(12) United States Patent
Cheung et al.

(10) Patent No.: US 11,168,150 B2
(45) Date of Patent: Nov. 9, 2021

(54) T CELL RECEPTOR-LIKE ANTIBODY AGENTS SPECIFIC FOR EBV LATENT MEMBRANE PROTEIN 2A PEPTIDE PRESENTED BY HUMAN HLA

(71) Applicants: Memorial Sloan Kettering Cancer Center, New York, NY (US); Eureka Therapeutics, Inc., Emeryville, CA (US)

(72) Inventors: Nai-Kong V. Cheung, New York, NY (US); Mahiuddin Ahmed, Verona, NJ (US); Andres Lopez-Albaitero, New York, NY (US); Cheng Liu, Emeryville, CA (US); Su Yan, State College, PA (US); Jingyi Xiang, Walnut Creek, CA (US); Hong Liu, El Sobrante, CA (US)

(73) Assignees: Memorial Sloan Kettering Cancer Center, New York, NY (US); Eureka Therapeutics, Inc., Emeryville, CA (US)

( * ) Notice: Subject to any disclaimer, the term of this patent is extended or adjusted under 35 U.S.C. 154(b) by 28 days.

(21) Appl. No.: 16/665,708

(22) Filed: Oct. 28, 2019

(65) Prior Publication Data
US 2020/0115470 A1   Apr. 16, 2020

Related U.S. Application Data

(62) Division of application No. 15/735,133, filed as application No. PCT/US2016/036735 on Jun. 9, 2016, now Pat. No. 10,501,559.

(60) Provisional application No. 62/173,330, filed on Jun. 9, 2015.

(51) Int. Cl.
| | |
|---|---|
| C07K 16/08 | (2006.01) |
| C07K 16/46 | (2006.01) |
| C07K 16/28 | (2006.01) |
| G01N 33/68 | (2006.01) |
| A61K 39/00 | (2006.01) |

(52) U.S. Cl.
CPC .......... *C07K 16/468* (2013.01); *C07K 16/085* (2013.01); *C07K 16/2809* (2013.01); *G01N 33/6854* (2013.01); *A61K 2039/505* (2013.01); *A61K 2039/572* (2013.01); *C07K 2317/21* (2013.01); *C07K 2317/31* (2013.01); *C07K 2317/32* (2013.01); *C07K 2317/33* (2013.01); *C07K 2317/34* (2013.01); *C07K 2317/40* (2013.01); *C07K 2317/41* (2013.01); *C07K 2317/56* (2013.01); *C07K 2317/565* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,218,149 | B1 | 4/2001 | Morrison et al. |
| 6,472,511 | B1 | 10/2002 | Leung et al. |
| 6,602,684 | B1 | 8/2003 | Umana et al. |
| 7,446,190 | B2 | 11/2008 | Sadelain et al. |
| 7,741,465 | B1 | 6/2010 | Eshhar et al. |
| 2002/0028486 | A1 | 3/2002 | Morrison et al. |
| 2003/0115614 | A1 | 6/2003 | Kanda et al. |
| 2006/0257427 | A1 | 11/2006 | Harley et al. |
| 2012/0213783 | A1 | 8/2012 | Rosenberg et al. |
| 2012/0294874 | A1 | 11/2012 | Macary et al. |
| 2018/0258187 | A1 | 9/2018 | Cheung et al. |

FOREIGN PATENT DOCUMENTS

| | | |
|---|---|---|
| EP | 0359096 B1 | 11/1997 |
| JP | 2014-512812 A | 5/2014 |
| WO | WO-00/61739 A1 | 10/2000 |
| WO | WO-2001/072768 A2 | 10/2001 |
| WO | WO-02/30954 A1 | 4/2002 |
| WO | WO-03/035835 A2 | 5/2003 |
| WO | WO-2004/041849 A1 | 5/2004 |
| WO | WO-2011/039508 A2 | 4/2011 |
| WO | WO-2011/062560 A1 | 5/2011 |
| WO | WO-2012/079000 A1 | 6/2012 |
| WO | WO-2012/109659 A1 | 8/2012 |
| WO | WO-2012/135854 A2 | 10/2012 |
| WO | WO-2013/126726 A1 | 8/2013 |
| WO | WO-2014/047231 A1 | 3/2014 |
| WO | WO-2015/018527 A1 | 2/2015 |
| WO | WO-2015/026892 A1 | 2/2015 |

(Continued)

OTHER PUBLICATIONS

Ahmed, M. et al., Human derived dimerization tag enhances tumor killing potency of a T-cell engaging bispecific antibody, Oncoimmunology, 4(4):e989776 (2015).

(Continued)

*Primary Examiner* — Stacy B Chen
(74) *Attorney, Agent, or Firm* — Choate, Hall & Stewart LLP; Brenda Herschbach Jarrell; Tracy L. Vrablik

(57) ABSTRACT

Described herein are antibodies, fragments thereof and multi-specific binding agents that bind an Epstein-Barr virus (EBV) latent membrane protein 2 (LMP2) peptide presented by HLA class I molecules, in particular, HLA-A02. Also provided herein are methods of using the same or compositions thereof for the detection, prevention and/or therapeutic treatment of diseases characterized by expression of an EBV-LMP2 peptide presented by HLA-A02, in particular, Burkit's lymphoma, Hodgkin's lymphoma and nasopharyngeal carcinoma.

16 Claims, 34 Drawing Sheets

Specification includes a Sequence Listing.

(56) References Cited

FOREIGN PATENT DOCUMENTS

| WO | WO-2015/080981 A1 | 6/2015 |
|---|---|---|
| WO | WO-2015/199618 A1 | 12/2015 |
| WO | WO-2016/201124 A2 | 12/2016 |

OTHER PUBLICATIONS

Altman, J. and Davis, M., MHC-peptide tetramers to visualize antigen-specific T cells, Curr Protoc Immunol., Chapter 17:Unit 17.3 (2003).
Andersen, P. et al., A recombinant antibody with the antigen-specific, major histocompatibility complex-restricted specificity of T cells, Proc Natl Acad Sci USA, 93(5):1820-4 (1996).
Biddison, W. et al., Tax and M1 peptide/HLA-A2-specific Fabs and T cell receptors recognize nonidentical structural features on peptide/HLA-A2 complexes, J Immunol., 171(6):3064-74 (2003).
Bollard, C. et al., T-cell therapy in the treatment of post-transplant lymphoproliferative disease, Nat Rev Clin Oncol., 9(9):510-9 (2012).
Borbulevych, O. et al., Conformational melding permits a conserved binding geometry in TCR recognition of foreign and self molecular mimics, J Immunol., 186(5):2950-8 (2011).
Borbulevych, O. et al., T cell receptor cross-reactivity directed by antigen-dependent tuning of peptide-MHC molecular flexibility, Immunity, 31(6):885-96 (2009).
Brischwein, K., et al. MT110: a novel bispecific single-chain antibody construct with high efficacy in eradicating established tumors, Mol. Immunol., 43(8):1129-43 (2006).
Burrows, S. et al., Have we cut ourselves too short in mapping CTL epitopes?, Trends Immunology, 27(1):11-16 (2006).
Chen, J. et al., Structural and kinetic basis for heightened immunogenicity of T cell vaccines, J Exp Med., 201(8):1243-55 (2005).
Cheung, W. et al., Conjugation of latent membrane protein (LMP)-2 epitope to gold nanoparticles as highly immunogenic multiple antigenic peptides for induction of Epstein-Barr virus-specific cytotoxic T-lymphocyte responses in vitro, Bioconjug Chem., 20(1):24-31 (2009).
Coghill, A. and Hildesheim, A., Epstein-Barr virus antibodies and the risk of associated malignancies: review of the literature, Am J Epidemiol., 180(7):687-95 (2014).
Cohen, C. et al., Direct detection and quantitation of a distinct T-cell epitope derived from tumor-specific epithelial cell-associated mucin using human recombinant antibodies endowed with the antigen-specific, major histocompatibility complex-restricted specificity of T cells, Cancer Res., 62(20):5835-44 (2002).
Cohen, C. et al., Direct phenotypic analysis of human MHC class I antigen presentation: visualization, quantitation, and in situ detection of human viral epitopes using peptide-specific, MHC-restricted human recombinant antibodies, J Immunol., 170(8):4349-61 (2003).
Dahan, R. and Reiter, Y., T-cell-receptor-like antibodies—generation, function and applications, Expert Rev Mol Med., 14:e6 (2012).
Dao, T. et al., Targeting the intracellular WT1 oncogene product with a therapeutic human antibody, Sci Transl Med., 5(176):176ra33 (2013).
Davies, J. et al., Expression of GnTIII in a recombinant anti-CD20 CHO production cell line: Expression of antibodies with altered glycoforms leads to an increase in ADCC through higher affinity for FC gamma RIII, Biotechnol Bioeng., 74(4):288-94 (2001).
Denkberg, G. et al., Direct visualization of distinct T cell epitopes derived from a melanoma tumor-associated antigen by using human recombinant antibodies with MHC-restricted T cell receptor-like specificity, Proc Natl Acad Sci USA, 99(14):9421-6 (2002).
Ding, Y. et al., Two human T cell receptors bind in a similar diagonal mode to the HLA-A2/Tax peptide complex using different TCR amino acids, Immunity, 8(4):403-11 (1998).
Donermeyer, D. et al., The study of high-affinity TCRs reveals duality in T cell recognition of antigen: specificity and degeneracy, J Immunol., 177(10):6911-9 (2006).

Epel, M. et al., Targeting TARP, a novel breast and prostate tumor-associated antigen, with T cell receptor-like human recombinant antibodies, Eur J Immunol., 38(6):1706-20 (2008).
Garboczi, D. et al., Structure of the complex between human T-cell receptor, viral peptide and HLA-A2, Nature, 384(6605):134-41 (1996).
Glaser, S. et al., Epstein-Barr virus-associated Hodgkin's disease: epidemiologic characteristics in international data, Int J Cancer, 70(4):375-82 (1997).
Gras, S. et al., Structural bases for the affinity-driven selection of a public TCR against a dominant human cytomegalovirus epitope, J Immunol., 183(1):430-7 (2009).
Grywalska, E. and Rolinski, J., Epstein-Barr virus-associated lymphomas, Semin Oncol., 42(2):291-303 (2015).
Haigh, T. et al., EBV latent membrane proteins (LMPs) 1 and 2 as immunotherapeutic targets: LMP-specific CD4+ cytotoxic T cell recognition of EBV-transformed B cell lines, J Immunol., 180(3):1643-54 (2008).
Hislop, A. et al., Cellular responses to viral infection in humans: lessons from Epstein-Barr virus. Annu Rev Immunol., 25:587-617 (2007).
International Search Report for PCT/US2016/036735, 7 pages (dated Feb. 9, 2017).
Jilek, S. et al., HLA-B7-Restricted EBV-Specific CD8+ T Cells Are Dysregulated in Multiple Sclerosis, The Journal of Immunology, 188(9):4671-4680 (2012).
Klechevsky, E. et al., Antitumor activity of immunotoxins with T-cell receptor-like specificity against human melanoma xenografts, Cancer Res., 68(15):6360-7 (2008).
Lee, S.E. et al., HLA A2.1-Restricted Cytotoxic T Cells Recognizing a Range of Epstein-Barr Virus Isolates through a Defined Epitope in Latent Membrane Protein LMP2, Journal of Virology, 61(12):7428-7435 (1993).
Liddy, N. et al., Monoclonal TCR-redirected tumor cell killing, Nat Med., 18(6):980-7 (2012).
Liu, Z. et al., Fine mapping of the antigen-antibody interaction of scFv215, a recombinant antibody inhibiting RNA polymerase II from *Drosophila melanogaster*, J Mol Recognit., 12(2):103-11 (1999).
Long, H. et al., Cytotoxic CD4+ T cell responses to EBV contrast with CD8 responses in breadth of lytic cycle antigen choice and in lytic cycle recognition, J Immunol., 187(1):92-101 (2011).
Long, H. et al., Immune defence against EBV and EBV-associated disease, Curr Opin Immunol., 23(2):258-64 (2011).
Louis, C. et al., Adoptive transfer of EBV-specific T cells results in sustained clinical responses in patients with locoregional nasopharyngeal carcinoma, J Immunother., 33(9):983-90 (2010).
Low, J. et al., Binding of TCR multimers and a TCR-like antibody with distinct fine-specificities is dependent on the surface density of HLA complexes, PLoS One, 7(12):e51397 (2012).
Lutzky, V. et al., Novel approach to the formulation of an Epstein-Barr virus antigen-based nasopharyngeal carcinoma vaccine, J Virol., 84(1):407-17 (2010).
Madden, D. et al., The antigenic identity of peptide-MHC complexes: a comparison of the conformations of five viral peptides presented by HLA-A2, Cell, 75(4):693-708 (1993).
Maloney, D. et al., IDEC-C2B8 (Rituximab) anti-CD20 monoclonal antibody therapy in patients with relapsed low-grade non-Hodgkin's lymphoma, Blood, 90(6):2188-95 (1997).
Massimo, D. et al., A Functional Hot Spot for Antigen Recognition in a Superagonist TCR/MHC Complex, Immunity 12:251-261 (2000).
Menezes, J. et al., Establishment and characterization of an Epstein-Barr virus (EBC)-negative lymphoblastoid B cell line (BJA-B) from an exceptional, EBV-genome-negative African Burkitt's lymphoma, Biomedicine, 22(4):276-84 (1975).
Miller, K. et al., T cell receptor-like recognition of tumor in vivo by synthetic antibody fragment, PLoS One, 7(8):e43746 (2012).
Morrison, K. and Weiss, G., Combinatorial alanine-scanning, Curr Opin Chem Biol., 5(3):302-7 (2001).
Ning, R. et al., Long-term carriers generate Epstein-Barr virus (EBV)-specific CD4(+) and CD8(+) polyfunctional T-cell responses which show immunodominance hierarchies of EBV proteins, Immunology, 134(2):161-71 (2011).

(56) References Cited

OTHER PUBLICATIONS

Ok, C. et al., EBV-driven B-cell lymphoproliferative disorders: from biology, classification and differential diagnosis to clinical management, Exp Mol Med., 47:e132 (2015).
Okazaki, A. et al., Fucose depletion from human IgG1 oligosaccharide enhances binding enthalpy and association rate between IgG1 and FcgammaRIIIa, J Mol Biol., 336(5):1239-49 (2004).
Oren, R. et al., Functional comparison of engineered T cells carrying a native TCR versus TCR-like antibody-based chimeric antigen receptors indicates affinity/avidity thresholds, J Immunol., 193(11):5733-43 (2014).
Parker, K. et al., Sequence motifs important for peptide binding to the human MHC class I molecule, HLA-A2, J Immunol., 149(11):3580-7 (1992).
Petersson, F., Nasopharyngeal carcinoma: a review, Semin Diagn Pathol., 32(1):54-73 (2015).
Rasche, L. et al., EBV-induced post transplant lymphoproliferative disorders: a persisting challenge in allogeneic hematopoetic SCT, Bone Marrow Transplant, 49(2):163-7 (2014).
Reali, et al., A single specific amino acid residue in peptide antigens is sufficient to activate memory CTL: potential role of cross-reactive peptides in memory T cell maintenance, J Immunol., 162(1):106-13 (1999).
Rudikoff, S. et al., Singl amino acid substitution altering antigen-binding specificity, Proc. Natl. Acad. Sci. USA, 79:1979-1983 (1982).
Rudolph, M. and Wilson, I., The specificity of TCR/pMHC interaction, Curr Opin Immunol., 14(1):52-65 (2002).
Rudolph, M. et al., How TCRs bind MHCs, peptides, and coreceptors, Annu Rev Immunol., 24:419-66 (2006).
Salter, R. et al., Genes regulating HLA class I antigen expression in T-B lymphoblast hybrids, Immunogenetics, 21(3):235-46 (1985).
Sergeeva, A., et al., An anti-PR1/HLA-A2 T-cell receptor-like antibody mediates complement-dependent cytotoxicity against acute myeloid leukemia progenitor cells, Blood, 117(16):4262-72 (2011).
Shanmugaratnam, K., Histological typing of nasopharyngeal carcinoma, IARC Sci Publ., (20):3-12 (1978).
Shields, R. et al., Lack of fucose on human IgG1 N-linked oligosaccharide improves binding to human Fcgamma RIII and antibody-dependent cellular toxicity, J Biol Chem., 277(30):26733-40 (2002).
Shinkawa,T. et al., The absence of fucose but not the presence of galactose or bisecting N-acetylglucosamine of human IgG1 complex-type oligosaccharides shows the critical role of enhancing antibody-dependent cellular cytotoxicity, J Biol Chem., 278(5):3466-73 (2003).
Sim, A. et al., Defining the expression hierarchy of latent T-cell epitopes in Epstein-Barr virus infection with TCR-like antibodies, Scientific Reports, 3:3232, 1-7 (2013).
Simpson, A. et al., Structural and energetic evidence for highly peptide-specific tumor antigen targeting via allo-MHC restriction, Proc Natl Acad Sci USA, 108(52):21176-81 (2011).
Sondermann, P. et al., The 3.2-A crystal structure of the human IgG1 Fc fragment-Fc gammaRIII complex, Nature, 406(6793):267-73 (2000) . . . .
Stewart-Jones, G. et al., A structural basis for immunodominant human T cell receptor recognition, Nat Immunol., 4(7):657-63 (2003).
Stewart-Jones, G. et al., Rational development of high-affinity T-cell receptor-like antibodies, Proc Natl Acad Sci USA, 106(14):5784-8 (2009).
Su, Z. et al., The generation of LMP2a-specific cytotoxic T lymphocytes for the treatment of patients with Epstein-Barr virus-positive Hodgkin disease, Eur. J. Immunol., 31:947-958 (2001).
Tassev, D. et al., Retargeting NK92 cells using an HLA-A2-restricted, EBNA3C-specific chimeric antigen receptor Cancer Gene Ther., 19(2):84-100 (2012).
Thorpe, I. and Brooks, C., Molecular evolution of affinity and flexibility in the immune system, Proc Natl Acad Sci USA, 104(21):8821-6 (2007).
Townsend, A. and Bodmer, H., Antigen recognition by class I-restricted T lymphocytes, Annu Rev Immunol., 7:601-24 (1989).
Tsao, S. et al., The role of Epstein-Barr virus in epithelial malignancies, J Pathol., 235(2):323-33 (2015).
Umana, P. et al., Engineered glycoforms of an antineuroblastoma IgG1 with optimized antibody-dependent cellular cytotoxic activity, Nat Biotechnol., 17(2):176-80 (1999).
Verma, B. et al., TCR mimic monoclonal antibodies induce apoptosis of tumor cells via immune effector-independent mechanisms, J Immunol., 186(5):3265-76 (2011).
Weidanz, J. et al., Levels of specific peptide-HLA class I complex predicts tumor cell susceptibility to CTL killing, J Immunol., 177(8):5088-97 (2006).
Weidanz, J. et al., TCR-like biomolecules target peptide/MHC Class I complexes on the surface of infected and cancerous cells, Int Rev Immunol., 30(5-6):328-40 (2011).
Weiss, G. et al., Rapid mapping of protein functional epitopes by combinatorial alanine scanning, Proc Natl Acad Sci USA, 97(16):8950-4 (2000).
Willemsen, R. et al., A phage display selected fab fragment with MHC class I-restricted specificity for MAGE-A1 allows for retargeting of primary human T lymphocytes, Gene Ther., 8(21):1601-8 (2001).
Written Opinion for PCT/US2016/036735, 18 pages (dated Feb. 9, 2017).
Xu, H. et al., Retargeting T cells to GD2 pentasaccharide on human tumors using Bispecific humanized antibody, Cancer Immunol Res., 3(3):266-77 (2015).
Zhang, G. et al., Anti-melanoma activity of T cells redirected with a TCR-like chimeric antigen receptor, Sci Rep., 4:3571, 1-8 (2014).
Ziegler, A. et al., Monoclonal and recombinant antibodies with T cell receptor-like reactivity, Recent Results Cancer Res., 176:229-41 (2007).
Kunik, V. et. al., Structural Consensus among Antibodies Defines the Antigen Binding Site, PLoS Computational Biology, 8(2) p. e1002388, (2012).

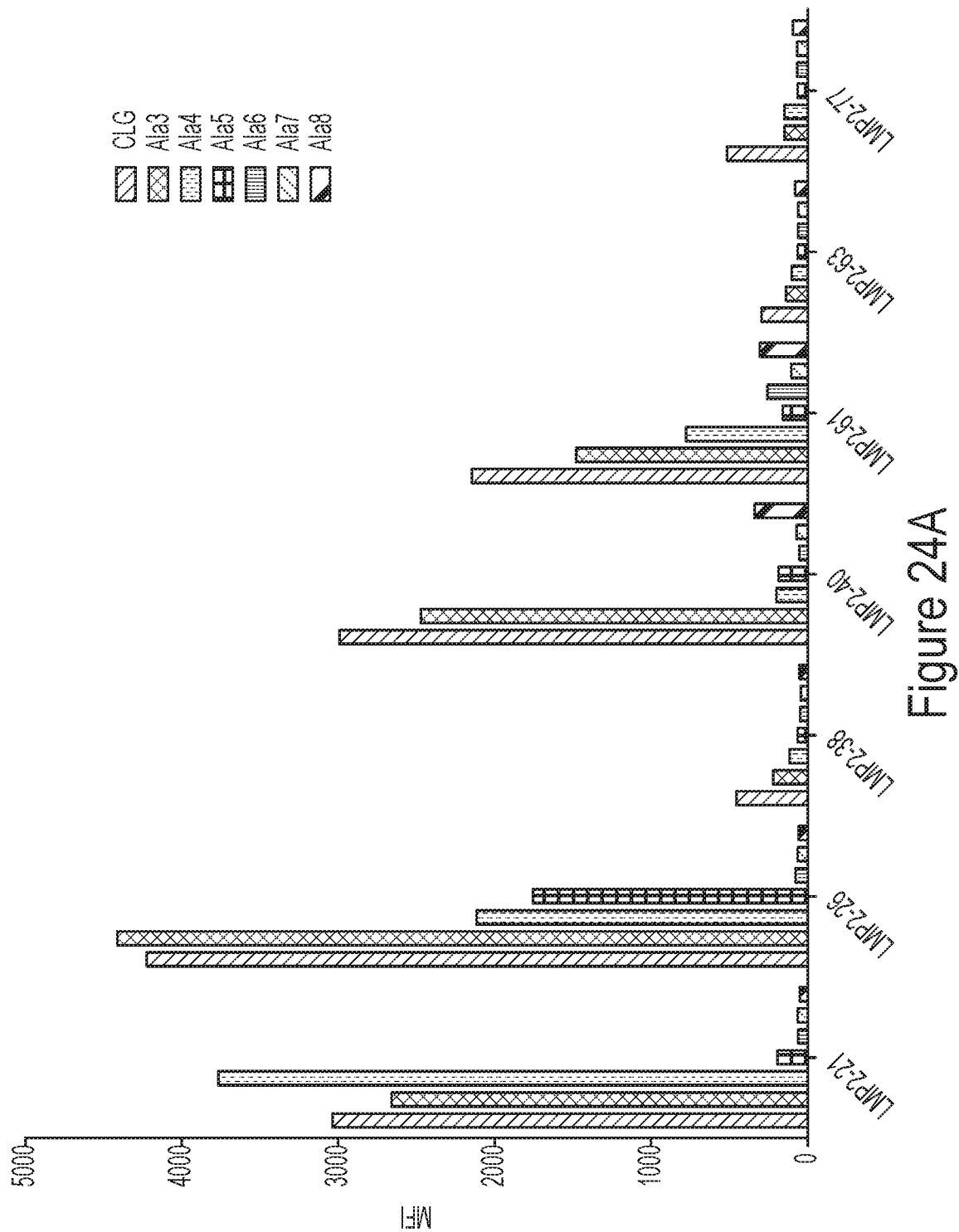

SEQUENCE LISTING

<160> NUMBER OF SEQ ID NOS: 144

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      EBV LMP2 peptide

<400> SEQUENCE: 1

Cys Leu Gly Gly Leu Leu Thr Met Val
1               5

<210> SEQ ID NO 2
<211> LENGTH: 327
<212> TYPE: DNA
<213> ORGANISM: Artificial Sequence
<220> FEATURE:
<223> OTHER INFORMATION: Description of Artificial Sequence: Synthetic
      LMP2-21 LCVR polynucleotide

<400> SEQUENCE: 2
acctatgagc tgactcagcc accctcagtg tcagtggccc caggagagac ggccaggatt      60
acctgtgggg gaaacaacat tggaggcaaa agtgtgcact ggtaccagca gaagccaggc     120 caggccctg tactggtcat ctcttatgat agcgaccggc cctcagggat ccctgagcga      180
atctccggct ccaactctgg gaacacggcc accctgacca tcagcagggt cgaagccggg     240
gatgaggccg actattactg tcaggtgtgg gatagtagta gtgatcattg ggtgttcggc     300
ggagggacca agctgaccgt cctaggt                                          327

<210> SEQ ID NO 3
<211> LENGTH: 109
<212> TYPE: PRT
<213> ORGANISM: Artificial Sequence
<220> FEATURE:
<223> OTHER INFORMATION: Description of Artificial Sequence: Synthetic
      LMP2-21 LCVR polypeptide

<400> SEQUENCE: 3

Ser Tyr Glu Leu Thr Gln Pro Pro Ser Val Ser Val Ala Pro Gly Glu
1               5                   10                  15

Thr Ala Arg Ile Thr Cys Gly Gly Asn Asn Ile Gly Gly Lys Ser Val
            20                  25                  30

His Trp Tyr Gln Gln Lys Pro Gly Gln Ala Pro Val Leu Val Ile Ser
        35                  40                  45

Tyr Asp Ser Asp Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly
            100                 105

<210> SEQ ID NO 4
<211> LENGTH: 360
<212> TYPE: DNA
<213> ORGANISM: Artificial Sequence
<220> FEATURE:
<223> OTHER INFORMATION: Description of Artificial Sequence: Synthetic
      LMP2-21 HCVR polynucleotide

<400> SEQUENCE: 4

```
taggtccagc tggtgcagtc tggggctgag gtgaagaagc tgggtcctc ggtgaaggtc      60 tcctgcaagg cttctggagg caccttcagc agctatgcta tcagctgggt gcgacaggcc    120
cctggacaag ggcttgagtg gatgggaagg atcatcccta tccttggtat agcaaactac    180
gcacagaagt tccagggcag agtcacgatt accgcggaca aatccacgag cacagcctac    240
atggagctga gcagcctgag atctgaggac accgccatgt attactgtgc gcgcggttct    300
taccatcagc attcttactc tgatgtttgg ggtcaaggta ctctggtgac cgtctcctca    360
```

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      LMP2-21 HCVR polypeptide

<400> SEQUENCE: 5

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Ser Tyr His Gln His Ser Tyr Ser Asp Val Trp Gly Gln
            100                 105                 110

Gly Thr Leu Val Thr Val Ser Ser
        115                 120
```

<210> SEQ ID NO 6
<211> LENGTH: 327
<212> TYPE: DNA
<213> ORGANISM: Artificial Sequence
<220> FEATURE:
<223> OTHER INFORMATION: Description of Artificial Sequence: Synthetic
      LMP2-26 LCVR polynucleotide

<400> SEQUENCE: 6

```
acctatgtgc tgactcagcc accctcagtc tcagtggccc caggaaagac ggccagagtt     60
acctgtgggg gaaataagat tggaagcaaa catgtgcact ggtaccaaca caaggcaggc    120
caggcccctg tgttggtcat ctattataat actgaccggc cctcgggat ccctgagcga     180 atctctggct ccaactctgg ggacacggcc accctgacca tcaccggggt cgaggccggc    240
gatgaggccg actattactg tcaggtgtgg gatagtagtt atgatcatgt gatattcggc    300
ggagggacca agctgaccgt cctaggt                                        327
```

<210> SEQ ID NO 7
<211> LENGTH: 109
<212> TYPE: PRT
<213> ORGANISM: Artificial Sequence
<220> FEATURE:

<223> OTHER INFORMATION: Description of Artificial Sequence: Synthetic
LMP2-26 LCVR polypeptide

<400> SEQUENCE: 7

Ser Tyr Val Leu Thr Gln Pro Pro Ser Val Ser Val Ala Pro Gly Lys
1               5                   10                  15

Thr Ala Arg Val Thr Cys Gly Gly Asn Lys Ile Gly Ser Lys His Val
            20                  25                  30

His Trp Tyr Gln His Lys Ala Gly Gln Ala Pro Val Leu Val Ile Tyr
        35                  40                  45

Tyr Asn Thr Asp Arg Pro Ser Gly Ile Pro Glu Arg Ile Ser Gly Ser
    50                  55                  60

Asn Ser Gly Asp Thr Ala Thr Leu Thr Ile Thr Gly Val Glu Ala Gly
65                  70                  75                  80

Asp Glu Ala Asp Tyr Tyr Cys Gln Val Trp Asp Ser Ser Tyr Asp His
                85                  90                  95

Val Ile Phe Gly Gly Gly Thr Lys Leu Thr Val Leu Gly
            100                 105

<210> SEQ ID NO 8
<211> LENGTH: 357
<212> TYPE: DNA
<213> ORGANISM: Artificial Sequence
<220> FEATURE:
<223> OTHER INFORMATION: Description of Artificial Sequence: Synthetic
LMP2-26 HCVR polynucleotide

<400> SEQUENCE: 8
aaggtgcagc tggtgcagtc tggggctgag gtgaagaagc ctgggtcctc ggtgaaggtc      60
tcctgcaagg cttctggagg caccttcagc agctatgcta tcaactgggt gcgacaggcc     120
cctggacaag gtcttgagtg gatgggaagg atcatcccta tccttggtat agcaaactac     180
gcacagaagt tccaggccag agtcacgatt accgcggaca atccacgag cacagcctac      240 atggagctga gcagcctgag atctgaggac acggccgtat attactgtgc gcgctcttac     300
ccgctgtact ctggttggga ttactggggt caaggtactc tggtgaccgt ctcctca         357

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
LMP2-26 HCVR polypeptide

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Pro Leu Tyr Ser Gly Trp Asp Tyr Trp Gly Gln Gly

Thr Leu Val Thr Val Ser Ser
              115

<210> SEQ ID NO 10
<211> LENGTH: 333
<212> TYPE: DNA
<213> ORGANISM: Artificial Sequence
<220> FEATURE:
<223> OTHER INFORMATION: Description of Artificial Sequence: Synthetic
      LMP2-38 LCVR polynucleotide

<400> SEQUENCE: 10
aaatctgccc tgactcagcc tgcctccgtg tctgggtctc caggacagtc gatcaccatc      60
tcctgcactg gaaccagcag tgacgttggt agttataacg atgtctcctg gtaccaacaa    120
cacccaggca agccccccaa actcatgatt tatgatgtca gtaatcggcc ctcagggott    180 tctaatcgct tctctggctc caagtctggc aacacggcct ccctgaccat ctctgggctc    240
cagactgagg acgaggctga ttattactgc aactcatata caagcagcaa cacttatgtc    300
ttcggaactg ggaccaaggt caccgtccta ggt                                  333

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      LMP2-38 LCVR polypeptide

<400> SEQUENCE: 11

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Asp Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Asn Ser Tyr Thr Ser Ser
                85                  90                  95

Asn Thr Tyr Val Phe Gly Thr Gly Thr Lys Val Thr Val Leu Gly
            100                 105                 110

<210> SEQ ID NO 12
<211> LENGTH: 348
<212> TYPE: DNA
<213> ORGANISM: Artificial Sequence
<220> FEATURE:
<223> OTHER INFORMATION: Description of Artificial Sequence: Synthetic
      LMP2-38 HCVR polynucleotide

<400> SEQUENCE: 12
taggtgcagc tggtgcagtc tggggctgag gtgaagaagc ctggggcctc agtgcaggtt      60
tcctgcaggg catctggata cacaatcacc tcctactata tgcactgggt gcgacaggcc    120
cctggacaag gcttgagtg gatgggagta atcaaccota atgctggcag cacaagatac    180
gcacagaaat tccagggcag agtcaccatg agcactgaca cgtccacgag cacagtctac    240

```
atggcgctga gtagtctgag atctgacgac actgccgtgt attactgtgc gcgcggtatg    300
taccgtatgt acgattgggg tcaaggtact ctggtgaccg tctcctca                 348
```

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      LMP2-38 HCVR polypeptide

<400> SEQUENCE: 13

Gln Val Gln Leu Val Gln Ser Gly Ala Glu Val Lys Lys Pro Gly Ala
1               5                   10                  15

Ser Val Gln Val Ser Cys Arg Ala Ser Gly Tyr Thr Ile Thr Ser Tyr
                20                  25                  30

Tyr Met His Trp Val Arg Gln Ala Pro Gly Gln Gly Leu Glu Trp Met
            35                  40                  45

Gly Val Ile Asn Pro Asn Ala Gly Ser Thr Arg Tyr Ala Gln Lys Phe
        50                  55                  60

Gln Gly Arg Val Thr Met Ser Thr Asp Thr Ser Thr Ser Thr Val Tyr
65                  70                  75                  80

Met Ala Leu Ser Ser Leu Arg Ser Asp Asp Thr Ala Val Tyr Tyr Cys
                85                  90                  95

Ala Arg Gly Met Tyr Arg Met Tyr Asp Trp Gly Gln Gly Thr Leu Val
                100                 105                 110

Thr Val Ser Ser
        115

<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      LMP2-40 LCVR polynucleotide

<400> SEQUENCE: 14

```
aagtctgtgt tgactcagcc accctcagtg tcagtggccc caggagagac ggccagaatt    60
acctgtgggg gaaacaacat tggaagtaga agtgtgcact ggtaccagca gaaggcaggc   120
caggcccctg ttctggtcat ctcttataat aacgaccggc cctcagggat ccctgagcga   180
atctctggct ccaactctgg gaacacggcc accctgacca tcagcagggt cgaagccggg   240
gatgaggccg acttttactg tcaggtgtgg gatagtatta gtgaccatta tgtcttcgga   300
actgggacca aggtcaccgt cctaggt                                       327
```

<210> SEQ ID NO 15
<211> LENGTH: 109
<212> TYPE: PRT
<213> ORGANISM: Artificial Sequence
<220> FEATURE:
<223> OTHER INFORMATION: Description of Artificial Sequence: Synthetic
      LMP2-40 LCVR polypeptide

<400> SEQUENCE: 15

Gln Ser Val Leu Thr Gln Pro Pro Ser Val Ser Val Ala Pro Gly Glu
1               5                   10                  15

Thr Ala Arg Ile Thr Cys Gly Gly Asn Asn Ile Gly Ser Arg Ser Val
                20                  25                  30

His Trp Tyr Gln Gln Lys Ala Gly Gln Ala Pro Val Leu Val Ile Ser
            35                  40                  45

Tyr Asn Asn Asp Arg Pro Ser Gly Ile Pro Glu Arg Ile Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Phe Tyr Cys Gln Val Trp Asp Ser Ile Ser Asp His
                85                  90                  95

Tyr Val Phe Gly Thr Gly Thr Lys Val Thr Val Leu Gly
               100                 105

<210> SEQ ID NO 16
<211> LENGTH: 360
<212> TYPE: DNA
<213> ORGANISM: Artificial Sequence
<220> FEATURE:
<223> OTHER INFORMATION: Description of Artificial Sequence: Synthetic
      LMP2-40 HCVR polynucleotide

<400> SEQUENCE: 16
taggtgcagc tggtggagtc tggggctgag gtgaagaaac ctgggtcctc ggtgaaggtc      60
gcctgcaagg gttctggagg caccttcagc aactatcata tcagctgggt gcgacaggcc     120
cctggacaag gcttgagtg gatgggtggg atcatcccca tccttggcac accaaactac     180
gcaccgaaat tcctggacag agtcacgatt tccgcgacg attccacgag cacagcctac     240
atggagctga gcagcctcac agctgacgac acggccgtat attactgtgc gcgcggtcgt     300
acttggtggt ctggtactct ggattcttgg ggtcaaggta ctctggtgac cgtctcctca     360

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      LMP2-40 HCVR polypeptide

<400> SEQUENCE: 17

Gln Val Gln Leu Val Glu Ser Gly Ala Glu Val Lys Lys Pro Gly Ser
 1               5                  10                  15

Ser Val Lys Val Ala Cys Lys Gly Ser Gly Gly Thr Phe Ser Asn Tyr
                20                  25                  30

His Ile Ser Trp Val Arg Gln Ala Pro Gly Gln Gly Leu Glu Trp Met
            35                  40                  45

Gly Gly Ile Ile Pro Ile Leu Gly Thr Pro Asn Tyr Ala Pro Lys Phe
 50                  55                  60

Leu Asp Arg Val Thr Ile Ser Ala Asp Asp Ser Thr Ser Thr Ala Tyr
 65                  70                  75                  80

Met Glu Leu Ser Ser Leu Thr Ala Asp Asp Thr Ala Val Tyr Tyr Cys
                85                  90                  95

Ala Arg Gly Arg Thr Trp Trp Ser Gly Thr Leu Asp Ser Trp Gly Gln
               100                 105                 110

Gly Thr Leu Val Thr Val Ser Ser
           115                 120

<210> SEQ ID NO 18
<211> LENGTH: 327
<212> TYPE: DNA
<213> ORGANISM: Artificial Sequence
<220> FEATURE:

<223> OTHER INFORMATION: Description of Artificial Sequence: Synthetic
    LMP2-61 LCVR polynucleotide

<400> SEQUENCE: 18
gcttctgagc tgactcagga ccctgctgtg tctgtggcct tgggacagac agtcaggatc      60
acatgccaag agacagcct cagaagctat tatgcaagct ggtaccagca aaagccagga     120
caggcccctg tacttgtcat ctatggtaaa acaaccggc cctcagggat cccagaccga     180
ttctctggct ccagctcagg aaacacagct tccttgacca tcactgggc tcaggcggaa     240 gatgaggctg actattactg taactcccgg acagcagtg gtaaccatct ggtattcggc     300
ggagggacca agctgaccgt cctaggt                                         327

<210> SEQ ID NO 19
<211> LENGTH: 109
<212> TYPE: PRT
<213> ORGANISM: Artificial Sequence
<220> FEATURE:
<223> OTHER INFORMATION: Description of Artificial Sequence: Synthetic
    LMP2-61 LCVR polypeptide

<400> SEQUENCE: 19

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly
            100                 105

<210> SEQ ID NO 20
<211> LENGTH: 351
<212> TYPE: DNA
<213> ORGANISM: Artificial Sequence
<220> FEATURE:
<223> OTHER INFORMATION: Description of Artificial Sequence: Synthetic
    LMP2-61 HCVR polynucleotide

<400> SEQUENCE: 20
taggtgcagc tggtgcagtc tggggctgag gtgaagaggc ctggggcctc agtgaaggtc      60
tcctgcaagg catctggata caccttcacc aactattata tccactgggt gcgacaggcc     120
cctggacaag gcttgagtg gatgggaaga atcaaccccta gtggtgggag cacaaattac     180
gcaccgaagt tccagggcag agtcaccatg accaggaca cgtccacgaa cacagtctac     240
atggaactga gcagcctgag atctgaggac actgccgtgt attactgtgc gcgctcttac     300
tacggttcta tggatgcttg gggtcaaggt actctggtga ccgtctcctc a              351

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic LMP2-61 HCVR polypeptide

<400> SEQUENCE: 21

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Arg Ile Asn Pro Ser Gly Gly Ser Thr Asn Tyr Ala Pro Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Gly Ser Met Asp Ala Trp Gly Gln Gly Thr Leu
            100                 105                 110

Val Thr Val Ser Ser
        115

<210> SEQ ID NO 22
<211> LENGTH: 327
<212> TYPE: DNA
<213> ORGANISM: Artificial Sequence
<220> FEATURE:
<223> OTHER INFORMATION: Description of Artificial Sequence: Synthetic
      LMP2-63 LCVR polynucleotide

<400> SEQUENCE: 22
tcctatgtgc tgactcagcc accctcggtg tcagtggccc caggaaagac ggccagactt      60
acctgtgggg gaaacaacat tggaagtgaa agtgtacatt ggtaccagca gaagccaggc     120
caggcccctt tactggtcgt ctatgatgat gacgaccggc cctccgggat ccctgagcga     180
ttctctggct ccaactctgg gaacacggcc accctgacca tcagcagggt cgaggccggc     240
gatgaggccg actattactg tcaggtgtgg gatcgaagta gtgatcattg gttttcggc      300 ggagggacca aggtcaccgt cctaggt                                         327

<210> SEQ ID NO 23
<211> LENGTH: 109
<212> TYPE: PRT
<213> ORGANISM: Artificial Sequence
<220> FEATURE:
<223> OTHER INFORMATION: Description of Artificial Sequence: Synthetic
      LMP2-63 LCVR polypeptide

<400> SEQUENCE: 23

Ser Tyr Val Leu Thr Gln Pro Pro Ser Val Ser Val Ala Pro Gly Lys
1               5                   10                  15

Thr Ala Arg Leu Thr Cys Gly Gly Asn Asn Ile Gly Ser Glu Ser Val
            20                  25                  30

His Trp Tyr Gln Gln Lys Pro Gly Gln Ala Pro Leu Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp His
                85                  90                  95

Trp Phe Phe Gly Gly Gly Thr Lys Val Thr Val Leu Gly
            100                 105

<210> SEQ ID NO 24
<211> LENGTH: 354
<212> TYPE: DNA
<213> ORGANISM: Artificial Sequence
<220> FEATURE:
<223> OTHER INFORMATION: Description of Artificial Sequence: Synthetic
      LMP2-63 HCVR polynucleotide

<400> SEQUENCE: 24
aaggtccagc tggtacagtc tggggctgag gtgaagaagc tggggcctc  agtgcaggtt    60 tcctgcaggg catctggata caatcacc tcctactata tgcactgggt gcgacaggcc    120
cctggacaag gcttgagtg gatgggagta atcaaccct  atgctggcag cacaagatac    180
gcacagaaat tccagggcag agtcaccatg agcactgaca cgtccacgag cacagtctac    240
atggcgctga gtagtctgag atctgacgac acggccgtgt attactgtgc gcgcggtgac    300
gtttacaacg gttgggatga atggggtcaa ggtactctgg tgaccgtctc ctca          354

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      LMP2-63 HCVR polypeptide

<400> SEQUENCE: 25

Glu Val Gln Leu Val Gln Ser Gly Ala Glu Val Lys Lys Pro Gly Ala
1               5                   10                  15

Ser Val Gln Val Ser Cys Arg Ala Ser Gly Tyr Thr Ile Thr Ser Tyr
            20                  25                  30

Tyr Met His Trp Val Arg Gln Ala Pro Gly Gln Gly Leu Glu Trp Met
        35                  40                  45

Gly Val Ile Asn Pro Asn Ala Gly Ser Thr Arg Tyr Ala Gln Lys Phe
    50                  55                  60

Gln Gly Arg Val Thr Met Ser Thr Asp Thr Ser Thr Ser Thr Val Tyr
65                  70                  75                  80

Met Ala Leu Ser Ser Leu Arg Ser Asp Asp Thr Ala Val Tyr Tyr Cys
                85                  90                  95

Ala Arg Gly Asp Val Tyr Asn Gly Trp Asp Glu Trp Gly Gln Gly Thr
            100                 105                 110

Leu Val Thr Val Ser Ser
        115

<210> SEQ ID NO 26
<211> LENGTH: 327
<212> TYPE: DNA
<213> ORGANISM: Artificial Sequence
<220> FEATURE:
<223> OTHER INFORMATION: Description of Artificial Sequence: Synthetic
      LMP2-77 LCVR polynucleotide

<400> SEQUENCE: 26
gcttctgagc tgactcagga ccctgctgtg tctgtggcct tgggacagac agtcaggttc    60
acatgccaag agacagcct  cagaacgcat tatgcaagtt ggtaccagca gaagccagga    120 caggccctc  aacttgtcat ctatggtaaa acaggcggc  cctcagggat cccagaccga    180

```
ttctctggct ccacctcagg aaacaccgct tccttgacca tcactggggc tcaggcggaa    240
gatgagggtg actattactg taactcccgg cacagcagtg gtaatcattg tgtgtttggc    300
ggagggacca agctgaccgt cctaggt                                         327
```

<210> SEQ ID NO 27
<211> LENGTH: 109
<212> TYPE: PRT
<213> ORGANISM: Artificial Sequence
<220> FEATURE:
<223> OTHER INFORMATION: Description of Artificial Sequence: Synthetic
   LMP2-77 LCVR polypeptide

<400> SEQUENCE: 27

```
Ser Ser Glu Leu Thr Gln Asp Pro Ala Val Ser Val Ala Leu Gly Gln
1               5                   10                  15

Thr Val Arg Phe Thr Cys Gln Gly Asp Ser Leu Arg Thr His Tyr Ala
            20                  25                  30

Ser Trp Tyr Gln Gln Lys Pro Gly Gln Ala Pro Gln Leu Val Ile Tyr
        35                  40                  45

Gly Lys Asn Arg Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Gly Asp Tyr Tyr Cys Asn Ser Arg His Ser Ser Gly Asn His
                85                  90                  95

Cys Val Phe Gly Gly Gly Thr Lys Leu Thr Val Leu Gly
            100                 105
```

<210> SEQ ID NO 28
<211> LENGTH: 360
<212> TYPE: DNA
<213> ORGANISM: Artificial Sequence
<220> FEATURE:
<223> OTHER INFORMATION: Description of Artificial Sequence: Synthetic
   LMP2-77 HCVR polynucleotide

<400> SEQUENCE: 28

```
taggtgcagc tggtggagtc tggcccagga ctggtgaaac cttcacagac cctgtccctc    60
acctgcactg tctctggtgg ctccatcacc agtggtaatt actactggag ctggatccgt    120
cagcccccag gaaggggct ggagtggatt ggggagatca atcatagcgg aagccccaag    180
tacaatccgt ccctcaagag tcgagtcacc atatcagaag acacgtcccg gaaccagttc    240
tccctgaagc tgagctctgt gaccgccgcg gacacggccg tgtattactg tgcgcgccag    300
tcttcttacg gtggttacat agatcagtgg ggtcaaggta ctctggtgac cgtctcctca    360
```

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
   LMP2-77 HCVR polypeptide

<400> SEQUENCE: 29

```
Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Asn Tyr Tyr Trp Ser Trp Ile Arg Gln Pro Pro Gly Lys Gly Leu Glu
```

```
                35                  40                  45
Trp Ile Gly Glu Ile Asn His Ser Gly Ser Pro Lys Tyr Asn Pro Ser
        50                  55                  60

Leu Lys Ser Arg Val Thr Ile Ser Glu Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Ser Ser Tyr Gly Gly Tyr Ile Asp Gln Trp Gly Gln
            100                 105                 110

Gly Thr Leu Val Thr Val Ser Ser
        115                 120

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-21 HCDR1 polynucleotide

<400> SEQUENCE: 30
ggaggcacct tcagcagcta tgct                                              24

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-21 HCDR1 polypeptide

<400> SEQUENCE: 31

Gly Gly Thr Phe Ser Ser Tyr Ala
1               5

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-21 HCDR2 polynucleotide

<400> SEQUENCE: 32
atcatcccta tccttggtat agca                                              24

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-21 HCDR2 polypeptide

<400> SEQUENCE: 33

Ile Ile Pro Ile Leu Gly Ile Ala
1               5

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      LMP2-21 HCDR3 polynucleotide
```

<400> SEQUENCE: 34
gcgcgcggtt cttaccatca gcattcttac tctgatgtt                    39

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      LMP2-21 HCDR3 polypeptide

<400> SEQUENCE: 35

Ala Arg Gly Ser Tyr His Gln His Ser Tyr Ser Asp Val
1               5                   10

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-26 HCDR1 polynucleotide

<400> SEQUENCE: 36
ggaggcacct tcagcagcta tgct                                    24

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-26 HCDR1 polypeptide

<400> SEQUENCE: 37

Gly Gly Thr Phe Ser Ser Tyr Ala
1               5

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-26 HCDR2 polynucleotide

<400> SEQUENCE: 38
atcatcccta tccttggtat agca                                    24

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-26 HCDR2 polypeptide

<400> SEQUENCE: 39

Ile Ile Pro Ile Leu Gly Ile Ala
1               5

<210> SEQ ID NO 40
<211> LENGTH: 36
<212> TYPE: DNA
<213> ORGANISM: Artificial Sequence
<220> FEATURE:

```
<223> OTHER INFORMATION: Description of Artificial Sequence: Synthetic
      LMP2-26 HCDR3 polynucleotide

<400> SEQUENCE: 40
gcgcgctctt acccgctgta ctctggttgg gattac                              36

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      LMP2-26 HCDR3 polypeptide

<400> SEQUENCE: 41

Ala Arg Ser Tyr Pro Leu Tyr Ser Gly Trp Asp Tyr
1               5                   10

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-38 HCDR1 polynucleotide

<400> SEQUENCE: 42
ggatacacaa tcacctccta ctat                                          24

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-38 HCDR1 polypeptide

<400> SEQUENCE: 43

Gly Tyr Thr Ile Thr Ser Tyr Tyr
1               5

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-38 HCDR2 polynucleotide

<400> SEQUENCE: 44
atcaacccta atgctggcag caca                                          24

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-38 HCDR2 polypeptide

<400> SEQUENCE: 45

Ile Asn Pro Asn Ala Gly Ser Thr
1               5

<210> SEQ ID NO 46
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      LMP2-38 HCDR3 polynucleotide

<400> SEQUENCE: 46
gcgcgcggta tgtaccgtat gtacgat                                          27

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      LMP2-38 HCDR3 polypeptide

<400> SEQUENCE: 47

Ala Arg Gly Met Tyr Arg Met Tyr Asp
1               5

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-40 HCDR1 polynucleotide

<400> SEQUENCE: 48
ggaggcacct tcagcaacta tcat                                             24

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-40 HCDR1 polypeptide

<400> SEQUENCE: 49

Gly Gly Thr Phe Ser Asn Tyr His
1               5

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-40 HCDR2 polynucleotide

<400> SEQUENCE: 50
atcatcccca tccttggcac acca                                             24

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-40 HCDR2 polypeptide

<400> SEQUENCE: 51

Ile Ile Pro Ile Leu Gly Thr Pro
1               5

<210> SEQ ID NO 52
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      LMP2-40 HCDR3 polynucleotide

<400> SEQUENCE: 52
gcgcgcggtc gtacttggtg gtctggtact ctggattct                          39

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      LMP2-40 HCDR3 polypeptide

<400> SEQUENCE: 53

Ala Arg Gly Arg Thr Trp Trp Ser Gly Thr Leu Asp Ser
1               5                   10

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-61 HCDR1 polynucleotide

<400> SEQUENCE: 54
ggatacacct tcaccaacta ttat                                         24

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-61 HCDR1 polypeptide

<400> SEQUENCE: 55

Gly Tyr Thr Phe Thr Asn Tyr Tyr
1               5

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-61 HCDR2 polynucleotide

<400> SEQUENCE: 56
atcaacccta gtggtgggag caca                                         24

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-61 HCDR2 polypeptide

<400> SEQUENCE: 57

Ile Asn Pro Ser Gly Gly Ser Thr
1               5
```

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      LMP2-61 HCDR3 polynucleotide

<400> SEQUENCE: 58
gcgcgctctt actacggttc tatggatgct                                         30

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      LMP2-61 HCDR3 polypeptide

<400> SEQUENCE: 59

Ala Arg Ser Tyr Tyr Gly Ser Met Asp Ala
1               5                   10

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-63 HCDR1 polynucleotide

<400> SEQUENCE: 60
ggatacacaa tcacctccta ctat                                               24

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-63 HCDR1 polypeptide

<400> SEQUENCE: 61

Gly Tyr Thr Ile Thr Ser Tyr Tyr
1               5

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      LMP2-63 HCDR2 polynucleotide

<400> SEQUENCE: 62
atcaacccta atgctggcag caca                                               24

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      LMP2-63 HCDR2 polypeptide

<400> SEQUENCE: 63

Ile Asn Pro Asn Ala Gly Ser Thr

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-63 HCDR3 polynucleotide

<400> SEQUENCE: 64
gcgcgcggtg acgtttacaa cggttgggat gaa                              33

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-63 HCDR3 polypeptide

<400> SEQUENCE: 65

Ala Arg Gly Asp Val Tyr Asn Gly Trp Asp Glu
1               5                   10

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      LMP2-77 HCDR1 polynucleotide

<400> SEQUENCE: 66
ggtggctcca tcaccagtgg taattactac                                  30

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      LMP2-77 HCDR1 polypeptide

<400> SEQUENCE: 67

Gly Gly Ser Ile Thr Ser Gly Asn Tyr Tyr
1               5                   10

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      LMP2-77 HCDR2 polynucleotide

<400> SEQUENCE: 68
atcaatcata gcggaagccc c                                           21

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      LMP2-77 HCDR2 polypeptide

<400> SEQUENCE: 69

Ile Asn His Ser Gly Ser Pro
1               5

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      LMP2-77 HCDR3 polynucleotide

<400> SEQUENCE: 70
gcgcgccagt cttcttacgg tggttacata gatcag                                36

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      LMP2-77 HCDR3 polypeptide

<400> SEQUENCE: 71

Ala Arg Gln Ser Ser Tyr Gly Gly Tyr Ile Asp Gln
1               5                   10

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-21 LCDR1 polynucleotide

<400> SEQUENCE: 72
aacattggag gcaaaagt                                                    18

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-21 LCDR1 polypeptide

<400> SEQUENCE: 73

Asn Ile Gly Gly Lys Ser
1               5

<210> SEQ ID NO 74
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-21 LCDR2 polynucleotide

<400> SEQUENCE: 74 tatgatagc                                                              9

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      LMP2-21 LCDR2 polypeptide

<400> SEQUENCE: 75

Tyr Asp Ser
1

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-21 LCDR3 polynucleotide

<400> SEQUENCE: 76
caggtgtggg atagtagtag tgatcattgg gtg                                    33

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-21 LCDR3 polypeptide

<400> SEQUENCE: 77

Gln Val Trp Asp Ser Ser Ser Asp His Trp Val
1               5                   10

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-26 LCDR1 polynucleotide

<400> SEQUENCE: 78
aagattggaa gcaaacat                                                     18

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-26 LCDR1 polypeptide

<400> SEQUENCE: 79

Lys Ile Gly Ser Lys His
1               5

<210> SEQ ID NO 80
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-26 LCDR2 polynucleotide

<400> SEQUENCE: 80 tataatact                                                                9

<210> SEQ ID NO 81
<211> LENGTH: 3
<212> TYPE: PRT
<213> ORGANISM: Artificial Sequence
<220> FEATURE:

<223> OTHER INFORMATION: Description of Artificial Sequence: Synthetic
      LMP2-26 LCDR2 polypeptide

<400> SEQUENCE: 81

Tyr Asn Thr
1

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-26 LCDR3 polynucleotide

<400> SEQUENCE: 82
caggtgtggg atagtagtta tgatcatgtg ata                                33

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-26 LCDR3 polypeptide

<400> SEQUENCE: 83

Gln Val Trp Asp Ser Ser Tyr Asp His Val Ile
1               5                   10

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      LMP2-38 LCDR1 polynucleotide

<400> SEQUENCE: 84
agcagtgacg ttggtagtta taacgat                                       27

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      LMP2-38 LCDR1 polypeptide

<400> SEQUENCE: 85

Ser Ser Asp Val Gly Ser Tyr Asn Asp
1               5

<210> SEQ ID NO 86
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-38 LCDR2 polynucleotide

<400> SEQUENCE: 86 gatgtcagt                                                            9

<210> SEQ ID NO 87
<211> LENGTH: 3
<212> TYPE: PRT

```
<213> ORGANISM: Artificial Sequence
<220> FEATURE:
<223> OTHER INFORMATION: Description of Artificial Sequence: Synthetic
      LMP2-38 LCDR2 polypeptide

<400> SEQUENCE: 87

Asp Val Ser
1

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      LMP2-38 LCDR3 polynucleotide

<400> SEQUENCE: 88
aactcatata caagcagcaa cacttatgtc                                      30

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      LMP2-38 LCDR3 polypeptide

<400> SEQUENCE: 89

Asn Ser Tyr Thr Ser Ser Asn Thr Tyr Val
1               5                   10

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-40 LCDR1 polynucleotide

<400> SEQUENCE: 90
aacattggaa gtagaagt                                                   18

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-40 LCDR1 polypeptide

<400> SEQUENCE: 91

Asn Ile Gly Ser Arg Ser
1               5

<210> SEQ ID NO 92
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-40 LCDR2 polynucleotide

<400> SEQUENCE: 92 tataataac                                                              9

<210> SEQ ID NO 93
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      LMP2-40 LCDR2 polypeptide

<400> SEQUENCE: 93

Tyr Asn Asn
1

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-40 LCDR3 polynucleotide

<400> SEQUENCE: 94
caggtgtggg atagtattag tgaccattat gtc                                   33

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-40 LCDR3 polypeptide

<400> SEQUENCE: 95

Gln Val Trp Asp Ser Ile Ser Asp His Tyr Val
1               5                   10

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-61 LCDR1 polynucleotide

<400> SEQUENCE: 96
agcctcagaa gctattat                                                    18

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-61 LCDR1 polypeptide

<400> SEQUENCE: 97

Ser Leu Arg Ser Tyr Tyr
1               5

<210> SEQ ID NO 98
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-61 LCDR2 polynucleotide

<400> SEQUENCE: 98 ggtaaaaac                                                               9
```

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      LMP2-61 LCDR2 polypeptide

<400> SEQUENCE: 99

Gly Lys Asn
1

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-61 LCDR3 polynucleotide

<400> SEQUENCE: 100
aactcccggg acagcagtgg taaccatctg gta                                33

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-61 LCDR3 polypeptide

<400> SEQUENCE: 101

Asn Ser Arg Asp Ser Ser Gly Asn His Leu Val
1               5                   10

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-63 LCDR1 polynucleotide

<400> SEQUENCE: 102
aacattggaa gtgaaagt                                                 18

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-63 LCDR1 polypeptide

<400> SEQUENCE: 103

Asn Ile Gly Ser Glu Ser
1               5

<210> SEQ ID NO 104
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-63 LCDR2 polynucleotide

<400> SEQUENCE: 104 gatgatgac                                                                          9

<210> SEQ ID NO 105
<211> LENGTH: 3
<212> TYPE: PRT
<213> ORGANISM: Artificial Sequence
<220> FEATURE:
<223> OTHER INFORMATION: Description of Artificial Sequence: Synthetic
      LMP2-63 LCDR2 polypeptide

<400> SEQUENCE: 105

Asp Asp Asp
1

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-63 LCDR3 polynucleotide

<400> SEQUENCE: 106
caggtgtggg atcgaagtag tgatcattgg ttt                                              33

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-63 LCDR3 polypeptide

<400> SEQUENCE: 107

Gln Val Trp Asp Arg Ser Ser Asp His Trp Phe
1               5                   10

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      LMP2-77 LCDR1 polynucleotide

<400> SEQUENCE: 108
agcctcagaa cgcattat                                                               18

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      LMP2-77 LCDR1 polypeptide

<400> SEQUENCE: 109

Ser Leu Arg Thr His Tyr
1               5

<210> SEQ ID NO 110
<211> LENGTH: 9
<212> TYPE: DNA
<213> ORGANISM: Artificial Sequence
<220> FEATURE:
<223> OTHER INFORMATION: Description of Artificial Sequence: Synthetic
      LMP2-77 LCDR2 polynucleotide

```
<400> SEQUENCE: 110 ggtaaaaac                                                               9

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      LMP2-77 LCDR2 polypeptide

<400> SEQUENCE: 111

Gly Lys Asn
1

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
      LMP2-77 LCDR3 polynucleotide

<400> SEQUENCE: 112
aactcccggc acagcagtgg taatcattgt gtg                                   33

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      LMP2-77 LCDR3 polypeptide

<400> SEQUENCE: 113

Asn Ser Arg His Ser Ser Gly Asn His Cys Val
1               5                   10

<210> SEQ ID NO 114
<211> LENGTH: 318
<212> TYPE: DNA
<213> ORGANISM: Homo sapiens

<400> SEQUENCE: 114
aagcctaagg ccaaccctac cgtgaccctg ttccccccat cctccgagga actgcaggcc      60
aacaaggcca cctcgtgtg cctgatctcc gacttctacc ctggcgccgt gaccgtggcc     120
tggaaggctg atggatctcc tgtgaaggcc ggcgtggaaa ccaccaagcc ctccaagcag    180
tccaacaaca aatacgccgc ctcctcctac ctgtccctga ccctgagca gtggaagtcc     240 caccggtcct acagctgcca agtgacccac gagggctcca ccgtggaaaa gaccgtggct   300
cctaccgagt gctcctag                                                  318

<210> SEQ ID NO 115
<211> LENGTH: 105
<212> TYPE: PRT
<213> ORGANISM: Homo sapiens

<400> SEQUENCE: 115

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30
```

```
Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 116
<211> LENGTH: 321
<212> TYPE: DNA
<213> ORGANISM: Homo sapiens

<400> SEQUENCE: 116
accgtggccg ctccctccgt gttcatcttc ccaccttccg acgagcagct gaagtccggc      60
accgcttctg tcgtgtgcct gctgaacaac ttctaccccc gcgaggccaa ggtgcagtgg     120
aaggtggaca acgccctgca gagcggcaac tcccaggaat ccgtgaccga gcaggactcc     180
aaggacagca cctactccct gtcctccacc ctgaccctgt ccaaggccga ctacgagaag     240
cacaaggtgt acgcctgcga agtgacccac cagggcctgt ctagccccgt gaccaagtct     300
ttcaaccggg gcgagtgcta g                                               321

<210> SEQ ID NO 117
<211> LENGTH: 106
<212> TYPE: PRT
<213> ORGANISM: Homo sapiens

<400> SEQUENCE: 117

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 118
<211> LENGTH: 1002
<212> TYPE: DNA
<213> ORGANISM: Homo sapiens

<400> SEQUENCE: 118
gtctcctcag cttccaccaa gggcccatcg gtcttccccc tggcaccctc ctccaagagc      60
acctctgggg gcacagcggc cctgggctgc ctggtcaagg actacttccc cgaaccggtg     120
acggtgtcgt ggaactcagg cgccctgacc agcggcgtgc acaccttccc ggccgtccta     180
cagtcctcag gactctactc cctcagcagc gtggtgaccg tgccctccag cagcttgggc     240
```

```
acccagacct acatctgcaa cgtgaatcac aagcccagca acaccaaggt ggacaagaag    300
gttgagccca atcttgtga caaaactcac acatgcccac cgtgcccagc acctgaactc    360
ctggggggac cgtcagtctt cctcttcccc ccaaaaccca aggacaccct catgatctcc    420
cggacccctg aggtcacatg cgtggtggtg gacgtgagcc acgaagaccc tgaggtcaag    480
ttcaactggt acgtggacgg cgtggaggtg cataatgcca agacaaagcc gcgggaggag    540
cagtacaaca gcacgtaccg tgtggtcagc gtcctcaccg tcctgcacca ggactggctg    600
aatggcaagg agtacaagtg caaggtctcc aacaaagccc tcccagcccc catcgagaaa    660
accatctcca aagccaaagg gcagcccga gaaccacagg tgtacaccct gcccccatcc    720
cgggaggaga tgaccaagaa ccaggtcagc ctgacctgcc tggtcaaagg cttctatccc    780
agcgacatcg ccgtggagtg ggagagcaat gggcagccgg agaacaacta caagaccacg    840
cctcccgtgc tggactccga cggctccttc ttcctctaca gcaagctcac cgtggacaag    900
agcaggtggc agcaggggaa cgtcttctca tgctccgtga tgcatgaggc tctgcacaac    960
cactacacgc agaagagcct ctccctgtct ccgggtaaat ga                      1002
```

<210> SEQ ID NO 119
<211> LENGTH: 330
<212> TYPE: PRT
<213> ORGANISM: Homo sapiens

<400> SEQUENCE: 119

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Tyr Met Leu Asp Leu Gln Pro Glu Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ser Cys Ser Ser Cys Pro Leu Ser Lys
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Pro Tyr Leu Phe Trp Leu Ala Ala
1               5

<210> SEQ ID NO 123
<211> LENGTH: 729
<212> TYPE: DNA
<213> ORGANISM: Artificial Sequence
<220> FEATURE:
<223> OTHER INFORMATION: Description of Artificial Sequence: Synthetic
      Anti-CD3 scFv polynucleotide

<400> SEQUENCE: 123
gacgtgcagc tggtgcagag cggagctgaa gtgaagaaac ctggcgcctc cgtgaaggtg      60
tcctgcaaag ctagcggcta ccttcacc cggtacacca tgcactgggt gcgccaggca     120
cctggacagg gactggaatg gatcggctac atcaacccct cccggggcta caccaactac    180
gccgactctg tgaagggccg gttcaccatc accaccgata agtccaccag caccgcttac    240
```

```
atggaactgt cctccctgag atccgaggac accgctacct actattgcgc ccggtactac    300
gacgaccact actgcctgga ctactgggga cagggaacca cagtgaccgt gtcctctggc    360
gagggcacct ctactggatc tgggggaagt ggtggttctg gcggcgctga cgacatcgtg    420
ctgacccagt ctccagccac cctgtctctg agcccaggcg agagagctac cctgtcctgc    480
agagcctccc agtccgtgtc ctacatgaat tggtatcagc agaagcctgg caaggcccct    540
aagcggtgga tctacgacac ctccaaggtg gcctctggcg tgccagcccg gttttccgga    600
tctggctctg gcaccgacta ctccctgacc atcaacagcc tggaagccga ggacgctgcc    660
acctattact gccagcagtg gtcctccaac cccctgacct ttggaggcgg caccaaggtg    720
gaaatcaag                                                            729
```

<210> SEQ ID NO 124
<211> LENGTH: 243
<212> TYPE: PRT
<213> ORGANISM: Artificial Sequence
<220> FEATURE:
<223> OTHER INFORMATION: Description of Artificial Sequence: Synthetic Anti-CD3 scFv polypeptide

<400> SEQUENCE: 124

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys
```

<210> SEQ ID NO 125

```
<211> LENGTH: 243
<212> TYPE: PRT
<213> ORGANISM: Artificial Sequence
<220> FEATURE:
<223> OTHER INFORMATION: Description of Artificial Sequence: Synthetic
      Anti-CD3 scFv amino acid sequence with free cysteine to
      serine mutation polypeptide

<400> SEQUENCE: 125
```

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

```
<210> SEQ ID NO 126
<211> LENGTH: 56
<212> TYPE: PRT
<213> ORGANISM: Artificial Sequence
<220> FEATURE:
<223> OTHER INFORMATION: Description of Artificial Sequence: Synthetic
      Homodimerization tag sequence based on HNF1-alpha
      polypeptide

<400> SEQUENCE: 126
```

Arg Thr Pro Leu Gly Asp Thr Thr His Thr Ser Gly Met Val Ser Lys
1               5                   10                  15

Leu Ser Gln Leu Gln Thr Glu Leu Leu Ala Ala Leu Leu Glu Ser Gly
            20                  25                  30

Leu Ser Lys Glu Ala Leu Ile Gln Ala Leu Gly Glu Gly Ser Gly Gly
        35                  40                  45

Ala Pro His His His His His His
    50                  55

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ile Leu Gly Phe Val Phe Thr Leu
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Leu Phe Gly Tyr Pro Val Tyr Val
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Leu Leu Met Trp Ile Thr Gln Val
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Met Leu Trp Gly Tyr Leu Gln Tyr Val
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Leu Gly Tyr Gly Phe Val Asn Tyr Ile
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Asn Leu Val Pro Met Val Ala Thr Val
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ala Gly Ile Gly Ile Leu Thr Val
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Phe Leu Arg Gly Arg Ala Tyr Gly Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

His Ser Lys Lys Lys Cys Asp Glu Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Glu Tyr Leu Gln Ala Phe Thr Tyr
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Leu Ala Gly Ile Gly Ile Leu Thr Val
1               5                   10

<210> SEQ ID NO 138

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Glu Glu Asn Leu Leu Asp Phe Val Arg Phe
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Leu Trp Gly Pro Asp Pro Ala Ala Ala
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Tyr Pro Leu Thr Phe Gly Trp Cys Phe
1               5                   10

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      3xGS linker

<400> SEQUENCE: 141

Gly Gly Gly Gly Ser Gly Gly Gly Ser Gly Gly Gly Gly Ser
1               5                   10                  15

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 142

His His His His His His
1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      1xGS linker

<400> SEQUENCE: 143
```

```
Gly Gly Gly Gly Ser
1               5

<210> SEQ ID NO 144
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(75)
<223> OTHER INFORMATION: This sequence may encompass 1-15 "Gly Gly Gly
      Gly Ser" repeating units
<220> FEATURE:
<223> OTHER INFORMATION: See specification as filed for detailed
      description of substitutions and preferred embodiments

<400> SEQUENCE: 144

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser
65                  70                  75
```

T CELL RECEPTOR-LIKE ANTIBODY AGENTS SPECIFIC FOR EBV LATENT MEMBRANE PROTEIN 2A PEPTIDE PRESENTED BY HUMAN HLA

CROSS REFERENCE TO RELATED APPLICATIONS

This application is a divisional of U.S. application Ser. No. 15/735,133, filed Dec. 8, 2017, which is a U.S. National Application of PCT Application No.: PCT/US16/36735, filed Jun. 9, 2016, which claims the benefit of U.S. Provisional Application No. 62/173,330, filed Jun. 9, 2015, the contents of which are hereby incorporated herein in their entirety.

GOVERNMENT SUPPORT

This invention was made with government support under CA008748 awarded by the National Institutes of Health. The government has certain rights in the invention.

REFERENCE TO SEQUENCE LISTING

The specification includes a Sequence Listing in the form of an ASCII compliant text file named "Sequence Listing.txt", which was created on Oct. 12, 2016 and has a size of 63.6 kilobytes. The content of the aforementioned "Sequence Listing.txt" file is hereby incorporated by reference in its entirety.

BACKGROUND

T cell based immunotherapy is highly effective for cancer treatment as evidenced by recent reports with chimeric antigen receptors, bispecific antibodies, and checkpoint blockade antibodies. Both chimeric antigen receptors and bispecific antibodies have relied on antibody-based targeting of surface antigens. T cell receptor (TCR)-based approaches, however, have been slower in their development due in part to insufficient clonal frequency or clonal deletion of tumor-specific T cells and dwarfed by the rapid advances in antibody libraries and platform technologies. Unfortunately, clinically approved therapeutic monoclonal antibodies recognize structures of cell surface proteins. Moreover, antibody-based targetable antigens are limited in number. Of the candidates on the National Cancer Institute (NCI) cancer antigen priority list, the majority are found in the cytoplasmic compartment. Development of antibody agents targeting such candidates remains a challenge.

SUMMARY

The present invention provides, among other things, human antibody agents (and affinity matured versions thereof) that bind an Epstein-Barr virus (EBV) latent membrane protein 2 (LMP2) peptide in the context of human MHC (e.g., class I) molecules. In some embodiments, provided antibody agents demonstrate high specificity for a center portion (e.g., a center peptide position) of an EBV-LMP2 peptide in a peptide-MHC class I (e.g., an HLA-A02) binding pocket. In some embodiments, provided antibody agents demonstrate high specificity for an end portion (e.g., an end peptide position) of an EBV-LMP2 peptide in a peptide-MHC class I binding pocket. In some embodiments, provided antibody agents effectively carry out antibody-dependent cell-mediated cytotoxicity (ADCC) of target cells that carry an EBV-LMP2 peptide via HLA-A02 molecules on their surface. In some embodiments, provided antibody agents overcome suboptimal affinity associated with antibodies having specificity for a center portion(s) of a peptide presented in a binding pocket of an MHC molecule (e.g., an MHC class I molecule).

In some embodiments, the present invention also provides human antibody agents that bind an EBV-LMP2/HLA-A02 complex. In some embodiments, provided antibody agents bind a center portion (e.g., position 5) in an EBV-LMP2 peptide in an EBV-LMP2/HLA-A02 complex. In some embodiments, provided antibody agents bind position 1 (P1), position 5 (P5), position 8 (P8), and/or combinations thereof, of an EBV-LMP2 peptide in an EBV-LMP2/HLA-A02 complex. In some embodiments, provided antibody agents bind positions 1-5 (P1-P5), positions 4-7 (P4-P7) or positions 4-8 (P4-P8) of an EBV-LMP2 peptide in an EBV-LMP2/HLA-A02 complex.

The present invention also provides, multi-specific binding agents that include binding moieties that interact with a particular target. In many embodiments, such binding moieties are or comprise antibody components. In some embodiments, multi-specific binding agents are bispecific binding agents (e.g., bispecific antibodies). In some embodiments, multi-specific binding agents of the present invention comprise antibody components that have high specificity for a center and/or end portion of an EBV-LMP2 peptide in a peptide-MHC (e.g., a MHC class I) binding pocket. In some embodiments, multi-specific binding agents of the present invention comprise a first binding moiety based on an antibody component that has high specificity for an EBV-LMP2 peptide in a peptide-MHC class I binding pocket (e.g., an HLA-A02 binding pocket) and a second binding moiety that interacts with an immune effector cell (e.g., a T cell). In some embodiments, provided multi-specific binding agents have a high potency in cytotoxicity assays against EBV$^+$ and tumor cell lines. In some embodiments, provided multi-specific binding agents overcome low affinity barriers associated with TCR-like monoclonal antibodies. Such provided agents have improved functional characteristics as compared to parental binding agents that lack components as described herein.

The present invention also provides, methods of generating, selecting and/or identifying antibody agents and/or multi-specific binding agents that bind an EBV-LMP2 peptide in a peptide-MHC binding pocket (e.g., an MHC class I binding pocket). In many embodiments, methods of the present invention include generating, selecting and/or identifying antibody agents and/or multi-specific binding agents that bind a center and/or end portion of an EBV-LMP2 peptide presented by a human MHC class I molecule (e.g., an HLA-A02 molecule).

In some embodiments, methods include selecting antibody agents based on binding (or lack of binding) peptides having non-native amino acid substitutions at a center and/or end portion(s) of a peptide presented by an MHC class I molecule. In some embodiments, methods include selecting antibody agents based on lack of binding peptides having non-native amino acid substitutions at a center and/or end portion and further having extra native flanking residues at the N- and/or C-termini of the peptide presented by an MHC class I molecule. In some embodiments, methods include negatively selecting antibody agents based on binding a peptide at a position(s) outside of a center portion of the peptide (e.g., position 5). In some embodiments, peptide positions outside a center portion of the peptide are mutated. In some embodiments, peptides are nonamer or decamer peptides. In many embodiments, an MHC class I molecule is a human HLA-A02 molecule.

In some embodiments, the present invention provides a human antibody agent that binds an EBV-LMP2/HLA peptide complex, wherein the human antibody agent interacts directly with amino acid residues at one or more positions selected from the group consisting of position 1, position 5, position 8, and combinations thereof, in the EBV-LMP2 peptide.

In some embodiments, the present invention provides a human antibody agent that binds an EBV-LMP2/HLA peptide complex, wherein the human antibody agent has a $K_D$ of about 2.0 to about 170 nM.

In some embodiments, an EBV-LMP2 peptide has an amino acid sequence that is or comprises CLGGLLTMV (SEQ ID NO: 1).

In some embodiments, a human antibody agent interacts directly with amino acid residues at one or more positions selected from the group consisting of position 1, 2, 3, 4, 5, 6, 7, 8, and combinations thereof, in the EBV-LMP2 peptide.

In some embodiments, a human antibody agent comprises heavy chain CDR1 of SEQ ID NO:31, CDR2 of SEQ ID NO:33 and CDR3 of SEQ ID NO:35; and wherein the human antibody agent comprises light chain CDR1 of SEQ ID NO:73, CDR2 of SEQ ID NO:75 and CDR3 of SEQ ID NO:77. In some embodiments, a human antibody agent comprises heavy chain CDR1 of SEQ ID NO:37, CDR2 of SEQ ID NO:39 and CDR3 of SEQ ID NO:41; and wherein the human antibody agent comprises light chain CDR1 of SEQ ID NO:79, CDR2 of SEQ ID NO:81 and CDR3 of SEQ ID NO:83. In some embodiments, a human antibody agent comprises heavy chain CDR1 of SEQ ID NO:43, CDR2 of SEQ ID NO:45 and CDR3 of SEQ ID NO:47; and wherein the human antibody agent comprises light chain CDR1 of SEQ ID NO:85, CDR2 of SEQ ID NO:87 and CDR3 of SEQ ID NO:89. In some embodiments, a human antibody agent comprises heavy chain CDR1 of SEQ ID NO:49, CDR2 of SEQ ID NO:51 and CDR3 of SEQ ID NO:53; and wherein the human antibody agent comprises light chain CDR1 of SEQ ID NO:91, CDR2 of SEQ ID NO:93 and CDR3 of SEQ ID NO:95. In some embodiments, a human antibody agent comprises heavy chain CDR1 of SEQ ID NO:55, CDR2 of SEQ ID NO:57 and CDR3 of SEQ ID NO:59; and wherein the human antibody agent comprises light chain CDR1 of SEQ ID NO:97, CDR2 of SEQ ID NO:99 and CDR3 of SEQ ID NO: 101. In some embodiments, a human antibody agent comprises heavy chain CDR1 of SEQ ID NO:61, CDR2 of SEQ ID NO:63 and CDR3 of SEQ ID NO:65; and wherein the human antibody agent comprises light chain CDR1 of SEQ ID NO: 103, CDR2 of SEQ ID NO: 105 and CDR3 of SEQ ID NO: 107. In some embodiments, a human antibody agent comprises heavy chain CDR1 of SEQ ID NO:67, CDR2 of SEQ ID NO:69 and CDR3 of SEQ ID NO:71; and wherein the human antibody agent comprises light chain CDR1 of SEQ ID NO: 109, CDR2 of SEQ ID NO:111 and CDR3 of SEQ ID NO: 113.

In some embodiments, a human antibody agent comprises one or more amino acid substitutions in a heavy chain CDR and/or light chain CDR. In some certain embodiments, a human antibody agent comprises at least one or up to five amino acid substitutions in a heavy chain CDR and/or light chain CDR. In some certain embodiments, a human antibody agent comprises at least one or up to three amino acid substitutions in a heavy chain CDR and/or light chain CDR.

In some embodiments, a human antibody agent comprises a heavy chain variable region having a sequence at least 95% identical to a heavy chain variable region sequence that appears in Table 3. In some embodiments, a human antibody agent comprises a light chain variable region having a sequence at least 95% identical to a light chain variable region sequence that appears in Table 3. In some embodiments, a human antibody agent comprises (a) a heavy chain variable region having a sequence at least 95% identical to a heavy chain variable region sequence that appears in Table 3, and (b) a light chain variable region having a sequence at least 95% identical to a light chain variable region sequence that appears in Table 3. In some embodiments, a human antibody agent comprises a heavy chain variable region or light chain variable region selected from Table 3.

In some embodiments, a human antibody agent comprises the light chain variable region of SEQ ID NO:3 and the heavy chain variable region of SEQ ID NO:5. In some embodiments, a human antibody agent comprises the light chain variable region of SEQ ID NO:7 and the heavy chain variable region of SEQ ID NO:9. In some embodiments, a human antibody agent comprises the light chain variable region of SEQ ID NO: 11 and the heavy chain variable region of SEQ ID NO:13. In some embodiments, a human antibody agent comprises the light chain variable region of SEQ ID NO:15 and the heavy chain variable region of SEQ ID NO:17. In some embodiments, a human antibody agent comprises the light chain variable region of SEQ ID NO: 19 and the heavy chain variable region of SEQ ID NO:21. In some embodiments, a human antibody agent comprises the light chain variable region of SEQ ID NO:23 and the heavy chain variable region of SEQ ID NO:25. In some embodiments, a human antibody agent comprises the light chain variable region of SEQ ID NO:27 and the heavy chain variable region of SEQ ID NO:29.

In some embodiments, a human antibody agent is a human monoclonal antibody that is defucosylated and/or glycosylated with terminal mannose, N-acetylglucose or glucose.

In some embodiments, the present invention provides a human antibody agent that binds an EBV-LMP2/HLA peptide complex, which human antibody agent comprises one or more amino acid substitutions that increase affinity to the EBV-LMP2/HLA peptide complex, and wherein the human antibody agent is characterized by (a) a KA of at least about 1.6 higher affinity than affinity to a reference peptide/HLA complex, and/or (b) no cross-reactivity to a reference peptide/HLA complex. In some embodiments, a human antibody agent is characterized by (a) a KA of at least about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or at least about 9.0 higher affinity than affinity to a reference peptide/HLA complex, and/or (b) no cross-reactivity to a reference peptide/HLA complex.

In some certain embodiments, a human antibody agent comprises a light chain variable region that comprises one or more amino acid substitutions at any of amino acid positions 48, 52, 55, 66, 95 and combinations thereof. In some embodiments, one or more amino acid substitutions is I48V/S52G, P55H, K66R or N95I.

In some certain embodiments, a human antibody agent comprises a heavy chain variable region that comprises one or more amino acid substitutions at any of amino acid positions 5, 10, 26, 51, 78 and combinations thereof. In some embodiments, one or more amino acid substitutions is V5E, E10D, G26E/I51V or V78A.

In various embodiments, a human antibody agent is a human monoclonal antibody or a fragment thereof. In some embodiments, a human monoclonal antibody is an IgG1, IgG2, IgG3 or IgG4 antibody. In some certain embodiments, a human monoclonal antibody is an IgG1. In some embodiments, a human monoclonal antibody fragment is an scFv.

In some embodiments, the present invention provides a bispecific antibody comprising a first antigen-binding site that binds an EBV-LMP2/HLA peptide complex and a second antigen-binding site.

In some embodiments, a bispecific antibody is characterized by an $EC_{50}$ of about 0.2 to about 135 pM in T2 cells pulsed with EBV-LMP2 peptide CLGGLLTMV (SEQ ID NO:1). In some embodiments, a bispecific antibody has a $K_D$ of about 10 to about 130 nM.

In some embodiments, first and/or second antigen-binding sites are selected from the group consisting of an immunoglobulin molecule, scFv, scFab, Fab, Fv or a combination thereof. In some embodiments, first and second antigen-binding sites are configured such that they form a single polypeptide chain. In some embodiments, first and second antigen-binding sites are each scFvs. In some embodiments, first and second antigen-binding sites are linked by a peptide linker. In some embodiments, a second antigen-binding site is linked to the C-terminal end of a first antigen-binding site.

In some embodiments, a second antigen-binding site binds an immunological cell selected from the group consisting of a T cell, B cell, NK cell, dendritic cell, monocyte, macrophage, neutrophil, mesenchymal stem cell and neural stem cell. In some certain embodiments, a second antigen-binding site binds CD3 on T cells. In some embodiments, a second antigen-binding site is or comprises SEQ ID NO: 124.

In some embodiments, the present invention provides a bispecific antibody comprising a first scFv that binds to EBV-LMP2 peptide CLGGLLTMV (SEQ ID NO: 1) presented by an HLA-A02 molecule, and a second scFv that binds CD3 on T cells, wherein the bispecific antibody is characterized by an $EC_{50}$ of about 0.2 to about 135 pM in T2 cells pulsed with the EBV-LMP2 peptide.

In some embodiments, a first scFv comprises (a) the light chain variable region of SEQ ID NO:3 and the heavy chain variable region of SEQ ID NO:5; (b) the light chain variable region of SEQ ID NO:7 and the heavy chain variable region of SEQ ID NO:9; (c) the light chain variable region of SEQ ID NO: 11 and the heavy chain variable region of SEQ ID NO: 13; (d) the light chain variable region of SEQ ID NO: 15 and the heavy chain variable region of SEQ ID NO: 17; (e) the light chain variable region of SEQ ID NO: 19 and the heavy chain variable region of SEQ ID NO:21; (f) the light chain variable region of SEQ ID NO:23 and the heavy chain variable region of SEQ ID NO:25; or (g) the light chain variable region of SEQ ID NO:27 and the heavy chain variable region of SEQ ID NO:29.

In some embodiments, a second scFv is linked to the C-terminal end of a first scFv. In some certain embodiments, a second scFv is or comprises SEQ ID NO: 124.

In some embodiments, a first scFv of a bispecific antibody interacts directly with amino acid residues at one more positions selected from the group consisting of position 1, 2, 3, 4, 5, 6, 7, 8, and combinations thereof, in the EBV-LMP2 peptide. In some embodiments, a first scFv of the bispecific antibody interacts directly with at least position 1, at least position 5, or at least position 8 of the EBV-LMP2 peptide.

In some embodiments, the present invention provides a chimeric antigen receptor comprising an antigen-binding site of a human antibody agent that binds an EBV-LMP2/HLA peptide complex.

In some embodiments, an antigen-binding site is an scFv. In some embodiments, an antigen-binding site is expressed by an immune effector cell. In some embodiments, an immune effector cell is a T cell.

In some embodiments, the present invention provides an isolated nucleic acid molecule encoding, in whole or in part, a human antibody agent, a bispecific antibody, or a chimeric antigen receptor as described herein.

In some embodiments, the present invention provides a recombinant vector encoding a nucleic acid molecule as described herein.

In some embodiments, the present invention provides a host cell comprising a recombinant vector as described herein or a nucleic acid molecule as described herein. In some embodiments, a host cell is selected from a bacterial, yeast, insect or mammalian cell. In some embodiments, a host cell is selected from the group consisting of *E. coli, P. pastoris*, Sf9, COS, HEK293, CHO and a mammalian lymphocyte. In some certain embodiments, a mammalian lymphocyte is a human lymphocyte.

In some embodiments, the present invention provides a method for producing a human antibody agent, bispecific antibody, or chimeric antigen receptor as described herein, comprising culturing a host cell as described herein in a culture medium under conditions suitable for expression of the human antibody agent, bispecific antibody, or chimeric antigen receptor and recovering the human antibody agent, bispecific antibody, or chimeric antigen receptor (or a host cell expressing the chimeric antigen receptor) from the culture medium.

In some embodiments, the present invention provides a composition comprising a human antibody agent, bispecific antibody, or chimeric antigen receptor as described herein.

In some embodiments, the present invention provides a pharmaceutical composition comprising a human antibody agent, bispecific antibody, or chimeric antigen receptor as described herein, or a composition as described herein, and further comprising a pharmaceutically acceptable carrier or diluent.

In some embodiments, the present invention provides a kit comprising a human antibody agent, bispecific antibody, or chimeric antigen receptor as described herein.

In some embodiments, the present invention provides a method of treating a medical condition in a subject characterized by expression of an EBV-LMP2/HLA peptide complex, comprising a step of administering a therapeutically effective amount of a human antibody agent, bispecific antibody, chimeric antigen receptor (or an immune effector cell expressing the chimeric antigen receptor) as described herein, a composition as described herein, or a pharmaceutical composition as described herein.

In some embodiments, a medical condition is Hodgkin's disease, non-Hodgkin's disease or infectious mononucleosis. In some embodiments, a medical condition is selected from Burkitt's lymphoma, immunosuppressive lymphoma, diffuse large B-cell lymphoma, diffuse large B-cell lymphoma associated with chronic inflammation, lymphomatoid granulomatosis, plasmablastic lymphoma, primary effusion lymphoma, post-transplant lymphoproliferative disorder, nasopharyngeal carcinoma, gastric adenocarcinoma, lymphoepithelioma-associated carcinoma, and immunodeficiency-related leiomyosarcoma.

In some embodiments, the present invention provides use of a human antibody agent as, bispecific antibody or chimeric antigen receptor (or an immune effector cell expressing the chimeric antigen receptor) as described herein for the treatment or detection of a condition related to EBV infection.

In some embodiments, the present invention provides a method of directing T cells to kill target cells expressing an EBV-LMP2/HLA peptide complex, the method comprising a step of contacting one or more target cells expressing an EBV-LMP2/HLA peptide complex with a bispecific antibody as described herein, the contacting being performed under conditions and for a time sufficient that T cells to which the bispecific antibody has bound mediates killing of the target cells. In some embodiments, a bispecific antibody comprises a first antigen-binding site that binds an EBV-LMP2/HLA peptide complex and a second antigen-binding site that binds CD3 on T cells.

In some embodiments, an EBV-LMP2 peptide is or comprises CLGGLLTMV (SEQ ID NO: 1). In some embodiments, a first antigen-binding site of a bispecific antibody interacts directly with amino acid residues at one more positions selected from the group consisting of position 1, 2, 3, 4, 5, 6, 7, 8, and combinations thereof, in the EBV-LMP2 peptide.

In some embodiments, the present invention provides a method of selecting an antibody agent that binds a central residue of a peptide presented by a human HLA class I molecule of interest from a population, the method comprising the steps of (a) selecting one or more antibody agents from a population that bind a peptide-HLA class I complex of interest; and (b) screening the one or more antibody agents from (a) for binding a peptide-HLA class I complex that includes a peptide having one or more amino acid substitutions at a residue selected from the group consisting of position 1, position 5, position 8, and combinations thereof; wherein loss of binding of an antibody agent to a peptide-HLA class I complex that includes a peptide having a substitution at position 5 indicates an antibody agent that binds a central residue of a peptide presented by a human HLA class I molecule.

In some embodiments, the present invention provides a method of selecting an antibody agent that binds a central residue of a peptide presented by a human HLA class I molecule of interest from a population, the method comprising the steps of (a) selecting one or more antibody agents from a population that do not bind a first peptide-HLA class I complex, which first peptide-HLA class I complex includes a peptide having an amino acid substitution at position 5 and/or one or more additional amino acids at the N- and/or C-terminus of the peptide; and (b) screening the one or more antibody agents from (a) for binding a second peptide-HLA class I complex, which second peptide-HLA class I complex includes a peptide having a wild-type sequence of interest; wherein binding of an antibody agent to the second peptide-HLA class I complex indicates an antibody agent that binds a central residue of a peptide presented by a human HLA class I molecule.

In some embodiments, a peptide of a peptide/HLA class I complex is an Epstein-Barr virus (EBV)-related peptide. In some embodiments, a peptide/HLA class I complex is an EBV-LMP2/HLA-A02 complex.

In some embodiments, an antibody agent is a human monoclonal antibody. In some embodiments, an antibody agent is a human monoclonal antibody fragment.

In some embodiments, in a method of providing a high affinity human monoclonal antibody that binds a peptide/HLA complex, the present invention provides an improvement comprising providing a human monoclonal antibody that interacts directly with or prefers one or more amino acids at the center of a peptide in a peptide/HLA complex.

In some embodiments, in a method of providing a high affinity human monoclonal antibody that binds a peptide/HLA complex, the present invention provides an improvement comprising providing a human monoclonal antibody that interacts directly with or prefers one or more amino acids at the center of a peptide in an HLA binding pocket, wherein the peptide/HLA complex is not generated using an in silico prediction method.

In some embodiments, in a method of providing a high affinity bispecific antibody composition comprising a bispecific antibody that includes first and second antigen-binding sites, which first antigen-binding site binds a peptide/HLA complex, the present invention provides an improvement comprising providing at least one of such first antigen-binding sites as a human monoclonal antibody or fragment thereof that interacts directly with one or more amino acids at the center of a peptide in a peptide/HLA complex.

In some embodiments, in a method of providing a chimeric antigen receptor composition comprising one or more antigen binding sites, wherein at least one of the one or more antigen binding sites binds a peptide/HLA complex, the present invention provides an improvement comprising providing an antigen-binding site of a human antibody agent that interacts directly with one or more amino acids at the center of a peptide in an HLA binding pocket. In some certain embodiments, a chimeric antigen receptor composition is expressed by an immune effector cell. In some embodiments, an immune effector cell is a T cell.

In various embodiments, an HLA is a class I HLA molecule.

In various embodiments, a peptide is a nonamer peptide.

In various embodiments, a peptide is a decamer peptide.

In various embodiments, a peptide is an Epstein-Barr virus (EBV)-related peptide.

In various embodiments, a peptide/HLA complex is an EBV-LMP2/HLA-A02 complex.

In various embodiments, an HLA of an EBV-LMP2/HLA peptide complex is an HLA class I molecule. In various embodiments, an HLA class I molecule is HLA-A02. In various embodiments, an HLA-A02 is selected from HLA-A*02:01, HLA-A*02:02, HLA-A*02:03, HLA-A*02:04, HLA-A*02:05 and HLA-A*02:06.

In some embodiments, the present invention provides use of a human antibody agent, bispecific antibody, or chimeric antigen receptor (or an immune effector cell expressing the chimeric antigen receptor) as described herein in the manufacture of a medicament for use in medicine.

In some embodiments, the present invention provides use of a human antibody agent, bispecific antibody, or chimeric antigen receptor (or an immune effector cell expressing the chimeric antigen receptor) as described herein in the manufacture of a medicament for use in a diagnostic test or assay.

In some embodiments, the present invention provides use of a human antibody agent, bispecific antibody, or chimeric antigen receptor (or an immune effector cell expressing the chimeric antigen receptor) as described herein in the manufacture of a medicament for use in the diagnosis or treatment of cancer.

In some embodiments, the present invention provides use of a human antibody agent, bispecific antibody, or chimeric antigen receptor (or an immune effector cell expressing the chimeric antigen receptor) as described herein in the manufacture of a medicament for use in the diagnosis or treatment of a medical condition characterized by expression of an EBV-LMP2/HLA peptide complex.

BRIEF DESCRIPTION OF THE DRAWING

The Drawing included herein, which is composed of the following Figures, is for illustration purposes only not for limitation.

FIG. 13A: LMP2-38xCD3 (top) and LMP2-63xCD3 (bottom); FIG. 13B: LMP2-40xCD3 (top) and LMP2-61xCD3 (bottom); FIG. 13C: LMP2-21xCD3 (top) and LMP2-26xCD3 (bottom); FIG. 13D: LMP2-77xCD3. KBAB: HLA-A02$^-$; 900D: HLA-A02$^-$; AK: HLA-A02$^-$; KS: HLA-A02$^-$; OKO: HLA-A02$^+$; BV: HLA-A02$^+$; 6/28: HLA-A02$^+$.

FIG. 24A and FIG. 24B show exemplary peptide binding of anti-EBV-LMP2(CLG)/HLA-A*02:01 IgG antibody clones to HLA-A*02:01 that is loaded with either wild-type CLG peptide or Ala-substituted CLG peptides at positions P3 through P8. FIG. 24A shows the binding data as detected by flow cytometry. FIG. 24B shows the binding data from FIG. 24A, where the binding to Ala-substituted peptide/HLA*02:01 complexes is normalized to the wild-type CLG peptide.

DEFINITIONS

Figure 1:
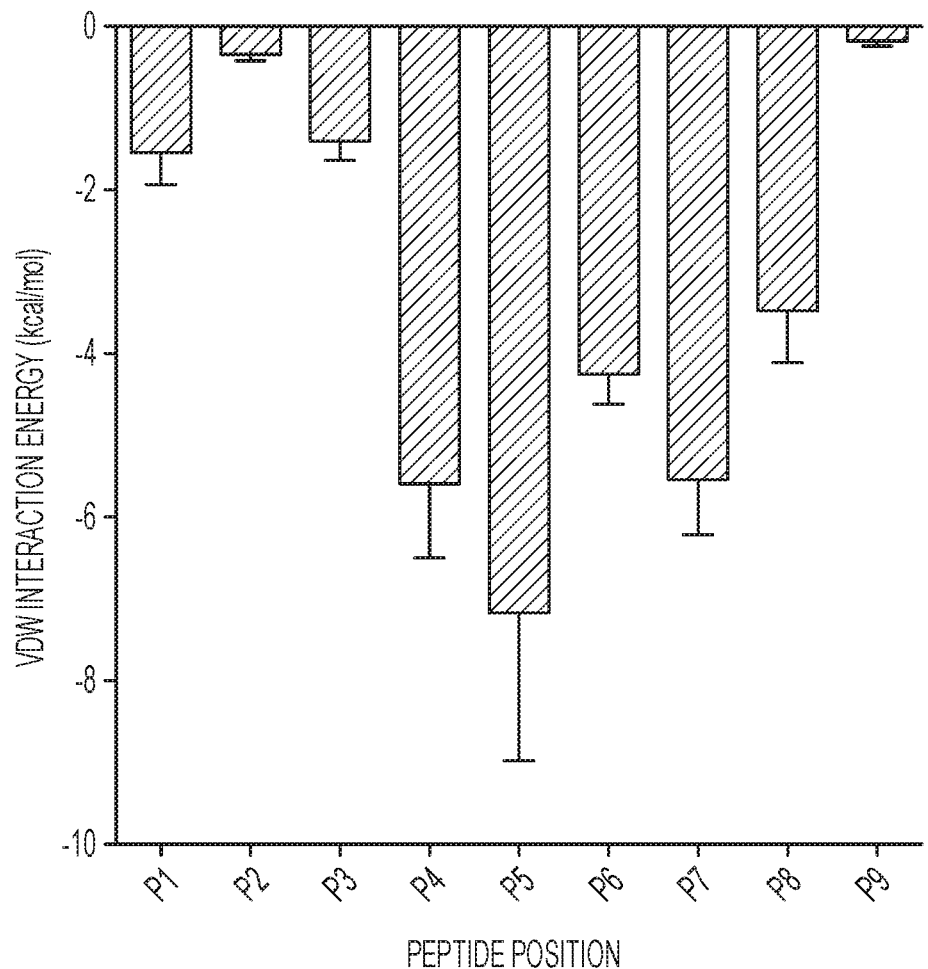
FIG. 1 shows a graph depicting average per residue van der Waals interaction energies of T cell receptor:nonamer-peptide/MHC class I complexes. The peptide position (P1, P2, etc.) is indicated on the x-axis of the graph.

The scope of present invention is defined by the claims appended hereto and is not limited by particular embodiments described herein; those skilled in the art, reading the present disclosure, will be aware of various modifications that may be equivalent to such described embodiments, or otherwise within the scope of the claims.

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

References cited within this specification, or relevant portions thereof, are incorporated herein by reference.

In order that the present invention may be more readily understood, certain terms are first defined below. Additional definitions for the following terms and other terms are set forth throughout the specification.

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human) may be bronchial (including by bronchial instillation), buccal, enteral, interdermal, intraarterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Affinity: As is known in the art, "affinity" is a measure of the tightness with which a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Affinity matured (or affinity matured antibody): As used herein, refers to an antibody with one or more alterations in one or more CDRs (or, in some embodiments, framework regions) thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., 1992, BioTechnology 10:779-783 describes affinity maturation by $V_H$ and $V_L$ domain shuffling. Random mutagenesis of CDR and/or framework residues is described by: Barbas et al., 1994, Proc. Nat. Acad. Sci, U.S.A. 91:3809-3813; Schier et al., 1995, Gene 169: 147-155; Yelton et al., 1995. J. Immunol. 155:1994-2004; Jackson et al., 1995, J. Immunol. 154(7): 3310-9; and Hawkins et al., 1992, J. Mol. Biol. 226:889-896.

Agent: As used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Amelioration: As used herein, refers to the prevention, reduction or palliation of a state, or improvement of the state of a subject. Amelioration includes, but does not require complete recovery or complete prevention of a disease, disorder or condition (e.g., radiation injury).

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by EBV. In some embodiments, an animal may be a transgenic animal, genetically engineered animal, and/or a clone.

Antibody: As used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a CH4 domain in the case of IgM and IgE). The constant region of a light chain is comprised of one domain, CL. The $V_H$ and $V_L$ regions further contain regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

Antibody agent: As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bispecific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins), Small Modular Immuno-Pharmaceuticals ("SMIPsTM"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

Antibody component: As used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component" encompasses polypeptides having a binding domain that shows at least 99% identity with an immunoglobulin-binding domain. In some embodiments, an included "antibody component" is any polypeptide having a binding domain that shows at least 70%, 75%, 80%, 85%, 90%, 95% or 98% identity with an immunoglobulin-binding domain, for example a reference immunoglobulin-binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and CL domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al, 1989, Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al., 1988, Science 242:423-426; and Huston et al., 1988, Proc. Natl. Acad. Sci. U.S.A. 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. U.S.A. 90:6444-6448; Poljak, R. J., et al., 1994, Structure 2:1121-1123). Such antibody binding portions are known in the art (Kontermann and Dubel eds., Antibody Engineering, 2001, Springer-Verlag. New York. 790 pp. ISBN 3-540-41354-5). In some embodiments, an antibody component is or comprises a single chain "linear antibody" comprising a pair of tandem Fv segments ($V_H$-$C_H1$-$V_H$-$C_H1$) which, together with complementary light chain polypeptides, form a pair of antigen binding regions (Zapata et al., 1995, Protein Eng. 8(10):1057-1062; and U.S. Pat. No. 5,641,870). In some embodiments, an antibody component may have structural elements characteristic of chimeric, humanized or human antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

Biological activity: As used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Bispecific antibody: As used herein, refers to a bispecific binding agent in which at least one, and typically both, of the binding moieties is or comprises an antibody component. A variety of different bi-specific antibody structures are known in the art. In some embodiments, each binding moiety in a bispecific antibody that is or comprises an antibody component includes $V_H$ and/or $V_L$ regions; in some such embodiments, the $V_H$ and/or $V_L$ regions are those found in a particular monoclonal antibody. In some embodiments, where the bispecific antibody contains two antibody component-binding moieties, each includes $V_H$ and/or $V_L$ regions from different monoclonal antibodies. In some embodiments, a bispecific antibody is a dimeric bispecific antibody.

Bispecific binding agent: As used herein, refers to a polypeptide agent with two discrete binding moieties, each of which binds a distinct target. In some embodiments, a bispecific binding agent is a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) the same target (e.g., antigen); in some embodiments, they recognize different targets. In some embodiments, a bispecific binding agent is capable of binding simultaneously to two targets, which are of different structure.

Carrier: As used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

CDR: As used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Boundaries of CDRs have been defined differently depending on the system, of which several are known in the art (e.g., Kabat, Chothia, etc.).

CDR-grafted antibody: As used herein, refers to an antibody whose amino acid sequence comprises heavy and light chain variable region sequences from one species but in which the sequences of one or more of the CDR regions of $V_H$ and/or $V_L$ are replaced with CDR sequences of another species, such as antibodies having murine $V_H$ and $V_L$ regions in which one or more of the murine CDRs (e.g., CDR3) has been replaced with human CDR sequences. Likewise, a "CDR-grafted antibody" may also refer to antibodies having human $V_H$ and $V_L$ regions in which one or more of the human CDRs (e.g., CDR3) has been replaced with mouse CDR sequences.

Chimeric antibody: As used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody".

Comparable: As used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Control: As used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control antibody". A "control antibody" may be a human, non-human (e.g. murine), chimeric, humanized, CDR-grafted, multi-specific, or bispecific antibody as described herein, an antibody that is different as described herein, an antibody fragment or antibody component, or a parental antibody. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Corresponding to: As used herein with reference to amino acids within a polypeptide sequence designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Effector function: As used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

Effector cell: As used herein refers to a cell of the immune system that expresses one or more Fc receptors and mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

Engineered. As used herein refers, in general, to the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively or additionally, in some embodiments, "engineering" may involve use of in vitro chemical synthesis methodologies and/or recombinant nucleic acid technologies such as, for example, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.)) are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y., 1989).

Epitope: As used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Fc ligand: As used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcεRII (CD23), FcRn, C1q, C3, staphylococcal protein A, streptococcal protein G, and viral FcγR. Fc ligands may include undiscovered molecules that bind Fc.

Framework or framework region: As used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Host cell: As used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, a host cell is a human, monkey, ape, hamster, rat, or mouse cell. In some embodiments, a host cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, a host cell comprises one or more viral genes, e.g., a retinal cell that expresses a viral gene (e.g., a PER.C6™ cell).

Human antibody: As used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example, that may (originally) have been introduced by random or site-specific mutagenesis in vitro or by somatic mutation in vivo), for example in one or more CDRs and in particular CDR3.

Humanized: As is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Improve, increase or reduce: As used herein, or grammatical equivalents thereof, indicate values that are relative to a baseline measurement, such as a measurement in the same individual prior to initiation of a treatment described herein, or a measurement in a control individual (or multiple control individuals) in the absence of the treatment described herein. A "control individual" is an individual afflicted with the same form of disease or injury as the individual being treated.

In vitro: As used herein refers to events that occur in an artificial environment, e.g., in a test tube or reaction vessel, in cell culture, etc., rather than within a multi-cellular organism.

In vivo: As used herein refers to events that occur within a multi-cellular organism, such as a human and a non-human animal. In the context of cell-based systems, the term may be used to refer to events that occur within a living cell (as opposed to, for example, in vitro systems).

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

KA: As used herein, refers to the association (or affinity) constant of a binding agent (e.g., an antibody agent or binding component thereof) from a complex with its partner (e.g., the epitope to which the antibody agent or binding component thereof binds).

$K_D$: As used herein, refers to the dissociation constant of a binding agent (e.g., an antibody agent or binding component thereof) from a complex with its partner (e.g., the epitope to which the antibody agent or binding component thereof binds).

$k_{off}$: As used herein, refers to the off rate constant for dissociation of a binding agent (e.g., an antibody agent or binding component thereof) from a complex with its partner (e.g., the epitope to which the antibody agent or binding component thereof binds).

$k_{on}$: As used herein, refers to the on rate constant for association of a binding agent (e.g., an antibody agent or binding component thereof) with its partner (e.g., the epitope to which the antibody agent or binding component thereof binds).

Linker: As used herein, is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al., 1993, Proc. Natl. Acad. Sci. U.S.A. 90:6444-6448; Poljak, R. J. et al., 1994, Structure 2:1121-1123).

Multivalent binding agent (or multispecific binding agent): As used herein, refers a binding agent capable of binding to two or more antigens, which can be on the same molecule or on different molecules. Multivalent binding agents as described herein are, in some embodiments, engineered to have the two or more antigen binding sites, and are typically not naturally occurring proteins. Multivalent binding agents as described herein refer to binding agents capable of binding two or more related or unrelated targets. Multivalent binding agents may be composed of multiple copies of a single antibody component or multiple copies of different antibody components. Such binding agents are capable of binding to two or more antigens and are tetravalent or multivalent binding agents. Multivalent binding agents may additionally comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, or a hapten and/or an antigen or epitope. In many embodiments, multivalent binding agents of the present invention are proteins engineered to have characteristics of multivalent binding agents as described herein. Multivalent binding agents of the present invention may be monospecific (capable of binding one antigen) or multispecific (capable of binding two or more antigens), and may be composed of two heavy chain polypeptides and two light chain polypeptides. Each binding site, in some embodiments, is composed of a heavy chain variable domain and a light chain variable domain with a total of six CDRs involved in antigen binding per antigen binding site.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Operably linked: As used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with a gene of interest and expression control sequences that act in trans or at a distance to control said gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Peptide: As used herein, a peptide refers to a polypeptide that is typically relatively short, for example having a length of less than about 100 amino acids, less than about 50 amino acids, less than 20 amino acids, or less than 10 amino acids. In some embodiments a peptide is 5, 6, 7, 8, 9, 10, 11, 12, 13, 14 or 15 amino acids in length.

Physiological conditions: As used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20–40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: As used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30 to 40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least three to four and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice-versa, and/or fragments may be present in a different order in the polypeptide of interest than in the parent), so that the polypeptide of interest is a derivative of its parent polypeptide.

Prevent or prevention: As used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Recombinant: As used herein, is intended to refer to polypeptides (e.g., antibodies or antibody components, or multi-specific binding agents as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997, TIB Tech. 15:62-70; Azzazy H., and Highsmith W. E., 2002, Clin. Biochem. 35:425-445; Gavilondo J. V., and Larrick J. W., 2002, BioTechniques 29:128-145; Hoogenboom H., and Chames P., 2000, Immunol. Today 21:371-378), antibodies isolated from an animal (e.g., a mouse) that is transgenic for human immunoglobulin genes (see e.g., Taylor, L. D., et al., 1992, Nucl. Acids Res. 20:6287-6295; Kellermann S-A., and Green L. L., 2002, Curr. Opin. Biotech. 13:593-597; Little, M. et al., 2000, Immunol. Today 21:364-370; Murphy, A. J. et al., 2014, Proc. Natl. Acad. Sci. U.S.A. 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

Recovering: As used herein, refers to the process of rendering an agent or entity substantially free of other previously-associated components, for example by isolation, e.g., using purification techniques known in the art. In some embodiments, an agent or entity is recovered from a natural source and/or a source comprising cells.

Reference: As used herein describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

Risk: As will be understood from context, "risk" of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 and up to 100%. In some embodiments risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0, 1, 2, 3, 4, 5, 6, 7, 8, 9, 10 or more.

Specific binding: As used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, means any mammal, including humans. In certain embodiments of the present invention the subject is an adult, an adolescent or an infant. In some embodiments, terms "individual" or "patient" are used and are intended to be interchangeable with "subject." Also contemplated by the present invention are the administration of the pharmaceutical compositions and/or performance of the methods of treatment in utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial sequence homology: As used herein, the phrase "substantial homology" to refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized as follows:

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, J. Mol. Biol., 215(3):403-410; Altschul et al., 1996, Meth. Enzymology 266:460-480; Altschul et al., 1997, Nucleic Acids Res. 25:3389-3402; Baxevanis et al, Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: As used herein, the phrase "substantial identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al, 1990, J. Mol. Biol, 215(3):403-410, 1990; Altschul et al, 1996, Methods in Enzymology 266:460-480; Altschul et al, 1997, Nucleic Acids Res. 25:3389-3402; Baxevanis et al, Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

Surface plasmon resonance: As used herein, refers to an optical phenomenon that allows for the analysis of specific binding interactions in real-time, for example through detection of alterations in protein concentrations within a biosensor matrix, such as by using a BIAcore system (Pharmacia Biosensor AB, Uppsala, Sweden and Piscataway, N.J.). For further descriptions, see Jonsson, U. et al., 1993, Ann. Biol. Clin. 51:19-26; Jonsson, U. et al., 1991, Biotechniques 11:620-627; Johnsson, B. et al., 1995, J. Mol. Recognit. 8:125-131; and Johnnson, B. et al., 1991, Anal. Biochem. 198:268-277.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vector: As used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

DETAILED DESCRIPTION OF CERTAIN EMBODIMENTS

The present invention is based, in part, on the recognition that high affinity human antibody agents (e.g., human monoclonal antibodies) that mimic TCR interaction with peptides presented by MHC molecules (e.g., class I molecules) can be made having preferential binding to end portions (i.e., the N-terminal or C-terminal ends of the antigenic peptide; e.g., positions 1 and position 8) of a peptide in an MHC binding-pocket (referred to herein as type I antibodies). Further, antibody agents having preferential binding to a middle or center portion (e.g., position 5) of a peptide in an MHC binding-pocket (referred to herein as type II antibodies) generally demonstrate lower affinity, and are not easily affinity matured. The present invention is also based on the recognition that naturally processed peptides on tumor cell lines may vary from in silico predictions and such naturally processed peptides are recognized by type II antibodies, but not by type I antibodies. To give but one example, the present disclosure demonstrates that Epstein-Barr virus (EBV)-infected cell lines are preferentially killed by type II antibodies, but not by type I antibodies when human antibody agents are employed in the context of multi-specific binding agents (e.g., bispecific antibodies) that bind (1) an EBV latent membrane 2 peptide presented by a human MHC class I molecule (e.g., HLA-A02) and (2) non-specific immune effector cells (e.g., T cells).

The present invention demonstrates, among other things, the successful production and selection of type II human monoclonal antibodies that bind a center portion of an Epstein-Barr virus (EBV)-associated antigen presented in a human MHC molecule-binding pocket. The present invention is based, in part, on the recognition that T cell receptors (TCRs) specific for an EBV-associated antigen interact preferentially with position 5 of the antigenic peptide in the context of HLA-A02 (e.g., HLA-A*02:01). Thus, the present invention provides, among other things, human antibody agents that mimic TCR interaction with an EBV-associated antigen in that human antibody agents described herein bind a center portion (e.g., position 5) of an EBV latent membrane protein 2 (LMP2) peptide presented in an HLA-A02 binding pocket. The present invention specifically provides human antibody agents that target a peptide derived from EBV-LMP2 (CLGGLLTMV; SEQ ID NO: 1) in the context of a human HLA-A02 (e.g., HLA-A*02:01) molecule. LMP2 is expressed in both EBV infected B-cells and nasopharyngeal and gastric epithelial cells, and thus such human antibody agents are useful for the treatment and diagnosis of EBV-associated diseases and malignancies.

Among other things, the present invention also demonstrates the successful production of multi-specific binding agents (e.g., bispecific antibodies) that bind an EBV-LMP2 peptide presented in a human MHC molecule-binding pocket. In particular, the present invention specifically provides multi-specific binding agents that bind a center portion (e.g., position 5) of an EBV-LMP2 peptide presented in an HLA-A02 binding pocket. Such multi-specific binding agents are characterized by high specificity and potency in cytotoxicity assays including EBV+ B-lymphoblastoid cell lines (BLCLs) and tumor cell lines.

Without wishing to be bound by any particular theory, we note that the only known methodology to reach cytoplasmic antigens is through their peptide-HLA complex presented on the cell surface, which is first discovered through interaction with a TCR. Specific antibodies, termed TCR mimics, have been reported, but few, if any, have realized their clinical potential. Based on a detailed meta-analysis of crystallographic structures of known TCR-peptide-HLA structures and experimental data using an EBV-LMP2 peptide, the present disclosure demonstrates, among other things, that (1) TCRs consistently demonstrate preferential binding of a center position (positions 4-7), but not end positions of peptides in an HLA pocket, (2) antibody agents having specificity to positions 4-7 (P4-P7) of a peptide-HLA complex (i.e., a type II TCR mimic) are highly specific, but typically associated with low affinity, which is similar to natural TCRs, (3) antibodies that preferentially bind end positions of peptides in an HLA pocket (i.e., a type I TCR mimic) are associated with high affinity, yet lose affinity when peptide ends are blocked by native amino acid(s), (4) type I TCR mimics made against nonamer peptides fail to recognize naturally presented peptide-HLA complexes in transformed cells because peptides presented on such cells likely do not present nonamer peptides having free ends, but rather present decamer, undecamer, or dodecamer peptides, and (5) TCR mimics having specificity to end portions of peptides in a peptide-HLA complex demonstrate a higher likelihood to cross-react with irrelevant peptide-HLA complexes that include an HLA-A02 allele. Moreover, the low affinity characteristic of both natural TCRs and type II TCR mimics is a result of the entropic freedom of the middle (or center) position of a peptide as compared to the end positions where residues are anchored. Such low affinity ensures T cells to dissociate from targets to continue serial killing and is counterbalanced by the presence of multiple copies of TCRs freely mobile on the cell surface. Thus, the present disclosure, in at least some embodiments, embraces the development of type II TCR mimics for cancer diagnosis and therapy based on the recognition that such agents are more specific and analogous to natural TCRs, and bivalent and tetravalent forms of such agents should enhance avidity and clinical utility without suffering cross-reactivity.

Epstein-Barr Virus Infection and Cancer

The association of Epstein Barr Virus (EBV) with malignancy has been reported (e.g., reviewed in Coghill, A. E. and A. Hildesheim, 2014, Am. J. Epidemiol. 180:687-95). EBV was one of the first viruses to be identified as oncogenic. EBV is extremely effective in infecting B cells through its interaction with CD21 and MHC class II (Hislop, A. D., G. S. Taylor, and D. Sauce et al., 2007, Ann. Rev. Immunol. 25:587-617). However, EBV can also infect and be retained in epithelial cells, a process that is less efficient and not well understood.

Virtually all adults in the world have been exposed to EBV. In the absence of immune compromise, initial exposure in childhood results in a self-limited illness controlled by a cellular immune response (Hislop, A. D., G. S. Taylor, and D. Sauce et al., 2007, Ann. Rev. Immunol. 25:587-617). The presence of an immune defense against Epstein Barr Virus (EBV) and EBV-associated disease is well known (Hislop, A. D. et al., 2007, Ann. Rev. Immunol. 25:587-617; Long, H. M. et al., 2011, J. Immunol. 187:92-101). The host's generation of antigen specific T-cells against viral proteins is very effective against the virus. However, EBV can persist in epithelial or B cells without being completely eliminated (Long, H. M. et al., 2011, J. Immunol. 187:92-101). Any changes in the immune status of the host can lead to re-activation and depending on the degree of immune compromise, this re-activation can lead to malignancy.

Viral replication can occur by two mechanisms: lytic replication or replication through latency. The former requires a linear viral genome, produces active virions and destroys the host cell. Replication through latency, on the other hand, occurs when the viral genome creates an episome that is replicated by the host's cell DNA polymerase. It perpetuates replication of the cell and with it of EBV infection. Replication through latency can generate three different latency programs, each varying in the EBV gene repertoire that is expressed.

EBV has been best studied in the setting of solid organ and hematopoietic cell transplantation (HSCT) where the decreased number or absence of T-cells may cause unrestricted proliferation of B-cells harboring EBV (Rasche, L. et al., 2014, Bone Marrow Transplant 49:163-7). Such uncontrolled expansion can lead to post transplant lymphoproliferative disease (PTLD), the most common post-transplant malignancy. The frequency and intensity of this syndrome varies within each patient and the effects of their immune suppression on their T-cell population (Bollard, C. M. et al., 2012, Nat. Rev. Clin. Oncol. 9:510-9).

However, EBV is also involved in other malignancies. Several lines of research have implicated EBV in the pathogenesis of various epithelial and lymphoid malignancies. For example, it is well known that Hodgkin (Glaser, S. L. et al., 1997, Int. J. Cancer 70:375-82) and non-Hodgkin Lymphomas are related to EBV but its role in the development of these diseases is not well understood. Likewise, although there is a clear causal relationship between EBV and nasopharyngeal carcinoma (NPC; Shanmugaratnam, K., 1978, IARC Sci. Publ:3-12), EBV's role in the pathogenesis of this neoplasm is not entirely understood. Tumor samples of patients with Hodgkin Lymphoma and NPC express EBV derived proteins including the latent membrane protein 2

(LMP2). LMP-2 has also been found in 40% of EBV-related gastric carcinoma. Because these are non-self and are also the main targets of the cellular immune response against EBV, these represent ideal targets for immunotherapy approaches.

The list of LMP2(+) human malignancies associated with EBV includes Burkitt's lymphoma, immunosuppressive lymphoma, diffuse large B-cell lymphoma, diffuse large B-cell lymphoma associated with chronic inflammation, lymphomatoid granulomatosis, plasmablastic lymphoma, primary effusion lymphoma, post-transplant lymphoproliferative disorder, nasopharyngeal carcinoma, gastric adenocarcinoma, lymphoepithelioma-associated carcinoma, and immunodeficiency-related leiomyosarcoma (Ok, C Y et al., 2015, Exp. Mol. Med. 47:e132; Grywalska, E. and J. Rolinski, 2015, Semin. Oncol. 42:291-303; Petersson, F, 2015, Semin. Diagn. Pathol. 32:54-73; Tsao, S. W. et al., 2015, J. Pathol. 235(2):323-33).

Expression of EBV Latent Proteins

The EBV infection/transformation of resting B-cells produces Latent Lymphoblastoma Lines (LCL). This process has been accurately replicated in vitro with the use of the B95-8 strain of EBV present in the marmoset B-lymphoblastoid line B95-8 (Menezes, J. et al., 1975, Biomedicine 22:276-84). The production of BLCL in the laboratory has been invaluable in the understanding and characterization of EBV infection and the immune response to it. In contrast, in vitro infection of epithelial cells is not effective, and there is no current model to understand this interaction.

LCLs present in latent replication and carry multiple copies of the viral genome as an episome. They express a number of viral gene products denominated latent proteins that vary according to latency stage.

A total of ten latency proteins have been described: Six Epstein Virus Nuclear Antigens (EBNA 1, 2, 3A, 3B, 3C and LP), three Latent Membrane Proteins (LMP 1, 2A and 2B) and BARF1. Initial EBV infection activates B-cells and induces latency III when EBNA1, EBNA2, EBNA3, LMP1, LMP2 and BARF1 are expressed (Bollard et al., Nat. Rev. Clin. Oncol. 9:510, 2012). This is followed by a more limited expression of the viral products and conversion of the infected B-cell into a memory B-cell, termed Latency II, where EBNA1, LMP1 and LMP2 are expressed. Further restriction in the expression of these antigens leads to latency I where only EBNA-1, LMP2 and BARF1 are expressed.

B-cells can have latency programs I through III. However, epithelial cells only present latency I and II. LMP-2A is expressed in latency I, II and III (Bollard, C. M. et al., 2012, Nat. Rev. Clin. Oncol. 9(9):510-9), and thus is an appealing target for multiple solid and non-solid malignancies.

Immune Response Against EBV and Adoptive T Cell Therapy

Almost all nucleated cells in the body express Human Leukocyte Antigen—class I (HLA class I) molecules. These molecules have the ability to present peptides derived from any protein expressed by cells whether the protein is present on the cell surface or within the cytoplasm. The present invention is based on the recognition that immune response mounted against these peptide-HLA complexes forms the foundation for a successful cellular immunity that can distinguish self from non-self. To give but one example, Hodgkin's lymphoma (HL) and nasopharyngeal carcinoma (NPC) cells constitutively express EBV-derived proteins and the immunogenic peptides derived from these proteins presented in the context of HLA molecules offers a unique opportunity to exploit cellular immunity in therapeutic strategies against these EBV associated malignancies.

T cells recognize these peptide-HLA complexes through their clonal T cell receptors (TCR; Haigh, T. A. et al., 2008, J. Immunol. 180:1643-54.). In fact, a highly effective treatment for EBV-recrudescence in recipients of allogeneic marrow or stem cell transplant (HSCT) or solid organ transplants is adoptive T-cell therapy. More importantly, post transplant lymphoproliferative disease (PTLD) especially with T-depleted grafts, is a consequence of loss of T cell control of EBV-infected B cells, and can now be successfully treated by donor T cell infusions, or EBV-specific allogeneic T cell infusions in 70% of cases (Bollard, C. M. et al., 2012, Nat. Rev. Clin. Oncol. 9:510-9).

Immune defense against Epstein Barr Virus (EBV) and EBV-associated disease is well known (Hislop, A. D. et al., 2007, Ann. Rev. Immunol. 25:587-617; Long, H. M. et al., 2011, Curr. Opin. Immunol. 23:258-64, 2011. EBV carriers generate EBV-specific $CD4^+$ and $CD8^+$ polyfunctional T-cell responses, which show immunodominant hierarchies of EBV proteins: (EBNA1>EBNA3/LMP2 for CD4+ T cells and EBNA3>LMP2>EBNA1 for CD8+ T cells; Ning, R. J. et al., 2011, Immunology 134:161-71.). The EBV-latent membrane proteins (LMPs) 1 and 2, together with EBNA1 are three viral proteins expressed in EBV-associated Hodgkin's lymphoma (HL) and nasopharyngeal carcinoma (NPC). Since these tumors are HLA class I and class II-positive, the LMPs and EBNA1 could serve as both CD8 and CD4 T cell targets (Haigh, T. A. et al., 2008, J. Immunol. 180:1643-54). Despite the subdominant frequencies of CTLs specific for epitopes derived from these latent gene products (0.05%-1%), they are implicated in the control of EBV infection in vivo (Hislop, A. D. et al., 2007, Ann. Rev. Immunol. 25:587-617). DNA vaccines targeting these three antigens have been tested in patients with NPC (Lutzky, V. P. et al., 2010, J. Virol. 84:407-17). The LMP2 SSC peptide (SSCSSCPLSK; SEQ ID NO: 121) for A11 elicited response in most of the NPC patients. Peptide APYL (APYLFWLAA; SEQ ID NO: 122) for B55 (high frequency allele in Asian populations) is also of interest. Adoptive T cell therapy for NPC has also been proven safe and has clinical potential (Louis, C. U. et al., 2010, J. Immunother. 33:983-90). LMP2 and EBNA3-specific T cells were more common than EBNA1 or LMP1-specific T cells. LMP-2 peptide CLG-GLLTMV (340-349; SEQ ID NO: 1) for HLA-A02 and SSCSSCPLSK (426-434; SEQ ID NO:121) for HLA-A11 are highly relevant T cell epitopes (TCE).

In an effort to improve the generation and activation of T-cells that are specific against EBV derived proteins, vaccines targeting LMP2 have been tested in patients with NPC. Lutzky et al. (2010, supra) used a scrambled peptide including sequences for EBNA1, LMP1 and LMP2 with an adenovirus, generating LMP2 specific responses in normal donors and NPC patients (Lutzky, V. P. et al., 2010, J. Virol. 84:407-17). Cheung et al. demonstrated responses against EBV transformed cells when the LMP2 derived peptide (SSCSSCPLSK; SEQ ID NO: 121) was used in a construct with a gold nanoparticle (Cheung, W. H. et al., 2009, Bioconjug. Chem. 20:24-31). Likewise the use of the APYL peptide (SEQ ID NO: 122), containing sequences from EBNA1, LMP1 and LMP2, has also shown some responses. Furthermore, adoptive T cell therapy for NPC has been proven safe and has had a suggestion of clinical activity (Louis, C. U. et al., 2010, J. Immunother. 33:983-90). The LMP-2 peptide CLGGLLTMV (340-349; SEQ ID NO: 1) specific for HLA-A*02:01 has been reported effective for EBV-related solid and non-solid malignancies that have stage II latency. In fact, this peptide is the most immunogenic within the full sequence of LMP2A for HLA-A*02:01 donors.

Despite these preclinical and clinical successes, there is uncertainty regarding the expression of EBV latency epitopes in EBV-associated malignancies. While mass spectrometry can assess the presence or absence of these epitopes at a population level (Weidanz, J. A. et al., 2011, Int. Rev. Immunol. 30:328-40), heterogeneity from cell to cell within a tumor and between tumors has been difficult to assess. The discovery of antibodies specific for peptide-HLA complexes (referred to as TCR mimics) offers a new opportunity to reexamine such issues (Sim, A. C. et al., 2013, Sci. Rep. 3:3232). Three TCR-like murine monoclonal antibodies targeting the latent epitopes LMP1(125-133), LMP2A(340-349) or EBNA1(562-570) in association with HLA-A*02:01 were recently described to map the expression hierarchy of endogenously generated EBV epitopes. The dominance of EBNA(1562-570) in association with HLA-A*02:01 was consistently observed in cell lines and EBV-associated tumor biopsies.

T Cell Receptor-Like Monoclonal Antibodies

The lack of surface expression of most cytoplasmic proteins makes them nearly impossible to be targeted with regular antibodies. However, antigenic peptides derived from these proteins are presented in the cell surface within MHC class I molecules and can be targeted with antibodies that resemble or replicate TCR binding (Dahan, R. and Y. Reiter, 2012, Expert Rev. Mol. Med. 14:e6; Denkberg, G. et al., 2002, Proc. Natl. Acad. Sci. U.S.A. 99:9421-6; Sergeeva, A. et al., 2011, Blood 117:4262-72; Tassev, D. V. et al., 2012, Cancer Gene Ther. 19:84-100; Dao, T. et al., 2013, Sci. Transl. Med. 5:176ra33). These peptide-HLA complexes contain a short peptide sequence that can vary in length but is usually nine amino acids for class I alleles (Townsend, A. and H. Bodmer, 1989, Ann. Rev. Immunol. 7:601-24; Rudolph, M. G. et al., 2005, Ann. Rev. Immunol. 24:419-466). Within these nonamers there are usually two anchoring residues that are located in position 2 and 9 (P2 and P9) for the HLA-A*02:01 allele (Parker, K. C. et al., 1992, J. Immunol. 149:3580-7). Co-crystallization structures of several TCR-peptide-HLA complexes have permitted a better understanding of the interaction of these three members of the complex (peptide, HLA, TCR) at the immunological synapse.

For example, the TCR in $CD8^+$ T cells binds to a peptide-HLA complex diagonally at an average angle of 35 degrees with several interaction sites carried by these three members of the complex. However, T cell activation itself depends on only a few contact amino acids that are indispensible for mounting a successful immune response. These primary and secondary contact sites are determined by the side chains of two to five amino acid residues that are located in the middle portion of the antigenic peptide (Rudolph, M G and Wilson I A, Curr. Opin. Immunol. 14(1):52-65, 2002), the so-called functional hotspots (Massimo, D. et al., 2000, Immunity 12:251-261). In the case of nonamer peptides, the most frequent peptide length presented in class I alleles, the most important residue for TCR interaction is located at position 5 of the antigenic peptide (P5) with P6, P7 and P8 playing a secondary role (Rudolph, M. G. et al., 2005, Ann. Rev. Immunol. 24:419-466; Rudolph, M G and Wilson I A, Curr. Opin. Immunol. 14(1):52-65, 2002; Massimo, D. et al., 2000, Immunity 12:251-261). In octamer peptides, the most relevant residues are P4, P6 and P7 (Rudolph, M. G. et al., 2005, Ann. Rev. Immunol. 24:419-466; Rudolph, M G and Wilson I A, Curr. Opin. Immunol. 14(1):52-65, 2002; Massimo, D. et al., 2000, Immunity 12:251-261). Besides the structural evidence, the functional significance of these regions within the antigenic peptide has been consistently demonstrated. For example, EBV-specific memory T-cell activation can occur with as little as one amino acid, as long as this residue is one of the primary contact sites (Reali, E. et al., 1999, J. Immunol. 162:106-113).

Antibodies targeting peptide-MHC complexes are loosely termed "TCR mimics" because they bind to a peptide-MHC complex, and are thought to replicate TCR binding. Though initially difficult to generate, the availability of soluble peptide-MHC monomers and phage display technology has greatly facilitated their generation (Dahan, R. and Y. Reiter Y, 2011, Expert Rev. Mol. Med. 14). Soluble TCRs have been successfully generated and affinity matured (Liddy, N. et al., 2012, Nat. Med. 18:980-987). However, TCR mimic antibody reagents have distinct advantages over these for the following reasons: (1) larger libraries than TCR libraries to screen from, (2) both naïve and artificial libraries can be used, the latter of which is ideal for finding clones deleted during maturation of the immune system, (3) fine-tuning of epitope preference by choosing antibodies directed at each of the amino acid position in the peptide, (4) affinity maturation using standard phage or yeast display techniques, (5) control of valence by using Fab, scFv, or IgG, or even multimeric formats, and (6) ease of manufacture and genetic engineering for antibody-based versus TCR-based platforms. With engineering, both diagnostic and therapeutic drug candidates can be derived from such TCR mimics, including, but not limited to antibody-drug conjugates, radio-conjugates, toxin conjugates and bispecific antibodies to artificially generate T cell responses.

Since Andersen et al. first produced a monoclonal antibody with TCR specificity (Andersen, P. S. et al., 1996, Proc. Natl. Acad. Sci. U.S.A. 93:1820-4), there have been more than 60 TCR mimic monoclonal antibodies generated against human peptide-HLA class I complexes. Such monoclonal antibodies have been successfully used to characterize antigen presentation and as therapeutic agents in preclinical models. However, there is a lack of information on the specificity of these reagents to specific portions of antigenic peptides, and none of these have been generated to specifically target the primary and secondary contact residues (Townsend, A. and H. Bodmer, 1989, Ann. Rev. Immunol. 7:601-24; Willemsen, R A et al., 2001, Gene Ther. 8(21):1601-8, 2001; Low, J L et al., 2012, PLOS ONE 7(12):e51397; Miller, K R et al., 2012, PLOS ONE 7(8): e43746; Biddison, W E et al., 2003, J. Immunol. 171(6): 3064-74; Cohen, C J et al., 2002, Cancer Res. 62(20):5835-44; Cohen, C J et al. 2003, J. Immunol. 170(8):4349-61; Dao, T et al., 2013, Sci. Transl. Med. 5(176):176ra33; Denkberg, G et al., 2002, Proc. Natl. Acad. Sci. U.S.A. 99(14):9421-6; Epel, M et al., 2008, Eur. J. Immunol. 38:1706-20; Zhang, G et al., 2014, Scientific Reports 4:3571; Klechevsky, E et al., 2008, Cancer Res. 68(15): 6360-7; Oren, R et al., 2014, J. Immunol. 193(11):5733-43; Sergeeva, A et al., 2011, Blood 117(16):4262-72; Stewart-Jones, G et al., 2009, Proc. Natl. Acad. Sci. U.S.A. 106(14): 5784-8; Verma, B et al., 2011, J. Immunol. 186(5):3265-76; Weidanz, J A et al., 2006, J. Immunol. 177(8):5088-97; Ziegler, A et al., 2007, Recent Results Cancer Res. 176:229-41). Thus, even though such monoclonal antibodies bind to a peptide-HLA complex, they do not necessarily replicate the binding of TCR to peptide-HLA.

Not targeting the most important residues for antigen recognition has far reaching implications that are of particular importance when developing TCR mimics as therapeutic agents. By not targeting the functional hotspots, such reagents are prone to non-specific interaction or epitope spread, especially when multivalent engagement (e.g. as chimeric antigen receptor) is introduced (Oren, R. et al., 2014, J. Immunol. 193:5733-43). Furthermore, the generation of TCR monoclonal antibody mimics usually employs peptide sequences that are generated in silico, which may differ from the antigenic peptides presented in vivo (Scott, R. B. et al., 2006, Trends Immunol. 27:11-16) producing a selection bias that could compromise relevance.

Generation of True Second Generation T Cell Receptor Monoclonal Antibody Mimics

To create a true TCR-like monoclonal antibody, the present inventors first determined how TCRs natively bind peptide-HLA complexes. The inventors identified 14 unique TCR:nonamer-peptide/HLA Class I co-crystal structures from the protein data bank (Table 1; Stewart-Jones, G. B. et al., 2003; Nat. Immunol. 4:657-63; Garboczi, D. N. et al., 1996, Nature 384:134-41; Ding, Y. H. et al., 1998, Immunity 8:403-11; Chen, J. L. et al., 2005, J. Exp. Med. 201:1243-55; Borbulevych, O. Y. et al., 2009, Immunity 31:885-96; Borbulevych, O. Y. et al., 2011, J. Immunol. 186:2950-8; Gras, S. et al. 2009, J. Immunol. 183:430-7). Only native human TCR:HLA interactions were considered, while non-human TCRs, unnatural peptide variants, and artificially affinity-enhanced TCRs were excluded. The present inventors also identified 5 unique TCR:decamer-peptide/HLA Class I co-crystal structures from the protein data bank (Table 2). Because of the smaller size of the decamer-data set, the present inventors included two structures with heteroclitic peptides. All of these structures demonstrated that TCRs share a common geometry of binding, where TCRs bind diagonally to the peptide in the HLA binding pocket (or cleft). The present inventors then performed a more detailed molecular analysis of this interaction by calculating the per residue interaction energies of the peptide with the bound TCR using CHARMM force field simulations.

Molecular modeling and interaction energy calculations were done using Discovery Studio 4.1 (Accelrys, San Diego, Calif., U.S.A). The crystal structures of TCR-peptide-HLA complexes were energy-minimized using CHARMM (Chemistry at Harvard Molecular mechanics) force fields simulations, and the atomic interaction energies were then calculated as the sum of van der Waals and electrostatic energies.

TABLE 1

| PDB | MHC | TCR | Peptide | Source | Reference |
|-----|-----|-----|---------|--------|-----------|
| 1OGA | HLA-A2 | JM22 | GILGFVFTL | Viral MP (58-66) | (1) |
| 1AO7 | HLA-A2 | A6 | LLFGYPVYV | Tax viral peptide | (2) |
| 1BD2 | HLA-A2 | B7 | LLFGYPVYV | Tax viral peptide | (3) |
| 2BNQ | HLA-A2 | 1G4 | SLLMWITQV | NY-ESO-1 | (4) |
| 3H9S | HLA-A2 | A6 | MLWGYLQYV | Tel1p | (5) |
| 3PWP | HLA-A2 | A6 | LGYGFVNYI | Hud | (6) |
| 3GSN | HLA-A2 | RA14 | NLVPMVATV | CMV-pp65 | (7) |
| 3QEQ | HLA-A2 | DMF4 | AAGIGILTV | MART-1 | (8) |
| 3QDJ | HLA-A2 | DMF5 | AAGIGILTV | MART-1 | (8) |
| 1MI5 | HLA-B8 | LC13 | FLRGRAYGL | EBV/EBNA-3 | (9) |
| 3SJV | HLA-B8 | RL42 | FLRGRAYGL | EBV/EBNA-3 | (10) |
| 4QRP | HLA-B8 | DD31 | HSKKKCDEL | HCV/NS3-4A | (11) |
| 3FFC | HLA-B8 | CF34 | FLRGRAYGL | EBV/EBNA-3 | (12) |
| 3KPS | HLA-B44 | LC13 | EEYLQAFTY | ABCD3 | (13) |

TABLE 2

| PDB | MHC | TCR | Peptide | Source | Reference |
|-----|-----|-----|---------|--------|-----------|
| 3QDM | HLA-A2 | DMF4 | ELAGIGILTV | MART-1 (A2L) | (8) |
| 3QDG | HLA-A2 | DMF5 | ELAGIGILTV | MART-1 (A2L) | (8) |
| 3DXA | HLA-B44 | DM1 | EENLLDFVRF | EBV | (14) |
| 3UTT | HLA-A2 | 1E6 | ALWGPDPAAA | Insulin | (15) |
| 3VXR | HLA-A24 | H27-14 | RYPLTFGWCF | HIV-1 Nef | (16) |

To understand the short-range molecular contacts at the TCR-peptide-HLA interface, the van der Waals interaction energies were analyzed for each residue of the nonamer and decamer peptides. The per residue van der Waals interaction energies are set forth in FIG. 1 for TCR:nonamer-peptide/HLA structures and FIG. 2 for TCR:decamer-peptide/HLA structures (more negative values indicate more favorable interactions). The van der Waals interaction energies for the nonamer structures demonstrate a dominant cluster of interaction involving residues P4-P7, with the highest interaction occurring with residue P5. As the present inventors expected, the least interaction with the TCR occurs with the peptide anchor residues P2 and P9. For the decamer structures, a similar pattern was observed where the largest cluster of interaction with the TCR occurring at residues P4-P7, with the highest interaction at P5. In the case of the decamer where the last anchor residue is at P10 instead of P9, there was a wider distribution of high interaction energies at the P5 and P6 positions due to the presence of the extra residue, compared to the nonamer structures. Based on this unique structural analysis on a large number of native human TCR-peptide-HLA complexes, the present inventors generated human antibody agents (e.g., human monoclonal antibodies) that mimic the precise peptide-MHC binding modes of a TCR.

Human antibody agents of the present invention are based on the recognition that antigen recognition by TCRs is different when compared to antigen recognition by B cell receptors and antibodies. In particular, B cell receptors and antibodies recognize the surface of antigens, often contacting discontinuous amino acids brought together in a folded protein structure. Typically, antibodies are often selected based on affinity for a particular antigen, with binders having the highest affinity being chosen as the "best" therapeutics. In contrast, TCRs recognize short continuous amino acids (peptides) that are often buried within the structure of a folded protein, which would otherwise be unrecognizable if not for the presentation of such peptides on the cell surface via MHC molecules. TCRs bind peptides presented in an MHC binding pocket with relatively low affinity (usually in the micromolar range; e.g., see Donermeyer, D L et al., 2006, J. Immunol. 177(10):6911-9). Also, most of the diversity of TCRs resides in CDR3, which interacts directly with peptide, while other CDRs (e.g., CDR1, CDR2) are less variable and interact directly with MHC amino acids. Such low affinity is important for, among other things, disengagement from peptide-MHC complexes to resume serial killing of cells presenting such peptides as well as other T cell functions. Thus, human antibody agents of the present invention encompass the recognition that overreliance on affinity and in silico predictions as the central criteria when generating antibody agents specific for peptides presented by MHC molecules represents a flawed and misguided methodology. Such a methodology has lead to the production of several antibodies that have high affinity yet predominantly interact with the end portions of peptides presented by MHC molecules and suffer from cross-reactivity with irrelevant peptide-MHC complexes.

Among other things, the present invention specifically provides an improved methodology for developing human antibody agents that recognize a peptide presented by an MHC molecule. In particular, the present invention provides human antibody agents generated using a methodology that focuses on interaction with amino acids at the center position of a peptide presented by an MHC molecule in vivo, and furthermore provides human antibody agents characterized by high specificity and potency in cytotoxicity against cells expressing the peptide-MHC complex. Thus, the present disclosure, in at least some embodiments, embraces the development of an improved methodology for the development of human antibody agents using the location of antibody agent-peptide interaction in vivo as a central criterion to achieve natural TCR-like interaction without unwanted cross-reactivity.

As described herein, phage display technology was employed by the present inventors to generate high affinity human antibody agents (e.g., human monoclonal antibodies) specific for an LMP2 derived antigenic peptide (CLGGLLTMV, 340-349; SEQ ID NO: 1) in the context of an HLA-A*02:01 allele. The present invention offers distinct advantages that allow generalizations to other HLA alleles and antigens: (1) structural evidence demonstrates that EBV-LMP2-HLA-A*02:01 complex has prototypical behavior for a centrally located region of importance within the antigenic peptide (Simpson, A A et al., 2011, Proc. Natl. Acad. Sci. U.S.A. 108(52):21176-81) and (2) availability of several cell lines that have been fully genotyped for HLA and transformed in vitro for EBV positivity. Human monoclonal antibodies described herein have been selected not only for their affinity and specificity for a peptide-HLA complex, but have also been characterized for their ability to bind specific amino acid residues in a peptide present in such complex. The data presented in the present disclosure demonstrates that targeting different amino acid positions has important implications for specificity and affinity of TCR mimics, which confirms their utility not only in the diagnosis and therapy of EBV-associated malignancies but also provide important insight into how such an approach can be applied to other peptide-HLA class I complexes.

Anti-EBV-LMP2/HLA Class I Antibody Agents

The present invention provides methods and compositions for treating EBV-associated diseases, disorders and conditions and related malignancies, based on administration of anti-EBV-LMP2/HLA-A02 antibody agents (e.g., monoclonal antibodies), and, in some embodiments, multi-specific binding agents (e.g., bispecific antibodies) having a first antigen binding site that binds an EBV-LMP2/HLA-A02 complex and a second antigen-binding site that binds an immune effector cell (e.g., a T cell).

Exemplary human antibody agents (e.g., human monoclonal antibodies) that bind an EBV-LMP2/HLA-A02 complex are presented in Table 3 (LCVR: light chain variable region; HCVR: heavy chain variable region; scFv: single chain variable fragment).

TABLE 3

LMP2-21 LCVR DNA (SEQ ID NO: 2)
ACCTATGAGCTGACTCAGCCACCCTCAGTGTCAGTGGCCCCAGGAGAGAC

GGCCAGGATTACCTGTGGGGGAAACAACATTGGAGGCAAAAGTGTGCACT

GGTACCAGCAGAAGCCAGGCCAGGCCCCTGTACTGGTCATCTCTTATGAT

AGCGACCGGCCCTCAGGGATCCCTGAGCGAATCTCCGGCTCCAACTCTGG

GAACACGGCCACCCTGACCATCAGCAGGGTCGAAGCCGGGGATGAGGCCG

ACTATTACTGTCAGGTGTGGGATAGTAGTAGTGATCATTGGGTGTTCGGC

GGAGGGACCAAGCTGACCGTCCTAGGT

TABLE 3-continued

LMP2-21 LCVR amino acid (SEQ ID NO: 3)
SYELTQPPSVSVAPGETARITCGGNNIGGKSVHWYQQKPGQAPVLVISYD
SDRPSGIPERISGSNSGNTATLTISRVEAGDEADYYCQVWDSSSDHWVFG
GGTKLTVLG LMP2-21 HCVR DNA (SEQ ID NO: 4)
TAGGTCCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAG
AGTCACGATTACCGCGGACAAATCCACGAGCACAGCCTACATGGAGCTGA
GCAGCCTGAGATCTGAGGACACCGCCATGTATTACTGTGCGCGCGGTTCT
TACCATCAGCATTCTTACTCTGATGTTTGGGGTCAAGGTACTCTGGTGAC
CGTCTCC TCA LMP2-21 HCVR amino acid (SEQ ID NO: 5)
QVQLVQSGAEVKKPGSSVKVSCKASGGTFSSYAISWVRQAPGQGLEWMGR
IIPILGIANYAQKFQGRVTITADKSTSTAYMELSSLRSEDTAMYYCARGS
YHQHSYSDVWGQGTLVTVSS LMP2-26 LCVR DNA (SEQ ID NO: 6)
ACCTATGTGCTGACTCAGCCACCCTCAGTCTCAGTGGCCCCAGGAAAGAC
GGCCAGAGTTACCTGTGGGGGAAATAAGATTGGAAGCAAACATGTGCACT
GGTACCAACACAAGGCAGGCCAGGCCCTGTGTTGGTCATCTATTATAAT
ACTGACCGGCCCTCGGGGATCCCTGAGCGAATCTCTGGCTCCAACTCTGG
GGACACGGCCACCCTGACCATCACCGGGGTCGAGGCCGGCGATGAGGCCG
ACTATTACTGTCAGGTGTGGGATAGTAGTTATGATCATGTGATATTCGGC
GGAGGGACCAAGCTGACCGTCCTAGGT LMP2-26 LCVR amino acid (SEQ ID NO: 7)
SYVLTQPPSVSVAPGKTARVTCGGNKIGSKHVHWYQHKAGQAPVLVIYYN
TDRPSGIPERISGSNSGDTATLTITGVEAGDEADYYCQVWDSSYDHVIFG
GGTKLTVLG LMP2-26 HCVR DNA (SEQ ID NO: 8)
AAGGTGCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAACTGGGTGCGACAGGCCCCTGGACAAGGTCTTGAGTGGATGGGAAGG
ATCATCCCTATCCTTGGTATAGCAAACTACGCACAGAAGTTCCAGGCCAG
AGTCACGATTACCGCGGACAAATCCACGAGCACAGCCTACATGGAGCTGA
GCAGCCTGAGATCTGAGGACACCGCCGTATATTACTGTGCGCGCTCTTAC
CCGCTGTACTCTGGTTGGGATTACTGGGGTCAAGGTACTCTGGTGACCGT
CTCCTCA LMP2-26 HCVR amino acid (SEQ ID NO: 9)
QVQLVQSGAEVKKPGSSVKVSCKASGGTFSSYAINWVRQAPGQGLEWMGR
IIPILGIANYAQKFQGRVTITADKSTSTAYMELSSLRSEDTAVYYCARSY
PLYSGWDYWGQGTLVTVSS LMP2-38 LCVR DNA (SEQ ID NO: 10)
AAATCTGCCCTGACTCAGCCTGCCTCCGTGTCTGGGTCTCCAGGACAGTC
GATCACCATCTCCTGCACTGGAACCAGCAGTGACGTTGGTAGTTATAACG
ATGTCTCCTGGTACCAACAACACCCAGGCAAAGCCCCCAAACTCATGATT
TATGATGTCAGTAATCGGCCCTCAGGGGTTTCTAATCGCTTCTCTGGCTC
CAAGTCTGGCAACACGGCCTCCCTGACCATCTCTGGGCTCCAGACTGAGG
ACGAGGCTGATTATTACTGCAACTCATATACAAGCAGCAACACTTATGTC
TTCGGAACTGGGACCAAGGTCACCGTCCTAGGT LMP2-38 LCVR amino acid (SEQ ID NO: 11)
QSALTQPASVSGSPGQSITISCTGTSSDVGSYNDVSWYQQHPGKAPKLMI
YDVSNRPSGVSNRFSGSKSGNTASLTISGLQTEDEADYYCNSYTSSNTYV
FGTGTKVTVLG LMP2-38 HCVR DNA (SEQ ID NO: 12)
TAGGTGCAGCTGGTGCAGTCTGGGGCTGAGGTGAAGAAGCCTGGGGCCTC
AGTGCAGGTTTCCTGCAGGGCATCTGGATACACAATCACCTCCTACTATA
TGCACTGGGTGCGACAGGCCCCTGGACAAGGGCTTGAGTGGATGGGAGTA
ATCAACCCTAATGCTGGCAGCACAAGATACGCACAGAAATTCCAGGGCAG
AGTCACCATGAGCACTGACACGTCCACGAGCACAGTCTACATGGCGCTGA
GTAGTCTGAGATCTGACGACACTGCCGTGTATTACTGTGCGCGCGGTATG
TACCGTATGTACGATTGGGGTCAAGGTACTCTGGTGACCGTCTCCTCA LMP2-38 HCVR amino acid (SEQ ID NO: 13)
QVQLVQSGAEVKKPGASVQVSCRASGYTITSYYMEIWVRQAPGQGLEWMG
VINPNAGSTRYAQKFQGRVTMSTDTSTSTVYMALSSLRSDDTAVYYCARG
MYRMYDWGQGTLVTVSS LMP2-40 LCVR DNA (SEQ ID NO: 14)
AAGTCTGTGTTGACTCAGCCACCCTCAGTGTCAGTGGCCCCAGGAGAGAC
GGCCAGAATTACCTGTGGGGGAAACAACATTGGAAGTAGAAGTGTGCACT
GGTACCAGCAGAAGGCAGGCCAGGCCCCTGTTCTGGTCATCTCTTATAAT
AACGACCGGCCCTCAGGGATCCCTGAGCGAATCTCTGGCTCCAACTCTGG
GAACACGGCCACCCTGACCATCAGCAGGGTCGAAGCCGGGGATGAGGCCG
ACTTTTACTGTCAGGTGTGGGATAGTATTAGTGACCATTATGTCTTCGGA
ACTGGGACCAAGGTCACCGTCCTAGGT LMP2-40 LCVR amino acid (SEQ ID NO: 15)
QSVLTQPPSVSVAPGETARITCGGNNIGSRSVHWYQQKAGQAPVLVISYN
NDRPSGIPERISGSNSGNTATLTISRVEAGDEADFYCQVWDSISDHYVFG
TGTKVTVLG LMP2-40 HCVR DNA (SEQ ID NO: 16)
TAGGTGCAGCTGGTGGAGTCTGGGGCTGAGGTGAAGAAACCTGGGTCCTC
GGTGAAGGTCGCCTGCAAGGGTTCTGGAGGCACCTTCAGCAACTATCATA
TCAGCTGGGTGCGACAGGCCCCTGGACAAGGGCTTGAGTGGATGGGTGGG
ATCATCCCCATCCTTGGCACACCAAACTACGCACCGAAATTCCTGGACAG
AGTCACGATTTCCGCGGACGATTCCACGAGCACAGCCTACATGGAGCTGA TABLE 3-continued GCAGCCTCACAGCTGACGACACGGCCGTATATTACTGTGCGCGCGGTCGT
ACTTGGTGGTCTGGTACTCTGGATTCTTGGGGTCAAGGTACTCTGGTGAC
CGTCTCCTCA LMP2-40 HCVR amino acid (SEQ ID NO: 17)
QVQLVESGAEVKKPGSSVKVACKGSGGTFSNYHISWVRQAPGQGLEWMGG
IIPILGTPNYAPKFLDRVTISADDSTSTAYMELSSLTADDTAVYYCARGR
TWWSGTLDSWGQGTLVTVSS LMP2-61 LCVR DNA (SEQ ID NO: 18)
GCTTCTGAGCTGACTCAGGACCCTGCTGTGTCTGTGGCCTTGGGACAGAC
AGTCAGGATCACATGCCAAGGAGACAGCCTCAGAAGCTATTATGCAAGCT
GGTACCAGCAGAAGCCAGGACAGGCCCCTGTACTTGTCATCTATGGTAAA
AACAACCGGCCCTCAGGGATCCCAGACCGATTCTCTGGCTCCAGCTCAGG
AAACACAGCTTCCTTGACCATCACTGGGGCTCAGGCGGAAGATGAGGCTG
ACTATTACTGTAACTCCCGGGACAGCAGTGGTAACCATCTGGTATTCGGC
GGAGGGACCAAGCTGACCGTCCTAGGT LMP2-61 LCVR amino acid (SEQ ID NO: 19)
SSELTQDPAVSVALGQTVRITCQGDSLRSYYASWYQQKPGQAPVLVIYGK
NNRPSGIPDRFSGSSSGNTASLTITGAQAEDEADYYCNSRDSSGNHLVFG
GGTKLTVLG LMP2-61 HCVR DNA (SEQ ID NO: 20)
TAGGTGCAGCTGGTGCAGTCTGGGGCTGAGGTGAAGAGGCCTGGGGCCTC
AGTGAAGGTCTCCTGCAAGGCATCTGGATACACCTTCACCAACTATTATA
TCCACTGGGTGCGACAGGCCCCTGGACAAGGGCTTGAGTGGATGGGAAGA
ATCAACCCTAGTGGTGGGAGCACAAATTACGCACCGAAGTTCCAGGGCAG
AGTCACCATGACCAGGGACACGTCCACGAACACAGTCTACATGGAACTGA
GCAGCCTGAGATCTGAGGACACTGCCGTGTATTACTGTGCGCGCTCTTAC
TACGGTTCTATGGATGCTTGGGGTCAAGGTACTCTGGTGACCGTCTCCTC
A LMP2-61 HCVR amino acid (SEQ ID NO: 21)
QVQLVQSGAEVKRPGASVKVSCKASGYTFTNYYIHWVRQAPGQGLEWMGR
INPSGGSTNYAPKFQGRVTMTRDTSTNTVYMELSSLRSEDTAVYYCARSY
YGSMDAWGQGTLVTVSS LMP2-63 LCVR DNA (SEQ ID NO: 22)
TCCTATGTGCTGACTCAGCCACCCTCGGTGTCAGTGGCCCCAGGAAAGAC
GGCCAGACTTACCTGTGGGGGAAACAACATTGGAAGTGAAAGTGTACATT
GGTACCAGCAGAAGCCAGGCCAGGCCCCTTTACTGGTCGTCTATGATGAT
GACGACCGGCCCTCCGGGATCCCTGAGCGATTCTCTGGCTCCAACTCTGG
GAACACGGCCACCCTGACCATCAGCAGGGTCGAGGCCGGCGATGAGGCCG
ACTATTACTGTCAGGTGTGGGATCGAAGTAGTGATCATTGGTTTTTCGGC
GGAGGGACCAAGGTCACCGTCCTAGGT LMP2-63 LCVR amino acid (SEQ ID NO: 23)
SYVLTQPPSVSVAPGKTARLTCGGNNIGSESVHWYQQKPGQAPLLVVYDD
DDRPSGIPERFSGSNSGNTATLTISRVEAGDEADYYCQVWDRSSDHWFFG
GGTKVTVLG LMP2-63 HCVR DNA (SEQ ID NO: 24)
AAGGTCCAGCTGGTACAGTCTGGGGCTGAGGTGAAGAAGCCTGGGGCCTC
AGTGCAGGTTTCCTGCAGGGCATCTGGATACACAATCACCTCCTACTATA
TGCACTGGGTGCGACAGGCCCCTGGACAAGGGCTTGAGTGGATGGGAGTA
ATCAACCCTAATGCTGGCAGCACAAGATACGCACAGAAATTCCAGGGCAG
AGTCACCATGAGCACTGACACGTCCACGAGCACAGTCTACATGGCGCTGA
GTAGTCTGAGATCTGACGACACGGCCGTGTATTACTGTGCGCGCGGTGAC
GTTTACAACGGTTGGGATGAATGGGGTCAAGGTACTCTGGTGACCGTCTC
CTCA LMP2-63 HCVR amino acid (SEQ ID NO: 25)
EVQLVQSGAEVKKPGASVQVSCRASGYTITSYYMEIWVRQAPGQGLEWMG
VINPNAGSTRYAQKFQGRVTMSTDTSTSTVYMALSSLRSDDTAVYYCARG
DVYNGWDEWGQGTLVTVSS LMP2-77 LCVR DNA (SEQ ID NO: 26)
GCTTCTGAGCTGACTCAGGACCCTGCTGTGTCTGTGGCCTTGGGACAGAC
AGTCAGGTTCACATGCCAAGGAGACAGCCTCAGAACGCATTATGCAAGTT
GGTACCAGCAGAAGCCAGGACAGGCCCCTCAACTTGTCATCTATGGTAAA
AACAGGCGGCCCTCAGGGATCCCAGACCGATTCTCTGGCTCCACCTCAGG
AAACACCGCTTCCTTGACCATCACTGGGGCTCAGGCGGAAGATGAGGGTG
ACTATTACTGTAACTCCCGGCACAGCAGTGGTAATCATTGTGTGTTTGGC
GGAGGGACCAAGCTGACCGTCCTAGGT LMP2-77 LCVR amino acid (SEQ ID NO: 27)
SSELTQDPAVSVALGQTVRFTCQGDSLRTHYASWYQQKPGQAPQLVIYGK
NRRPSGIPDRFSGSTSGNTASLTITGAQAEDEGDYYCNSRHSSGNHCVFG
GGTKLTVLG LMP2-77 HCVR DNA (SEQ ID NO: 28)
TAGGTGCAGCTGGTGGAGTCTGGCCCAGGACTGGTGAAACCTTCACAGAC
CCTGTCCCTCACCTGCACTGTCTCTGGTGGCTCCATCACCAGTGGTAATT
ACTACTGGAGCTGGATCCGTCAGCCCCCAGGGAAGGGGCTGGAGTGGATT
GGGGAGATCAATCATAGCGGAAGCCCCAAGTACAATCCGTCCCTCAAGAG
TCGAGTCACCATATCAGAAGCACGTCCCGGAACCAGTTCTCCCTGAAGC
TGAGCTCTGTGACCGCCGCGGACACGGCCGTGTATTACTGTGCGCGCCAG
TCTTCTTACGGTGGTTACATAGATCAGTGGGGTCAAGGTACTCTGGTGAC
CGTCTCCTCA LMP2-77 HCVR amino acid (SEQ ID NO: 29)
EVQLVESGPGLVKPSQTLSLTCTVSGGSITSGNYYWSWIRQPPGKGLEWI
GEINHSGSPKYNPSLKSRVTISEDTSRNQFSLKLSSVTAADTAVYYCARQ
SSYGGYIDQWGQGTLVTVSS TABLE 3-continued

```
Anti-CD3 scFv DNA (SEQ ID NO: 123)
GACGTGCAGCTGGTGCAGAGCGGAGCTGAAGTGAAGAAACCTGGCGCCTC

CGTGAAGGTGTCCTGCAAAGCTAGCGGCTATACCTTCACCCGGTACACCA

TGCACTGGGTGCGCCAGGCACCTGGACAGGGACTGGAATGGATCGGCTAC

ATCAACCCCTCCCGGGGCTACACCAACTACGCCGACTCTGTGAAGGGCCG

GTTCACCATCACCACCGATAAGTCCACCAGCACCGCTTACATGGAACTGT

CCTCCCTGAGATCCGAGGACACCGCTACCTACTATTGCGCCCGGTACTAC

GACGACCACTACTGCCTGGACTACTGGGGACAGGGAACCACAGTGACCGT

GTCCTCTGGCGAGGGCACCTCTACTGGATCTGGGGGAAGTGGTGGTTCTG

GCGGCGCTGACGACATCGTGCTGACCCAGTCTCCAGCCACCCTGTCTCTG

AGCCCAGGCGAGAGAGCTACCCTGTCCTGCAGAGCCTCCCAGTCCGTGTC

CTACATGAATTGGTATCAGCAGAAGCCTGGCAAGGCCCCTAAGCGGTGGA

TCTACGACACCTCCAAGGTGGCCTCTGGCGTGCCAGCCCGGTTTTCCGGA

TCTGGCTCTGGCACCGACTACTCCCTGACCATCAACAGCCTGGAAGCCGA

GGACGCTGCCACCTATTACTGCCAGCAGTGGTCCTCCAACCCCCTGACCT

TTGGAGGCGGCACCAAGGTGGAAATCAAG

Anti-CD3 scFv amino acid (SEQ ID NO: 124)
DVQLVQSGAEVKKPGASVKVSCKASGYTFTRYTMHWVRQAPGQGLEWIGY

INPSRGYTNYADSVKGRFTITTDKSTSTAYMELSSLRSEDTATYYCARYY

DDHYCLDYWGQGTTVTVSSGEGTSTGSGGSGGSGGADDIVLTQSPATLSL

SPGERATLSCRASQSVSYMNWYQQKPGKAPKRWIYDTSKVASGVPARFSG

SGSGTDYSLTINSLEAEDAATYYCQQWSSNPLTFGGGTKVEIK
```

In various embodiments, a human anti-EBV-LMP2/HLA-A02 monoclonal antibody according to the present invention is composed of heavy and light chain variable regions, wherein the heavy chain variable region contains at least one of the CDRs found in a heavy chain variable region that appears in Table 3 and the light chain variable region contains at least one of the CDRs found in a light chain variable region that appears in Table 3.

In various embodiments, a human anti-EBV-LMP2/HLA-A02 monoclonal antibody according to the present invention is composed of heavy and light chain variable regions, wherein the heavy chain variable region contains at least two of the CDRs found in a heavy chain variable region that appears in Table 3 and the light chain variable region contains at least two of the CDRs found in a light chain variable region that appears in Table 3.

In various embodiments, a human anti-EBV-LMP2/HLA-A02 monoclonal antibody according to the present invention is composed of heavy and light chain variable regions, wherein the heavy chain variable region contains three CDRs found in a heavy chain variable region that appears in Table 3 and the light chain variable region contains three CDRs found in a light chain variable region that appears in Table 3.

In various embodiments, a human anti-EBV-LMP2/HLA-A02 monoclonal antibody according to the present invention is composed of heavy and light chain variable regions, wherein the heavy chain variable region contains three CDRs, which CDRs each have a sequence that is at least about 50% (e.g., at least about 55%, 60%, 65%, 70%, 75%, 80%, 85%, 90%, 95%, 96%, 97%, 98%, or 99%) identical to heavy chain CDRs that appear in Table 5.

In various embodiments, a human anti-EBV-LMP2/HLA-A02 monoclonal antibody according to the present invention is composed of heavy and light chain variable regions, wherein the heavy chain variable region contains three CDRs, which CDRs each have a sequence that is substantially identical or identical to heavy chain CDRs that appear in Table 5.

In various embodiments, a human anti-EBV-LMP2/HLA-A02 monoclonal antibody according to the present invention is composed of heavy and light chain variable regions, wherein the light chain variable region contains three CDRs, which CDRs each have a sequence that is at least about 50% (e.g., at least about 55%, 60%, 65%, 70%, 75%, 80%, 85%, 90%, 95%, 96%, 97%, 98%, or 99%) identical to light chain CDRs that appear in Table 6.

In various embodiments, a human anti-EBV-LMP2/HLA-A02 monoclonal antibody according to the present invention is composed of heavy and light chain variable regions, wherein the light chain variable region contains three CDRs, which CDRs each have a sequence that is substantially identical or identical to light chain CDRs that appear in Table 6.

In various embodiments, a human anti-EBV-LMP2/HLA-A02 monoclonal antibody according to the present invention is composed of heavy and light chain variable regions, wherein the heavy chain variable region contains three CDRs that appear in Table 5 and the light chain variable region contains three CDRs that appear in Table 6.

In various embodiments, a human anti-EBV-LMP2/HLA-A02 monoclonal antibody according to the present invention is composed of heavy and light chain variable regions, wherein the heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 3.

In various embodiments, a human anti-EBV-LMP2/HLA-A02 monoclonal antibody according to the present invention is composed of heavy and light chain variable regions, wherein the heavy chain variable region has a sequence that is substantially identical or identical to a heavy chain variable region that appears in Table 3.

In various embodiments, a human anti-EBV-LMP2/HLA-A02 monoclonal antibody according to the present invention is composed of heavy and light chain variable regions, wherein the light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 3.

In various embodiments, a human anti-EBV-LMP2/HLA-A02 monoclonal antibody according to the present invention is composed of heavy and light chain variable regions, wherein the light chain variable region has a sequence that is substantially identical or identical to a light chain variable region that appears in Table 3.

In various embodiments, a human anti-EBV-LMP2/HLA-A02 monoclonal antibody according to the present invention is composed of heavy and light chain variable regions, which heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 3, and which light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 3.

In various embodiments, a human anti-EBV-LMP2/HLA-A02 monoclonal antibody according to the present invention is composed of heavy and light chain variable regions, which heavy chain variable region has a sequence that is substantially identical or identical to a heavy chain variable region that appears in Table 3, and which light chain variable region has a sequence that is substantially identical or identical to a light chain variable region that appears in Table 3.

In various embodiments, a human anti-EBV-LMP2/HLA-A02 monoclonal antibody according to the present invention is composed of heavy and light chain variable regions that are selected from heavy and light chain variable region sequences that appear in Table 3.

EBV-LMP2 peptides described herein, or fragments thereof, can be used to generate antibodies by methods known to those of skill in the art. As used herein, anti-EBV-LMP2/HLA-A02 antibodies include any antibodies or fragments of antibodies that bind specifically to any residues of EBV-LMP2 peptide CLGGLLTMV (SEQ ID NO: 1) in the context of HLA-A02.

As used herein, an "anti-EBV-LMP2/HLA-A02 antibody", "anti-EBV-LMP2/HLA-A02 antibody portion," or "anti-EBV-LMP2/HLA-A02 antibody fragment" and/or "anti-EBV-LMP2/HLA-A02 antibody variant" and the like include any protein or peptide containing molecule that comprises at least a portion of an immunoglobulin molecule, containing at least one complementarity determining region (CDR) of a heavy or light chain or a ligand binding portion thereof derived from any of the monoclonal antibodies described herein, in combination with a heavy chain or light chain variable region, a heavy chain or light chain constant region, a framework region, or any portion thereof, of non-murine origin, preferably of human origin, which can be incorporated into an antibody of the present invention. Alternatively, the term "anti-EBV-LMP2/HLA-A02 antibody" shall refer collectively or individually to LMP2-21, LMP2-21 IgG1, LMP2-26, LMP2-26 IgG1, LMP2-38, LMP2-38 IgG1, LMP2-40, LMP2-40 IgG1, LMP2-61, LMP2-61 IgG1, LMP2-63, LMP2-63 IgG1, LMP2-77, LMP2-77 IgG1, and combinations thereof, as well fragments and regions thereof such as single chain variable fragments of the present invention including LMP2-21 scFv, LMP2-26 scFv, LMP2-38 scFv, LMP2-40 scFv, LMP2-61 scFv, LMP2-63 scFv, LMP2-77 scFv, and combinations thereof. Such human monoclonal antibody is capable of modulating, decreasing, antagonizing, mitigating, alleviating, blocking, inhibiting, abrogating and/or interfering with at least one cell function in vitro, in situ and/or in vivo, wherein said cell expresses an EBV-LMP2/HLA-A02 complex. As a non-limiting example, a suitable anti-EBV-LMP2/HLA-A02 antibody, specified portion or variant of the present invention can bind with high affinity to an epitope, in particular a peptide epitope, of an EBV-LMP2 peptide presented by a human HLA class I molecule.

Anti-EBV-LMP2/HLA-A02 antibodies can be generated using methods known in the art. For example, protocols for antibody production are described by Harlow and Lane, Antibodies: A Laboratory Manual, (1988). Typically, antibodies can be generated in mouse, rat, guinea pig, hamster, camel, llama, shark, or other appropriate host. Alternatively, antibodies may be made in chickens, producing IgY molecules (Schade et al., 1996, ALTEX 13(5):80-85). In some embodiments, antibodies suitable for the present invention are subhuman primate antibodies. For example, general techniques for raising therapeutically useful antibodies in baboons may be found, for example, in WO 91/11465 and in Losman et al., 1990, Int. J. Cancer 46:310. In some embodiments, monoclonal antibodies may be prepared using hybridoma methods (Milstein and Cuello, 1983, Nature 305(5934):537-40). In some embodiments, monoclonal antibodies may also be made by recombinant methods (see, e.g., U.S. Pat. No. 4,166,452).

Many of the difficulties associated with generating monoclonal antibodies by B-cell immortalization can be overcome by engineering and expressing antibody fragments in E. coli, using phage display. To ensure the recovery of high affinity, monoclonal antibodies a combinatorial immunoglobulin library must typically contain a large repertoire size. A typical strategy utilizes mRNA obtained from lymphocytes or spleen cells of immunized mice to synthesize cDNA using reverse transcriptase. The heavy and light chain genes are amplified separately by PCR and ligated into phage cloning vectors. Two different libraries are produced, one containing the heavy chain genes and one containing the light chain genes. Phage DNA is isolated from each library, and the heavy and light chain sequences are ligated together and packaged to form a combinatorial library. Each phage contains a random pair of heavy and light chain cDNAs and upon infection of E. coli directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from Stratagene Cloning Systems (La Jolla, Calif.).

A similar strategy can be employed to obtain high-affinity scFv (see, e.g., Vaughn et al., 1996, Nat. Biotechnol., 14:309-314). An scFv library with a large repertoire can be constructed by isolating V-genes from non-immunized human donors using PCR primers corresponding to all known $V_H$, Vκ and Vλ gene families. Following amplification, the Vκ and Vλ pools are combined to form one pool. These fragments are ligated into a phagemid vector. An scFv linker (e.g., [G4S]3) is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in P. pastoris (see, e.g., Ridder et al., 1995, Biotechnology, 13:255-260). Additionally, following isolation of an appropriate scFv, antibody fragments with higher binding affinities and slower dissociation rates can be obtained through affinity maturation processes such as CDR3 mutagenesis and chain-shuffling (see, e.g., Jackson et al., 1998, Br. J. Cancer, 78:181-188); Osbourn et al., 1996, Immunotechnology, 2:181-196).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, e.g., Larrick et al., 1991, Methods: A Companion to Methods in Enzymology 2:106; Courtenay-Luck, "Genetic Manipulation of Monoclonal Antibodies," in Monoclonal Antibodies: Production, Engineering And Clinical Application, Ritter et al., eds., p. 166-179, Cambridge University Press 1995; and Ward et al., "Genetic Manipulation and Expression of Antibodies," in Monoclonal Antibodies: Principles And Applications, Birch et al., eds., p. 137-185, Wiley-Liss, Inc. 1995).

In some embodiments, antibodies suitable for the invention may include humanized or human antibodies. Humanized forms of non-human antibodies are chimeric immunoglobulins (Igs), Ig chains or fragments (such as Fv, Fab, Fab', F(ab')$_2$ or other antigen-binding subsequences of antibodies) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., 1988, Nature 332(6162):323-7; Verhoeyen et al., 1988, Science 239 (4847):1534-6). Such "humanized" antibodies are chimeric antibodies (see, e.g., U.S. Pat. Nos. 4,816,567; 5,693,762; and 5,225,539), wherein substantially less than an intact human variable domain has been substituted by the corresponding sequence from a non-human species. In some embodiments, humanized antibodies are typically human antibodies in which some CDR residues and possibly some framework (FR) residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., 1988, Nature 332(6162):323-7; Verhoeyen et al., 1988, Science 239 (4847): 1534-6).

Human antibodies can be produced using various techniques, including phage display libraries (Hoogenboom et al., 1991, Mol. Immunol. 28(9):1027-37; Marks et al., 1991, J. Mol. Biol. 222(3):581-97) and the preparation of human monoclonal antibodies (Reisfeld and Sell, 1985, Cancer Surv. 4(1):271-90). Similarly, introducing human Ig genes into transgenic animals in which the endogenous Ig genes have been partially or completely inactivated can be exploited to synthesize human antibodies (see, e.g., Fishwild et al., 1996, Nat. Biotechnol. 14(7):845-51; Lonberg et al., 1994, Nature 368(6474):856-9; Lonberg and Huszar, 1995, Int. Rev. Immunol. 13:65-93; Taylor, L. D., et al., 1992, Nucl. Acids Res. 20:6287-6295; Kellermann S-A., and Green L. L., 2002, Curr. Opin. Biotechnol. 13:593-597; Little, M. et al., 2000, Immunol. Today 21:364-370; Murphy, A. J. et al., 2014, Proc. Natl. Acad. Sci. U.S.A. 111(14):5153-5158). Upon challenge, human antibody production is observed. In some embodiments, anti-EBV-LMP2/HLA-A02 human antibodies are made by immunization of non-human animals engineered to make human antibodies in response to antigen challenge with an EBV-LMP2 peptide having an amino acid sequence that is or comprises CLGGLLTMV (SEQ ID NO: 1).

In some embodiments, anti-EBV-LMP2/HLA-A02 human monoclonal antibodies for use in accordance with the present invention comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., 2000, Nature, 406: 267-273. Examples of positions within the Fc region that make a direct contact with an Fc receptor such as an FcγR are amino acids 234-239 (hinge region), amino acids 265-269 (B/C loop), amino acids 297-299 (C'/E loop), and amino acids 327-332 (F/G) loop. In some embodiments, anti-EBV-LMP2/HLA-A02 human monoclonal antibodies of the present invention comprising variant Fc regions comprise modification of at least one residue that makes a direct contact with an FcγR based on structural and crystallographic analysis.

In some embodiments, an anti-EBV-LMP2/HLA-A02 human monoclonal antibody for use in accordance with the present invention is an anti-EBV-LMP2/HLA-A02 human monoclonal antibody with an altered affinity for activating and/or inhibitory receptors, having variant Fc regions with one or more amino acid modifications, wherein said one or more amino acid modification is a substitution at position 297 with alanine; in some embodiments, a substitution at 239D, 330L, 332E to enhance FcR affinity; in some embodiments, a substitution at 322K to reduce or eliminate FcR binding. In some embodiments, anti-EBV-LMP2/HLA-A02 human monoclonal antibodies for use in accordance with the present invention have an Fc region with variant glycosylation as compared to a parent Fc region; in some embodiments, variant glycosylation includes absence of fucose; in some embodiments, variant glycosylation results from expression in GnT1-deficient CHO cells. In some embodiments, the present invention provides multi-specific binding agents having a human anti-EBV-LMP2/HLA-A02 antibody component that comprises a variant Fc region characterized by a K322A substitution. In some embodiments a provided multi-specific binding agent includes an antibody component that shows variant glycosylation (e.g., is aglycosylated) as compared with a parent antibody from which the component may be derived; in some such embodiments, such a variant may be or comprise a variant Fc region characterized by the K322A substitution.

In some embodiments, the present invention provides and/or utilizes antibodies or antibody agents comprising a variant Fc region (i.e., an Fc region includes one or more additions, deletions, and/or substitutions relative to an appropriate reference Fc) that are characterized in that alter effector function and/or affinity for an FcR is enhanced or diminished relative to a reference Fc. These variations are within the skill of a person in the art.

Therefore, among other things, the present invention provides antibody agents and multi-specific binding agents (e.g., antibody agents) comprising variant Fc regions that bind with a greater affinity to one or more FcγRs. Such agents preferably mediate effector function more effectively as discussed infra. In some embodiments, the present invention provides antibody agents and multi-specific binding agents (e.g., bispecific antibodies) comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Further, elimination of effector function is desirable, in some embodiments, when making bispecific antibodies as discussed infra. Reduction or elimination of effector function would be desirable in cases of autoimmune disease where one would block FcγR activating receptors in effector cells (This type of function would be present in the host cells). Generally, increased effector function may be directed to tumor and foreign cells; in some embodiments, effector function may be directed away from tumor cells.

Fc variants for use in accordance present invention may be combined with other Fc modifications, including but not limited to modifications that alter effector function. The invention encompasses combining an Fc variant as described herein with other Fc modifications to provide additive, synergistic, or novel properties in antibodies or Fc fusions. In some such embodiments, Fc variants may enhance the phenotype of the modification with which they are combined. For example, if an Fc variant is combined with a mutant known to bind FcγRIIIA with a higher affinity than a comparable molecule comprising a wild type Fc region, the combination with the mutant results in a greater fold enhancement in FcγRIIIA affinity.

In some embodiments, in accordance with the present invention Fc variants as described herein are incorporated into an antibody or Fc fusion to generate an engineered agent that comprises one or more Fc glycoforms (i.e., one or more Fc polypeptides to which one or more carbohydrates is covalently attached) to a molecule comprising an Fc region wherein the carbohydrate composition of the glycoform differs chemically from that of a parent molecule comprising an Fc region.

In some embodiments, a multi-specific binding agent (e.g., an antibody agent) as described herein may include an Fc variant that shows variant glycosylation and/or may be expressed in a glycosylation deficient cell line (e.g., a GnT1-deficient CHO cell) such an Fc region of the agent is produced lacking glycosylation as compared to an appropriate reference Fc region (e.g., a wild type), or an Fc region expressed in a cell line not deficient in glycosylation.

In some embodiments, antibodies utilized in accordance with the present invention, may have a modified glycosylation site relative to an appropriate reference antibody that binds to an antigen of interest (e.g., an EBV-LMP2 peptide), preferably without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform that lacks certain oligosaccharides including fucose and terminal N-acetylglucosamine may be produced in special CHO cells and exhibit enhanced ADCC effector function.

In some embodiments, the present invention encompasses methods of modifying the carbohydrate content of an antibody as described herein by adding or deleting a glycosylation site. Methods for modifying the carbohydrate content of antibodies are well known in the art and are included within the present invention (see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. No. 6,218,149; U.S. Pat. No. 6,472,511). In some embodiments, the present invention includes methods of modifying the carbohydrate content of an antibody (or relevant portion or component thereof) by deleting one or more endogenous carbohydrate moieties of the antibody. In some certain embodiments, the present invention includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol. 17:176-180; Davies et al., 2001, Biotechnol. Bioeng. 74:288-294; Shields et al., 2002, J. Biol. Chem. 277:26733-26740; Shinkawa et al., 2003, J. Biol. Chem. 278:3466-3473; U.S. Pat. No. 6,602,684; U.S. patent application Ser. No. 10/277,370; U.S. patent application Ser. No. 10/113,929; International Pat. Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland). See, e.g., International Pat. Application Publication WO 00/061739; EA01229125; U.S. Pat. Application Publication No. 2003/0115614; Okazaki et al., 2004, JMB, 336:1239-49.

Multivalent Binding Agents

As those skilled in the art are aware, a multivalent binding agent is a molecular entity or complex that includes binding components that bind specifically to two or more targets (e.g., epitopes). Such multivalent binding agents find a variety of uses in the art, including therapeutic uses. To give but one example, as those skilled in the art are aware, multivalent binding agents have been engineered to facilitate killing of tumor cells by directing (or recruiting) cytotoxic T cells to a tumor site. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo Dl, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

In some embodiments, multivalent binding agents for use in accordance with the present invention are bispecific binding agents. In many embodiments, such bispecific binding agents are capable of binding to tumor cells. In many embodiments, such bispecific binding agents are capable of binding to Epstein-Barr virus (EBV)-infected, EBV$^+$ cells, or cells that express an EBV-related peptide on the tumor cell surface via an MHC molecule (e.g., an HLA class I molecule).

In some embodiments, multivalent binding agents (e.g., bispecific binding agents) provided by the present invention are or comprise antibody components. A variety of technologies are known in the art for designing, constructing, and/or producing multi-specific binding agents comprising antibody components.

For example, multivalent binding agents have been constructed that either utilize the full immunoglobulin framework (e.g., IgG), single chain variable fragment (scFv), or combinations thereof. Bispecific binding agents composed of two scFv units in tandem has been shown to be a clinically successful bispecific antibody format. In the case of anti-tumor immunotherapy, bispecific binding agents that comprise two single chain variable fragments (scFvs) in tandem have been designed such that an scFv that binds a tumor antigen is linked with an scFv that engages T cells by binding CD3. In this way, T cells are recruited to a tumor site in the hope that they can mediate killing of the tumor cells by the cytotoxic properties that certain T cells have. An example of such a bispecific binding agent has been made that targets CD19 and CD3 for lymphoma (termed Bispecific T cell Engaging, or BiTE; e.g., see Dreier et al., 2003, J. Immunol. 170:4397-4402; Bargou et al., 2008, Science 321:974-977), which has been successful in preventing tumor growth in animal xenograft studies. In human studies, this bispecific binding agent demonstrated objective tumor response, including five partial and two complete remissions.

Exemplary bispecific binding agents include those with a first antibody component specific for a tumor antigen (e.g., an EBV-related peptide in a binding pocket of an MHC molecule) and a second antibody component specific for an immune effector cell (e.g., a T cell, NK cell, etc.). Bispecific binding agents can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

In some embodiments, bispecific binding agents of the present invention are characterized by the ability to bind simultaneously to two targets that are of different structure. In some embodiments, bispecific binding agents of the present invention have at least one component that specifically binds to, for example, a B-cell, T-cell, myeloid, plasma, or a mast cell antigen or epitope and at least one other component that specifically binds to a peptide-HLA complex, which peptide of the peptide-HLA complex is derived from an EBV protein.

Bispecific binding agents (e.g., bispecific antibodies) of the present invention are based on the particular insight that certain formats may be more beneficial for certain targets (e.g., a tumor antigen) when employed for the diagnosis and/or treatment of EBV-related disease and malignancies. For example, bispecific antibodies provided herein utilize a combination of scFvs having distinct binding characteristics. Such bispecific antibodies demonstrate specificity for an EBV-peptide/HLA complex via a first scFv and specificity for T cells via a second (e.g., anti-CD3). As described herein, bispecific antibodies having this format first bind to a cell that expresses an EBV-LMP2 peptide/HLA complex via a first scFv (e.g., anti-EBV-LMP2/HLA-A02) and CD3 on T cells via a second scFv. Such bispecific binding agents promote cytotoxicity of EBV$^+$ cells via T cells through the simultaneous binding of an EBV-LMP2 peptide/HLA complex and CD3. Further, bispecific antibodies of the present invention provide both diagnostic and therapeutic tumor targeting features.

In various embodiments, a bispecific binding agent (e.g., a bispecific antibody) according to the present invention is composed of a first binding component and a second binding component. In many embodiments, first and second binding components of a bispecific binding agent as described herein are each composed of antibody components characterized by different specificities. In many embodiments, antibody components are selected from Table 3.

In various embodiments, a bispecific binding agent according to the present invention comprises a first binding component and a second binding component. In various embodiments, a bispecific binding agent according to the present invention comprises a first binding component, a second binding component and a linker that is connected to both the first and second binding component (e.g., positioned between the first and second binding components).

In various embodiments, first and/or second binding components as described herein comprise or are antibody components. In various embodiments, first and/or second binding components as described herein comprise a linker sequence.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second binding components). In some embodiments, a linker is employed in a bispecific binding agent described herein based on specific properties imparted to the bispecific binding agent such as, for example, a reduction in aggregation and/or an increase in stability. In some embodiments, a bispecific binding agent of the present invention comprises a $G_4S$ linker. In some certain embodiments, a bispecific binding agent of the present invention comprises a $(G_4S)_n$ linker, wherein n is 1, 2, 3, 4, 5, 6, 7, 8, 9, 10, 11, 12, 13, 14, 15 or more.

In some embodiments, first and/or second binding components as described herein comprise or are immunoglobulins (e.g., IgGs). In some embodiments, first and/or second binding components binding components as described herein comprise or are antibody fragments (e.g., scFvs). In some embodiments, first binding components as described herein comprise or are immunoglobulins and second binding components comprise or are antibody fragments. In some certain embodiments, first binding components are immunoglobulins and second binding components are antibody fragments. In some certain embodiments, first binding components are IgGs and second binding components are scFvs.

In some certain embodiments, a bispecific binding agent according to the present invention comprises a first and a second scFv. In some certain embodiments, a first scFv is linked to the C-terminal end of a second scFv. In some certain embodiments, a second scFv is linked to the C-terminal end of a first scFv. In some certain embodiments, scFvs are linked to each other via a linker sequence.

In some embodiments, a bispecific binding agent of the present invention comprises one or more sequences that are at least about 50% (e.g., at least about 55%, 60%, 65%, 70%, 75%, 80%, 85%, 90%, 95%, 96%, 97%, 98%, or 99%) identical to one or more sequences that appear in Table 3.

In some embodiments, a bispecific binding agent of the present invention comprises one or more sequences that are substantially identical or identical to one or more sequences that appears in Table 3.

In some embodiments, a bispecific binding agent of the present invention is selected from one or more sequences that appear in Table 3. In some certain embodiments, a bispecific binding agent of the present invention is selected from two sequences that appear in Table 3, for example, a heavy chain and a light chain sequence. In some certain embodiments, a bispecific binding agent of the present invention is selected from three sequences that appear in Table 3, for example, a heavy chain sequence, a light chain sequence and an scFv sequence.

In various embodiments, a first binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 3.

In various embodiments, a first binding component of a bispecific binding agent as described herein comprises an antibody component having a sequence that is substantially identical or identical to an antibody component that appears in Table 3.

In various embodiments, a second binding component of a bispecific binding agent as described herein comprises an antibody component that binds a T cell. Exemplary T cell markers that can be employed as targets for a second binding component of a bispecific binding agent as described herein include CD3, CD4, CD8, CD28, etc. In some embodiments, a second binding component of a bispecific binding agent as described herein comprises an antibody component that binds CD3. In some certain embodiments, a second binding component of a bispecific binding agent as described herein comprises an antibody component that binds CD3c.

In various embodiments, a second binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 3.

In various embodiments, a second binding component of a bispecific binding agent as described herein comprises an antibody component having a sequence that is substantially identical or identical to an antibody component that appears in Table 3. In some certain embodiments, a second binding component of a bispecific binding agent as described herein is or comprises SEQ ID NO: 124.

As described herein, the present inventors provide improved monospecific and multi-specific binding agents (e.g., bispecific antibodies) that target an EBV-related peptide presented in an HLA class I binding pocket. Such multi-specific binding agents include binding components that, in some embodiments, mimic TCR interaction with peptides presented in an HLA class I binding pocket. Thus, binding components of multi-specific binding agents of the present invention can be described as more specific and analogous to natural TCRs that are specific to an EBV-related peptide presented in an HLA class I binding pocket. As described herein, such multi-specific binding agents demonstrate enhanced avidity and clinical utility without suffering cross-reactivity as compared to multi-specific binding agents that do not contain such binding components. Thus, the present invention specifically demonstrates the synthesis of bivalent and multivalent LMP2(CLG)/HLA-A02 specific type II antibodies, which antibodies are characterized by enhanced potency in vitro and in vivo. Further, the present invention specifically demonstrates a selection methodology for developing type II TCR antibody mimic characterized, in some embodiments, by specificity for target peptide positions 4-7 of an EBV-related peptide, which offers distinct advantages that allow generalizations to other HLA alleles and antigens.

Chimeric Antigen Receptors (CARs)

The present invention also provides chimeric antigen receptors comprising a human antibody agent and/or multispecific binding agent as described herein. CARs may be constructed by methods known in the art (see, e.g., WO 2012/079000, U.S. Patent Application Publication No. 2012/0213783, WO 2013/126726, WO 2015/177789 and WO 2015/080981; all of which are hereby incorporated by reference). Immune effector cells (e.g., T cells, NK cells, etc.) may be engineered to express a chimeric antigen receptor that contains an antibody component as described herein, thereby creating anti-tumor immune effector cells that overcome the surveillance mechanisms of the immune system employed by cancer cells to evade detection. In some embodiments, the present invention provides an immune effector cell that express a chimeric antigen receptor, which chimeric antigen receptor comprises one or more antigen-binding sites of a human antibody agent or multispecific binding agent as described herein. In some embodiments, immune effector cells include T cells engineered to express an antigen-binding site of an antibody component described herein. In some embodiments, an antigen-binding site is or comprises an antibody component as described herein.

In some embodiments, immune effector cells include a chimeric antigen receptor that is chimeric, humanized, human and/or engineered by the hand of man. In some embodiments, a chimeric antigen receptor comprises one, two, three, four, five, or more components (e.g., antibody components, binding components, signaling components, etc.). In some embodiments, components of a chimeric antigen receptor as described herein facilitate binding of an immune effector cell to an EBV$^+$ or EBV-infected cell. In some embodiments, a chimeric antigen receptor as described herein comprises an antibody component that binds EBV-LMP2/HLA-A complex (e.g., an EBV-LMP2(CLG)/HLA-A02 complex), and further comprises one or more cytoplasmic signaling domains, in whole or in part, and one or more co-stimulatory molecules, in whole or in part. In some embodiments, an antibody component of a chimeric antigen receptor as described herein is or comprises an scFv; in some certain embodiments, an scFv is selected from Table 3.

Targets

Among other things, the present invention encompasses the recognition that multi-specific binding agents (and/or chimeric antigen receptors), and particularly bispecific binding agents such as bispecific antibodies, are particularly useful and/or effective to facilitate cell killing. In particular, the present invention demonstrates that activity of multivalent binding agents that bind specifically to both a target-cell-associated epitope (e.g., an EBV-associated peptide antigen) and a lymphocyte-associated epitope (e.g., a T cell surface protein) can be an effective immunotherapy for EBV-associated disease and malignancies.

For example, in some embodiments of the present invention, a multivalent binding agent binds specifically to a tumor-cell-associated epitope and a T-cell epitope. In accordance with such embodiments, the multivalent binding agent can facilitate binding of the agent to one or both of its target epitopes and/or can enhance killing of the target tumor cell as mediated by the target T cell. To give but another example, in some embodiments of the present invention, a chimeric antigen receptor binds an EBV-associated epitope on an EBV$^+$ or EBV-infected cell. In accordance with such embodiments, the immune effector cell can facilitate killing of the EBV$^+$ or EBV-infected cell after engagement of the chimeric antigen receptor with its target eptitope.

In some embodiments, target cells to be killed include, for example, cells that express a viral peptide antigen (e.g., an EBV-associated viral peptide antigen). Those of ordinary skill in the art will be aware of appropriate target epitopes on such cells to which multivalent binding agents as described herein desirably bind.

In some embodiments, lymphocyte cells that can mediate killing of target cells as described herein include T cells (e.g., CD8$^+$ T cells), natural killer (NK) cells, macrophages, granulocytes and antibody-dependent cytotoxic cells. Those of ordinary skill in the art will be aware of appropriate target epitopes on such lymphocytes to which multivalent binding agents as described herein desirably bind. Representative such epitopes can be found on antigens such as, for example, Fc receptor of IgG (e.g., FcγRIIB), CD1d, CD3, CD4, CD7, CD8, CD13, CD14, CD16, CD31, CD38, CD56, CD68, MAC-1/MAC-3, IL-2Ra, OX40, Ly49, and CD94.

Nucleic Acid Construction and Expression

Human monoclonal antibodies, multi-specific binding agents (e.g., bispecific antibodies) and chimeric antigen receptors as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al., Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs include regions that encode multi-specific binding proteins (or chimeric antigen receptors) generated from antibodies and/or antibody components. Typically, such multi-specific binding proteins (or chimeric antigen receptors) will be generated from V$_H$ and/or V$_L$ regions. After identification and selection of antibodies exhibiting desired binding and/or functional properties, variable regions of each antibody are isolated, amplified, cloned and sequenced. Modifications may be made to the V$_H$ and V$_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, non-human (e.g., rodent), humanized or chimeric antibodies.

Nucleic acid constructs of the present invention are inserted into an expression vector or viral vector by methods known to the art, and nucleic acid molecules are operatively linked to an expression control sequence.

Where appropriate, nucleic acid sequences that encode human monoclonal antibodies, multi-specific binding agents, and chimeric antigen receptors as described herein may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a human or humanized heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., E. coli) and eukaryotes (e.g., a COS or CHO cell). Host cells transformed with an expression vector are grown under conditions permitting production of a human monoclonal antibody, multi-specific binding agent, or chimeric antigen receptor of the present invention followed by recovery of the human monoclonal antibody, multi-specific binding agent or chimeric antigen receptor.

Human monoclonal antibodies and/or multi-specific binding agents of the present invention may be purified by any technique, which allows for the subsequent formation of a stable antibody or binding agent molecule. For example, not wishing to be bound by theory, human monoclonal antibodies and/or multi-specific binding agents may be recovered from cells either as soluble polypeptides or as inclusion bodies, from which they may be extracted quantitatively by 8M guanidinium hydrochloride and dialysis. In order to further purify human monoclonal antibodies and/or multi-specific binding agents of the present invention, conventional ion exchange chromatography, hydrophobic interaction chromatography, reverse phase chromatography or gel filtration may be used. Human monoclonal antibodies and/or multi-specific binding agents of the present invention may also be recovered from conditioned media following secretion from eukaryotic or prokaryotic cells.

Chimeric antigen receptors expressed on an immune effector cell surface may be achieved by methods known in the art. Typically, an expression vector carrying the nucleic acid sequence that encodes the chimeric antigen receptor polypeptide is transformed into a microorganism for expression. As described above, such microorganisms can be prokaryotic (bacteria) or eukaryotic (e.g., yeast). The expression vector may also include a sequence that encodes a signal peptide such that the expression of the chimeric antigen receptor is targeted to a cell membrane or subcellular location depending on the desired outcome. Such signal peptides are known by persons of skill in the art. The expression vector that encodes the chimeric antigen receptor polypeptide is introduced into a host cell by methods known in the art, which include, for example, DNA transfection, electroporation, transfection and infection (e.g., with a virus such as an adenovirus or retrovirus).

In some embodiments, nucleic acid molecules encoding a chimeric antigen receptor as described herein provide for expression in a T cell thereby generating chimeric antigen receptor T cells. The nucleic acid molecule encoding the chimeric antigen receptor can be included in a vector (e.g., a lentiviral or retroviral vector) for expression in a host immune effector cell, such as a T cell. Exemplary immune effector cells include T cells, Natural Killer (NK) cells, cytotoxic T lymphocytes (CTLs), and regulatory T cells. Methods of generating nucleic acid molecules encoding chimeric antigen receptors and T cells including such chimeric antigen receptors are known in the art (see, e.g., Till, B. G. et al., 2008, Blood 112(6):2261-71; Brentjens, R. et al., 2010, Molecular Therapy 18(4):666-8; Morgan, R. A. et al., 2010, Molecular Therapy 18(4):843-51; Park, T. S. et al., 2011, Trends Biotechnol. 29(11):550-7; Grupp, S. A. et al., 2013, N. Engl. J. Med. 368(16):1509-18; Han, E. Q. et al., 2013, J. Hematol. Oncol. 6:47; WO 2012/079000, WO 2013/126726; and U.S. Patent Application Publication No. 2012/0213783, all of which are hereby incorporated by reference).

Screening and Detection Methods

Human monoclonal antibodies, multi-specific binding agents and/or chimeric antigen receptors of the present invention may also be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a human monoclonal antibody or a multi-specific binding agent which is bound to a target molecule (e.g., cell surface antigen). Detectable labels may be used in conjunction with assays using human monoclonal antibodies, multi-specific binding agents or chimeric antigen receptors of the present invention.

Therapeutic Methods

The ability of human monoclonal antibodies, multi-specific binding agents and/or chimeric antigen receptors of the present invention to exhibit high affinity binding for one of the target antigens makes them therapeutically useful for efficiently targeting cells expressing the target antigen (e.g., an EBV-associated peptide). Thus, it some embodiments, it may be desirable to increase the affinity of a human monoclonal antibody or multi-specific binding agent for one target antigen and not the other target antigen that is also bound by the multi-specific binding agent (or an Fc receptor in the case of a human monoclonal antibody). For example, in the context of tumor killing, certain conditions may benefit from an increase in affinity to a tumor antigen but not to an antigen on the surface of a cell capable of mediating killing of the tumor (e.g., a T cell). Thus, it may be beneficial to increase the binding affinity of a human monoclonal antibody, multi-specific binding agent or chimeric antigen receptor to a tumor antigen in a patient having a tumor that expresses the tumor antigen through the use of a human monoclonal antibody, multi-specific binding agent or chimeric antigen receptor as described herein.

The present invention provides a human monoclonal antibody, multi-specific binding agent and/or chimeric antigen receptor as described herein as a therapeutic for the treatment of patients having a tumor that expresses an antigen that is capable of being bound by such a multi-specific binding agent. Such human monoclonal antibodies, multi-specific binding agents and/or chimeric antigen receptors may be used in a method of treatment of the human or animal body, or in a method of diagnosis.

In some embodiments, a provided human monoclonal antibody, multi-specific binding agent, or chimeric antigen receptor is useful in medicine. In some embodiments, a provided human monoclonal antibody, multi-specific binding agent, or chimeric antigen receptor is useful as prophylactic agents in the treatment or prevention of EBV-associated disease or malignancies or of negative ramifications associated or correlated with EBV-associated disease or malignancies. In some embodiments, a provided human monoclonal antibody, multi-specific binding agent, or chimeric antigen receptor is useful in therapeutic applications, for example in individuals suffering from or susceptible to EBV-associated disease or malignancies.

Administration

The present invention provides methods of administering an effective amount of a therapeutic active described herein (e.g., a human monoclonal antibody, multi-specific binding agent, or chimeric antigen receptor) to a subject in need of treatment.

Human monoclonal antibodies, multi-specific binding agents, or chimeric antigen receptor as described herein may be administered through various methods known in the art for the therapeutic delivery of agents, such as proteins or nucleic acids can be used for the therapeutic delivery of a human monoclonal antibody, multi-specific binding agent or chimeric antigen receptor or a nucleic acid encoding a human monoclonal antibody, multi-specific binding agent, or chimeric antigen receptor of the present invention for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a multi-specific binding agent of the present invention.

Various delivery systems are known and can be used to administer a human monoclonal antibody, multi-specific binding agent, or chimeric antigen receptor of the present invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, multi-specific binding agents of the present invention are administered intravenously. In some embodiments, multi-specific binding agents of the present invention are administered subcutaneously. In some embodiments, multi-specific binding agents are administered together with other biologically active agents.

Pharmaceutical Compositions

The present invention further provides pharmaceutical compositions comprising human monoclonal antibodies, multi-specific binding agents or chimeric antigen receptors of the present invention and a pharmaceutically acceptable carrier or excipient. The composition, if desired, can also contain one or more additional therapeutically active substances.

In some embodiments, pharmaceutical compositions comprising a chimeric antigen receptor may be provided as a virus (e.g., a retrovirus) used to infect autologous T cells isolated from a subject. In such embodiments, autologous T cells are infected with a virus that has been engineered to express a chimeric antigen receptor as described herein, thereby creating chimeric antigen receptor T cells for reinfusion into the subject (e.g., a human patient).

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

For example, pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present invention further provides a pharmaceutical pack or kit comprising one or more containers filled with at least one human monoclonal antibody, multi-specific binding agent (e.g., a bispecific antibody), or chimeric antigen receptor (or chimeric antigen immune effector cell) as described herein. Kits may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Other features of the invention will become apparent in the course of the following descriptions of exemplary embodiments, which are given for illustration of the invention and are not intended to be limiting thereof.

EXEMPLARY EMBODIMENTS

1. A human antibody agent that binds an EBV-LMP2/HLA peptide complex, wherein the human antibody agent interacts directly with amino acid residues at one or more positions selected from the group consisting of position 1, position 5, position 8, and combinations thereof, in the EBV-LMP2 peptide.

2. A human antibody agent that binds an EBV-LMP2/HLA peptide complex, wherein the human antibody agent has a $K_D$ of about 2.0 to about 170 nM.

3. The human antibody agent of exemplary embodiment 1 or 2, wherein the EBV-LMP2 peptide has an amino acid sequence that is or comprises CLGGLLTMV (SEQ ID NO: 1).

4. The human antibody agent of exemplary embodiment 3, wherein the human antibody agent interacts directly with amino acid residues at one or more positions selected from the group consisting of position 1, 2, 3, 4, 5, 6, 7, 8, and combinations thereof, in the EBV-LMP2 peptide.

5. The human antibody agent of any one of exemplary embodiments 1-4, wherein the human antibody agent comprises heavy chain CDR1 of SEQ ID NO:31, CDR2 of SEQ ID NO:33 and CDR3 of SEQ ID NO:35; and wherein the human antibody agent comprises light chain CDR1 of SEQ ID NO:73, CDR2 of SEQ ID NO:75 and CDR3 of SEQ ID NO:77.

6. The human antibody agent of any one of exemplary embodiments 1-4, wherein the human antibody agent comprises heavy chain CDR1 of SEQ ID NO:37, CDR2 of SEQ ID NO:39 and CDR3 of SEQ ID NO:41; and wherein the human antibody agent comprises light chain CDR1 of SEQ ID NO:79, CDR2 of SEQ ID NO:81 and CDR3 of SEQ ID NO:83.

7. The human antibody agent of any one of exemplary embodiments 1-4, wherein the human antibody agent comprises heavy chain CDR1 of SEQ ID NO:43, CDR2 of SEQ ID NO:45 and CDR3 of SEQ ID NO:47; and wherein the human antibody agent comprises light chain CDR1 of SEQ ID NO:85, CDR2 of SEQ ID NO:87 and CDR3 of SEQ ID NO:89.

8. The human antibody agent of any one of exemplary embodiments 1-4, wherein the human antibody agent comprises heavy chain CDR1 of SEQ ID NO:49, CDR2 of SEQ ID NO:51 and CDR3 of SEQ ID NO:53; and wherein the human antibody agent comprises light chain CDR1 of SEQ ID NO:91, CDR2 of SEQ ID NO:93 and CDR3 of SEQ ID NO:95.

9. The human antibody agent of any one of exemplary embodiments 1-4, wherein the human antibody agent comprises heavy chain CDR1 of SEQ ID NO:55, CDR2 of SEQ ID NO:57 and CDR3 of SEQ ID NO:59; and wherein the human antibody agent comprises light chain CDR1 of SEQ ID NO:97, CDR2 of SEQ ID NO:99 and CDR3 of SEQ ID NO:101.

10. The human antibody agent of any one of exemplary embodiments 1-4, wherein the human antibody agent comprises heavy chain CDR1 of SEQ ID NO:61, CDR2 of SEQ ID NO:63 and CDR3 of SEQ ID NO:65; and wherein the human antibody agent comprises light chain CDR1 of SEQ ID NO: 103, CDR2 of SEQ ID NO: 105 and CDR3 of SEQ ID NO: 107.

11. The human antibody agent of any one of exemplary embodiments 1-4, wherein the human antibody agent comprises heavy chain CDR1 of SEQ ID NO:67, CDR2 of SEQ ID NO:69 and CDR3 of SEQ ID NO:71; and wherein the human antibody agent comprises light chain CDR1 of SEQ ID NO: 109, CDR2 of SEQ ID NO:111 and CDR3 of SEQ ID NO: 113.

12. The human antibody agent of any one of exemplary embodiments 5-11, wherein the human antibody agent comprises one or more amino acid substitutions in a heavy chain CDR and/or light chain CDR.

13. The human antibody agent of exemplary embodiment 12, wherein the human antibody agent comprises at least one or up to five amino acid substitutions in a heavy chain CDR and/or light chain CDR.

14. The human antibody agent of exemplary embodiment 12, wherein the human antibody agent comprises at least one or up to three amino acid substitutions in a heavy chain CDR and/or light chain CDR.

15. The human antibody agent of any one of exemplary embodiments 1-4, wherein the human antibody agent comprises a heavy chain variable region having a sequence at least 95% identical to a heavy chain variable region sequence that appears in Table 3.

16. The human antibody agent of any one of exemplary embodiments 1-4, wherein the human antibody agent comprises a light chain variable region having a sequence at least 95% identical to a light chain variable region sequence that appears in Table 3.

17. The human antibody agent of any one of exemplary embodiments 1-4, wherein the human antibody agent comprises
  (a) a heavy chain variable region having a sequence at least 95% identical to a heavy chain variable region sequence that appears in Table 3, and
  (b) a light chain variable region having a sequence at least 95% identical to a light chain variable region sequence that appears in Table 3.

18. The human antibody agent of any one of exemplary embodiments 1-4, wherein the human antibody agent comprises a heavy chain variable region selected from Table 3.

19. The human antibody agent of any one of exemplary embodiments 1-4, wherein the human antibody agent comprises a light chain variable region selected from Table 3.

20. The human antibody agent of any one of exemplary embodiments 1-4, wherein the human antibody agent comprises the light chain variable region of SEQ ID NO:3 and the heavy chain variable region of SEQ ID NO:5.

21. The human antibody agent of any one of exemplary embodiments 1-4, wherein the human antibody agent comprises the light chain variable region of SEQ ID NO:7 and the heavy chain variable region of SEQ ID NO:9.

22. The human antibody agent of any one of exemplary embodiments 1-4, wherein the human antibody agent comprises the light chain variable region of SEQ ID NO: 11 and the heavy chain variable region of SEQ ID NO:13.

23. The human antibody agent of any one of exemplary embodiments 1-4, wherein the human antibody agent comprises the light chain variable region of SEQ ID NO: 15 and the heavy chain variable region of SEQ ID NO: 17.

24. The human antibody agent of any one of exemplary embodiments 1-4, wherein the human antibody agent comprises the light chain variable region of SEQ ID NO: 19 and the heavy chain variable region of SEQ ID NO:21.

25. The human antibody agent of any one of exemplary embodiments 1-4, wherein the human antibody agent comprises the light chain variable region of SEQ ID NO:23 and the heavy chain variable region of SEQ ID NO:25.

26. The human antibody agent of any one of exemplary embodiments 1-4, wherein the human antibody agent comprises the light chain variable region of SEQ ID NO:27 and the heavy chain variable region of SEQ ID NO:29.

27. The human antibody agent of any one of the preceding exemplary embodiments, wherein the human antibody agent is a human monoclonal antibody that is defucosylated and/or glycosylated with terminal mannose, N-acetylglucose or glucose.

28. A human antibody agent that binds an EBV-LMP2/HLA peptide complex, which human antibody agent comprises one or more amino acid substitutions that increase affinity to the EBV-LMP2/HLA peptide complex, and wherein the human antibody agent is characterized by
  (a) a KA of at least about 1.6 higher affinity than affinity to a reference peptide/HLA complex, and/or
  (b) no cross-reactivity to a reference peptide/HLA complex.

29. The human antibody agent of exemplary embodiment 28, wherein the human antibody agent comprises a light chain variable region that comprises one or more amino acid substitutions at any of amino acid positions 48, 52, 55, 66, 95 and combinations thereof.

30. The human antibody agent of exemplary embodiment 29, wherein the one or more amino acid substitutions is I48V/S52G, P55H, K66R or N95I.

31. The human antibody agent of any one of exemplary embodiments 28-30, wherein the human antibody agent comprises a heavy chain variable region that comprises one or more amino acid substitutions at any of amino acid positions 5, 10, 26, 51, 78 and combinations thereof.

32. The human antibody agent of exemplary embodiment 31, wherein the one or more amino acid substitutions is V5E, E10D, G26E/I51V or V78A.

33. The human antibody agent of any one of the preceding exemplary embodiments, wherein the human antibody agent is a human monoclonal antibody or a fragment thereof.

34. The human antibody agent of exemplary embodiment 33, wherein the human monoclonal antibody is an IgG1, IgG2, IgG3 or IgG4 antibody.

35. The human antibody agent of exemplary embodiment 34, wherein the human monoclonal antibody is an IgG1.

36. The human antibody agent of exemplary embodiment 33, wherein the human monoclonal antibody fragment is an scFv.

37. The human antibody agent of any one of the preceding exemplary embodiments, wherein the HLA of the EBV-LMP2/HLA peptide complex is an HLA class I molecule.

38. The human antibody agent of exemplary embodiment 37, wherein the HLA class I molecule is HLA-A02.

39. The human antibody agent of exemplary embodiment 38, wherein the HLA-A02 is selected from HLA-A*02:01, HLA-A*02:02, HLA-A*02:03, HLA-A*02:04, HLA-A*02:05 and HLA-A*02:06.

40. An isolated nucleic acid molecule encoding, in whole or in part, a human antibody agent of any one of exemplary embodiments 1-39.

41. A recombinant vector comprising the nucleic acid molecule of exemplary embodiment 40.

42. A host cell comprising the recombinant vector of claim 41 or the nucleic acid molecule of exemplary embodiment 40.

43. The host cell of exemplary embodiment 42, wherein the host cell is selected from a bacterial, yeast, insect or mammalian cell.

44. The host cell of exemplary embodiment 43, wherein the host cell is selected from the group consisting of *E. coli*, *P. pastoris*, Sf9, COS, HEK293, CHO and a mammalian lymphocyte.

45. The host cell of exemplary embodiment 44, wherein the mammalian lymphocyte is a human lymphocyte.

46. A method for producing a human antibody agent according to any one of exemplary embodiments 1-39 comprising
  culturing a host cell according to any one of claims 42-45 in a culture medium under conditions suitable for expression of the human antibody agent, and
  recovering the human antibody agent from the culture medium.

47. A composition comprising a human antibody agent according to any one of exemplary embodiments 1-39.

48. A pharmaceutical composition comprising a human antibody agent according to any one of exemplary embodiments 1-39 or a composition according to exemplary embodiment 47, and further comprising a pharmaceutically acceptable carrier or diluent.

49. A kit comprising a human antibody agent according to any one of exemplary embodiments 1-39.

50. A method of treating a medical condition in a subject characterized by expression of an EBV-LMP2/HLA peptide complex, comprising a step of administering a therapeutically effective amount of a human antibody agent according to any one of exemplary embodiments 1-39, a composition of exemplary embodiment 47, or a pharmaceutical composition of exemplary embodiment 48.

51. The method of exemplary embodiment 50, wherein the medical condition is Hodgkin's disease, non-Hodgkin's disease or infectious mononucleosis.

52. The method of exemplary embodiment 50, wherein the medical condition is selected from Burkitt's lymphoma, immunosuppressive lymphoma, diffuse large B-cell lymphoma, diffuse large B-cell lymphoma associated with chronic inflammation, lymphomatoid granulomatosis, plasmablastic lymphoma, primary effusion lymphoma, post-transplant lymphoproliferative disorder, nasopharyngeal carcinoma, gastric adenocarcinoma, lymphoepithelioma-associated carcinoma, and immunodeficiency-related leiomyosarcoma.

53. The method of any one of exemplary embodiments 50-52, wherein the HLA of the EBV-LMP2/HLA peptide complex is an HLA class I molecule.

54. The method of exemplary embodiment 53, wherein the HLA class I molecule is HLA-A02.

55. The method of exemplary embodiment 54, wherein the HLA-A02 is selected from HLA-A*02:01, HLA-A*02:02, HLA-A*02:03, HLA-A*02:04, HLA-A*02:05, and HLA-A*02:06.

56. Use of a human antibody agent according to any one of exemplary embodiments 1-39 for the treatment or detection of a condition related to EBV infection.

57. A bispecific antibody comprising a first antigen-binding site that binds an EBV-LMP2/HLA peptide complex and a second antigen-binding site.

58. The bispecific antibody of exemplary embodiment 57, wherein the bispecific antibody is characterized by an $EC_{50}$ of about 0.2 to about 135 pM in T2 cells pulsed with EBV-LMP2 peptide CLGGLLTMV (SEQ ID NO: 1).

59. The bispecific antibody of exemplary embodiment 57 or 58, wherein the first and/or second antigen-binding sites are selected from the group consisting of an immunoglobulin molecule, scFv, scFab, Fab, Fv or a combination thereof.

60. The bispecific antibody of exemplary embodiment 57 or 58, wherein the first and second antigen-binding sites are configured such that they form a single polypeptide chain.

61. The bispecific antibody of exemplary embodiment 60, wherein the first and second antigen-binding sites are each scFvs.

62. The bispecific antibody of exemplary embodiment 60, wherein the first and second antigen-binding sites are linked by a peptide linker.

63. The bispecific antibody of exemplary embodiment 61 or 62, wherein the second antigen-binding site is linked to the C-terminal end of the first antigen-binding site.

64. The bispecific antibody of any one of exemplary embodiments 57-63, wherein the second antigen-binding site binds an immunological cell selected from the group consisting of a T cell, B cell, NK cell, dendritic cell, monocyte, macrophage, neutrophil, mesenchymal stem cell and neural stem cell.

65. The bispecific antibody of exemplary embodiment 64, wherein the second antigen-binding site binds CD3 on T cells.

66. The bispecific antibody of any one of exemplary embodiments 57-65, wherein the HLA of the EBV-LMP2/HLA peptide complex is an HLA class I molecule.

67. The bispecific antibody of exemplary embodiment 66, wherein the HLA class I molecule is HLA-A02.

68. The bispecific antibody of exemplary embodiment 67, wherein the HLA-A02 is selected from HLA-A*02:01, HLA-A*02:02, HLA-A*02:03, HLA-A*02:04, HLA-A*02:05 and HLA-A*02:06.

69. An isolated nucleic acid molecule encoding, in whole or in part, a bispecific antibody according to any one of exemplary embodiments 57-68.

70. A recombinant vector comprising the nucleic acid molecule of exemplary embodiment 69.

71. A host cell comprising the recombinant vector of exemplary embodiment 70 or the nucleic acid molecule of exemplary embodiment 69.

72. The host cell of exemplary embodiment 71, wherein the host cell is selected from a bacterial, yeast, insect or mammalian cell.

73. The host cell of exemplary embodiment 72, wherein the host cell is selected from the group consisting of *E. coli, P. pastoris*, Sf9, COS, HEK293, CHO, and a mammalian lymphocyte.

74. The host cell of exemplary embodiment 73, wherein the mammalian lymphocyte is a human lymphocyte.

75. A composition comprising a bispecific antibody according to any one of exemplary embodiments 57-68.

76. A pharmaceutical composition comprising a bispecific antibody according to any one of exemplary embodiments 57-68 or a composition according exemplary embodiment 75, and further comprising a pharmaceutically acceptable carrier or diluent.

77. A kit comprising a bispecific antibody according to any one of exemplary embodiments 57-68.

78. A method of treating a medical condition in a subject characterized by expression of an EBV-LMP2/HLA peptide complex, comprising a step of administering a therapeutically effective amount of a bispecific antibody according to any one of exemplary embodiments 57-68, a composition of exemplary embodiment 75, or a pharmaceutical composition of exemplary embodiment 76.

79. The method of exemplary embodiment 78, wherein the medical condition is Hodgkin's disease, non-Hodgkin's disease or infectious mononucleosis.

80. The method of exemplary embodiment 78, wherein the medical condition is selected from Burkitt's lymphoma, immunosuppressive lymphoma, diffuse large B-cell lymphoma, diffuse large B-cell lymphoma associated with chronic inflammation, lymphomatoid granulomatosis, plasmablastic lymphoma, primary effusion lymphoma, post-transplant lymphoproliferative disorder, nasopharyngeal carcinoma, gastric adenocarcinoma, lymphoepithelioma-associated carcinoma, and immunodeficiency-related leiomyosarcoma.

81. The method of any one of exemplary embodiments 78-80, wherein the HLA of the EBV-LMP2/HLA peptide complex is an HLA class I molecule.

82. The method of exemplary embodiment 81, wherein the HLA class I molecule is HLA-A02.

83. The method of exemplary embodiment 82, wherein the HLA-A02 is selected from HLA-A*02:01, HLA-A*02:02, HLA-A*02:03, HLA-A*02:04, HLA-A*02:05 and HLA-A*02:06.

84. Use of a bispecific antibody according to any one of exemplary embodiments 57-68 for the treatment or detection of a condition related to EBV infection.

85. A method of directing T cells to kill target cells expressing an EBV-LMP2/HLA peptide complex, the method comprising a step of contacting one or more target cells expressing an EBV-LMP2/HLA peptide complex with a bispecific antibody, which bispecific antibody comprises a first antigen-binding site that binds an EBV-LMP2/HLA peptide complex and a second antigen-binding site that binds CD3 on T cells, the contacting being performed under conditions and for a time sufficient that T cells to which the bispecific antibody has bound mediates killing of the target cells.

86. The method of exemplary embodiment 85, wherein the EBV-LMP2 peptide is or comprises CLGGLLTMV (SEQ ID NO: 1).

87. The method of exemplary embodiment 85 or 86, wherein the first antigen-binding site of the bispecific antibody interacts directly with amino acid residues at one more positions selected from the group consisting of position 1, 2, 3, 4, 5, 6, 7, 8, and combinations thereof, in the EBV-LMP2 peptide.

88. The method of any one of exemplary embodiments 85-87, wherein the HLA of the EBV-LMP2/HLA peptide complex is an HLA class I molecule.

89. The method of exemplary embodiment 88, wherein the HLA class I molecule is HLA-A02.

90. The method of exemplary embodiment 89, wherein the HLA-A02 is selected from HLA-A*02:01, HLA-A*02:02, HLA-A*02:03, HLA-A*02:04, HLA-A*02:05 and HLA-A*02:06.

91. A bispecific antibody comprising
a first scFv that binds to EBV-LMP2 peptide CLG-GLLTMV (SEQ ID NO: 1) presented by an HLA-A02 molecule, and
a second scFv that binds CD3 on T cells,
wherein the bispecific antibody is characterized by an $EC_{50}$ of about 0.2 to about 135 pM in T2 cells pulsed with the EBV-LMP2 peptide.

92. The bispecific antibody of exemplary embodiment 91, wherein the first scFv comprises
(a) the light chain variable region of SEQ ID NO:3 and the heavy chain variable region of SEQ ID NO:5;
(b) the light chain variable region of SEQ ID NO:7 and the heavy chain variable region of SEQ ID NO:9;
(c) the light chain variable region of SEQ ID NO: 11 and the heavy chain variable region of SEQ ID NO: 13;
(d) the light chain variable region of SEQ ID NO: 15 and the heavy chain variable region of SEQ ID NO: 17;
(e) the light chain variable region of SEQ ID NO: 19 and the heavy chain variable region of SEQ ID NO:21;
(f) the light chain variable region of SEQ ID NO:23 and the heavy chain variable region of SEQ ID NO:25; or
(g) the light chain variable region of SEQ ID NO:27 and the heavy chain variable region of SEQ ID NO:29.

93. The bispecific antibody of exemplary embodiment 91 or 92, wherein the second scFv is linked to the C-terminal end of the first scFv.

94. The bispecific antibody of any one of exemplary embodiments 91-93, wherein the HLA-A02 molecule is selected from HLA-A*02:01, HLA-A*02:02, HLA-A*02:03, HLA-A*02:04, HLA-A*02:05 and HLA-A*02:06.

95. The bispecific antibody of any one of exemplary embodiments 91-94, wherein the first scFv of the bispecific antibody interacts directly with amino acid residues at one more positions selected from the group consisting of position 1, 2, 3, 4, 5, 6, 7, 8, and combinations thereof, in the EBV-LMP2 peptide.

96. The bispecific antibody of any one of exemplary embodiments 91-94, wherein the first scFv of the bispecific antibody interacts directly with at least position 5 of the EBV-LMP2 peptide.

97. The bispecific antibody of any one of exemplary embodiments 91-94, wherein the first scFv of the bispecific antibody interacts directly with at least position 1 of the EBV-LMP2 peptide.

98. The bispecific antibody of any one of exemplary embodiments 91-94, wherein the first scFv of the bispecific antibody interacts directly with at least position 8 of the EBV-LMP2 peptide.

99. A chimeric antigen receptor comprising an antigen-binding site of a human antibody agent that binds an EBV-LMP2/HLA peptide complex.

100. The chimeric antigen receptor of exemplary embodiment 99, wherein the antigen-binding site is an scFv.

101. The chimeric antigen receptor of exemplary embodiment 99 or 100, wherein the antigen-binding site is expressed by an immune effector cell.

102. The chimeric antigen receptor of exemplary embodiment 101, wherein the immune effector cell is a T cell.

103. The chimeric antigen receptor of any one of exemplary embodiments 99-102, wherein the HLA of the EBV-LMP2/HLA peptide complex is an HLA class I molecule.

104. The chimeric antigen receptor of exemplary embodiment 103, wherein the HLA class I molecule is HLA-A*02.

105. The chimeric antigen receptor of exemplary embodiment 104, wherein the HLA-A02 is selected from HLA-A*02:01, HLA-A*02:02, HLA-A*02:03, HLA-A*02:04, HLA-A*02:05 and HLA-A*02:06.

106. An isolated nucleic acid molecule encoding, in whole or in part, a chimeric antigen receptor according to any one of exemplary embodiments 99-105.

107. A recombinant vector comprising the nucleic acid molecule of exemplary embodiment 106.

108. A host cell comprising the recombinant vector of exemplary embodiment 107 or the nucleic acid molecule of exemplary embodiment 106.

109. The host cell of exemplary embodiment 108, wherein the host cell is selected from a bacterial, yeast, insect or mammalian cell.

110. The host cell of exemplary embodiment 109, wherein the host cell is selected from the group consisting of *E. coli, P. pastoris*, Sf9, COS, HEK293, CHO, and a mammalian lymphocyte.

111. The host cell of exemplary embodiment 110, wherein the mammalian lymphocyte is a human lymphocyte.

112. A composition comprising a chimeric antigen receptor according to any one of exemplary embodiments 99-105.

113. A pharmaceutical composition comprising a chimeric antigen receptor according to any one of exemplary embodiments 99-105 or a composition according exemplary embodiment 112, and further comprising a pharmaceutically acceptable carrier or diluent.

114. A kit comprising a chimeric antigen receptor according to any one of exemplary embodiments 99-105.

115. A method of treating a medical condition in a subject characterized by expression of an EBV-LMP2/HLA peptide complex, comprising a step of
administering a therapeutically effective amount of a chimeric antigen receptor according to any one of exemplary embodiments 99-105, a composition of exemplary embodiment 112, or a pharmaceutical composition of exemplary embodiment 113.

116. The method of exemplary embodiment 115, wherein the medical condition is Hodgkin's disease, non-Hodgkin's disease or infectious mononucleosis.

117. The method of exemplary embodiment 115, wherein the medical condition is selected from Burkitt's lymphoma, immunosuppressive lymphoma, diffuse large B-cell lymphoma, diffuse large B-cell lymphoma associated with chronic inflammation, lymphomatoid granulomatosis, plasmablastic lymphoma, primary effusion lymphoma, post-transplant lymphoproliferative disorder, nasopharyngeal carcinoma, gastric adenocarcinoma, lymphoepithelioma-associated carcinoma, and immunodeficiency-related leiomyosarcoma.

118. The method of any one of exemplary embodiments 115-117, wherein the HLA of the EBV-LMP2/HLA peptide complex is an HLA class I molecule.

119. The method of exemplary embodiment 118, wherein the HLA class I molecule is HLA-A02.

120. The method of exemplary embodiment 119, wherein the HLA-A02 is selected from HLA-A*02:01, HLA-A*02:02, HLA-A*02:03, HLA-A*02:04, HLA-A*02:05 and HLA-A*02:06.

121. Use of a chimeric antigen receptor of any one of exemplary embodiments 99-105 for the treatment or detection of a condition related to EBV infection.

Figure 3:
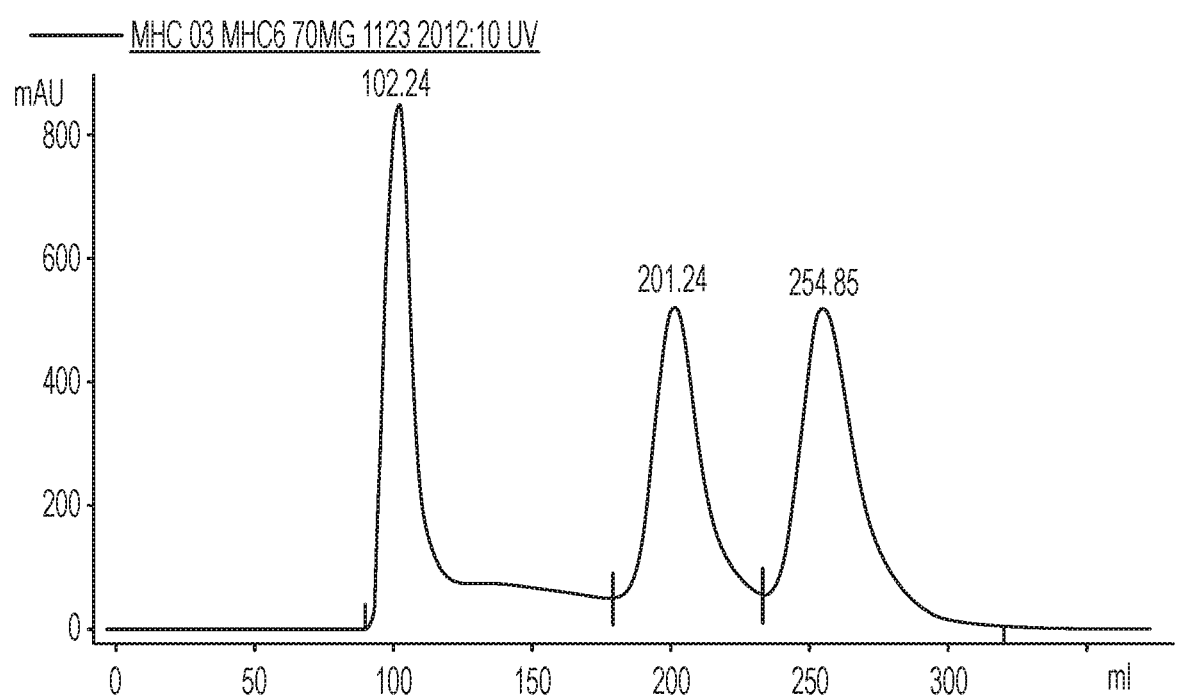
FIG. 3 shows a size exclusion chromatogram depicting the various species observed during purification of monomeric EBV-LMP2(CLG)/HLA-A*02:01 peptide complex.
Figure 4:
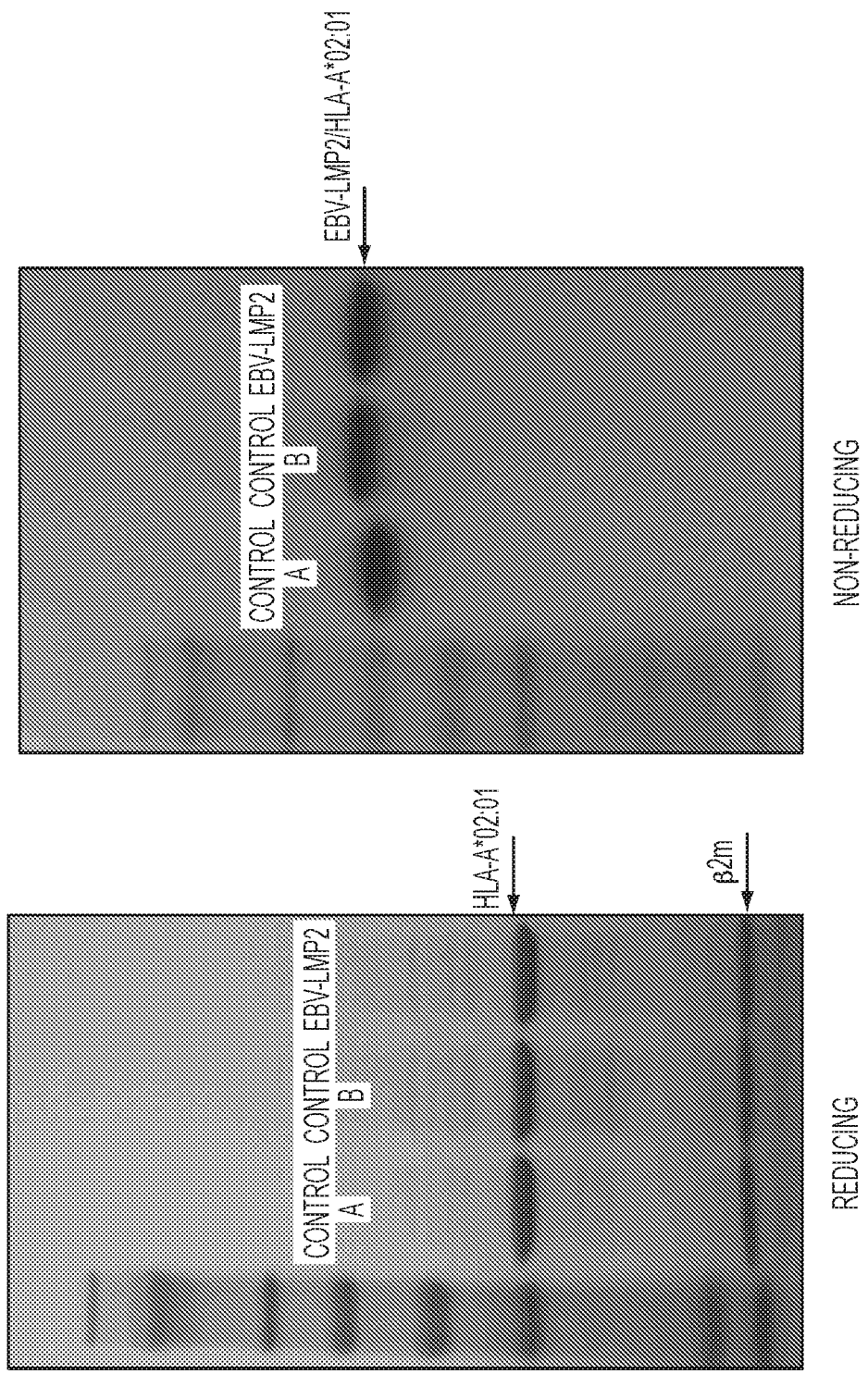
FIG. 4 shows an image of SDS-PAGE of monomeric EBV-LMP2(CLG)/HLA-A*02:01 peptide complex under reducing (left) and non-reducing (right) conditions. Identity of each sample is indicated for each column as well as the location of the monomer (EBV-LMP2/HLA-A*02:01), MHC molecule (HLA-A*02:01) and $\beta_2$ microglobulin ($\beta 2m$). Controls A and B: irrelevant peptide/HLA-A02 peptide complexes.

122. A method of selecting an antibody agent that binds a central residue of a peptide presented by a human HLA class I molecule of interest from a population, the method comprising the steps of
- (a) selecting one or more antibody agents from a population that bind a peptide/HLA class I complex of interest; and
- (b) screening the one or more antibody agents from (a) for binding a peptide/HLA class I complex that includes a peptide having one or more amino acid substitutions at a residue selected from the group consisting of position 1, position 5, position 8, and combinations thereof;

wherein loss of binding of an antibody agent to a peptide/HLA class I complex that includes a peptide having a substitution at position 5 indicates an antibody agent that binds a central residue of a peptide presented by a human HLA class I molecule.

123. A method of selecting an antibody agent that binds a central residue of a peptide presented by a human HLA class I molecule of interest from a population, the method comprising the steps of (a) selecting one or more antibody agents from a population that do not bind a first peptide/HLA class I complex, which first peptide/HLA class I complex includes a peptide having an amino acid substitution at position 5 and/or one or more additional amino acids at the N- and/or C-terminus of the peptide; and (b) screening the one or more antibody agents from (a) for binding a second peptide/HLA class I complex, which second peptide/HLA class I complex includes a peptide having a wild-type sequence of interest;

wherein binding of an antibody agent to the second peptide/HLA class I complex indicates an antibody agent that binds a central residue of a peptide presented by a human HLA class I molecule.

124. The method of exemplary embodiment 122 or 123, wherein the peptide of the peptide/HLA class I complex is an Epstein-Barr virus (EBV)-related peptide.

125. The method of exemplary embodiment 122 or 123, wherein the peptide/HLA class I complex is an EBV-LMP2/HLA-A02 complex.

126. The method of exemplary embodiment 125, wherein the HLA-A02 is selected from the group consisting of HLA-A*02:01, HLA-A*02:02, HLA-A*02:03, HLA-A*02:04, HLA-A*02:05 and HLA-A*02:06.

127. The method of exemplary embodiment 125 or 126, wherein the EBV-LMP2 peptide is or comprises CLGGLLTMV (SEQ ID NO:1).

128. The method of exemplary embodiment 122 or 123, wherein the peptide is a nonamer peptide.

129. The method of exemplary embodiment 122 or 123, wherein the peptide is a decamer peptide.

130. The method of any one exemplary embodiments 122-129, wherein the antibody agent is a human monoclonal antibody.

131. The method of any one exemplary embodiments 122-129, wherein the antibody agent is a human monoclonal antibody fragment.

132. In a method of providing a high affinity human monoclonal antibody that binds a peptide/HLA complex, the improvement comprising providing a human monoclonal antibody that interacts directly with or prefers one or more amino acids at the center of a peptide in a peptide/HLA complex.

133. In a method of providing a high affinity human monoclonal antibody that binds a peptide/HLA complex, the improvement comprising providing a human monoclonal antibody that interacts directly with or prefers one or more amino acids at the center of a peptide in an HLA binding pocket, wherein the peptide/HLA complex is not generated using an in silico prediction method.

134. In a method of providing a high affinity bispecific antibody composition comprising a bispecific antibody that includes first and second antigen-binding sites, which first antigen-binding site binds a peptide/HLA complex, the improvement comprising providing at least one of such first antigen-binding sites as a human monoclonal antibody or fragment thereof that interacts directly with one or more amino acids at the center of a peptide in a peptide/HLA complex.

135. In a method of providing a chimeric antigen receptor composition comprising one or more antigen binding sites, wherein at least one of the one or more antigen binding sites binds a peptide/HLA complex, the improvement comprising providing an antigen-binding site of a human antibody agent that interacts directly with one or more amino acids at the center of a peptide in an HLA binding pocket.

136. The method of exemplary embodiment 135, wherein the chimeric antigen receptor composition is expressed by an immune effector cell.

137. The method of exemplary embodiment 136, wherein the immune effector cell is a T cell.

138. The method of any one of exemplary embodiments 132-137, wherein the HLA is a class I HLA molecule.

139. The method of any one of exemplary embodiments 132-137, wherein the peptide is a nonamer peptide.

140. The method of any one of exemplary embodiments 132-137, wherein the peptide is a decamer peptide.

141. The method of any one of exemplary embodiments 132-137, wherein the peptide is an Epstein-Barr virus (EBV)-related peptide.

142. The method of any one of exemplary embodiments 132-137, wherein the peptide/HLA complex is an EBV-LMP2/HLA-A02 complex.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Production of Biotinylated Peptide/HLA-A*02:01 Complex Monomer

This example demonstrates the production of a MHC-peptide complex in the development and identification of antibodies and multi-specific binding agents (e.g., bispecific antibodies) that recognize an EBV-associated peptide presented by a class I human MHC molecule. In particular, this example specifically describes the production of monomeric EBV-LMP2(CLG)/HLA-A*02:01 complex, which was employed in the examples that follow for producing antibodies (i.e., antibody agents and full-length IgGs) and bispecific antibodies that recognize an EBV-LMP2 peptide presented by human HLA-A02.

Briefly, biotinylated peptide/HLA-A*02:01 complex monomers were prepared using methods known in the art (see, e.g., Altman, J. D. and M. M. Davis, 2003, MHC-peptide tetramers to visualize antigen-specific T cells. Curr.

Protoc. Immunol. Chapter 17: Unit 173). DNA encoding full-length human beta-2 microglobulin (β2m) was synthesized by Genewiz and cloned into vector pET-27b. A BirA substrate peptide (BSP) was added to the C-terminus of HLA-A*02:01 extracellular domain (ECD). DNA encoding HLA-A*02:01 ECD-BSP was synthesized by Genewiz and cloned into vector pET-27b. Vectors expressing human β2m and HLA-A*02:01 ECD-BSP were transformed into E. coli BL21 separately, and isolated as inclusion bodies from bacterial culture. Peptide ligand EBV-LMP2A(CLG) (full nonamer sequence CLGGLLTMV; SEQ ID NO: 1) was refolded with human β2m and HLA-A*02:01 ECD-BSP to form monomeric EBV-LMP2(CLG)/HLA-A*02:01 peptide complex. Folded peptide/HLA-A*02:01 monomers were concentrated by ultrafiltration and further purified through size-exclusion chromatography (FIG. 3). Purified peptide/HLA-A*02:01 monomer was also visualized through SDS-PAGE (FIG. 4) and biotinylated via BirA-mediated enzymatic reaction and subsequently purified by high-resolution anion-exchange chromatography. Biotinylated peptide/HLA-A*02:01 monomers were stored in PBS at −80° C.

HiPrep 26/60 Sephacryl S-300 HR was equilibrated with Hyclone Dulbecco's Phosphate Buffered Saline solution (Thermo Scientific, Cat No. SH3002802) with 1.5 column volumes. The unpurified sample was loaded and eluted with one column volume. As shown in FIG. 3, the first peak, consisting of misfolded aggregates, eluted at approximately 102.24 mL after loading. The peak corresponding to the properly folded MHC complex was observed at 201.24 mL. Lastly, the peak consisting of free β2m was observed at 254.85 mL.

Purified EBV-LMP2(CLG)/HLA-A*02:01 complex described above was used in the following example to produce human antibody components that recognize the LMP2 peptide in the context of HLA-A02.

Example 2. Screening of Phage scFv Specific for EBV-LMP2(CLG)/HLA-A*02:01 Complex This example demonstrates the construction of human antibody agents specific for an EBV-LMP2 peptide in the context of a human MHC class I molecule. In particular, this example demonstrates the production of human scFvs, and subsequent generation of full-length human IgG, that bind an EBV-LMP2 nonamer peptide having the sequence CLG-GLLTMV (SEQ ID NO: 1) presented by a human HLA-A02 molecule. LMP2 is expressed in both EBV infected B-cells and nasopharyngeal and gastric epithelial cells. Thus, such human antibody agents can be employed in the treatment and diagnosis of EBV-associated disease and malignancies.

Figure 5:
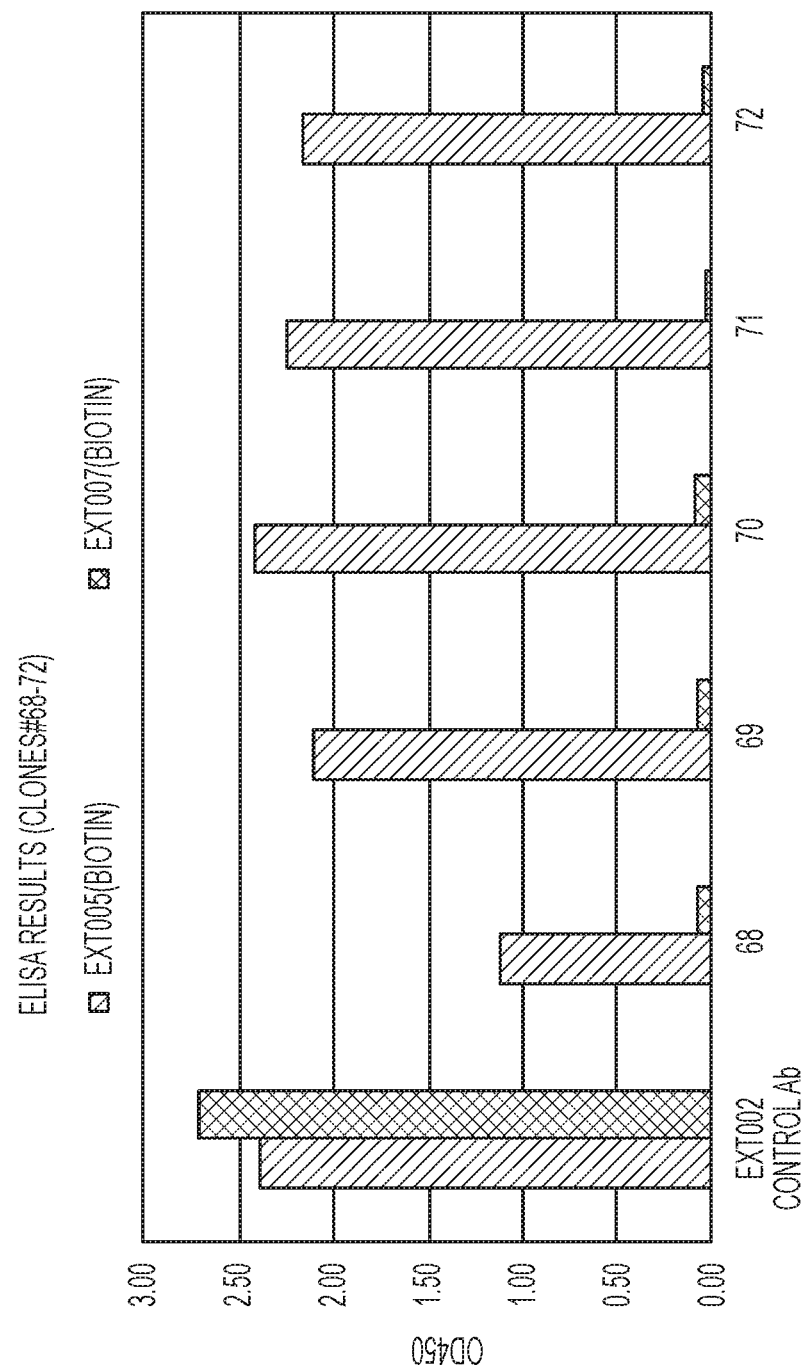
FIG. 5 shows an exemplary graph of the optical density at 450 nm ($OD_{450}$) of selected human scFv clones to soluble EBV-LMP2(CLG)/HLA-A*02:01 peptide complex in a phage ELISA assay described in Example 2. EXT005: EBV-LMP2(CLG)/HLA-A*02:01 complex; EXT007: control peptide/HLA-A*02:01 complex; EXT002 control Ab: positive control anti-HLA-A*02:01 antibody; 68-72: anti-EBV-LMP2(CLG)/HLA-A*02:01 antibody phage clones. Control peptide: irrelevant peptide.

Briefly, a human scFv antibody phage display library ($10 \times 10^{10}$ clones) constructed by Eureka Therapeutics (AL-PHA™ phage display) was used for selection of human monoclonal antibodies specific for EBV-LMP2(CLG)/HLA-A*02:01. To reduce any conformational change of MHC I complex introduced by immobilizing the protein complex onto plastic surfaces, solution panning was used in place of conventional plate panning. In solution panning, biotinylated antigens were first mixed with human scFv phage library after extended washing with PBS buffer, and then antigen-scFv antibody phage complexes were pulled down by streptavidin-conjugated Dynabeads M-280 through a magnetic rack. The bound clones were eluted and then used to infect E. coli XL1-Blue. The phage clones were expressed in bacteria and then purified. Panning was performed for 3-4 rounds to enrich scFv phage clones with specific binding to EBV-LMP2(CLG)/HLA-A*02:01. Table 4 sets forth a summary of phage panning against EBV-LMP2(CLG)/HLA-A*02:01. Positive clones were determined by an ELISA assay using biotinylated EBV-LMP2(CLG)/HLA-A*02:01 complexes (see, e.g., FIG. 5).

TABLE 4

| Panning Method | Clones Isolated | ELISA Positive Clones | Unique Clones |
|---|---|---|---|
| Panning-in-solution | 281 | 125 | 80 |

Figure 6:
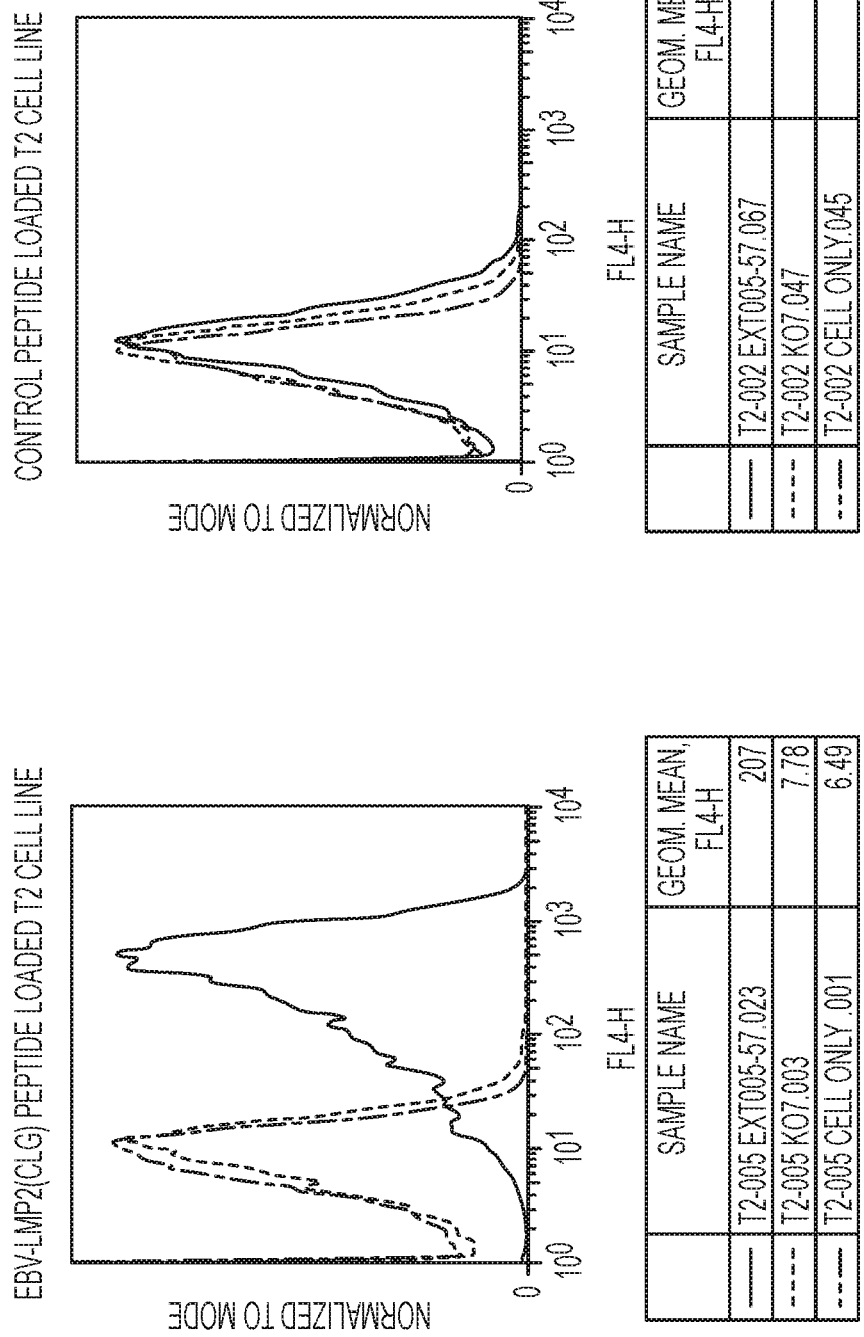
FIG. 6 shows exemplary phage binding of EBV-LMP2 peptide- and control peptide-loaded T2 cells by flow cytometry. Control peptide: irrelevant peptide; EXT005-57: anti-EBV-LMP2(CLG)/HLA-A*02:01 antibody phage clone; K07: helper phage, phage negative control; Cell only: mouse anti-M13 monoclonal antibody, and the R-PE conjugated horse anti-mouse IgG.

Positive clones were further tested for binding peptide/HLA-A02 complexes on surfaces of live cells by flow cytometry using a TAP-deficient HLA-A*02:01$^+$ cell line, T2. T2 cells only present exogenous peptides and are routinely used for presentation of peptides on HLA-A02 molecules. Briefly, T2 cells were pulsed overnight with LMP2 peptide (CLGGLLTMV; SEQ ID NO:1) at 50 µg/mL in serum-free RPMI-1640 medium with 20 µg/mL of β2m. Cells were then stained with purified scFv phage clones, followed by mouse anti-M13 monoclonal antibody, and R-PE conjugated horse anti-mouse IgG (Vector Labs). Each step of staining was done on ice with ~30-60 minutes incubation. Cells were washed twice between each step of staining. FIG. 6 sets forth exemplary binding of phage clones to EBV-LMP2(CLG)/HLA-A*02:01 loaded T2 cells.

Of 281 clones screened using an ELISA assay, 125 ELISA positive clones were identified. Of the 125 positive clones identified, 80 unique clones were isolated and characterized. Of the 80 unique clones, 54 were identified by ELISA and FACS to specifically bind the target complex at both protein level and cell surface level. The specificity of clones to positions in the EBV-LMP2 peptide was confirmed using alanine walking (see, e.g., Liu, Z et al., 1999, J. Mol. Recognit. 12(2):103-11; Weiss, G A et al., 2000, Proc. Nat. Acad. Sci. U.S.A. 97(16):8950-4; Morrison, K L and G A Weiss, 2001, Curr. Opin. Chem. Biol. 5(3):302-7). Briefly, the LMP2 peptide (CLGGLLTMV; SEQ ID NO: 1) was substituted with alanine residues at positions 1, 5 or 8. T2 cells were pulsed with the alanine mutant peptides at 50 µg/mL. Binding was measure by flow cytometry. DNA and amino acid sequences of heavy and light chains CDRs of selected clones are set forth in Tables 5 and 6, respectively.

TABLE 5

| | | Antibody HCDR DNA/Amino Acid Sequence (5'-3') | |
|---|---|---|---|
| LMP2-21 | 1 | GGAGGCACCTTCAGCAGCTATGCT | SEQ ID NO: 30 |
| | | GGTFSSYA | SEQ ID NO: 31 |
| | 2 | ATCATCCCTATCCTTGGTATAGCA | SEQ ID NO: 32 |
| | | IIPILGIA | SEQ ID NO: 33 |

TABLE 5-continued

| | | Antibody HCDR DNA/Amino Acid Sequence (5'-3') | |
|---|---|---|---|
| | 3 | GCGCGCGGTTCTTACCATCAGCATTCTTACTCTGATGTT | SEQ ID NO: 34 |
| | | ARGSYHQHSYSDV | SEQ ID NO: 35 |
| LMP2-26 | 1 | GGAGGCACCTTCAGCAGCTATGCT | SEQ ID NO: 36 |
| | | GGTFSSYA | SEQ ID NO: 37 |
| | 2 | ATCATCCCTATCCTTGGTATAGCA | SEQ ID NO: 38 |
| | | IIPILGIA | SEQ ID NO: 39 |
| | 3 | GCGCGCTCTTACCCGCTGTACTCTGGTTGGGATTAC | SEQ ID NO: 40 |
| | | ARSYPLYSGWDY | SEQ ID NO: 41 |
| LMP2-38 | 1 | GGATACACAATCACCTCCTACTAT | SEQ ID NO: 42 |
| | | GYTITSYY | SEQ ID NO: 43 |
| | 2 | ATCAACCCTAATGCTGGCAGCACA | SEQ ID NO: 44 |
| | | INPNAGST | SEQ ID NO: 45 |
| | 3 | GCGCGCGGTATGTACCGTATGTACGAT | SEQ ID NO: 46 |
| | | ARGMYRMYD | SEQ ID NO: 47 |
| LMP2-40 | 1 | GGAGGCACCTTCAGCAACTATCAT | SEQ ID NO: 48 |
| | | GGTFSNYH | SEQ ID NO: 49 |
| | 2 | ATCATCCCCATCCTTGGCACACCA | SEQ ID NO: 50 |
| | | IIPILGTP | SEQ ID NO: 51 |
| | 3 | GCGCGCGGTCGTACTTGGTGGTCTGGTACTCTGGATTCT | SEQ ID NO: 52 |
| | | ARGRTWWSGTLDS | SEQ ID NO: 53 |
| LMP2-61 | 1 | GGATACACCTTCACCAACTATTAT | SEQ ID NO: 54 |
| | | GYTFTNYY | SEQ ID NO: 55 |
| | 2 | ATCAACCCTAGTGGTGGGAGCACA | SEQ ID NO: 56 |
| | | INPSGGST | SEQ ID NO: 57 |
| | 3 | GCGCGCTCTTACTACGGTTCTATGGATGCT | SEQ ID NO: 58 |
| | | ARSYYGSMDA | SEQ ID NO: 59 |
| LMP2-63 | 1 | GGATACACAATCACCTCCTACTAT | SEQ ID NO: 60 |
| | | GYTITSYY | SEQ ID NO: 61 |
| | 2 | ATCAACCCTAATGCTGGCAGCACA | SEQ ID NO: 62 |
| | | INPNAGST | SEQ ID NO: 63 |
| | 3 | GCGCGCGGTGACGTTTACAACGGTTGGGATGAA | SEQ ID NO: 64 |
| | | ARGDVYNGWDE | SEQ ID NO: 65 |
| LMP2-77 | 1 | GGTGGCTCCATCACCAGTGGTAATTACTAC | SEQ ID NO: 66 |
| | | GGSITSGNYY | SEQ ID NO: 67 |
| | 2 | ATCAATCATAGCGGAAGCCCC | SEQ ID NO: 68 |
| | | INHSGSP | SEQ ID NO: 69 |

TABLE 5-continued

| | | Antibody HCDR DNA/Amino Acid Sequence (5'-3') | |
|---|---|---|---|
| | 3 | GCGCGCCAGTCTTCTTACGGTGGTTACATAGATCAG | SEQ ID NO: 70 |
| | | ARQSSYGGYIDQ | SEQ ID NO: 71 |

TABLE 6

| | | Antibody LCDR DNA/Amino Acid Sequence (5'-3') | |
|---|---|---|---|
| LMP2-21 | 1 | AACATTGGAGGCAAAAGT | SEQ ID NO: 72 |
| | | NIGGKS | SEQ ID NO: 73 |
| | 2 | TATGATAGC | SEQ ID NO: 74 |
| | | YDS | SEQ ID NO: 75 |
| | 3 | CAGGTGTGGGATAGTAGTAGTGATCATTGGGTG | SEQ ID NO: 76 |
| | | QVWDSSSDHWV | SEQ ID NO: 77 |
| LMP2-26 | 1 | AAGATTGGAAGCAAACAT | SEQ ID NO: 78 |
| | | KIGSKH | SEQ ID NO: 79 |
| | 2 | TATAATACT | SEQ ID NO: 80 |
| | | YNT | SEQ ID NO: 81 |
| | 3 | CAGGTGTGGGATAGTAGTTATGATCATGTGATA | SEQ ID NO: 82 |
| | | QVWDSSYDHVI | SEQ ID NO: 83 |
| LMP2-38 | 1 | AGCAGTGACGTTGGTAGTTATAACGAT | SEQ ID NO: 84 |
| | | SSDVGSYND | SEQ ID NO: 85 |
| | 2 | GATGTCAGT | SEQ ID NO: 86 |
| | | DVS | SEQ ID NO: 87 |
| | 3 | AACTCATATACAAGCAGCAACACTTATGTC | SEQ ID NO: 88 |
| | | NSYTSSNTYV | SEQ ID NO: 89 |
| LMP2-40 | 1 | AACATTGGAAGTAGAAGT | SEQ ID NO: 90 |
| | | NIGSRS | SEQ ID NO: 91 |
| | 2 | TATAATAAC | SEQ ID NO: 92 |
| | | YNN | SEQ ID NO: 93 |
| | 3 | CAGGTGTGGGATAGTATTAGTGACCATTATGTC | SEQ ID NO: 94 |
| | | QVWDSISDHYV | SEQ ID NO: 95 |
| LMP2-61 | 1 | AGCCTCAGAAGCTATTAT | SEQ ID NO: 96 |
| | | SLRSYY | SEQ ID NO: 97 |
| | 2 | GGTAAAAAC | SEQ ID NO: 98 |
| | | GKN | SEQ ID NO: 99 |
| | 3 | AACTCCCGGGACAGCAGTGGTAACCATCTGGTA | SEQ ID NO: 100 |
| | | NSRDSSGNHLV | SEQ ID NO: 101 |
| LMP2-63 | 1 | AACATTGGAAGTGAAAGT | SEQ ID NO: 102 |
| | | NIGSES | SEQ ID NO: 103 |

TABLE 6-continued

| | | Antibody LCDR DNA/Amino Acid Sequence (5'-3') | |
|---|---|---|---|
| | 2 | GATGATGAC | SEQ ID NO: 104 |
| | | DDD | SEQ ID NO: 105 |
| | 3 | CAGGTGTGGGATCGAAGTAGTGATCATTGGTTT | SEQ ID NO: 106 |
| | | QVWDRSSDHWF | SEQ ID NO: 107 |
| LMP2-77 | 1 | AGCCTCAGAACGCATTAT | SEQ ID NO: 108 |
| | | SLRTHY | SEQ ID NO: 109 |
| | 2 | GGTAAAAAC | SEQ ID NO: 110 |
| | | GKN | SEQ ID NO: 111 |
| | 3 | AACTCCCGGCACAGCAGTGGTAATCATTGTGTG | SEQ ID NO: 112 |
| | | NSRHSSGNHCV | SEQ ID NO: 113 |

Antibody clones 38 and 63 demonstrated selective binding for peptide position 5 through peptide position 8 (P5-P8) and had nearly identical heavy chains (~75% amino acid identity). Further, antibody clones 38 and 63 demonstrated identical heavy chain CDR1 and CDR2 sequences and similar CDR3 sequences; and shared some common residues within the light chain CDRs. Antibody clones 21 and 26 demonstrated selective binding for peptide position 8 (P8) and had similar heavy chains (~88% amino acid identity), while CDR1 and CDR2 were identical, and CDR3 was similar. The light chains for antibody clones 21 and 26 were similar as well. Antibody clones 40 and 61 demonstrated selective binding for peptide position 1 (P1) and had about 67% identity and similar CDRs overall. Antibody clone 77 demonstrated selective binding for peptide position 1 through peptide position 5 (P1-P5) and had sequence similarities with the light chains of antibody clone 63 (~40% identity). Antibody clones 21, 26, 40 and 61 were designated as type I TCR mimic, while clones 38 and 63 were designated as type II TCR mimic.

Taken together, this Example demonstrates the successful production of both type I and type II TCR-like monoclonal antibodies that bind to an EBV-associated peptide presented in the context of a human MHC class I molecule. In particular, this Example describes the generation of antibodies that selectively target the center region (e.g., peptide position 5) of a peptide presented by a human HLA-A02 molecule. As described below, such antibodies have high specificity and potency in cytotoxicity against EBV⁺ cell lines and can be used in the construction of multi-specific binding agents (e.g., bispecific antibodies).

Example 3. Construction of Full-Length Monoclonal Antibody Using scFv Fragments

This example demonstrates the construction of full-length antibody using selected human scFvs described in Example 2. In particular, this Example specifically describes the construction of full-length human IgG (e.g., IgG1) using selected human scFvs clones that appear in Tables 5 and 6.

Briefly, full-length human IgG1 of selected phage clones were produced in HEK293 and Chinese hamster ovary (CHO) cell lines, as previously described (Tomimatsu, K. et al., 2009, Biosci. Biotechnol. Biochem. 73:1465-9). Antibody variable regions were subcloned into mammalian expression vectors with cognate human lambda (λ) or kappa (κ) light chain constant region and human IgG1 constant region sequences.

Human Cλ DNA
(SEQ ID NO: 114)
AAGCCTAAGGCCAACCCTACCGTGACCCTGTTCCCCCCATCCTCCGAGGA

ACTGCAGGCCAACAAGGCCACCCTCGTGTGCCTGATCTCCGACTTCTACC

CTGGCGCCGTGACCGTGGCCTGGAAGGCTGATGGATCTCCTGTGAAGGCC

GGCGTGGAAACCACCAAGCCCTCCAAGCAGTCCAACAACAAATACGCCGC

CTCCTCCTACCTGTCCCTGACCCCTGAGCAGTGGAAGTCCCACCGGTCCT

ACAGCTGCCAAGTGACCCACGAGGGCTCCACCGTGGAAAAGACCGTGGCT

CCTACCGAGTGCTCCTAG

Human Cλ amino acid
(SEQ ID NO: 115)
QPKANPTVTLFPPSSEELQANKATLVCLISDFYPGAVTVAWKADGSPVKA

GVETTKPSKQSNNKYAASSYLSLTPEQWKSHRSYSCQVTHEGSTVEKTVA

PTECS

Human Cκ DNA
(SEQ ID NO: 116)
ACCGTGGCCGCTCCCTCCGTGTTCATCTTCCCACCTTCCGACGAGCAGCT

GAAGTCCGGCACCGCTTCTGTCGTGTGCCTGCTGAACAACTTCTACCCCC

GCGAGGCCAAGGTGCAGTGGAAGGTGGACAACGCCCTGCAGAGCGGCAAC

TCCCAGGAATCCGTGACCGAGCAGGACTCCAAGGACAGCACCTACTCCCT

GTCCTCCACCCTGACCCTGTCCAAGGCCGACTACGAGAAGCACAAGGTGT

ACGCCTGCGAAGTGACCCACCAGGGCCTGTCTAGCCCCGTGACCAAGTCT

TTCAACCGGGGCGAGTGCTAG

Human Cκ amino acid
(SEQ ID NO: 117)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

-continued

Human IgG1 DNA
(SEQ ID NO: 118)
GTCTCCTCAGCTTCCACCAAGGGCCCATCGGTCTTCCCCCTGGCACCCTC

CTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACC

AGCGGCGTGCACACCTTCCCGGCCGTCCTACAGTCCTCAGGACTCTACTC

CCTCAGCAGCGTGGTGACCGTGCCCTCCAGCAGCTTGGGCACCCAGACCT

ACATCTGCAACGTGAATCACAAGCCCAGCAACACCAAGGTGGACAAGAAG

GTTGAGCCCAAATCTTGTGACAAAACTCACACATGCCCACCGTGCCCAGC

ACCTGAACTCCTGGGGGACCGTCAGTCTTCCTCTTCCCCCCAAAACCCA

AGGACACCCTCATGATCTCCCGGACCCCTGAGGTCACATGCGTGGTGGTG

GACGTGAGCCACGAAGACCCTGAGGTCAAGTTCAACTGGTACGTGGACGG

CGTGGAGGTGCATAATGCCAAGACAAAGCCGCGGGAGGAGCAGTACAACA

GCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCC

CATCGAGAAACCATCTCCAAAGCCAAAGGGCAGCCCCGAGAACCACAGG

TGTACACCCTGCCCCCATCCCGGGAGGAGATGACCAAGAACCAGGTCAGC

CTGACCTGCCTGGTCAAAGGCTTCTATCCCAGCGACATCGCCGTGGAGTG

GGAGAGCAATGGGCAGCCGGAGAACAACTACAAGACCACGCCTCCCGTGC

TGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA

Human IgG1 amino acid
(SEQ ID NO: 119)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Figure 7:
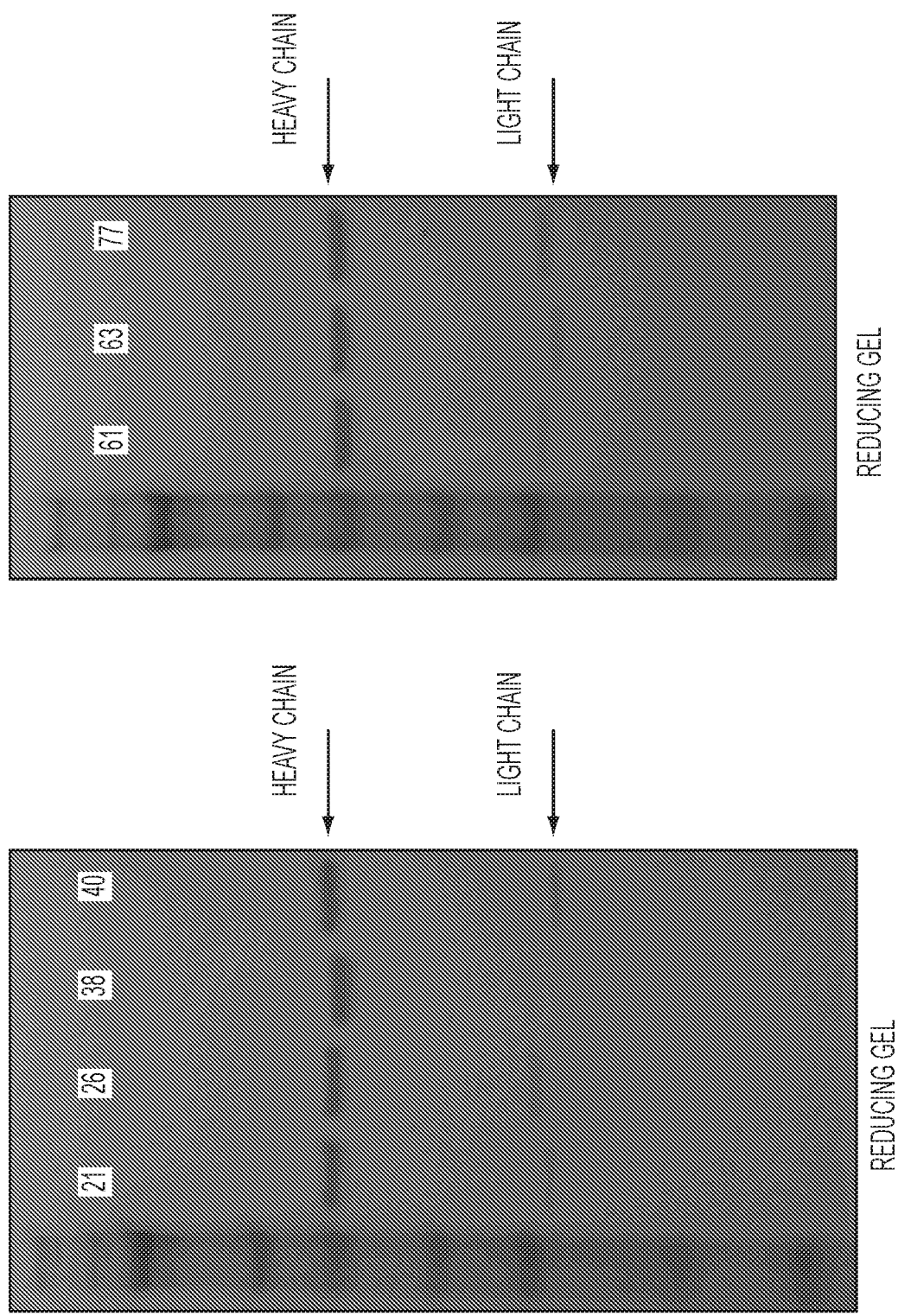
FIG. 7 shows an exemplary image of an SDS-PAGE of selected full-length human IgG1 antibodies made from scFvs specific for EBV-LMP2(CLG)/HLA-A*02:01 peptide complex under reducing conditions.

Molecular weight of purified full-length IgG1 antibodies was measured under both reducing and non-reducing conditions by electrophoresis (FIG. 7). Taken together, this example demonstrates the successful construction and expression of full-length human IgG1 using variable regions of selected scFvs specific for EBV-LMP2(CLG)/HLA-A02.

Example 4. Construction of Multi-Specific Binding Agents Using Single Chain Antibody Components This example demonstrates the construction of multi-specific binding agents using scFv fragments specific for an EBV-LMP2 peptide presented by a human MHC class I molecule. In particular, this example specifically demonstrates the construction of bispecific antibodies having a first antigen-binding site that binds to an EBV-LMP2 peptide (CLGGLLTMV; SEQ ID NO: 1) in the context of a human HLA-A02 molecule and a second antigen-binding site that binds CD3 on T cells. Thus, the present example illustrates that, in some embodiments, using multi-specific binding agents that contain antibody components as described herein, T cells can be directed to kill target cells that present a peptide (e.g., EBV-LMP2) on their surface via a human MHC class I molecules (e.g., HLA-A02; see, e.g., Brischwein, K. et al., 2006, Mol. Immunol. 43:1129-43).

Figure 8:
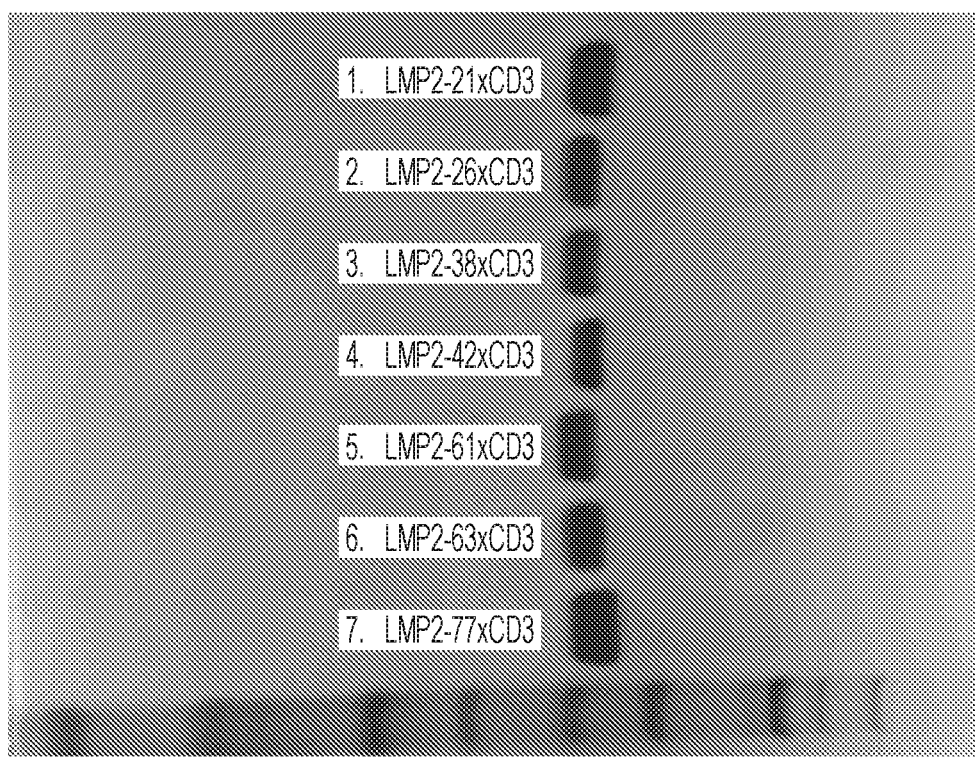
FIG. 8 shows an exemplary image of an SDS-PAGE of selected anti-EBV-LMP2(CLG)/HLA-A02 bispecific molecules under reducing conditions. Bispecific antibody molecules are indicated on each lane of the gel image.

Briefly, bispecific antibody constructs were constructed using a single-chain format such that scFvs specific for EBV-LMP2(CLG)/HLA-A*02:01 were linked at their C-terminal end to an scFv specific for human CD3 (i.e., CD3c; DNA: SEQ ID NO: 123; Amino acid: SEQ ID NO: 124). DNA fragments encoding EBV-LMP2(CLG)-specific scFv and human CD3-specific scFv were synthesized by Genewiz and subcloned into mammalian expression vector pGSN-Hyg (Eureka Therapeutics, Inc.). A hex-histamine tag was inserted at the C-terminal end of the bispecific constructs for purification and detection. HEK293 cells were transfected with bispecific antibody expression vectors for transient expression and supernatants containing secreted bispecific antibody molecules were collected. Stable expression of bispecific antibody molecules was achieved using Chinese hamster ovary (CHO) cells transfected with bispecific antibody expression vectors and grown in drug selection with methionine sulfoximine (MSX) using a glutamine synthetase(GS)-based system. CHO cell supernatants containing secreted anti-EBV-LMP2(CLG) bispecific antibody molecules were collected and purified using a HisTrap HP column (GE healthcare) using a FPLC AKTA system. CHO cell culture was clarified and loaded onto columns with a low imidazole concentration (20 mM), and anti-EBV-LMP2 (CLG) bispecific antibody molecules bound to the column were eluted with an isocratic high imidazole concentration elution buffer (500 mM). Molecular weight of the purified anti-EBV-LMP2(CLG) bispecific antibody molecules was measured under non-reducing conditions by electrophoresis (FIG. 8).

Taken together, this example demonstrates the successful construction of bispecific molecules having a first antigen-binding site that is specific for an EBV-LMP2 peptide presented by an HLA-A02 molecule and a second antigen-binding site that is specific for CD3. Further characterization of such bispecific molecules is described in the following examples.

Example 5. Antibody-Dependent Cell-Mediated Cytotoxicity (ADCC) of T2 Cells Mediated by TCR-Like Anti-EBV-LMP2(CLG) IgG1 Antibodies This example demonstrates that full-length IgG1 antibodies made from anti-EBV-LMP2(CLG) specific scFvs can both specifically recognize the EBV-LMP2 peptide presented on the surface of target cells and mediate antibody-dependent cell-mediated cytotoxicity (ADCC) of target cells that present the EBV-LMP2 peptide via human HLA-A02 molecules. The lymphoblastoid T2 cell line is a variant of the T1 cell line (ATCC CRL-1991) and HLA-A*02:01+ TAP1−. T2 cells are unable to present endogenous peptides, but can present exogenous peptides when incubated with them. Since T2 cells do not naturally produce it, β2m can be added when incubating with exogenous peptides. Thus, T2 cells are suitable for transfection and are routinely used for antigen processing and T cell recognition of MHC class I antigens (see, e.g., Salter, R. D. et al., 1985, Immunogenetics 21: 235-246).

Briefly, T2 cells were pulsed overnight with 100 μg of either a control peptide that is presented by HLA-A*02:01 (YMLDLQPET, $IC_{50}$=7.5; SEQ ID NO: 120) or an EBV-LMP2 peptide (CLGGLLTMV, $IC_{50}$=95.6; SEQ ID NO:1), and exogenous β2m in serum free IMDM media. Cells were then incubated with 5 μg/mL at 4° C. for an hour with selected full-length IgG1 anti-EBV-LMP2(CLG)/HLA-A*02:01 antibodies. A PE-labeled secondary antibody anti-human Fc antibody was used and cells were analyzed by flow cytometry.

For flow cytometry, T2 cells were washed once to remove excess peptide and incubated at 4° C. with 5 μg/mL of a given antibody (or isotype matched control). An anti-Fc PE-labeled secondary antibody was utilized and cells were run in a FACS calibur flow cytometer setting the isotype control at an MFI of 5. Data and overlays were prepared using Flowjo Software Version 6. Exemplary results are set forth in FIG. 9.

For cytotoxicity assays, T2 cells were incubated as described above, collected the morning after and labeled with 100 μCi of $^{51}$Cr for one hour and then plated at a density of 5×10³ per well in a round bottom 96-well plate with the specified concentration of each monoclonal antibody. NK92 cells, transfected with a 158V/V homozygous variant of CD16 (FcγRIIIa), were used as effector cells with an E:T ratio of 20:1. Plates were incubated four hours at 37° C., supernatants collected and then analyzed using a scintillation counter. Results were plotted using PRISM-Graphpad software. Cytotoxicity was calculated using the formula % specific lysis=((Experimental Lysis—Spontaneous release)/(Maximum Lysis-Spontaneous release)). Maximum lysis was obtained by incubating target cells on SDS; Spontaneous release represents the target cells incubated with media alone. Exemplary results are set forth in FIG. 9.

Figure 9:
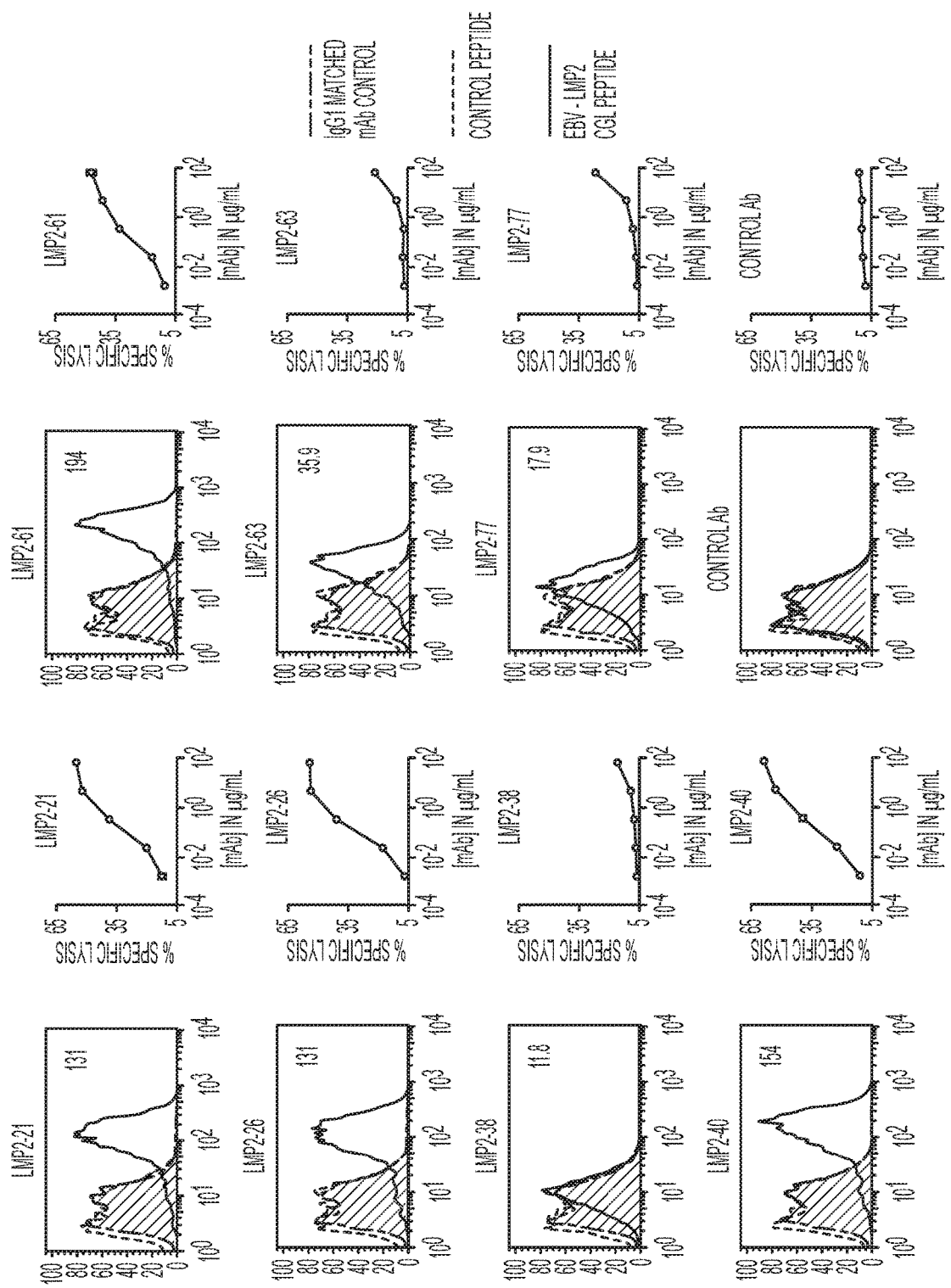
FIG. 9 shows exemplary FACS histograms (left in each pairing) illustrating positive staining for HLA-A02 presentation of an EBV-LMP2 peptide on the surface of T2 cells and antibody-dependent cellular cytotoxicity (ADCC; % specific lysis, right in each pairing) of T2 cells pulsed with a control (YMLDLQPET; SEQ ID NO: 120) or an EBV-LMP2 peptide (CLGGLLTMV; SEQ ID NO: 1). Control Ab: human IgG1 isotype matched control; NK92 effector cells were transfected with an FcγRIIIa 176V/V variant allele (CD16 176V/V) at an effector to target (E:T) ratio of 20:1; mAb: monoclonal antibody.

As shown in FIG. 9, each of the selected full-length IgG1 anti-EBV-LMP2(CLG)/HLA-A*02:01 antibodies demonstrated binding to the EBV-LMP2 peptide presented by HLA-A02 molecules on the surface of T2 cells (histograms, left side for each pairing), while no binding to the control peptide was observed for any of the antibodies. Further, ADCC was evident for each of the antibodies at comparable levels (% specific lysis, right side for each pairing) and correlated with the peptide binding observed for each antibody Taken together, these data demonstrate that the full-length IgG1 antibodies described in Example 3 retain the specificity to the EBV-LMP2 peptide of the parental antibody components (i.e., scFvs). Moreover, these full-length antibodies able to effectively mediate ADCC of target cells (e.g., T2 cells) that present the EBV-LMP2 peptide via HLA-A02 molecules on their surface.

Example 6. Affinity Measurement of TCR-Like Anti-EBV-LMP2(CLG) IgG1 Antibodies This example demonstrates that full-length IgG1 antibodies described in Example 3 bind to varying concentrations of an EBV-LMP2 peptide presented by HLA-A02 molecules on the surface of T2 cells.

Briefly, 1×10⁶ T2 cells were re-suspended in 1 mL of serum free IMDM media and loaded with different concentrations of EBV-LMP2 peptide (ranging from 0.0001 to 100 μg/mL) and exogenous β2m (25 μg/mL), and incubated overnight at 37° C. Cells were then incubated with g/mL of selected anti-EBV-LMP2(CLG)/HLA-A02 IgG1 antibodies and analyzed using flow cytometry. The MFI obtained with each of the antibodies was plotted against peptide concentration. Exemplary results are set forth in FIG. 10.

Figure 10:
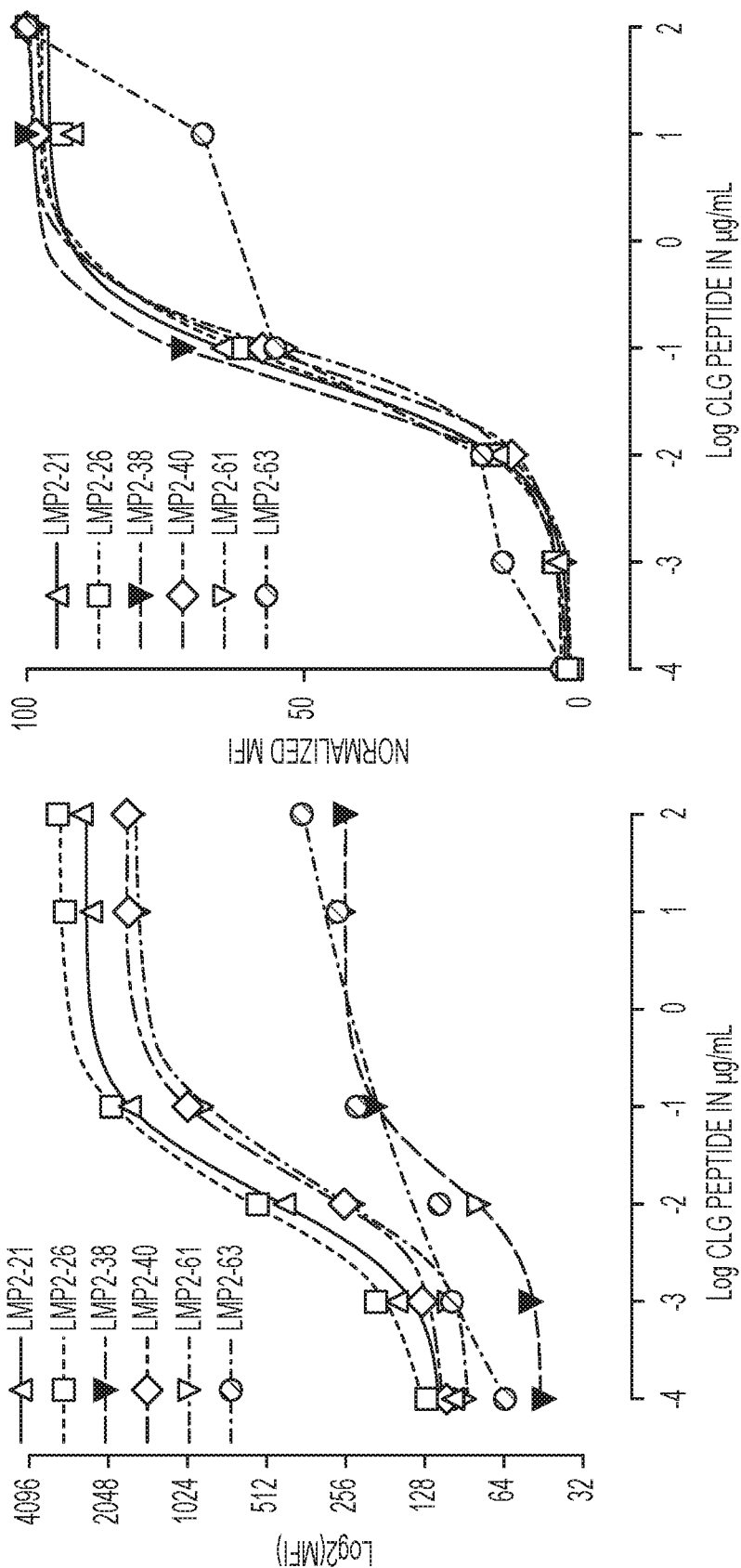
FIG. 10 shows exemplary binding of selected anti-EBV-LMP2(CLG)/HLA-A02 antibodies to EBV-LMP2 peptide on T2 cells pulsed with different concentrations of peptide.

As shown in FIG. 10, each of the antibodies binds with different affinities to the EBV-LMP2 peptide presented via HLA-A02 on the surface of T2 cells. Results were normalized to determine differences in the binding of the antibodies, which demonstrated consistent binding. Affinities of each of the antibodies were also determined using BIACORE (Table 7; nb: no binding).

TABLE 7

| Antibody | $K_{on}$ (s$^{-1}$M$^{-1}$) | $K_{off}$ (s$^{-1}$) | $K_D$ (nM) |
|---|---|---|---|
| LMP2-21 IgG1 | 2.244 × 10⁶ | 1.853 × 10⁻² | 8.3 |
| LMP2-26 IgG1 | 1.030 × 10⁷ | 2.103 × 10⁻² | 2.04 |
| LMP2-38 IgG1 | 1.144 × 10⁴ | 5.975 × 10⁻⁴ | 52.2 |
| LMP2-40 IgG1 | 2.793 × 10⁷ | 1.467 × 10⁻⁰ | 52.3 |
| LMP2-61 IgG1 | 6.876 × 10⁶ | 1.817 × 10⁻¹ | 26.4 |
| LMP2-63 IgG1 | 6.185 × 10⁴ | 7.770 × 10⁻³ | 125.6 |
| LMP2-77 IgG1 | 6.010 × 10⁵ | 1.016 × 10⁻¹ | 169.0 |
| IgG1-Control | nb | | |

Example 7. Antibody-Dependent Cell-Mediated Cytotoxicity (ADCC) of EBV-Transformed Cells Mediated by Anti-EBV-LMP2(CLG)/HLA-A02 IgG Antibodies This example describes the potential for full-length IgG1 antibodies made from anti-EBV-LMP2(CLG) specific scFvs to mediate antibody-dependent cell-mediated cytotoxicity (ADCC) of target cells transformed with the Epstein-Barr virus (EBV). In particular, this example specifically describes that selected anti-EBV-LMP2(CLG)/HLA-A02 IgG1 antibodies described in Example 3 do not mediate ADCC of EBV-transformed cells.

Briefly, an HLA-A*02:01+/EBV⁺ B lymphoblastoid cell line (BLCL), BV−, was generated by transforming PBMCs from a healthy donor with viral supernatant from B95-8 marmoset cells. This engineered BLCL cell line was used as a target in a chromium-based cytotoxicity assay with different concentrations of the anti-EBV-LMP2(CLG)/HLA-A02 IgG1 antibodies and NK92 cells as effectors (described above). Because the EBV-transformed BLCL are CD20⁺, Rituximab (an anti-CD20 antibody; see, e.g., Maloney, D. G. et al., 1997, Blood 90 (6): 2188-95) was employed as a positive control. An isotype matched negative control was also included in the assay. Exemplary results are shown in FIG. 11.

Figure 11:
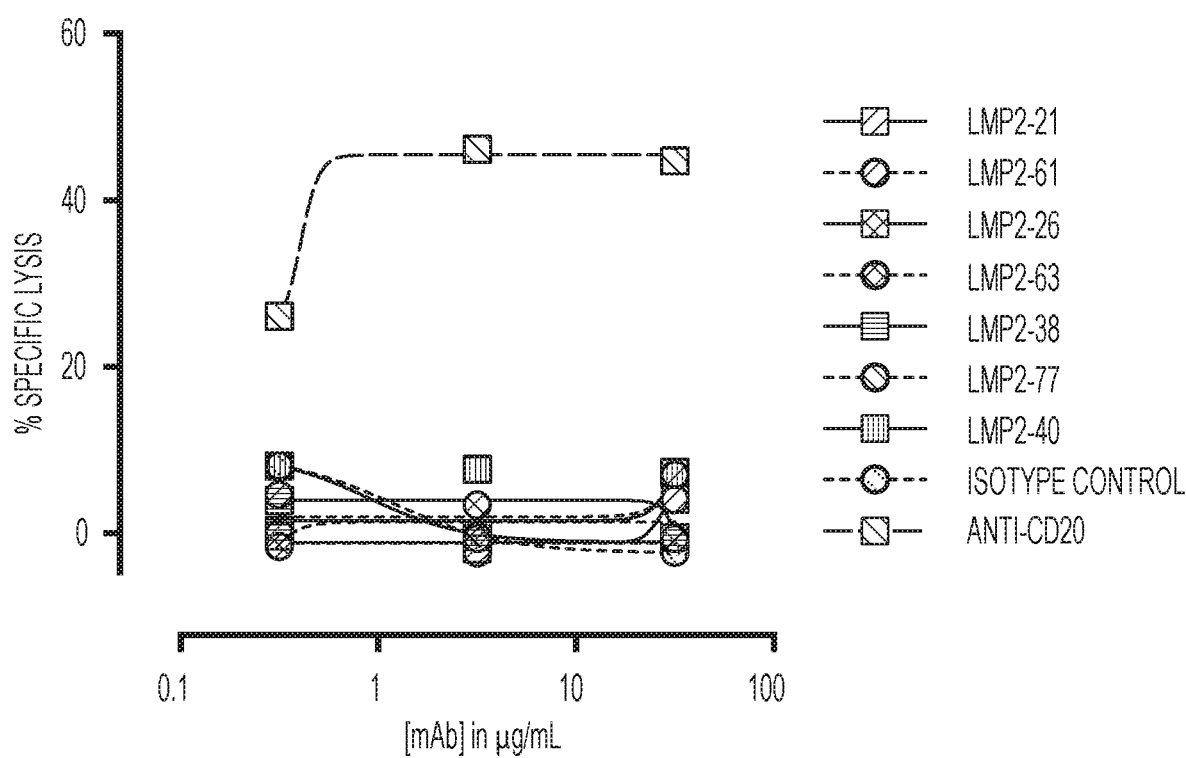
FIG. 11 shows exemplary percent specific lysis of EBV-transformed B lymphoblastoid cells (BLCL) mediated by selected anti-EBV-LMP2(CLG)/HLA-A02 IgG1 antibodies. mAb: monoclonal antibody.

As shown in FIG. 11, ADCC was present for RITUX-IMAB® (anti-CD20). However, no ADCC was observed for any of the anti-EBV-LMP2 IgG1 antibodies even when these IgG1 antibodies were used at high concentration (30 μg/mL).

Example 8. T Cell Cytotoxicity Assay Using Peptide-Pulsed T2 Cells

This example demonstrates experiments performed to determine the sensitivity of peptide loaded T2 cells to T cell cytotoxicity mediated by multi-specific binding agents that have a first antigen-binding site that binds an EBV-LMP2/HLA-A02 peptide complex and a second antigen-binding site that binds T cells. In particular, this example specifically demonstrates that bispecific antibodies that have a first antigen-binding site that binds an EBV-LMP2(CLG)/HLA-A*02:01 peptide complex and a second antigen-binding site that binds CD3 effectively mediate T cell cytotoxicity of peptide loaded T2 cells in the femtomolar range.

Briefly, peptide loaded T2 cells (described above) were tested for their sensitivity to T cell cytotoxicity by using different concentrations of EBV-LMP2(CLG)/HLA-A*02:01 bispecific antibody constructs described in Example 4. Target T2 cells were pulsed overnight with either 100 µg/mL of the LMP2 (CLGGLLTMV; SEQ ID NO: 1) or control (YMLDLQPET; SEQ ID NO: 120) peptide and 20 µg/mL of human β2m. Each of the bispecific antibodies was tested for specificity and affinity to the LMP2 peptide (Table 8). Exemplary affinity measurements of each of the bispecific antibodies to EBV-LMP2(CLG)/HLA-A*02:01, using BIACORE technology, is set forth in Table 9. Exemplary T cell cytotoxicity of T2 cells pulsed with EBV-LMP2 peptide using EBV-LMP2(CLG)/HLA-A*02:01 bispecific antibodies is set forth in FIG. 12.

TABLE 8

| Bispecific Antibody | $EC_{50}$ (ng/mL) | $EC_{50}$ (pM) |
| --- | --- | --- |
| LMP2-21xCD3 | 0.02059 | 0.4 |
| LMP2-26xCD3 | 0.0109 | 0.2 |
| LMP2-38xCD3 | 0.655 | 12.1 |
| LMP2-40xCD3 | 0.02361 | 0.4 |
| LMP2-61xCD3 | 0.4021 | 7.4 |
| LMP2-63xCD3 | 7.222 | 133.6 |
| LMP2-77xCD3 | 3.613 | 66.8 |

TABLE 9

| Bispecific Antibody | $K_{on}$ (s$^{-1}$M$^{-1}$) | $K_{off}$ (s$^{-1}$) | $K_D$ (nM) |
| --- | --- | --- | --- |
| LMP2-21xCD3 | $1.929 \times 10^5$ | $2.595 \times 10^{-3}$ | 20 |
| LMP2-26xCD3 | $1.399 \times 10^5$ | $2.818 \times 10^{-3}$ | 13 |
| LMP2-38xCD3 | $3.864 \times 10^4$ | $2.145 \times 10^{-3}$ | 117 |
| LMP2-40xCD3 | $1.358 \times 10^4$ | $1.587 \times 10^{-3}$ | 31 |
| LMP2-61xCD3 | $5.457 \times 10^4$ | $2.736 \times 10^{-3}$ | 128 |
| LMP2-63xCD3 | $4.987 \times 10^4$ | $6.389 \times 10^{-3}$ | 56 |
| LMP2-77xCD3 | $8.538 \times 10^4$ | $2.642 \times 10^{-3}$ | 50 |

Figure 12:
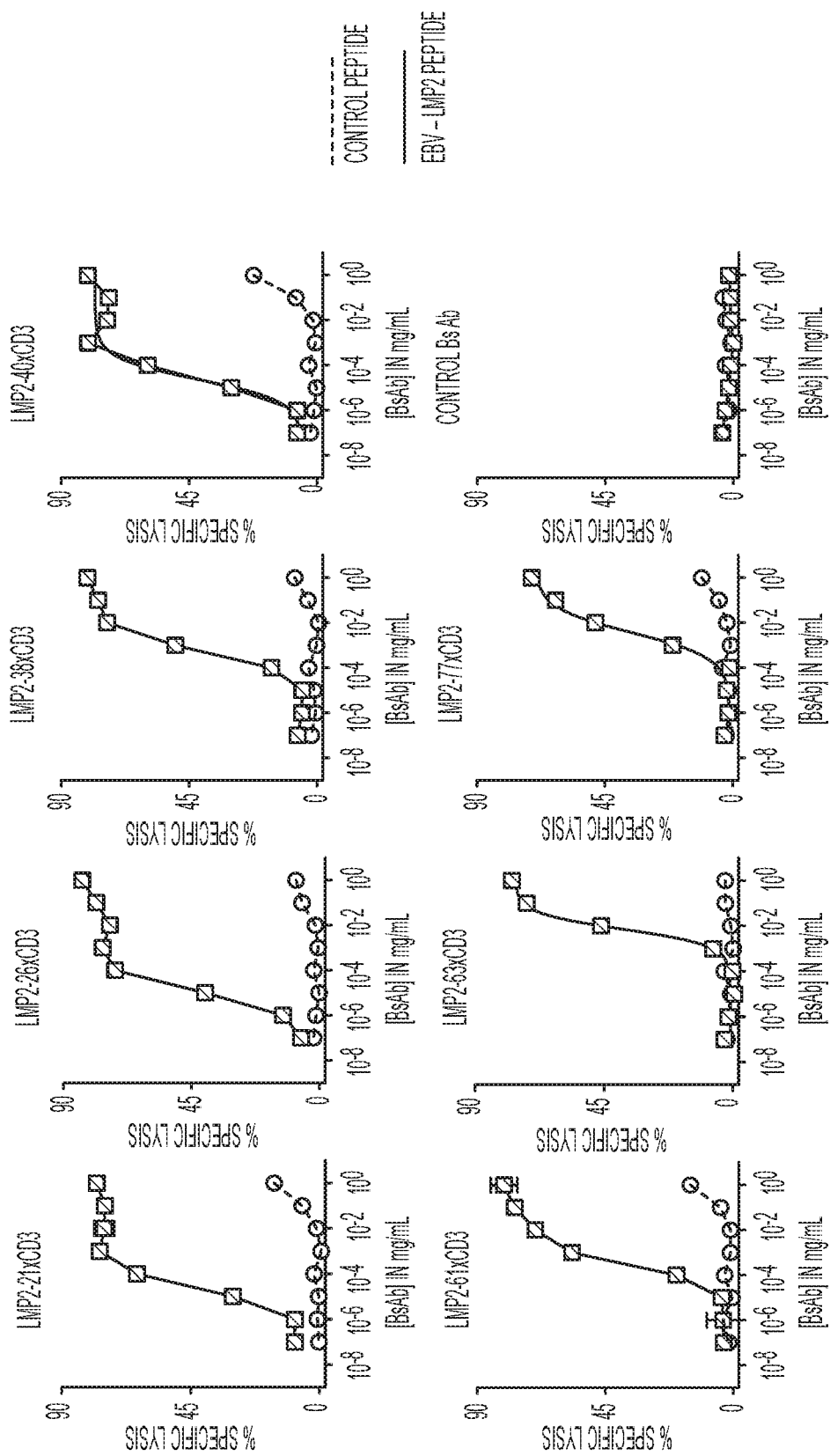
FIG. 12 shows exemplary T cell cytotoxicity against T2 cells pulsed with an EBV-LMP2 peptide (solid line; CLGGLLTMV, SEQ ID NO: 1) or a control peptide (dashed line; YMLDLQPET, SEQ ID NO: 120) using selected bispecific antibodies (BsAb) having a first antigen-binding site that binds EBV-LMP2(CLG)/HLA-A02 and a second antigen-binding site that binds CD3. Control BsAb: anti-HER2xCD3 bispecific antibody.
Figure 13A:
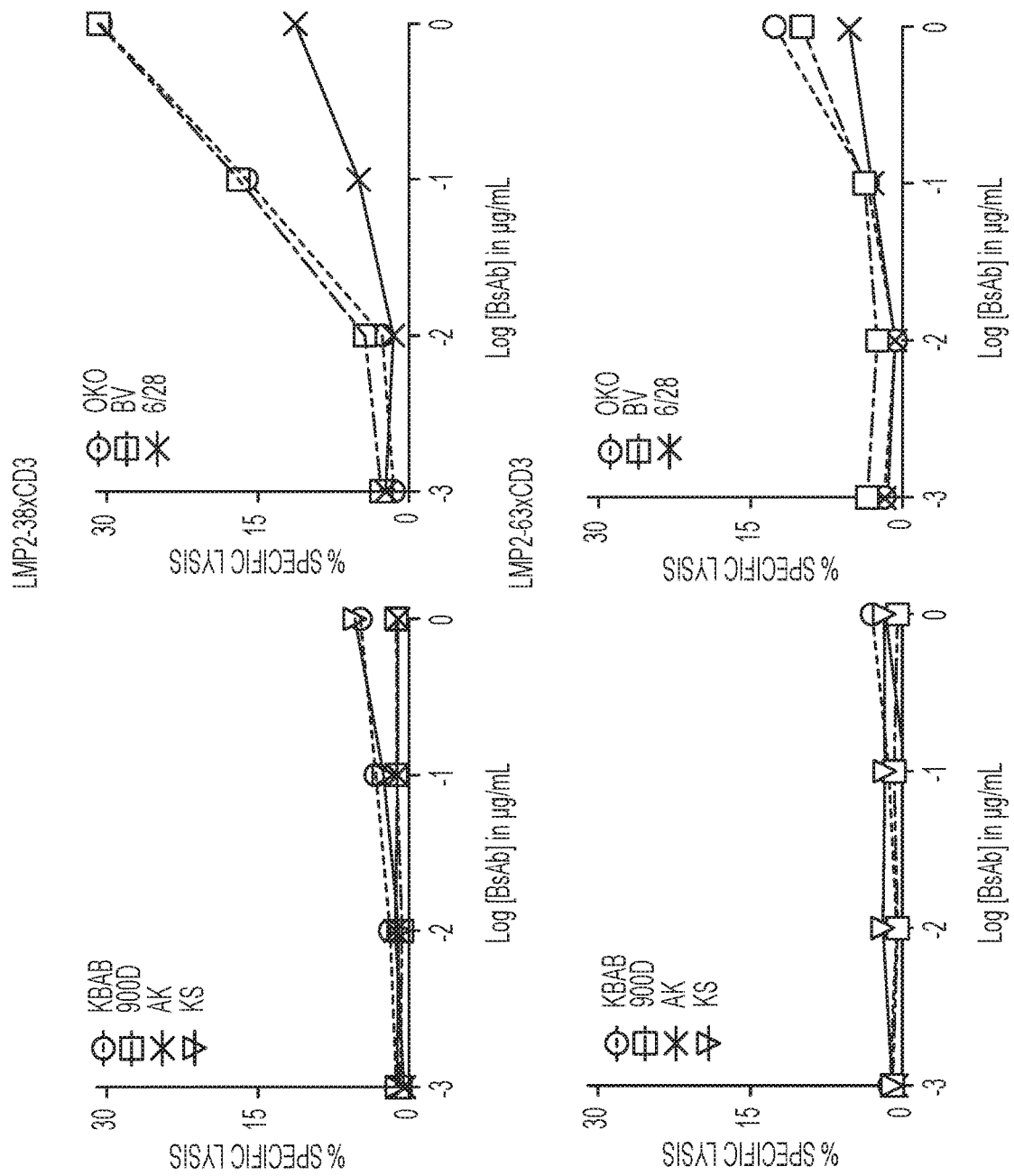
FIG. 13A to FIG. 13D show exemplary T cell cytotoxicity of EBV-transformed HLA-A02$^+$ (right panels) and HLA-A02$^-$ (left panels) cells using selected LMP2xCD3 bispecific antibodies (BsAb).
Figure 13B:
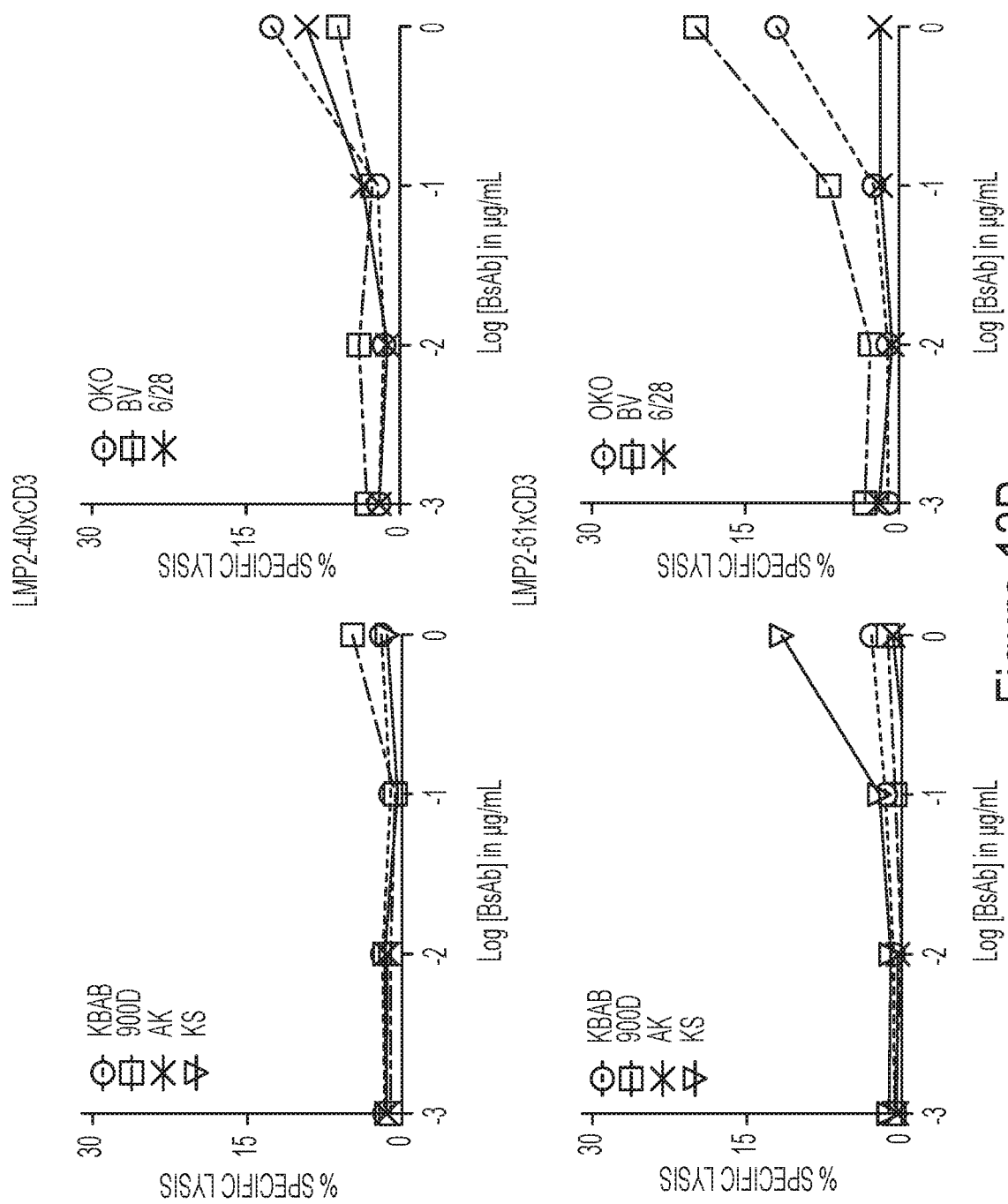
Figure 13C:
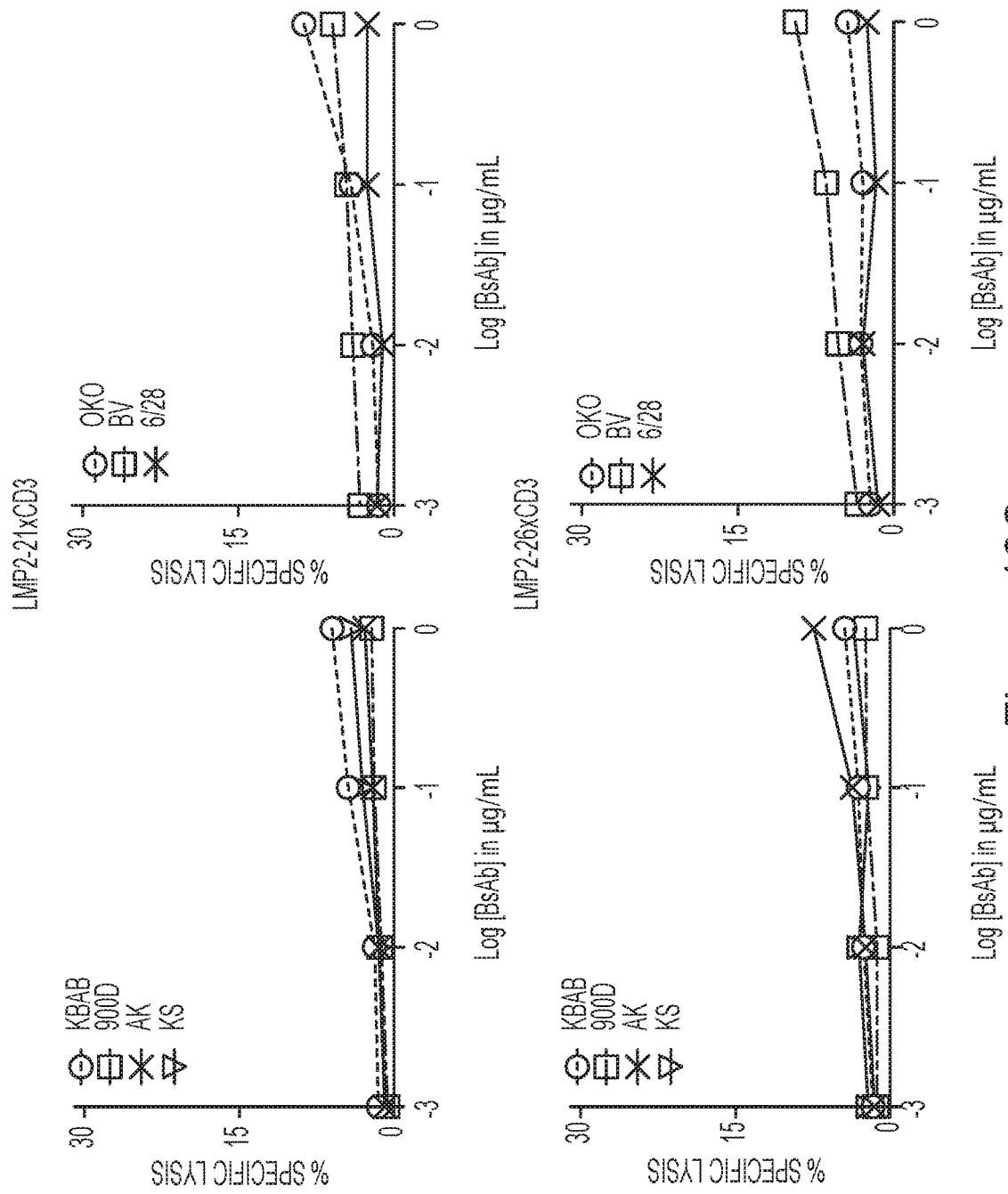
Figure 13D:
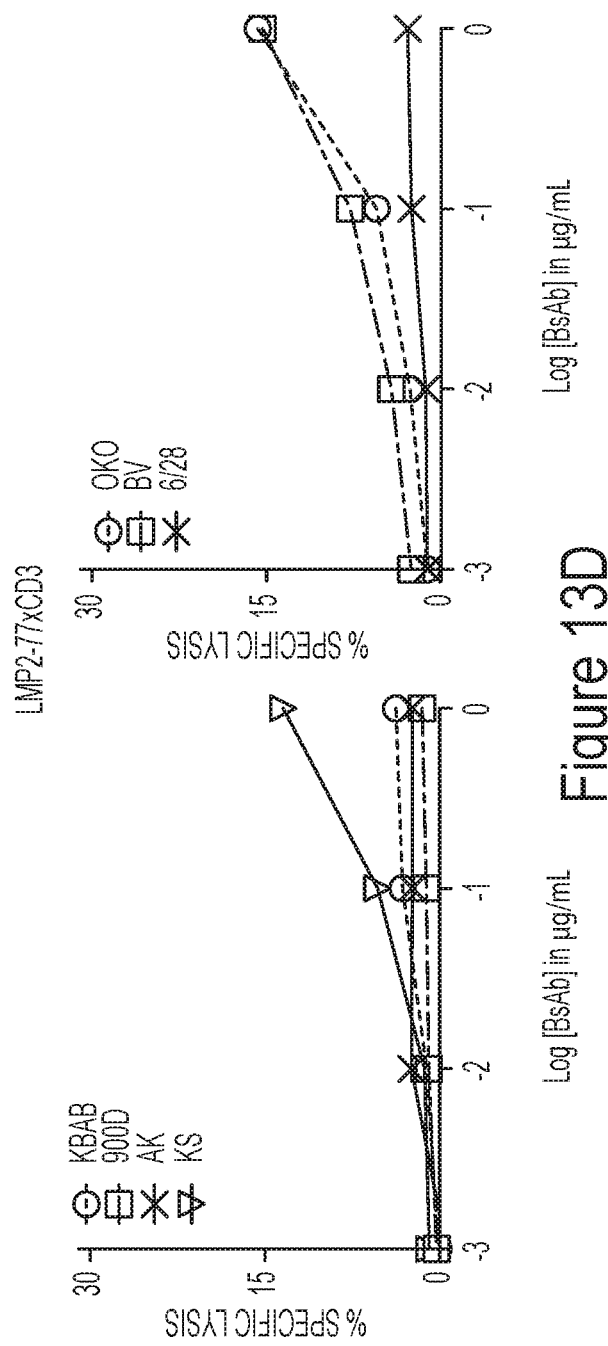
Figure 14:
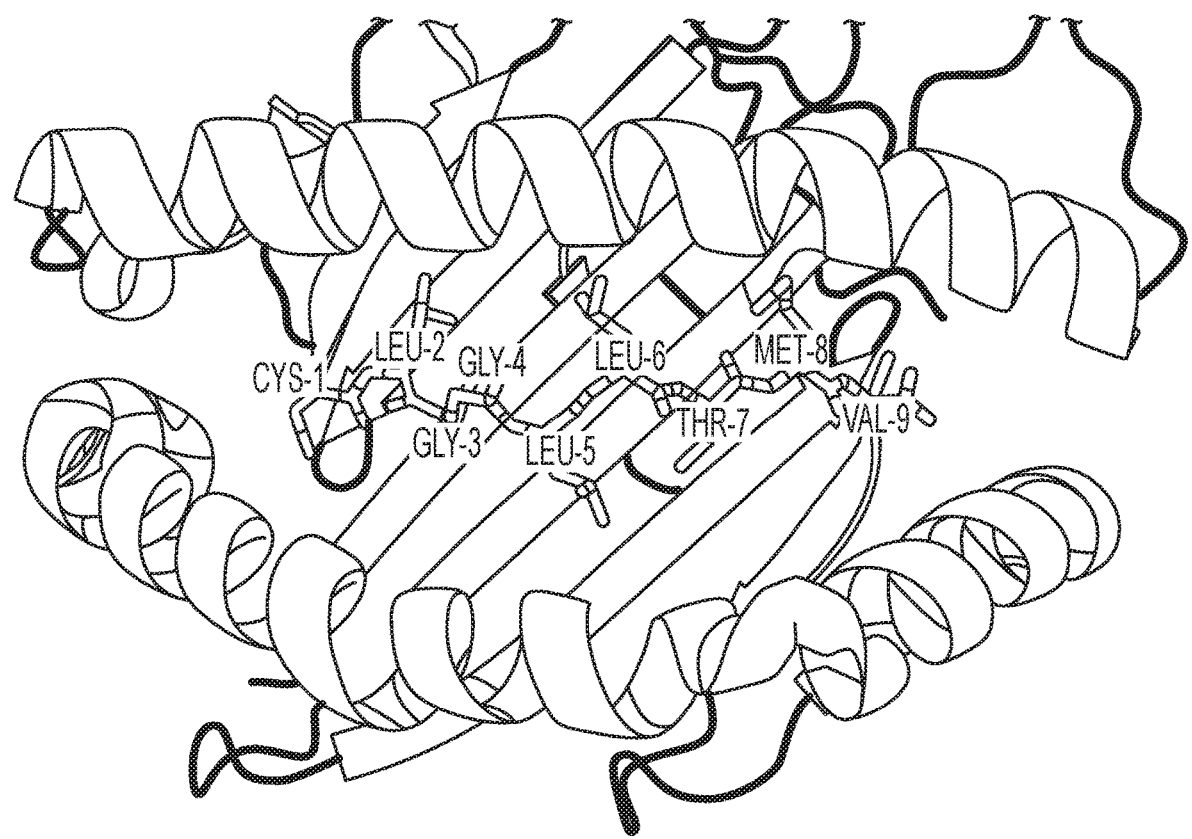
FIG. 14 shows a schematic illustration, not to scale, of the crystal structure of EBV-LMP2/HLA-A02 at 1.9 Å resolution generated using pdb 3REW. The orientation of the peptide position in the HLA-A02 binding pocket is shown.

As shown in Table 8, each of the bispecific antibodies were specific for the LMP2 peptide with an $EC_{50}$ ranging from 0.4 to about 133 pM. Further, each of the bispecific antibodies had similar affinities (Table 9) and effectively mediated T cell killing of T2 cells in a peptide specific manner (FIG. 12).

Example 9. T Cell Cytotoxicity Assay Using EBV-Transformed BLCLs

This example demonstrates that multi-specific binding agents of the present invention can mediate T cell cytotoxicity of EBV-transformed target cells that present an EBV peptide using multiple different EBV-transformed cells. In particular, this example specifically describes that selected EBV-LMP2(CLG)/HLA-A02xCD3 bispecific antibodies mediate T cell cytotoxicity against a panel of HLA-A02$^+$ EBV-transformed BLCLs.

A panel of seven different BLCL, generated in vitro by the B95-8 marmoset line and previously genotyped for their HLA-A*02:01 status by both flow cytometry and sequencing, were tested using activated T-cells (ATC) generated from cord blood donors in cytotoxicity assays using different concentrations of EBV-LMP2(CLG)/HLA-A*02:01 bispecific antibody. Cord blood cells were used because they are naïve to EBV and thus eliminate the potential of cross-reactivity from antigen-specific T-cells present in culture.

Briefly, BLCLs were generated from healthy donors (as described above) and then cultured in 10% FBS. For cytotoxicity assays, $1 \times 10^6$ BLCLs were incubated with 100 µCi of $^{51}$Cr for 60 minutes at 37° C. as described elsewhere (Xu, H. et al., 2015, Cancer Immunol. Res. 3(3):266-77). BLCLs were then washed twice and plated at a density of $5 \times 10^3$ per well in a round bottom 96-well plate. Each of the bispecific antibodies were added at the specified concentration at an E:T ratio of 10:1 and incubated for four hours at 37° C. Supernatants were harvested and read using a gamma counter. Specific lysis was calculated as described above. To generate effector cells, cord blood cells were obtained from the NY blood bank and processed using a ficoll gradient. The resulting lymphocyte enriched population was enriched for CD3 expression through magnetic columns using CD3 microbeads (Miltenyi Biotech). The cells were then plated with CD3/CD28 magnetic beads (Life Technologies) for seven days (×2) to generate ATCs. Exemplary results are shown in FIGS. 13A-D and Table 10 (bispecific antibodies grouped according to their specificity for amino acids of the EBV-LMP2 peptide).

TABLE 10

| Bispecific Antibody | Targets peptide positions(s) |
| --- | --- |
| LMP2-21xCD3 | 8 |
| LMP2-26xCD3 | 8 |
| LMP2-38xCD3 | 5-8 |
| LMP2-40xCD3 | 1 |
| LMP2-61xCD3 | 1 |
| LMP2-63xCD3 | 5-8 |
| LMP2-77xCD3 | 1-5 |

As shown in FIGS. 13A-D, the cytotoxicity against EBV-transformed cells by each of the bispecific antibodies varied with LMP2-38xCD3 demonstrating the highest cytotoxicity. LMP2-38xCD3 and LMP2-63xCD3 bispecific antibodies demonstrated the highest specificity for HLA-A*02:01$^+$ cells while several other bispecific antibodies (LMP2-21xCD3, LMP2-26xCD3, LMP2-40xCD3 and LMP2-77xCD3) demonstrated cross-reactivity with at least one of the HLA-A*02:01 negative cells. Also, bispecific antibodies that target residues 5-8 (Table 10) of the EBV-LMP2 peptide demonstrated the highest specificity against HLA-A*02:01$^+$ EBV$^+$ cells.

Taken together, this example confirms that EBV-LMP2 (CLG)/HLA-A02xCD3 bispecific antibodies effectively mediate T cell cytotoxicity against a panel of HLA-A02$^+$ EBV-transformed BLCLs.

Example 10. Characterization of LMP-2 Peptide Presented by HLA-A02 in BLCLs

This example demonstrates the characterization of LMP2 peptide (CLGGLLTMV; SEQ ID NO: 1) presented by HLA-A*02:01 in BLCLs using EBV-LMP2(CLG)/HLA-A*02:01 bispecific antibodies. Exemplary results are set forth in FIGS. 15 and 16.

Figure 15:
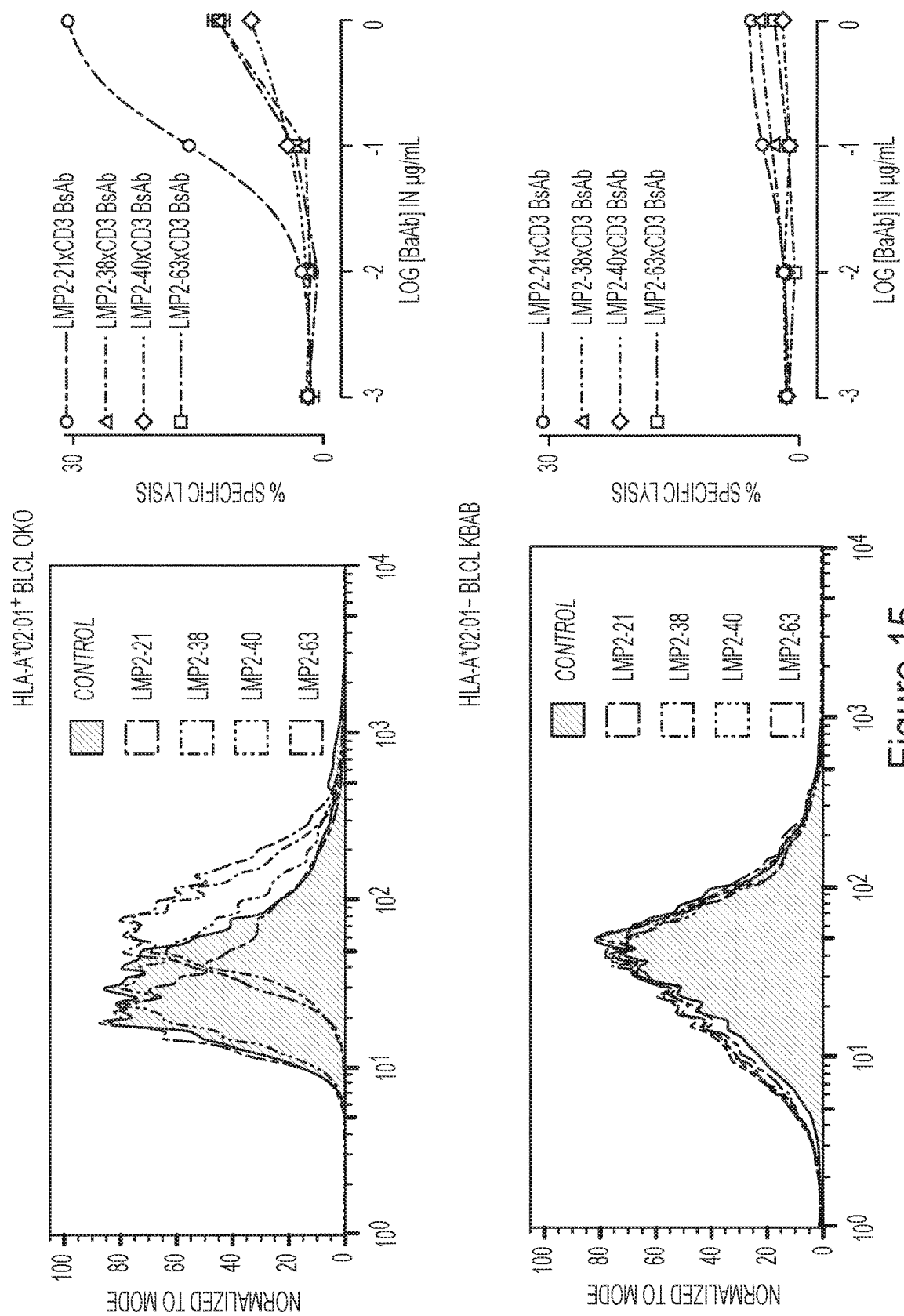
FIG. 15 shows exemplary peptide binding by flow cytometry of selected anti-EBV-LMP2(CLG)/HLA-A*02:01 specific IgG1 antibodies (left panel) and cytotoxicity against BLCL of corresponding bispecific antibodies (right panel). Control: human IgG1 isotype matched control.

As shown in FIG. 15, EBV-LMP2(CLG)/HLA-A*02:01 IgG1 antibodies that target position 8 of the EBV-LMP2 peptide (e.g., LMP2-21, LMP2-26) demonstrated minimal cytotoxicity against LMP2$^+$ HLA-A*02:01$^+$ cells. Interestingly, these same constructs demonstrated the lowest $EC_{50}$ (highest affinity) when tested against T2-peptide pulsed cells (described above). To determine a potential reason for this relationship, HLA-A*02:01+/EBV+ BLCL OKO cells were stained with selected antibodies targeting different peptide positions to determine their binding to HLA-A*02:01+ BLCL. Antibodies targeting position 1 of the EBV-LMP2 peptide demonstrated minimal to no binding by flow cytometry to BLCLs correlating with the results observed in cytotoxicity assays. The HLA-A*02:01− cell line KBAB-1 was used as a negative control (FIG. 15, lower panel).

Figure 16:
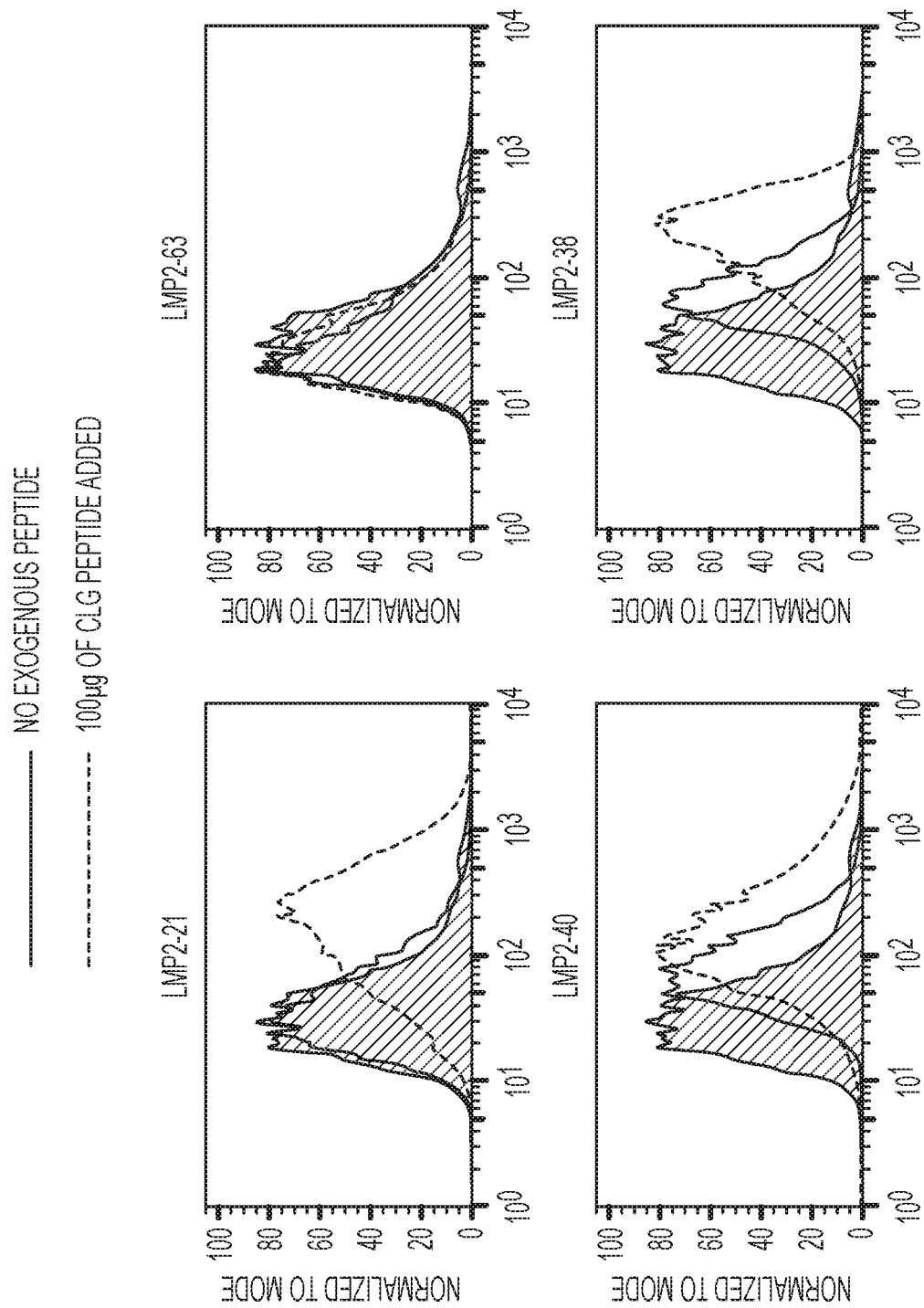
FIG. 16 shows exemplary binding by flow cytometry of selected EBV-LMP2(CLG)/HLA-A*02:01 specific IgG1 antibodies to HLA-A*02:01$^+$ BLCL OKO cells with (dotted line) and without (solid line) exogenous EBV-LMP2 peptide. The solid line represents binding of IgG1 antibodies to cells without exogenous peptide, and the dotted line represents the same OKO cells after incubation overnight with 100 µg/mL of peptide.

As shown in FIG. 16, when BLCL OKO cells were pulsed with 100 μg/mL of the EBV-LMP2 peptide overnight and stained with the same EBV-LMP2(CLG)/HLA-A*02:01 specific IgG1 antibodies, binding of constructs targeting position 8 of the EBV-LMP2 peptide was reconstituted. The inventors reasoned that such differences are due to a difference in the presentation of the CLGGLLTMV peptide in BLCL.

Example 11. Recognition of EBV-LMP2 Peptide Presented by Different HLA-A02 Sub-Alleles This example demonstrates that EBV-LMP2(CLG)/HLA-A*02:01 bispecific antibodies having specificity positions 5-8 of the EBV-LMP2 peptide can bind the EBV-LMP2 peptide when presented by multiple different sub-alleles of the HLA-A02 molecule. This example employs Artificial Antigen Presenting Cells (aAPCs), which are 3TC mouse fibroblast cells that have been engineered to stably express specific HLA class I alleles along with co-stimulatory molecules.

Briefly, six different aAPCs expressing sub-alleles of HLA-A02 (HLA-A*02:01, HLA-A*02:02, HLA-A*02:03, HLA-A*02:04, HLA-A*02:05 and HLA-A*02:06) were pulsed with 100 μg/mL of the EBV-LMP2 peptide at 37° C. overnight and used in cytotoxicity assays (described above) with EBV-LMP2(CLG)/HLA-A*02:01 bispecific antibodies targeting amino acids in positions 5-8 of the EBV-LMP2 peptide. These same cells were analyzed by flow cytometry after staining with these same EBV-LMP2(CLG)/HLA-A*02:01 bispecific antibodies as a full-length IgG1 antibody. To ensure that any differences in cytotoxicity were not due to differences in the expression of HLA-class I molecules, aAPCs were characterized for their expression of the HLA molecules by flow cytometry using a pan-HLA antibody (W6/32). Exemplary results are set forth in FIG. 17.

Figure 17:
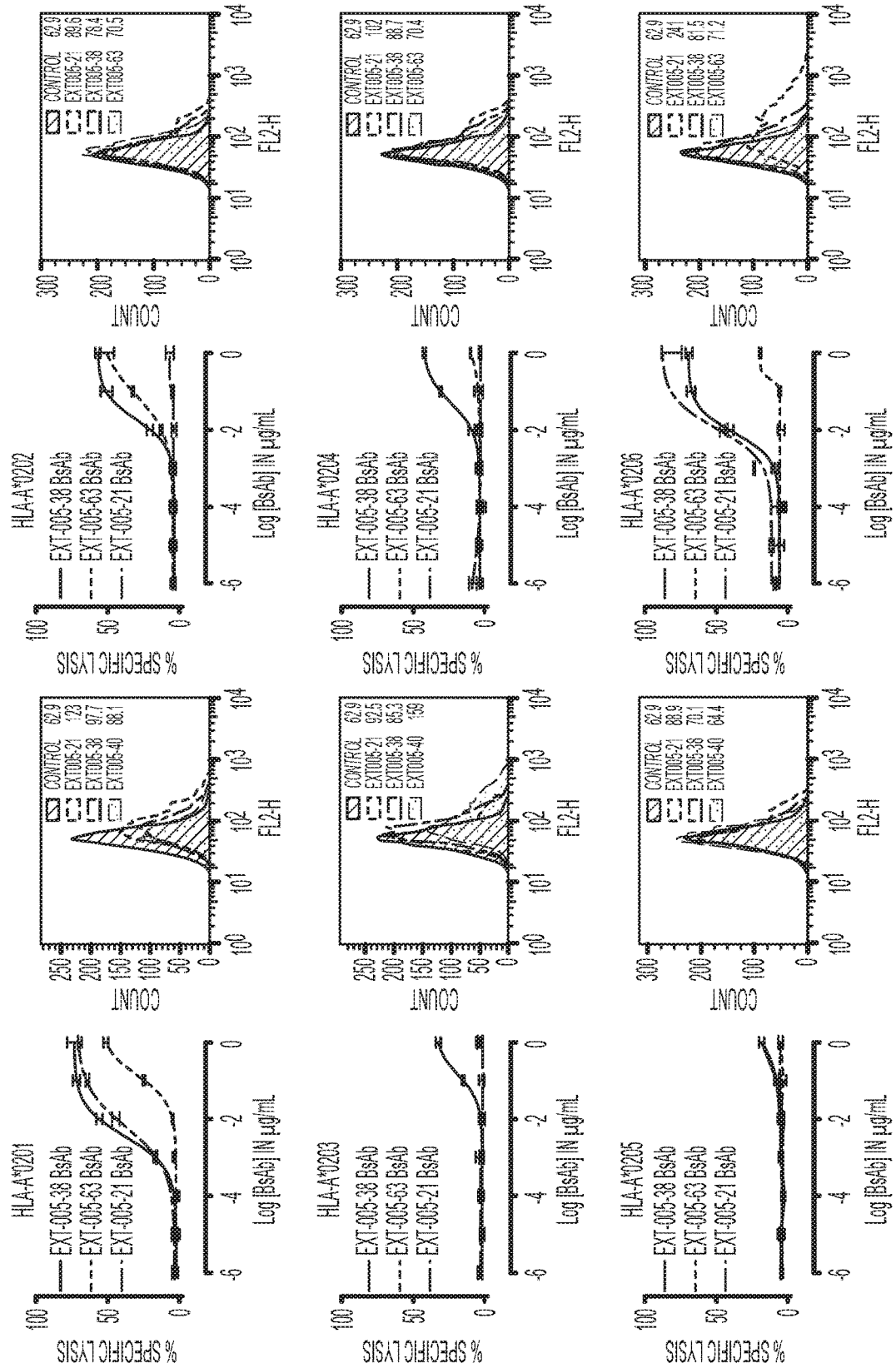
FIG. 17 shows exemplary cytotoxicity of bispecific antibodies (left in each pairing) and binding by flow cytometry of full-length IgG1 antibodies (right in each pairing) against peptide pulsed antigen-presenting cells expressing different HLA-A02 sub-alleles. Bispecific antibodies are labeled as, e.g., EXT005-38 BsAb which corresponds to LMP2-38xCD3 bispecific antibody, etc.; IgG1 antibodies are labeled as, e.g., EXT005-21, which corresponds to LMP2-21 IgG1 antibody, etc.

As shown in FIG. 17, several bispecific and IgG1 antibodies bound peptide presented by different HLA-A02 alleles. In particular, this example demonstrates that EBV-LMP2(CLG)/HLA-A*02:01 bispecific antibodies that bind to positions 5-8 of the EBV-LMP2 peptide are also reactive to HLA-A*02:02 and HLA-A*02:06.

To demonstrate that these cells do not cross react with aAPC not loaded with exogenous peptide, HLA-A*02:01 cells aAPC were used as target cells in a cytotoxicity assay (described above) after incubation with a low concentration (0.0001 μg/mL) or no exogenous peptide and tested with ATC using selected LMP2(CLG)/HLA-A*02:01 bispecific antibodies that bind to different positions of the EBV-LMP2 peptide. They were also stained using selected anti-EBV-LMP2(CLG)/HLA-A*02:01 IgG1 antibodies and analyzed by flow cytometry. Exemplary results are set forth in FIG. 18.

Figure 18:
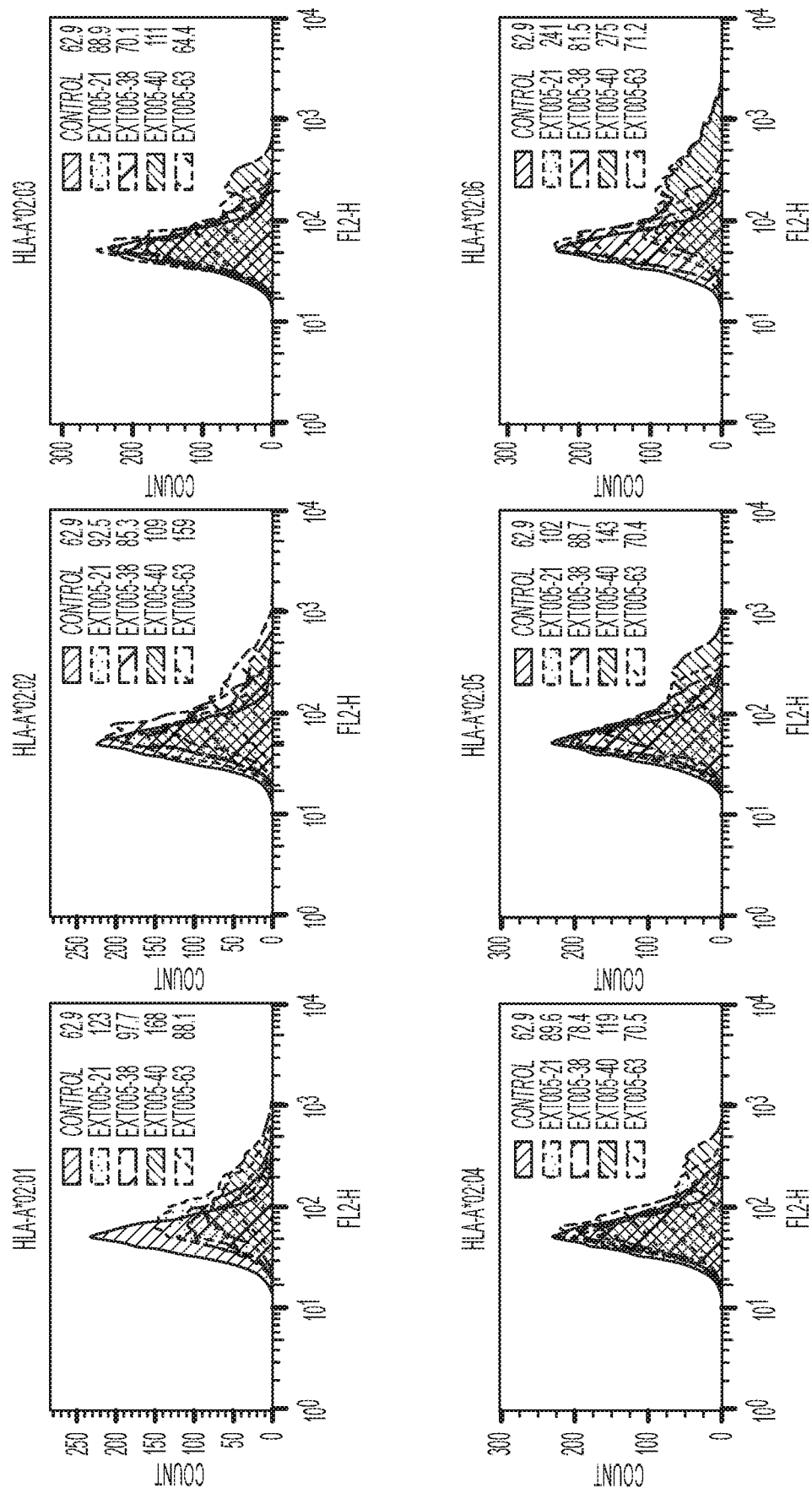
FIG. 18 shows exemplary binding by flow cytometry of selected full-length IgG1 antibodies against peptide pulsed antigen presenting cells expressing different HLA-A02 sub-alleles. IgG1 antibodies are labeled as, e.g., EXT005-21, which corresponds to LMP2-21 IgG1 antibody, etc.

As shown in FIG. 18, aAPC require a higher peptide concentration than peptide pulsed T2 cells to be recognized by either bispecific or full-length IgG1 antibodies. Further, this example demonstrates that similar cytotoxicity was observed between the bispecific and IgG1 antibodies tested.

Example 12. Affinity Maturation of Type I TCR Mimic Antibody

This example demonstrates the affinity maturation of an anti-EBV-LMP2(CLG)/HLA-A02 antibody. In particular, this example specifically demonstrates the generation of a series of antibody variants by incorporation of random mutations into a selected anti-EBV-LMP2(CLG)/HLA-A02 antibody (LMP2-38) followed by screening and characterization of the antibody variants using monomeric EBV-LMP2(CLG)/HLA-A02.

Using ALPHA™ phage display (described above), LMP2-38 IgG1 antibody was randomly mutated and selected with monomeric EBV-LMP2(CLG)/HLA-A*02:01. Of a total of 581 clones screened, 111 were specific for peptide-HLA complex. Of the 111 specific for the peptide-HLA complex, 34 were determined to be unique binders. Eleven demonstrated strong binding to peptide loaded T2 cells, i.e. [P19 peptide loaded T2 cell phage antibody FACS signal]/[negative control FACS signal]<5; Seventeen demonstrated T2 cell cross binding: [P19 peptide loaded T2 cell phage antibody FACS signal]/[negative control FACS signal]>5. In total, nine clones demonstrated improvement over the parental antibody, i.e. [LMP2-38 parental IC$_{50}$]/[mutated unique phage antibody IC$_{50}$ ]>2, and 24 showed no improvement, i.e. [EXT005-38 parental IC$_{50}$]/[mutated unique phage antibody IC$_{50}$ ]<2. Exemplary results are set forth in Tables 11 (Cell surface binding: [specific phage antibody FACS signal]/[negative control FACS signal]<2; +: [specific phage antibody FACS signal]/[negative control FACS signal]=2-10; ++: [specific phage antibody FACS signal]/[negative control FACS signal]>10; nd: not determined; affinity improvement: [LMP2-38 parental IC$_{50}$]/[mutated unique phage antibody IC$_{50}$]; P19 peptide: mixture of 19 endogenous control peptides) and 12 (BIACORE; nd: not determined).

TABLE 11

| Antibody Clone | Cell surface binding LMP2 peptide loaded T2 cell | P19 peptide loaded T2 cell | Affinity improvement |
|---|---|---|---|
| LMP2-38 parental | ++ | − | 1.00 |
| 1 | ++ | − | 0.79 |
| 2 | ++ | − | 1.67 |
| 3 | ++ | − | 1.58 |
| 4 | ++ | + | ND |
| 5 | ++ | − | 1.37 |
| 6 | ++ | − | 1.29 |
| 7 | nd | nd | 0.91 |
| 8 | ++ | + | 1.16 |
| 9 | ++ | ++ | 2.19 |
| 10 | ++ | ++ | 0.95 |
| 11 | ++ | + | 2.65 |
| 12 | ++ | ++ | 2.51 |
| 13 | ++ | − | 0.55 |
| 14 | nd | nd | 0.89 |
| 15 | nd | nd | 0.78 |
| 16 | ++ | ++ | 1.72 |
| 17 | ++ | ++ | 1.39 |
| 18 | nd | nd | 0.88 |
| 19 | ++ | ++ | 1.12 |
| 20 | nd | nd | 0.78 |
| 21 | ++ | − | 0.74 |
| 22 | ++ | + | 1.04 |
| 23 | ++ | ++ | 2.85 |
| 24 | ++ | ++ | 1.89 |

TABLE 11-continued

| | Cell surface binding | | |
|---|---|---|---|
| Antibody Clone | LMP2 peptide loaded T2 cell | P19 peptide loaded T2 cell | Affinity improvement |
| 25 | ++ | + | 1.44 |
| 26 | ++ | ++ | 4.25 |
| 27 | ++ | + | 1.37 |
| 28 | ++ | + | 1.49 |
| 29 | ++ | + | 1.46 |
| 30 | ++ | + | 2.22 |
| 31 | ++ | ++ | 2.36 |
| 32 | ++ | ++ | 3.55 |
| 33 | ++ | ++ | 6.20 |
| 34 | ++ | + | 1.66 |

TABLE 12

| Affinity matured clones | Retained specificity | ELISA enhancement | fold improvement | | |
|---|---|---|---|---|---|
| | | | $k_{on}$ | $k_{off}$ | KA |
| LMP2-38-1 | yes | 0.79 | 1.12 | 1.66 | 1.86 |
| LMP2-38-2 | yes | 1.67 | 2.36 | 2.07 | 4.90 |
| LMP2-38-3 | yes | 1.58 | 3.44 | 1.79 | 6.18 |
| LMP2-38-5 | yes | 1.37 | 2.44 | 1.36 | 3.31 |
| LMP2-38-6 | yes | 1.29 | 1.05 | 1.53 | 1.62 |
| LMP2-38-11 | no | 2.65 | 6.15 | 1.38 | 8.46 |
| LMP2-38-13 | nd | 0.55 | 2.35 | 1.23 | 2.89 |
| LMP2-38-21 | yes | 0.74 | 1.44 | 1.68 | 2.42 |
| LMP2-38 Parental | — | 1 | 1 | 1 | 1 |

Affinity improvement of LMP2-38 came with a sacrifice of specificity, i.e., when affinity improvement is >1.0, cross-reactivity with P19 peptide was observed for many antibody clones. Four antibody clones demonstrated marginal improvement in binding (1.29, 1.37, 1.58, 1.67) over the LMP2-38 parental antibody by ELISA while retaining specificity. When binding kinetics of these clones were analyzed in detail by SPR (BIACORE), the increase in affinity was not robust: ranging from 1.05-fold to 3.44-fold for $k_{on}$, and 1.36 to 2.07 for $k_{off}$, resulting in an improvement of KA of 1.62-fold to 6.2-fold (Table 12). Exemplary mutations in the $V_H$ and $V_L$ regions of selected affinity matured anti-EBV-LMP2(CLG)/HLA-A02 IgG1 antibody clones are set forth in Table 13 (amino acid numbering as in Kabat; see, e.g., E. A. Kabat et al., Sequences of Proteins of Immunological Interest, Fifth Edition, 1991, NIH).

TABLE 13

| | $V_L$ | | | | | | | $V_H$ | | | | | | |
|---|---|---|---|---|---|---|---|---|---|---|---|---|---|---|
| Clone | FR1 | CDR1 | FR2 | CDR2 | FR3 | CDR3 | FR4 | FR1 | CDR1 | FR2 | CDR2 | FR3 | CDR3 | FR4 |
| 38-1 | | | | | K66R | | | | | | | | | |
| 38-2 | | | P55H | | | | | | | | | | | |
| 38-3 | | | | | N95I | | | | | | | | | |
| 38-5 | | | | | | | | | | | | V78A | | |
| 38-6 | | I48V | S52G | | | | | | | | | | | |
| 38-11 | | | | | | | | | G26E | | I51V | | | |
| 38-13 | | | | | | | | | V5E | | | | | |
| 38-21 | | | | | | | | | E10D | | | | | |

The data presented in this example demonstrates that affinity maturation of KA and especially $k_{off}$ for type II TCR mimic antibodies can be difficult. This is analogous to a TCR having specificity to a center position of a peptide (i.e., around position 5) and typically low affinity (μM) even with repeated challenge in vitro or in vivo. Based on crystal structures of peptide-HLA-A02 complexes, the center of the peptide P4-6 (when anchored at P2 and P9) has the lowest number of contacts with the MHC class I protein (Madden, D. R. et al., 1993, Cell 75:693-708). This would allow a high degree of conformational flexibility at the center of the peptides around position P5, which is often the least anchored residue. TCR or antibody recognition of peptide position P5 region would result in a significant loss of entropy to this region. Reports of structural studies have demonstrated that a high entropic cost of binding is associated with low affinity of a protein-ligand interaction (Thorpe, I. F. and Brooks, C. L., 2007, Proc. Natl. Acad. Sci. U.S.A. 104:8821-6). The inventors of the present invention have recognized that, in some embodiments, based on the data presented herein, there is an inherent affinity barrier for generating type II TCR-like monoclonal antibodies.

Example 13. Selection Strategy for Generating TCR Mimic Monoclonal Antibodies

This example demonstrates multiple selection strategies for the development of TCR-like monoclonal antibodies, in particular, type II TCR mimics.

Figure 19:
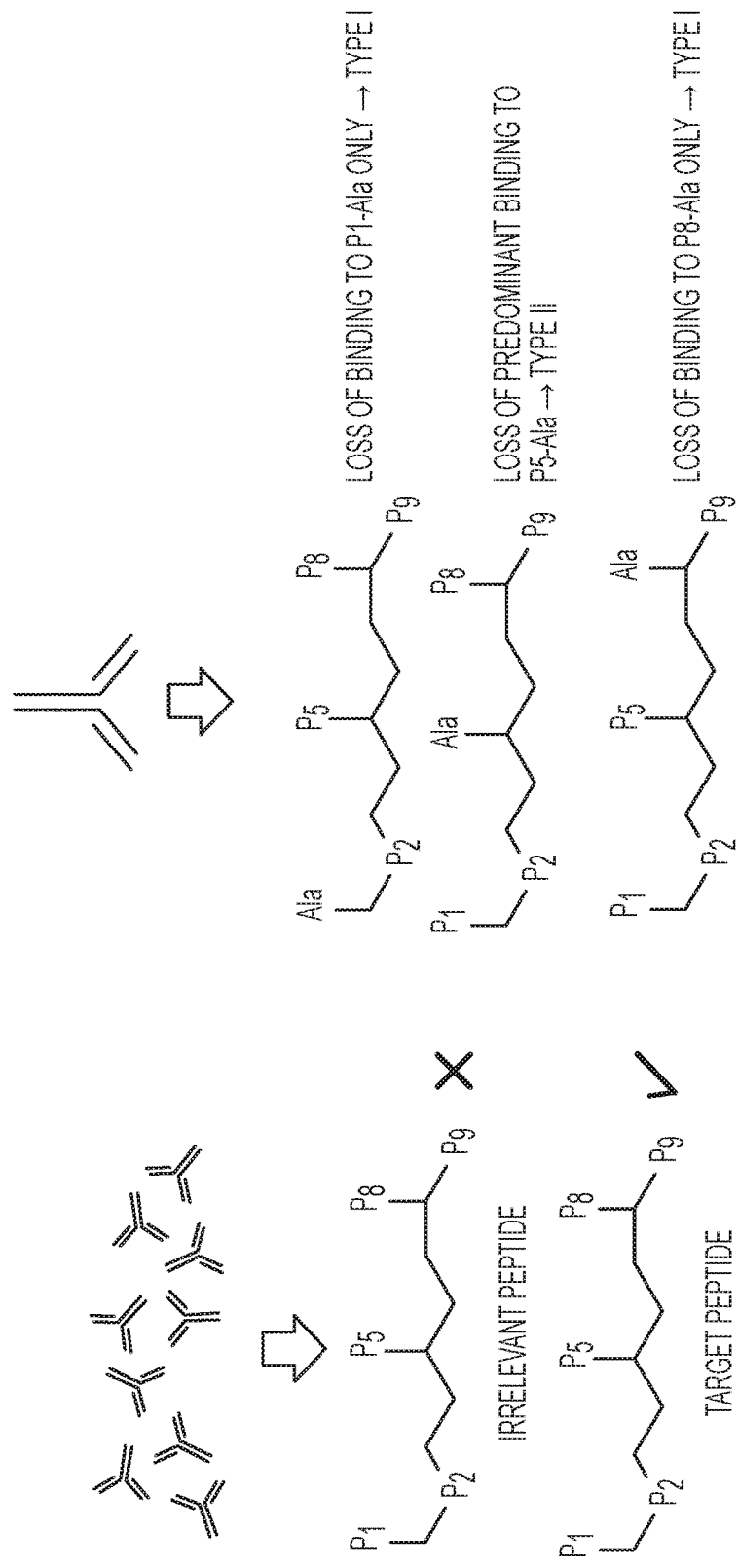
FIG. 19 shows an illustration, not to scale, of a selection strategy for generating type II TCR-like monoclonal antibodies using nonamer peptides with alanine substitutions at positions 1, 5 and 8 of the peptide.
Figure 20:
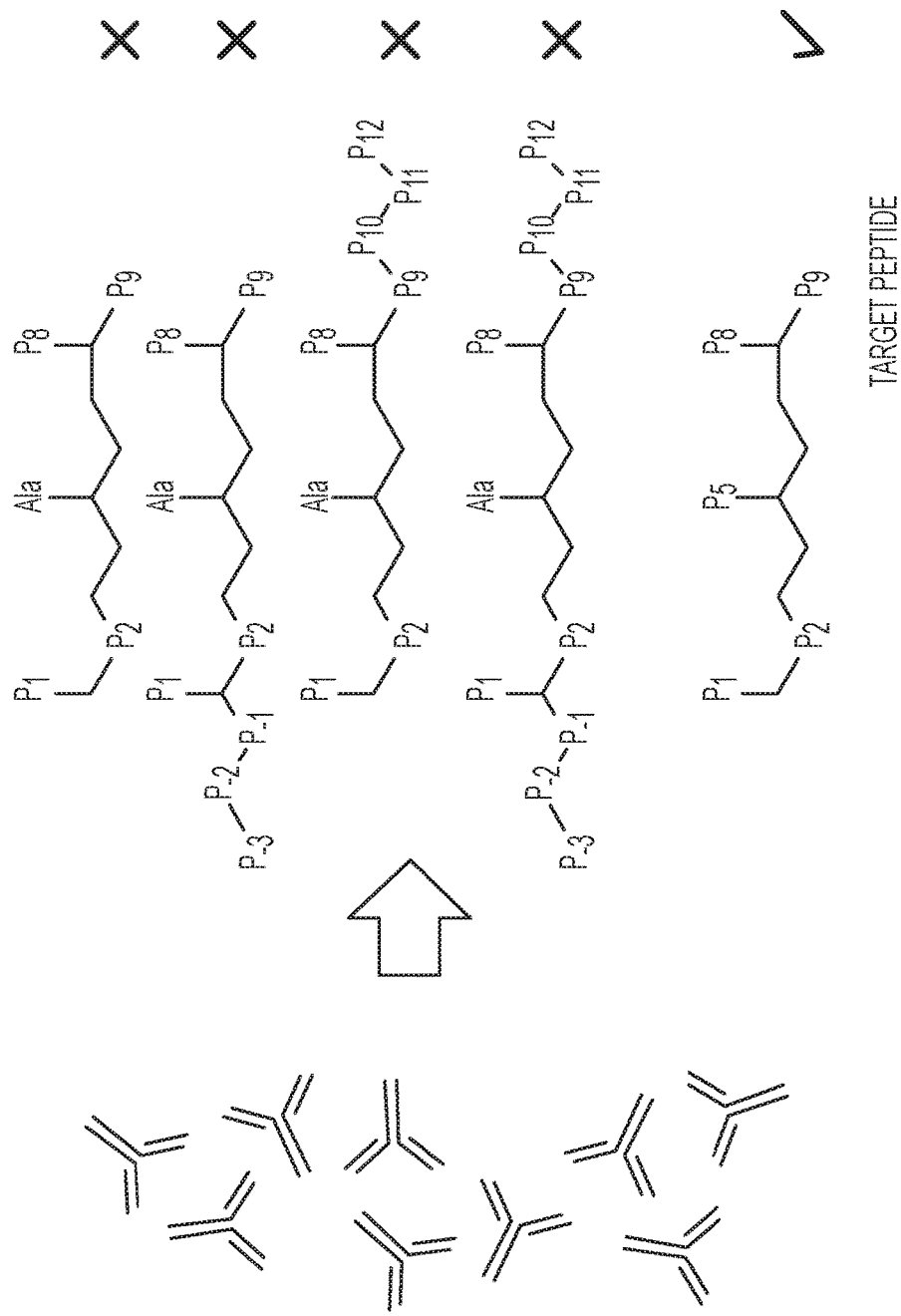
FIG. 20 shows an illustration, not to scale, of a selection strategy for generating type II TCR-like monoclonal antibodies using nonamer peptides with alanine substitutions at position 5 with native residues at the N- or C-terminus of the peptide.

Type II TCR-like monoclonal antibodies that are specific to a central epitope (at peptide position P5 when anchored at P2 and P9; see, e.g., FIGS. 19 and 20) can be efficiently generated using two selection strategies.

In a first strategy (FIG. 19), a library of candidate antibodies is first negatively selected for binding to an irrelevant peptide-MHC complex. The remaining library is then positively selected for binding to the target-peptide/MHC complex of interest. A second screening step is then utilized to distinguish Type I (antibodies that bind to the ends of the peptide), versus Type II (antibodies that bind near the center of the peptide at position P5) using Ala-substituted peptides at position P1, P5, or P8. Antibodies that lose binding only with the P1-Ala or P8-Ala substituted peptides are classified as Type I. Antibodies that lose the majority of their binding with the P5-Ala peptide are classified as Type II.

In a second strategy (FIG. 20), a library of antibodies is first negatively selected for binding to peptides with P5-Ala substitution and peptides that contain additional native flanking residues at the N- or C-terminus of the peptide. The remaining library of antibody candidates is then positively selected for binding to the wild-type target-peptide/MHC complex. The use of extended peptides ensures that only the native central epitope (centered on position P5), will be bound by the final antibody candidates.

Figure 21:
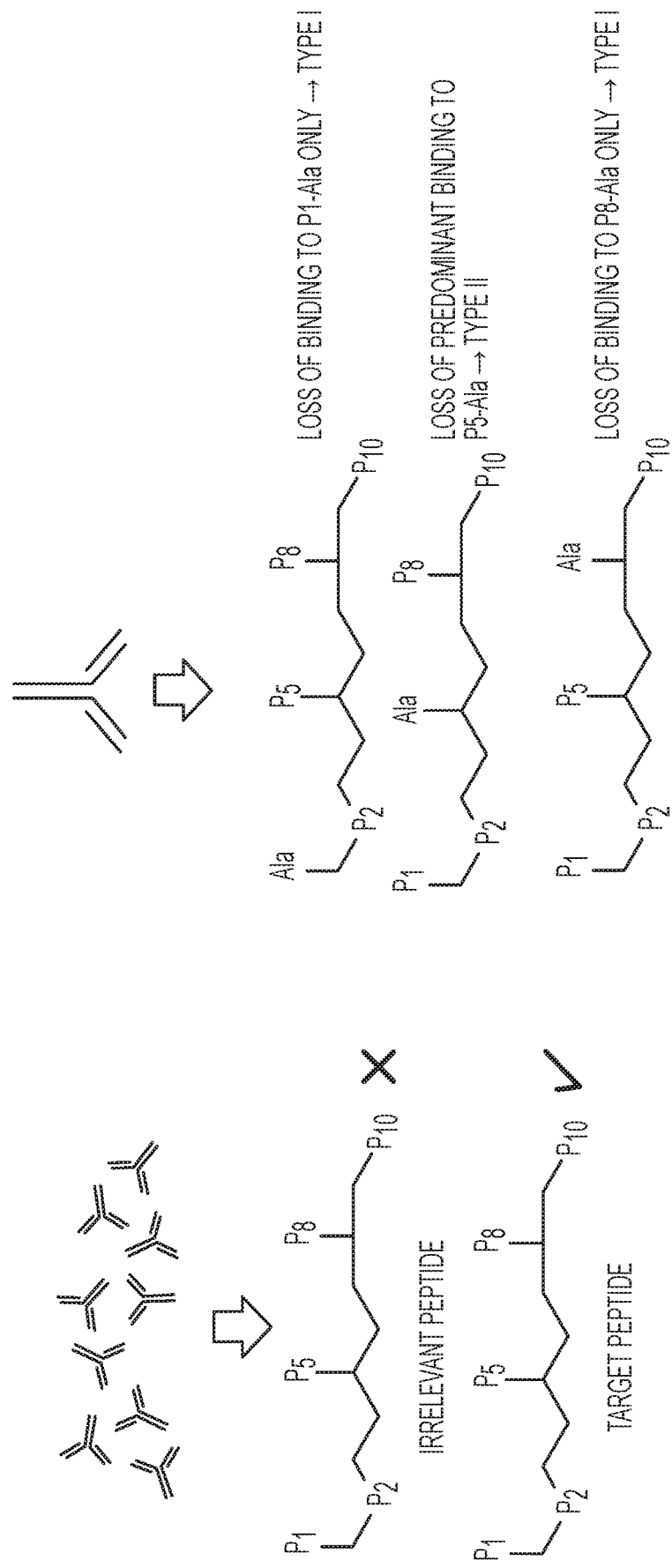
FIG. 21 shows an illustration, not to scale, of a selection strategy for generating type II TCR-like monoclonal antibodies using decamer peptides with alanine substitutions at positions 1, 5 and 8 of the peptide.
Figure 22:
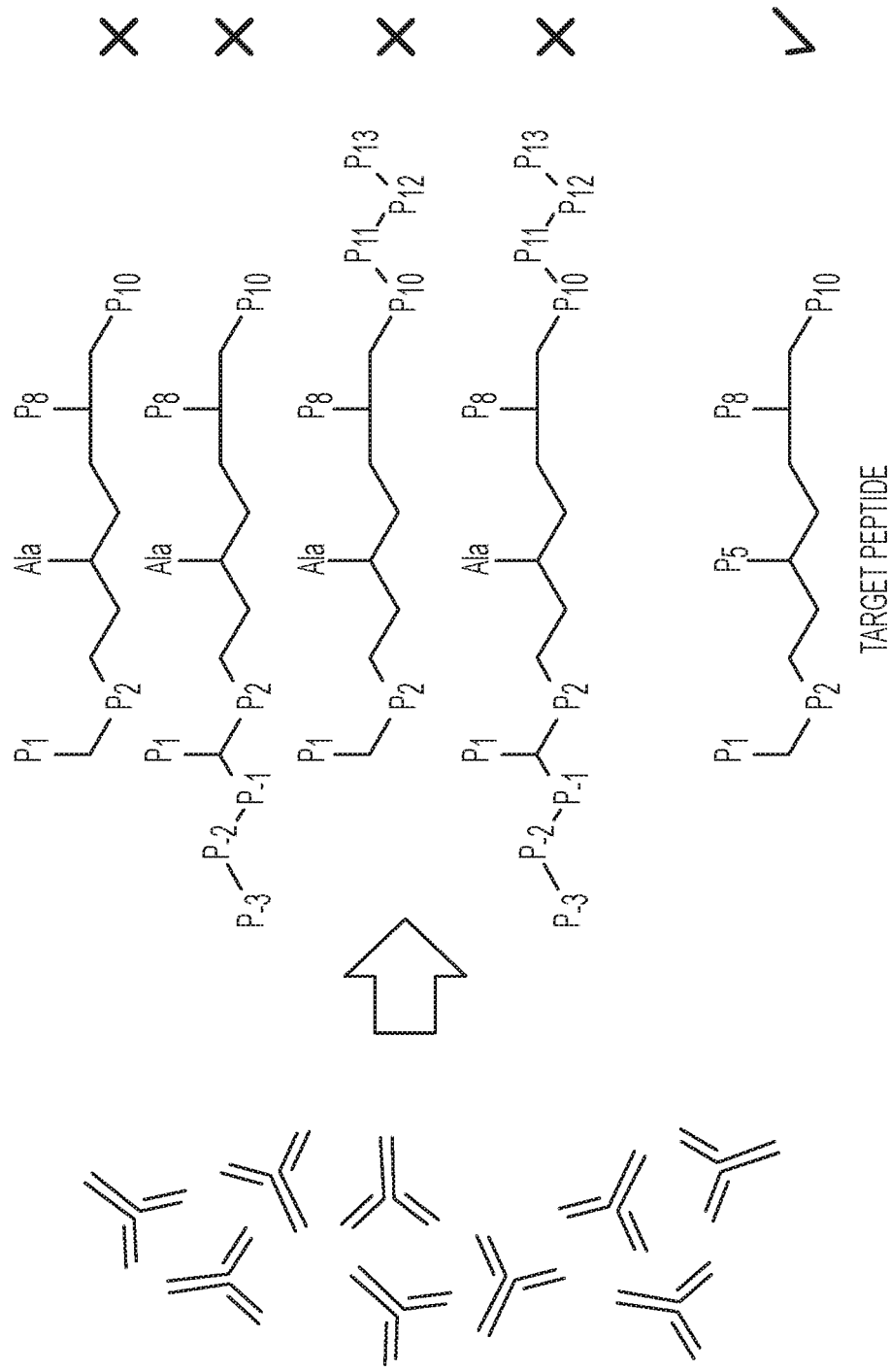
FIG. 22 shows an illustration, not to scale, of a selection strategy for generating type II TCR-like monoclonal antibodies using decamer peptides with alanine substitutions at position 5 with extra native residues at the N- or C-terminus of the peptide.

A combination of the strategies described above can also be employed. The same strategies can also utilize other non-native amino-acid substitutions other than Ala. In the case where the native sequence at P1, P5, or P8 is alanine, a different amino acid can be used. In the case where the anchor sites are P1 and P8, center position will be P(1+3)=P4, and the juxtaterminal position will be P(8-1)=P7. Strategies that can be employed for decapeptides are summarized in FIG. 21 and FIG. 22.

Example 14. Epitope Mapping of Anti-EBV-LMP2(CLG)/HLA-A*02:01 Clones

This example documents detailed binding characteristics of certain antibody agents as described herein that bind an EBV-LMP2/HLA peptide complex. Among other things, data provided in the present example confirms significance of binding, for example, to positions within a center portion of an EBV-LMP2 peptide in a peptide-MHC class I (e.g., an HLA-A02) binding pocket. Data provided herein also documents binding characteristics for certain agents that mimic one or more attributes of TCR binding. Without wishing to be bound by any particular theory, the present disclosure proposes that antibody agents that display binding characterized by inverted bell-shaped distribution of loss-of-binding to Ala-substituted positions across residues P3-P8 may be of particular interest.

Figure 23:
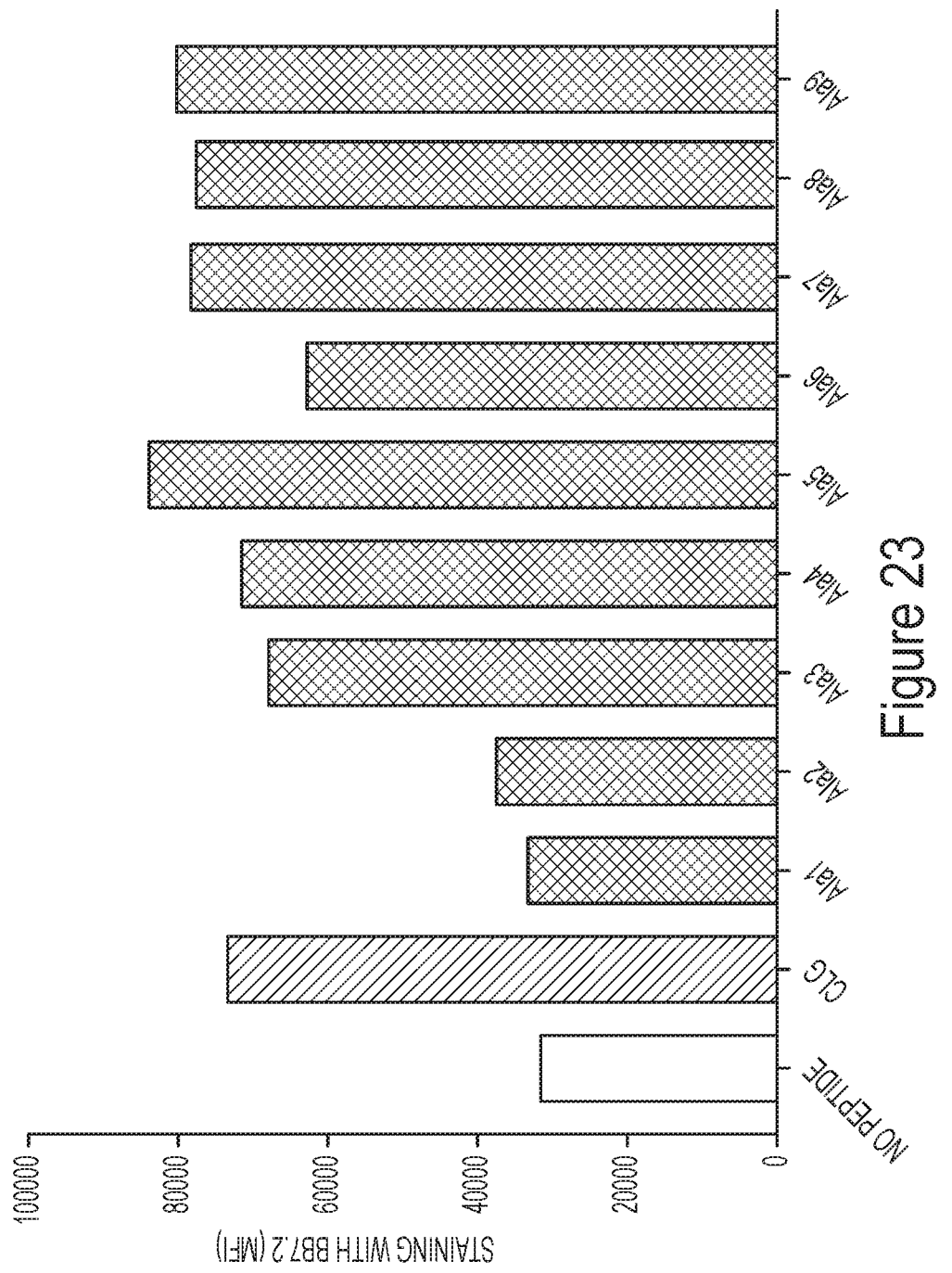
FIG. 23 shows exemplary peptide loading efficiency of Ala-substituted CLG peptides to HLA-A*02:01 as detected by flow cytometry.

In particular, the present Example describes detailed epitope mapping studies performed with full-length IgG1 antibodies as described herein that bind to EBV-LMP2 (CLG)/HLA-A*02:01 peptide complex. First, loading efficiency of EBV-LMP2(CLG) peptides with Alanine substitutions at each of positions P1, P2, P3, P4, P5, P6, P7, P8 or P9 to HLA-A*02:01 was tested (FIG. 23). T2 cells were pulsed with either the CLG wild-type peptide (SEQ ID NO: 1), or each of the P1 to P9 Ala-substituted peptides, and then stained for binding with antibody BB7.2, which shows enhanced binding to HLA-A*02:01 in the peptide-loaded state. Binding of BB7.2 was detected by flow cytometry (FIG. 23). Flow cytometry data presented in FIG. 23 shows that Ala-substitutions at positions P3-P9 are well tolerated and display comparable BB7.2 binding as the wild-type CLG peptide, whereas Ala-substitutions at positions P1 or P2 result in an inability to load onto HLA-A*02:01.

Figure 24B:
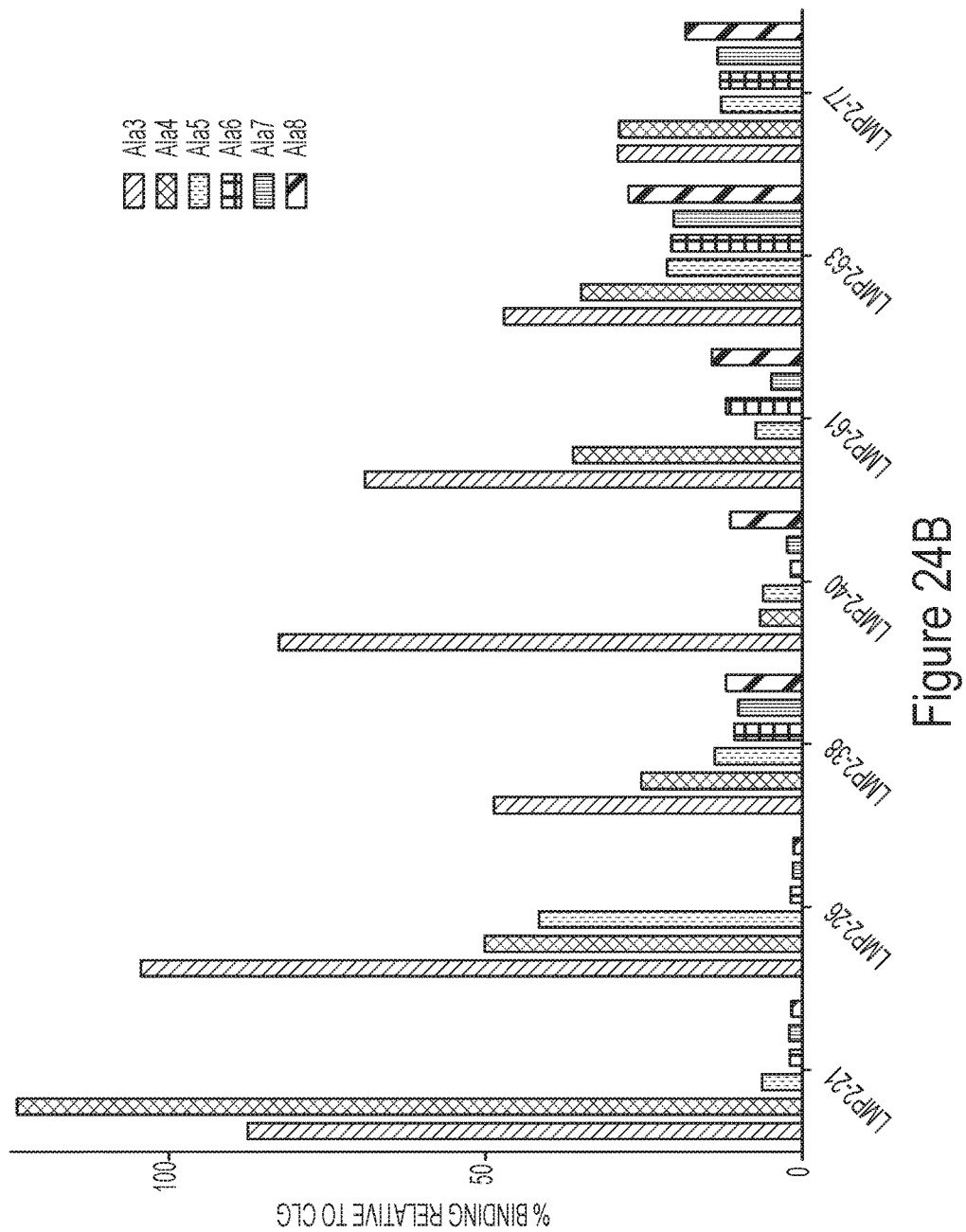

Because Ala substitution at CLG peptide positions P1 and P2 resulted in loss of loading to HLA-A*02:01, and because positions P2 and P9 are anchor residues that are buried away from T cell receptors or antibodies (as exemplified in crystal structure pdb 3REW), a detailed epitope mapping of IgG antibodies of clones 21, 26, 38, 61, 63 and 77 was performed using Ala-substituted peptides at positions P3, P4, P5, P6, P7, and P8 (FIGS. 24A and 24B). FIG. 24A shows binding of anti-EBV-LMP2(CLG)/HLA-A*02:01 IgG constructs to HLA-A*02:01 that is loaded with either wild-type CLG peptide or Ala-substituted CLG peptides at positions P3 through P8, as detected by flow cytometry. In FIG. 24B, binding of the IgG constructs to the Ala-substituted peptide/HLA-A*02:01 complex is normalized to binding of the respective IgG clone to the wild-type CLG/HLA-A*02:01 complex. Data presented in FIGS. 24A and 24B provide detailed epitope analyses, including by assessing binding to peptides with alanine substitutions at positions not tested in Example 2 and Table 10, where initial epitope mapping was performed with alanine substitutions only at CLG peptide positions P1, P5 and P8.

Data in FIG. 23 demonstrates that Ala-substitution at peptide position P1 prohibits loading onto HLA-A*02:01 and data presented in FIGS. 24A and 24B provide detailed insight into binding characteristics of tested LMP2 clones. Thus, data provided herein demonstrate and/or confirm that the high affinity LMP2-21 and LMP2-26 (which share strong sequence homology) bind predominantly to the C-terminus of the CLG peptide, and that LMP2-38 and LMP2-63 (which also share strong sequence homology) bind predominantly to the center of the CLG peptide.

Figure 2:
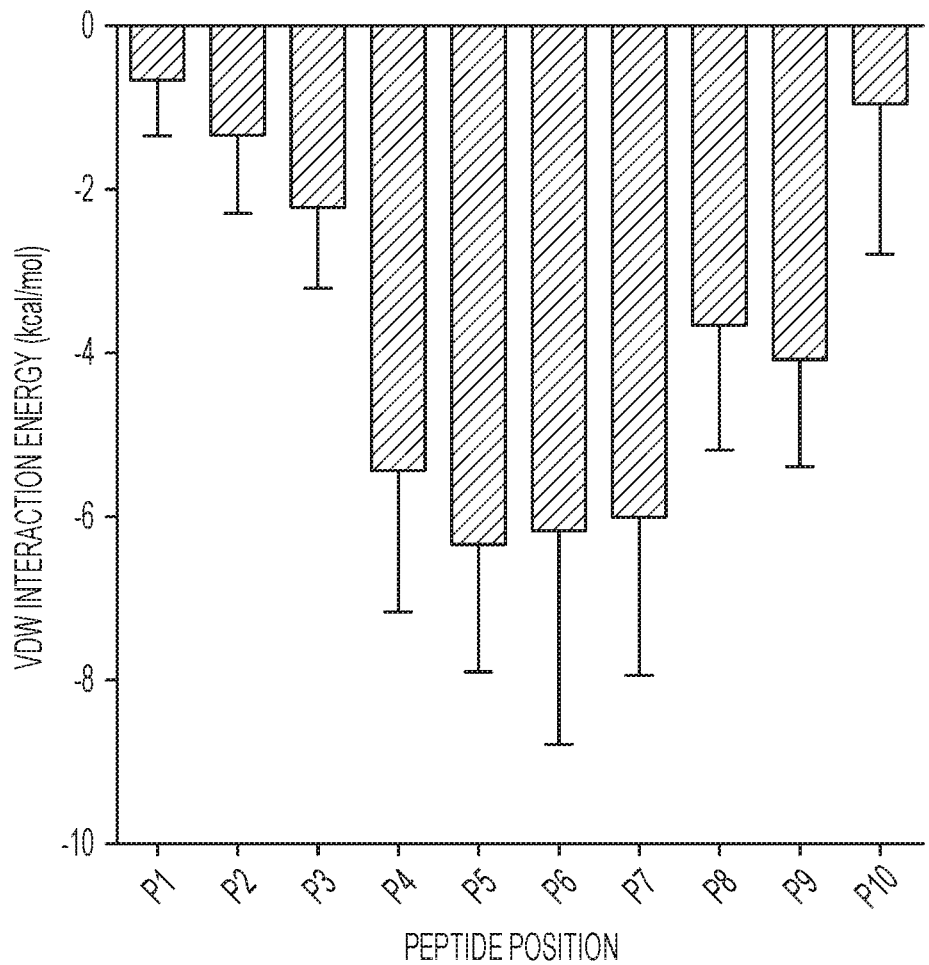
FIG. 2 shows a graph depicting average per residue van der Waals interaction energies of T cell receptor:decamer-peptide/MHC class I complexes. The peptide position (P1, P2, etc.) is indicated on the x-axis of the graph.

Importantly, the inverted bell-shaped distribution of loss-of-binding to the Ala-substituted positions across all of the residues P3-P8 for LMP2-38 and LMP2-63 is highly similar to the inverted bell shaped distribution of contact energy (van der Waals) of natural TCRs to HLA class I molecules (shown in FIG. 1). The present disclosure thus documents that various binding characteristics of LMP2-38 and LMP2-63 closely mimic a TCR. Without wishing to be bound by any particular theory, the present disclosure proposes that LMP2-38 and LMP2-63 likely bind with a similar crossing angle across the MHC class I pocket of a natural TCR. Epitope mapping data provided herein documents that LMP2-40 also binds predominantly to the center of the CLG peptide, but with a more narrow distribution than that observed for LMP2-38 and LMP2-63, centering on residues P4-P8. LMP2-61 and LMP2-77 also displayed epitopes near the center of CLG peptide, but with flatter distributions (not inverted bell shape) and with weak overall binding.

Example 15. Generation of Dimeric Bispecific Antibody Agents

This example demonstrates construction of dimeric bispecific antibodies specific for an EBV-LMP2 peptide presented by a human MHC class I molecule and CD3 in accordance with teachings provided by the present disclosure.

Without being bound to theory, it is envisioned that, in at least some embodiments, a dimerization format may stabilize and/or otherwise provide useful attributes to a bispecific (or other multispecific) antibody agent format. To mention but a few examples, in some embodiments, a dimeric bispecific format may improve and/or simplify analysis of one or more binding and/or pharmacokinetic properties, potentially at least in part due its larger size.

Five lead antibody LMP2 clones (26, 38, 38-2, 40, and 61) were selected for analysis in a dimeric bispecific format based on their binding specificity and overall affinity. The five lead antibody LMP2 clones were reformatted as dimeric bispecific antibody (DiBsAb) constructs based on the format described in Ahmed et al (2015) Oncoimmunology 4, e989776. To create dimeric BsAbs of LMP2 clones 26, 38, 38-2, 40 and 61, two changes were made to the LMP2xCD3 BsAbs described in Example 4. First, free cysteine in the anti-CD3 scFv (SEQ ID NO: 124) was mutated to serine (SEQ ID NO: 125), and a dimerization tag based on the transcription factor HNF1α and was added to the C-termini of the anti-CD3 scFv followed by a 6x-His tag (SEQ ID NO: 126).

Anti-CD3 scFv amino acid sequence with free cysteine to serine mutation (SEQ ID NO: 125)

```
Anti-CD3 scFv amino acid sequence with
free cysteine to serine mutation
                               (SEQ ID NO: 125)
DVQLVQSGAEVKKPGASVKVSCKASGYTFTRYTMEIWVRQAPGQGLEWIG

YINPSRGYTNYADSVKGRFTITTDKSTSTAYMELSSLRSEDTATYYCARY

YDDHYSLDYWGQGTTVTVSSGEGTSTGSGGSGGSGGADDIVLTQSPATLS

LSPGERATLSCRASQSVSYMNWYQQKPGKAPKRWIYDTSKVASGVPARFS

GSGSGTDYSLTINSLEAEDAATYYCQQWSSNPLTFGGGTKVEIK
```

Homodimerization tag sequence based on HNF1α (SEQ ID NO: 126)

```
Homodimerization tag sequence based on HNF1α
                                  (SEQ ID NO: 126)
RTPLGDTTHTSGMVSKLSQLQTELLAALLESGLSKEALIQALGEGSGGAP
HHHHHH
```

Figure 25:
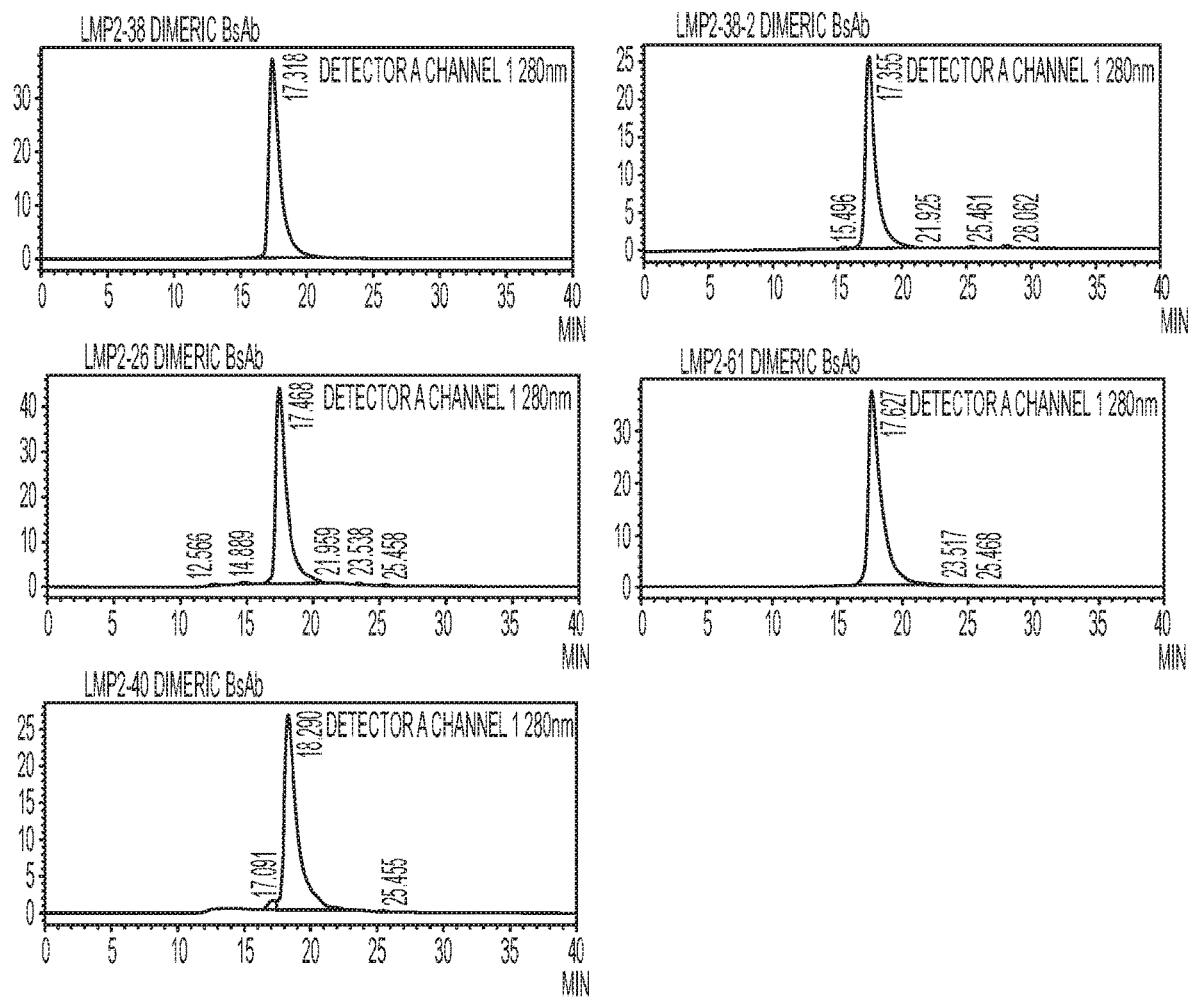
FIG. 25 shows exemplary chromatograms of dimeric bispecific antibodies from LMP2 clones 38 (top-left), 38-2 (top-right), 26 (middle-left), 61 (middle-right) and 40 (bottom-left) as an indication of the purity of these samples.

Resulting DiBsAbs were highly pure (97-100%) as shown by size exclusion chromatography data presented in FIG. 25.

Example 16. T Cell Cytotoxicity Assay of Certain Provided Antibody Agents Using Tumor Cell Lines This example demonstrates that certain antibody agents provided herein can mediate T cell cytotoxicity of tumor cells. In particular, this example specifically describes that selected EBV-LMP2(CLG)/HLA-A02xCD3 dimeric bispecific antibodies, utilized in a dimeric format as described in Example 15, mediate T cell cytotoxicity against a panel of HLA-A*02(+) EBV (+) tumor cell lines.

Figure 26:
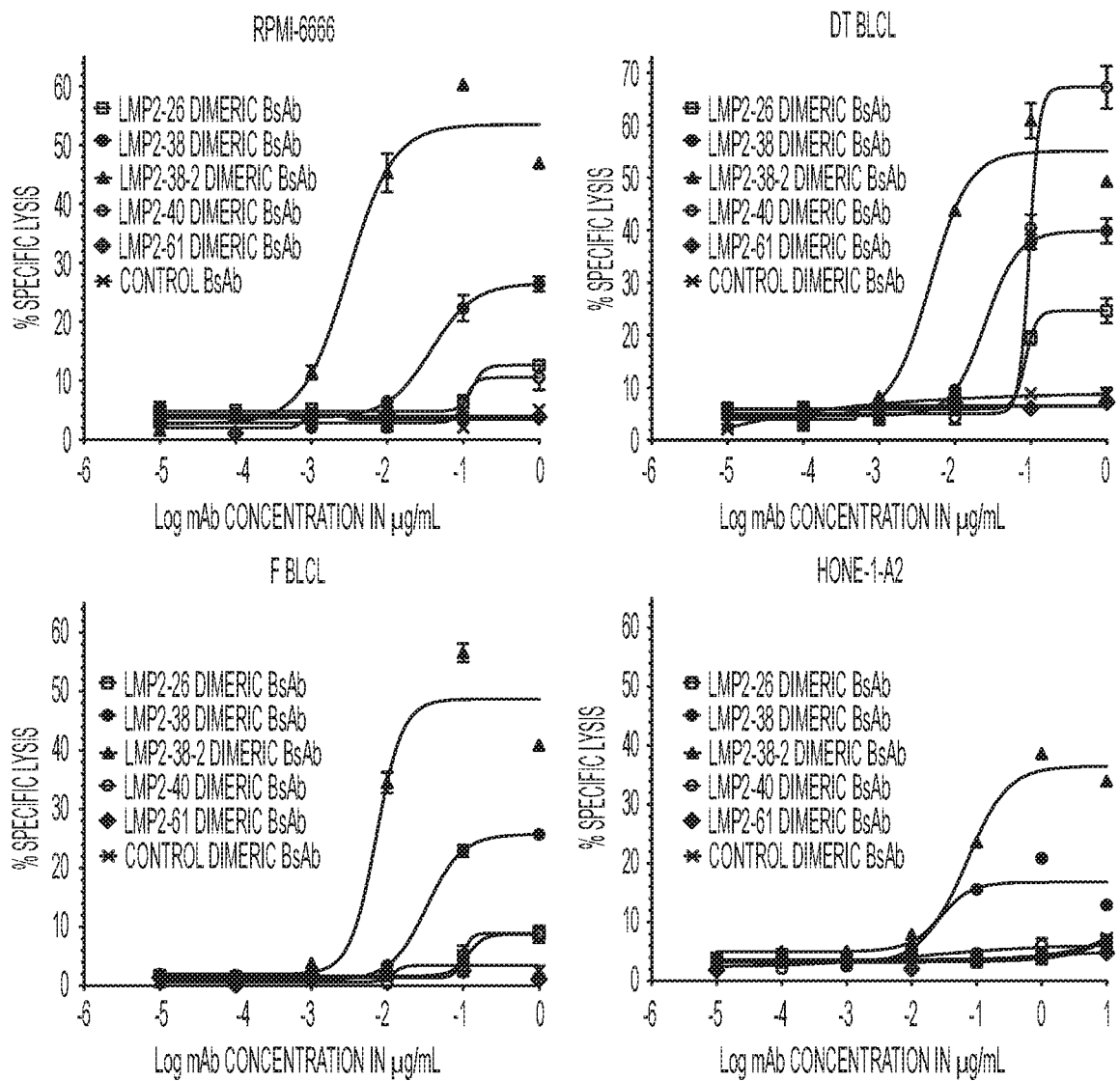
FIG. 26 shows exemplary cytotoxicity of dimeric bispecific antibodies against HLA-A*02(+) EBV (+) tumor cell lines, using cord blood T cells as effectors (10:1 ET ratio). Dimeric bispecific antibodies derived from clones 26, 28, 28-2, 40, 61 and a control were each tested and % specific lysis is shown in each of the following tumor cell lines: RPMI-6666 (top-left), DT BLCL (top-right), F BLCL (bottom-left) and HONE-1-A2 (bottom-right).

T cell dependent cytotoxicity assays of LMP2 DiBsAbs against HLA-A*02:01(+) EBV (+) tumor cell lines, including RPMI-6666 (Hodgkin's lymphoma), DT BLCL, F BLCL, HONE-1-A2 (nasopharyngeal carcinoma transfected with HLA-A*02:01) were completed. Activated cord blood T cells were used as effectors cells in a 10:1 effector-to-target ratio, and cytotoxicity was measured by $^{51}$Cr release after 4 hours of treatment (FIG. 26). LMP2-38 and LMP2-38-2 DiBsAbs displayed the highest levels of cytotoxicity against all four tumor cell lines. LMP2-26 and LMP2-61 displayed little to no cytotoxicity compared to the control BsAb. LMP-40 DiBsAb showed significant killing to the DT BLCL but not to F BLCL, RPMI-6666 or HONE-1-A2. The $EC_{50}$ and max killing data based on non-linear four parameter variable slope regression analysis (GraphPad Prism) is shown in Table 14. LMP2-38-2 DiBsAb had EC50 values of 0.003-0.07 g/mL and max killing of 37-55%, and LMP2-38 DiBsAb had $EC_{50}$ values of 0.02-0.04 μg/mL and max killing of 17-40%. Table 14 describes in vitro cytotoxicity results obtained with LMP2 dimeric BsAbs. "nd" indicates "not determined" by non-linear regression analysis due to poor curve fit.

T cell dependent cytotoxicity assays of LMP2 dimeric BsAbs were also done against antigen negative tumor cell lines, including HLA-A*02(−) EBV (+) tumor cell line KS BLCL and HLA-A*02(+) EBV(−) tumor cell lines COLO205 (colorectal cancer), MCF-7 (breast cancer), and HepG2 (hepatocellular cancer), using cord blood T cells as effectors. No substantial killing was observed compared to the control BsAb.

Example 17. Mouse Xenograft Studies of Certain Antibody Agents as Described Herein This example demonstrates in vivo efficacy of two exemplary bispecific antibody agents as described herein. In particular, this example specifically demonstrates that selected EBV-LMP2(CLG)/HLA-A02xCD3 bispecific antibodies (assessed in a dimeric format) are highly effective at reducing tumor growth and survival in a mouse xenograft model.

Figure 27:
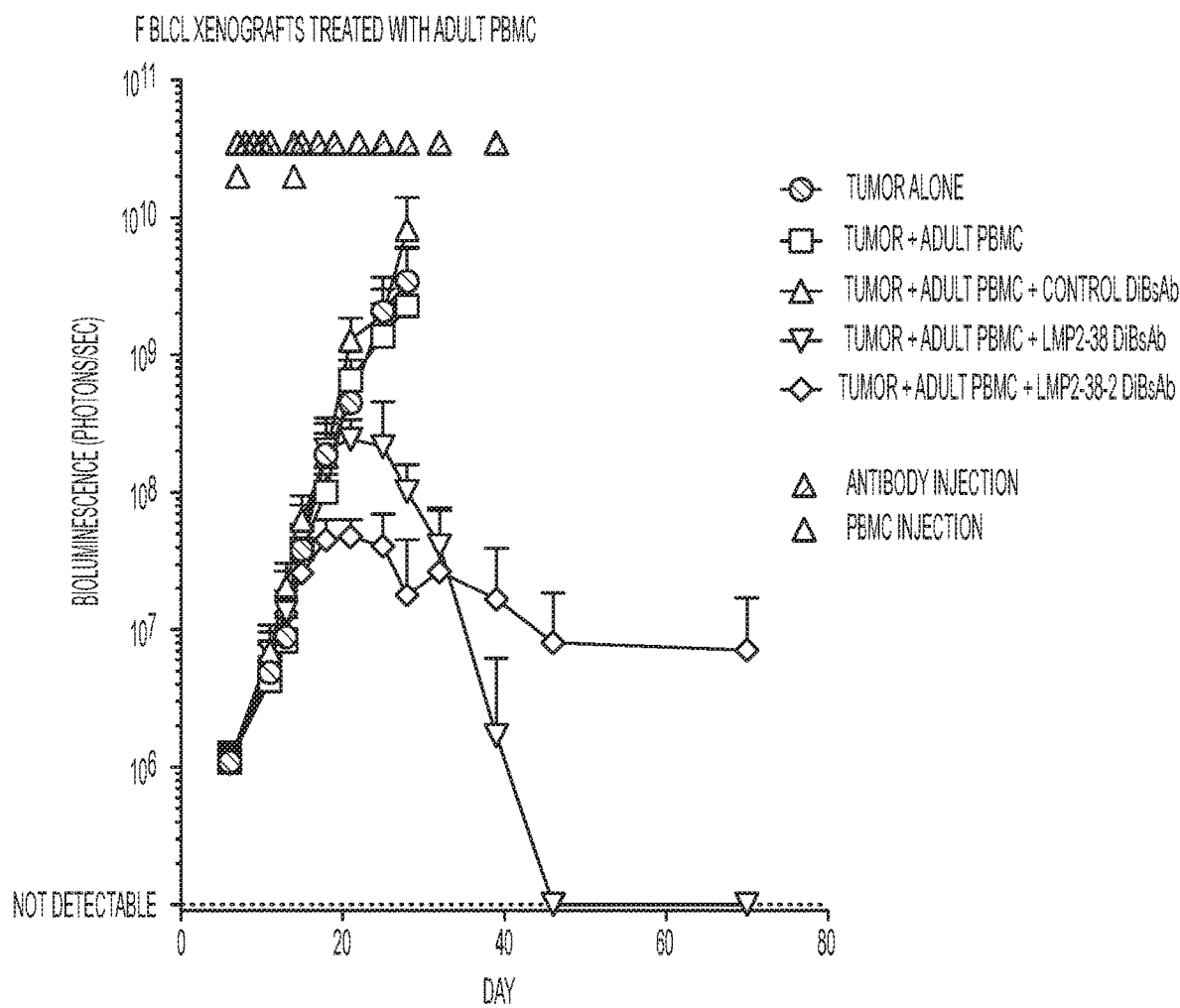
FIG. 27 shows exemplary tumor quantification data from a mouse xenograft study where immunodeficient mice were implanted with F BLCL and treated with LMP2 dimeric bispecific antibodies and human adult PBMC effector cells.

LMP-38 and LMP2-38-2 candidates, which, as documented herein, showed potent in vitro activit(ies) were tested in a dimeric bispecific format in described herein in mouse xenograft studies. In a first study, immunodeficient DKO mice (5 mice per group) were implanted with 1×10$^6$ F BLCL (with luciferase reporter gene) intravenously and then treated with two doses of intravenous injections of 10×10$^6$ million human adult PBMC at Day 7 (50% T cells) and Day 14 (50% T cells). 20 μg injections of either control DiBsAb, LMP2-38 DiBsAb or LMP2-38-2 DiBsAb were given at Days 7, 8, 9, 10, 11, 14, 15, 17, 19, 22, 25, 28, 32, and 39. Tumor growth was monitored by bioluminescence; results are shown in FIG. 27. As can be seen, luminescence signal of the non-treatment groups saturated after Day 28. Bioluminescence at Day 28 is shown in Table 15. LMP2-38 and LMP2-38-2 DiBsAbs were highly effective at reducing tumor growth (98.8% and 99.8% reduction compared to a control DiBsAb, respectively). Table 15 includes results from bioluminescence quantitation at day 28 of immunodeficient mice implanted with F BLCL and treated with human adult PBMC and LMP2 DiBsAbs.

TABLE 14

|  |  | LMP2-26 Dimeric BsAb | LMP2-38 Dimeric BsAb | LMP2-38-2 Dimeric BsAb | LMP2-40 Dimeric BsAb | LMP2-61 Dimeric BsAb | Control BsAb |
|---|---|---|---|---|---|---|---|
| RPMI-6666 | % Max Killing | 12.6 | 26.5 | 53.5 | 10.6 | 3.9 | 4.1 |
|  | EC50 (μg/mL) | nd | 3.7E−02 | 3.0E−03 | nd | nd | nd |
| DT BLCL | % Max Killing | 24.7 | 39.9 | 55.1 | 67.3 | 6.5 | 9.2 |
|  | EC50 (μg/mL) | nd | 2.5E−02 | 4.7E−03 | nd | nd | nd |
| F BLCL | % Max Killing | 8.8 | 25.8 | 48.7 | 8.9 | nd | 3.5 |
|  | EC50 (μg/mL) | nd | 3.3E−02 | 7.2E−03 | nd | nd | nd |
| HONE-1-A2 | % Max Killing | nd | 16.8 | 36.5 | 6.3 | 4.9 | nd |
|  | EC50 (μg/mL) | nd | 2.4E−02 | 7.4E−02 | 1.4E−02 | 1.2E+00 | nd |

TABLE 15

| Groups | Avg. Bioluminescence at Day 28 (photons/sec) | Standard Deviation | % change, compared to Group 3 | p value, compared to Group 3 |
|---|---|---|---|---|
| 1. Tumor Alone | 3.44E+09 | 2.73E+09 | — | — |
| 2. Tumor + Adult PBMC | 2.28E+09 | 3.73E+09 | — | — |
| 3. Tumor + Adult PBMC + Control BsAb | 8.24E+09 | 5.83E+09 | — | — |
| 4. Tumor + Adult PBMC + LMP2-38 DiBsAb | 1.02E+08 | 5.73E+07 | −98.8% | 0.03 |
| 5. Tumor + Adult PBMC + LMP2-38-2 DiBsAb | 1.79E+07 | 2.77E+07 | −99.8% | 0.01 |

Figure 28:
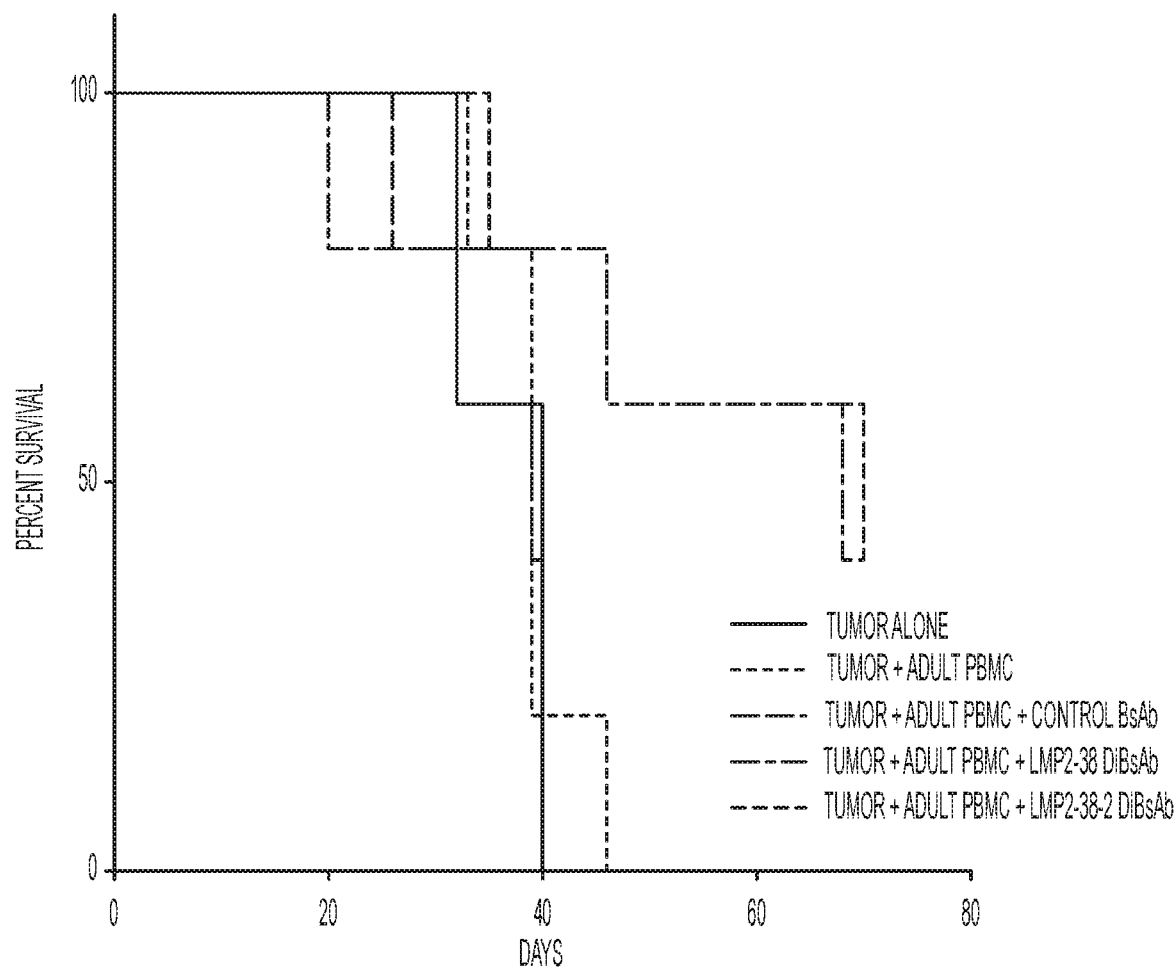
FIG. 28 shows exemplary survival data from a mouse xenograft study where immunodeficient mice were implanted with F BLCL and treated with LMP2 dimeric bispecific antibodies and human adult PBMC effector cells.

Survival data are shown in FIG. 28. Significant improvement in survival was observed for both the LMP2-38 DiBsAb group (p=0.04) and the LMP2-38-2 DiBsAb group (p=0.03).

Figure 29:
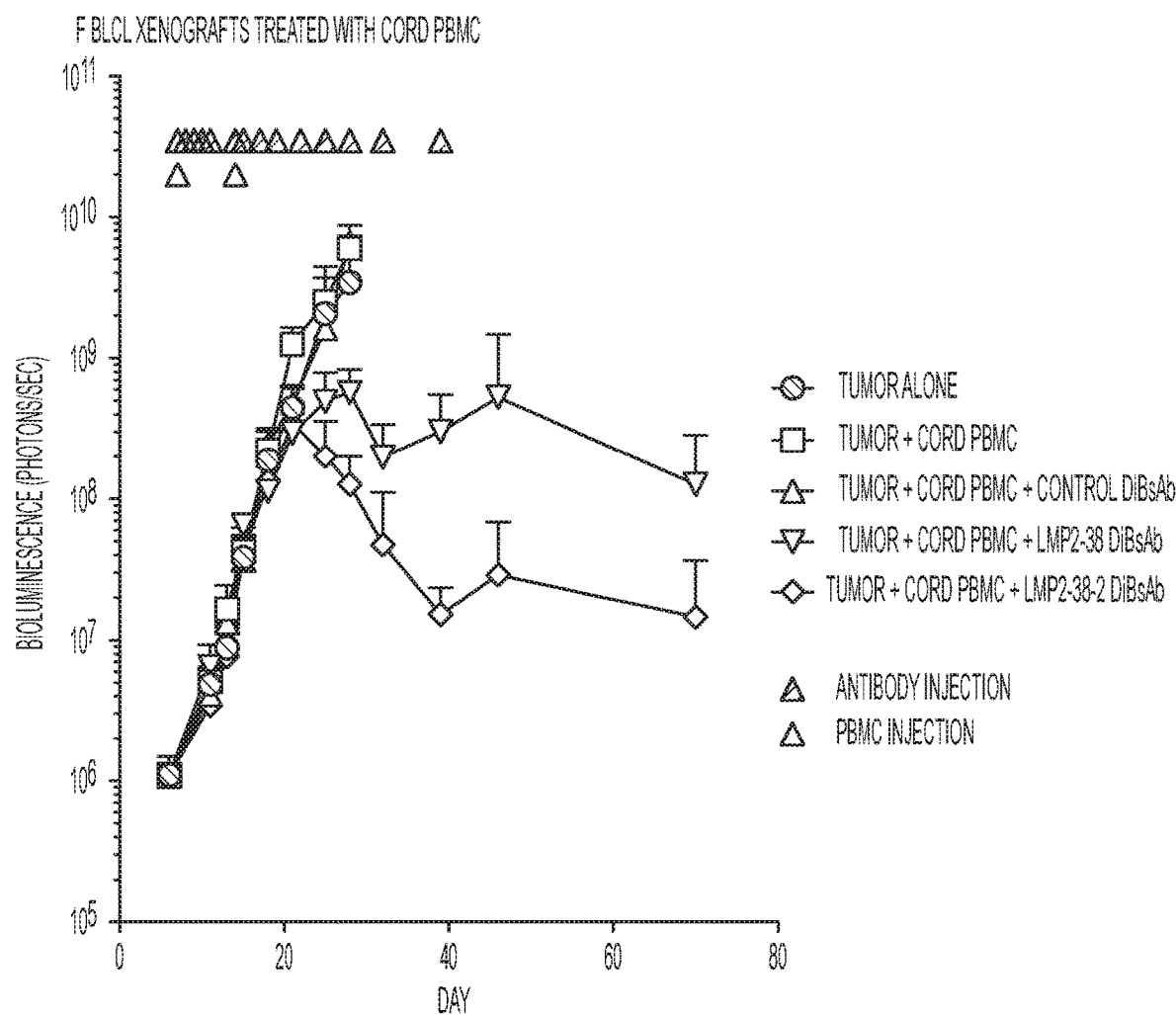
FIG. 29 shows exemplary tumor quantification data from a mouse xenograft study where immunodeficient mice were implanted with F BLCL and treated with LMP2 dimeric bispecific antibodies and human cord blood PBMC effector cells.

In a second study, immunodeficient DKO mice (5 mice per group) were implanted with $1\times10^6$ F BLCL (with luciferase reporter gene) intravenously and then treated with two doses of intravenous injections of $10\times10^6$ million human cord blood PBMC at Day 7 (20% T cells) and Day 14 (50% T cells). 20 µg injections of either control DiBsAb, LMP2-38 DiBsAb, or LMP2-38-2 DiBsAb were given at Days 7, 8, 9, 10, 11, 14, 15, 17, 19, 22, 25, 28, 32, and 39. Tumor growth was monitored by bioluminescence and shown in FIG. 29. Luminescence signal of the non-treatment groups saturated after Day 28, and the bioluminescence at Day 28 is shown in Table 16. LMP2-38 and LMP2-38-2 DiBsAbs were highly effective at reducing tumor growth (91.2% and 98.1% reduction compared to a control DiBsAb, respectively). Table 16 describes the bioluminescence quantitation at day 28 of immunodeficient mice implanted with F BLCL and treated with human cord blood PBMC and LMP2 DiBsAbs.

TABLE 16

| Groups | Avg. Bioluminescence at Day 28 (photons/sec) | Standard Deviation | % change, compared to Group 3 | p value, compared to Group 3 |
|---|---|---|---|---|
| 1. Tumor Alone | 3.44E+09 | 2.73E+09 | | |
| 2. Tumor + Cord PBMC | 5.97E+09 | 1.41E+09 | | |
| 3. Tumor + Cord PBMC + Control BsAb | 6.52E+09 | 2.22E+09 | | |
| 4. Tumor + Cord PBMC + LMP2-38 DiBsAb | 5.75E+08 | 2.59E+08 | −91.2% | <0.001 |
| 5. Tumor + Cord PBMC + LMP2-38-2 DiBsAb | 1.27E+08 | 7.40E+07 | −98.1% | <0.001 |

Figure 30:
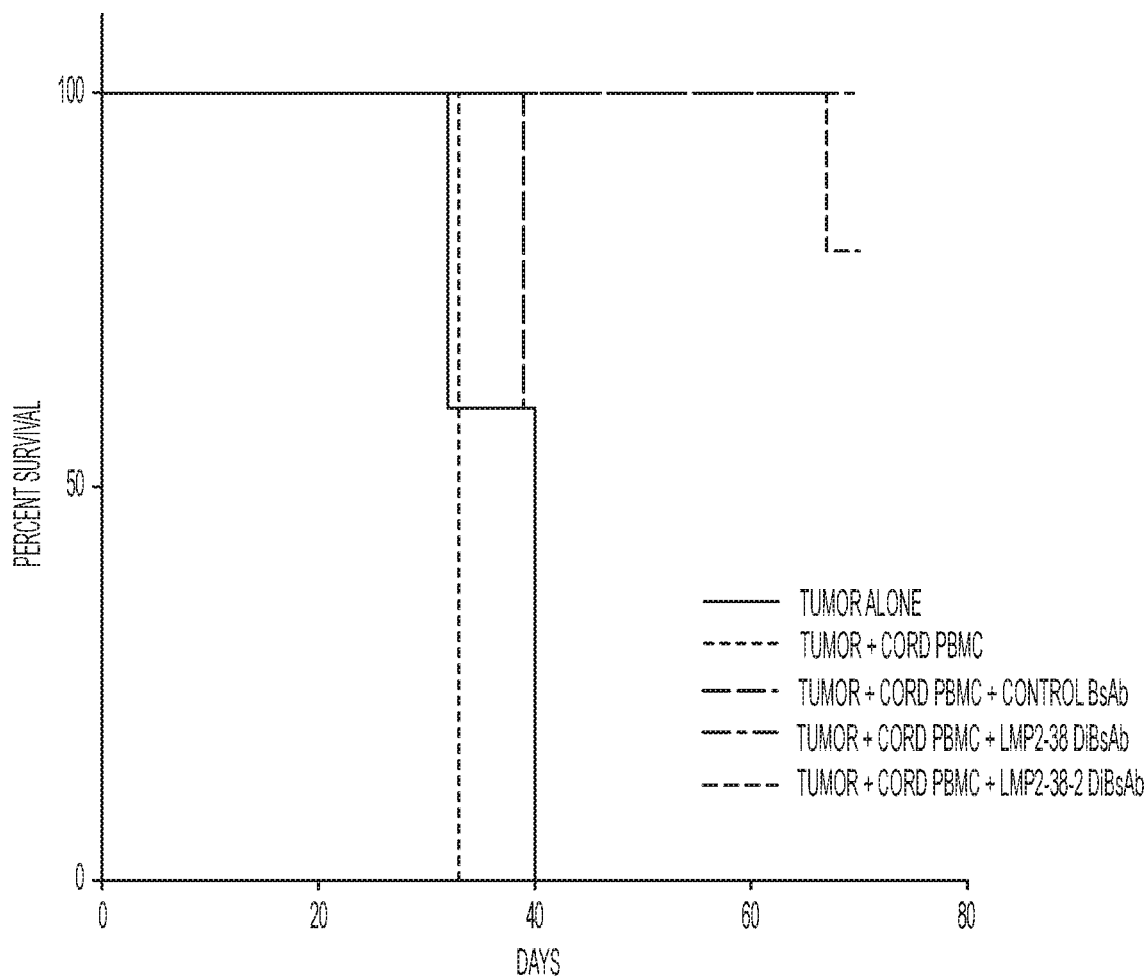
FIG. 30 shows exemplary survival data from a mouse xenograft study where immunodeficient mice were implanted with F BLCL and treated with LMP2 dimeric bispecific antibodies and human cord blood PBMC effector cells.

Survival data are shown in FIG. 30. As can be seen, significant improvement in survival was observed for both the LMP2-38 DiBsAb group (p=0.003) and the LMP2-38-2 DiBsAb group (p=0.003).

REFERENCES

Coghill A E, Hildesheim A: Epstein-Barr virus antibodies and the risk of associated malignancies: review of the literature, Am. J. Epidemiol. 180:687-95, 2014

Hislop A D, Taylor G S, Sauce D, et al.: Cellular responses to viral infection in humans: lessons from Epstein-Barr virus, Annu. Rev. Immunol. 25:587-617, 2007

Long H M, Leese A M, Chagoury O L, et al.: Cytotoxic CD4+ T cell responses to EBV contrast with CD8 responses in breadth of lytic cycle antigen choice and in lytic cycle recognition, J. Immunol. 187:92-101, 2011

Tsao S W, Tsang C M, To K F, et al.: The role of Epstein-Barr virus in epithelial malignancies, J. Pathol. 235:323-33, 2015

Rasche L, Kapp M, Einsele H, et al.: EBV-induced post transplant lymphoproliferative disorders: a persisting challenge in allogeneic hematopoetic SCT, Bone Marrow Transplant 49:163-7, 2014

Bollard C M, Rooney C M, Heslop H E: T-cell therapy in the treatment of post-transplant lymphoproliferative disease, Nat. Rev. Clin. Oncol. 9:510-9, 2012

Glaser S L, Lin R J, Stewart S L, et al.: Epstein-Barr virus-associated Hodgkin's disease: epidemiologic characteristics in international data, Int. J. Cancer 70:375-82, 1997

Shanmugaratnam K: Histological typing of nasopharyngeal carcinoma, IARC Sci Publ:3-12, 1978

Menezes J, Leibold W, Klein G, et al.: Establishment and characterization of an Epstein-Barr virus (EBC)-negative lymphoblastoid B cell line (BJA-B) from an exceptional, EBV-genome-negative African Burkitt's lymphoma, Biomedicine 22:276-84, 1975

Haigh T A, Lin X, Jia H, et al.: EBV latent membrane proteins (LMPs) 1 and 2 as immunotherapeutic targets: LMP-specific CD4+ cytotoxic T cell recognition of EBV-transformed B cell lines, J. Immunol. 180:1643-54, 2008

Long H M, Taylor G S, Rickinson A B: Immune defense against EBV and EBV-associated disease, Curr. Opin. Immunol. 23:258-64, 2011

Ning R J, Xu X Q, Chan K H, et al.: Long-term carriers generate Epstein-Barr virus (EBV)-specific CD4(+) and CD8(+) polyfunctional T-cell responses which show immunodominance hierarchies of EBV proteins, Immunology 134:161-71, 2011

Lutzky V P, Corban M, Heslop L, et al.: Novel approach to the formulation of an Epstein-Barr virus antigen-based nasopharyngeal carcinoma vaccine, J. Virol. 84:407-17, 2010

Louis C U, Straathof K, Bollard C M, et al.: Adoptive transfer of EBV-specific T cells results in sustained clinical responses in patients with locoregional nasopharyngeal carcinoma, J. Immunother. 33:983-90, 2010

Cheung W H, Chan V S, Pang H W, et al.: Conjugation of latent membrane protein (LMP)-2 epitope to gold nanoparticles as highly immunogenic multiple antigenic peptides for induction of Epstein-Barr virus-specific cytotoxic T-lymphocyte responses in vitro, Bioconjug. Chem. 20:24-31, 2009

Weidanz J A, Hawkins O, Verma B, et al.: TCR-like biomolecules target peptide/MHC Class I complexes on the surface of infected and cancerous cells, Int. Rev. Immunol. 30:328-40, 2011

Sim A C, Too C T, Oo M Z, et al.: Defining the expression hierarchy of latent T-cell epitopes in Epstein-Barr virus infection with TCR-like antibodies, Sci. Rep. 3:3232, 2013

Dahan R, Reiter Y: T-cell-receptor-like antibodies—generation, function and applications, Expert Rev. Mol. Med. 14:e6, 2012

Denkberg G, Cohen C J, Lev A, et al.: Direct visualization of distinct T cell epitopes derived from a melanoma tumor-associated antigen by using human recombinant antibodies with MHC-restricted T cell receptor-like specificity, Proc. Natl. Acad. Sci. U.S.A. 99:9421-6, 2002

Sergeeva A, Alatrash G, He H, et al.: An anti-PR1/HLA-A2 T-cell receptor-like antibody mediates complement-dependent cytotoxicity against acute myeloid leukemia progenitor cells, Blood 117:4262-72, 2011

Tassev D V, Cheng M, Cheung N K: Retargeting N K92 cells using an HLA-A2-restricted, EBNA3C-specific chimeric antigen receptor, Cancer Gene Ther. 19:84-100, 2012

Dao T, Yan S, Veomett N, et al.: Targeting the Intracellular WT1 Oncogene Product with a Therapeutic Human Antibody, Sci. Transl. Med. 5:176ra33, 2013

Townsend A, Bodmer H: Antigen Recognition by Class I-Restricted T Lymphocytes, Ann. Rev. Immunol. 7:601-24, 1989

Rudolph M G, Stanfield R L, Wilson I A: How TCRs bind MHCs, peptides, and coreceptors, Ann. Rev. Immunol. 24:419-466, 2005

Parker K C, Bednarek M A, Hull L K, et al.: Sequence motifs important for peptide binding to the human MHC class I molecule, HLA-A2, J. Immunol. 149:3580-7, 1992

Rudolph M G, Wilson I A: The specificity of TCR/pMHC interaction, Curr. Opin. Immunol. 14(1):52-65, 2002

Massimo D, Garcia K C, Vasso A, et al.: A Functional Hot Spot for Antigen Recognition in a Superagonist TCR/MHC Complex, Immunity 12:251-261, 2000

Reali E, Guerrini R, Marastoni M, et al.: A single specific amino acid residue in peptide antigens is sufficient to activate memory CTL: potential role of cross-reactive peptides in memory T cell maintenance, J. Immunol. 162:106-113, 1999

Liddy N, Bossi G, Adams K J, et al.: Monoclonal TCR-redirected tumor cell killing, Nat. Med. 18:980-987, 2012

Andersen P S, Stryhn A, Hansen B E, et al.: A recombinant antibody with the antigen-specific, major histocompatibility complex-restricted specificity of T cells, Proc. Natl. Acad. Sci. U.S.A. 93:1820-4, 1996

Willemsen R A, Debets R, Hart E, Hoogenboom H R, Bolhuis R L, Chames P: A phage display selected Fab fragment with MHC class I-restricted specificity for MAGE-A1 allows for retargeting of primary human T lymphocytes, Gene Ther. 8(21):1601-8, 2001

Low J L, Naidoo A, Yeo G, Gehring A J, Ho Z Z, Yau Y H, Shochat S G, Kranz D M, Bertoletti A, Grotenbreg G M: Binding of TCR Multimers and a TCR-Like Antibody with Distinct Fine-Specificities Is Dependent on the Surface Density of HLA Complexes, PLOS ONE 7(12): e51397, Miller K R, Koide A, Leung B, Fitzsimmons J, Yoder B, Yuan H, Jay M, Sidhu S S, Koide S, Collins E J: T Cell Receptor-Like Recognition of Tumor In Vivo by Synthetic Antibody Fragment, PLOS ONE 7(8):e43746, 2012

Biddison W E, Turner R V, Gagnon S J, et al.: Tax and M1 Peptide/HLA-A2-Specific Fabs and T Cell Receptors Recognize Nonidentical Structural Features on Peptide/HLA-A2 Complexes, J. Immunol. 171(6):3064-74, 2003

Cohen C J, Hoffmann N, Farago M, et al.: Direct Detection and Quantitation of a Distinct T-Cell Epitope Derived from Tumor-specific Epithelial Cell-associated Mucin Using Human Recombinant Antibodies Endowed with the Antigen-specific, Major Histocompatibility Complex-restricted Specificity of T Cells, Cancer Res. 62(20):5835-44, 2002

Cohen C J, Sarig O, Yamano Y, et al.: Direct Phenotypic Analysis of Human MHC Class I Antigen Presentation: Visualization, Quantitation, and In Situ Detection of Human Viral Epitopes Using Peptide-Specific, MHC-Restricted Human Recombinant Antibodies, J. Immunol. 170(8):4349-61, 2003

Dao T, Yan S, Veomett N, et al.: Targeting the Intracellular WT1 Oncogene Product with a Therapeutic Human Antibody, Sci. Transl. Med. 5(176):176ra33, 2013

Denkberg G, Cohen C J, Lev A, et al.: Direct visualization of distinct T cell epitopes derived from a melanoma tumor-associated antigen by using human recombinant antibodies with MHC-restricted T cell receptor-like specificity, Proc. Natl. Acad. Sci. U.S.A. 99(14):9421-6, 2002

Epel M, Carmi I, Soueid-Baumgarten S, et al.: Targeting TARP, a novel breast and prostate tumor-associated antigen, with T-cell receptor-like human recombinant antibodies, Eur. J. Immunol. 38:1706-20, 2008

Zhang G, Wang L I, Cui H, Wang X, Zhang G, Ma J, Han H, He W, Wang W, Zhao Y, Liu C, Sun M, Gao B: Anti-melanoma activity of T cells redirected with a TCR-like chimeric antigen receptor, Scientific Reports 4:3571, 2014

Klechevsky E, Gallegos M, Denkberg G, et al.: Antitumor activity of immunotoxins with T-cell receptor-like specificity against human melanoma xenografts, Cancer Res. 68(15):6360-7, 2008

Oren R, Hod-Marco M, Haus-Cohen M, et al.: Functional comparison of engineered T cells carrying a native TCR versus TCR-like antibody-based chimeric antigen receptors indicates affinity/avidity thresholds, J. Immunol. 193 (11):5733-43, 2014

Sergeeva A, Alatrash G, He H, et al.: An anti-PR1/HLA-A2 T-cell receptor-like antibody mediates complement-dependent cytotoxicity against acute myeloid leukemia progenitor cells, Blood 117(16):4262-72, 2011

Stewart-Jones G, Wadle A, Hombach A, et al.: Rational development of high-affinity T-cell receptor-like antibodies, Proc. Natl. Acad. Sci. U.S.A. 106(14):5784-8, 2009

Verma B, Jain R, Caseltine S, et al.: TCR Mimic Monoclonal Antibodies Induce Apoptosis of Tumor Cells via Immune Effector-Independent Mechanisms, J. Immunol. 186(5): 3265-76, 2011

Weidanz J A, Nguyen T, Woodburn T, et al.: Levels of Specific Peptide-HLA Class I Complex Predicts Tumor Cell Susceptibility to CTL Killing, J. Immunol. 177(8): 5088-97, 2006

Ziegler A, Coulie P G, Uchanska-Ziegler B: Monoclonal and recombinant antibodies with T cell receptor-like reactivity, Recent Results Cancer Res. 176:229-41, 2007

Oren R, Hod-Marco M, Haus-Cohen M, et al.: Functional comparison of engineered T cells carrying a native TCR versus TCR-like antibody-based chimeric antigen receptors indicates affinity/avidity thresholds, J. Immunol. 193: 5733-43, 2014

Scott R B, Jamie R, James M: Have we cut ourselves too short in mapping CTL epitopes?Trends in Immunology 27:11-16, 2006

Stewart-Jones G B, McMichael A J, Bell J I, et al.: A structural basis for immunodominant human T cell receptor recognition, Nat. Immunol. 4:657-63, 2003

Garboczi D N, Ghosh P, Utz U, et al.: Structure of the complex between human T-cell receptor, viral peptide and HLA-A2, Nature 384:134-41, 1996

Ding Y H, Smith K J, Garboczi D N, et al.: Two human T cell receptors bind in a similar diagonal mode to the HLA-A2/Tax peptide complex using different TCR amino acids, Immunity 8:403-11, 1998

Chen J L, Stewart-Jones G, Bossi G, et al.: Structural and kinetic basis for heightened immunogenicity of T cell vaccines, J. Exp. Med. 201:1243-55, 2005

Borbulevych O Y, Piepenbrink K H, Gloor B E, et al.: T cell receptor cross-reactivity directed by antigen-dependent tuning of peptide-MHC molecular flexibility, Immunity 31:885-96, 2009

Borbulevych O Y, Piepenbrink K H, Baker B M: Conformational melding permits a conserved binding geometry in TCR recognition of foreign and self-molecular mimics, J. Immunol. 186:2950-8, 2011

Gras S, Saulquin X, Reiser J B, et al.: Structural bases for the affinity-driven selection of a public TCR against a dominant human cytomegalovirus epitope, J. Immunol. 183: 430-7, 2009

Simpson A A, Mohammed F, Salim M et al.: Structural and energetic evidence for highly peptide-specific tumor antigen targeting via allo-MHC restriction, Proc. Natl. Acad. Sci. U.S.A. 108(52):21176-81, 2011

Altman J D, Davis M M: MHC-peptide tetramers to visualize antigen-specific T cells, Curr. Protoc. Immunol. Chapter 17:Unit 17 3, 2003

Tomimatsu K, Matsumoto S E, Yamashita M, et al.: Production of human monoclonal antibodies against Fc(epsilon)RI(alpha) by a method combining in vitro immunization with phage display, Biosci. Biotechnol. Biochem. 73:1465-9, 2009

Brischwein K, Schlereth B, Guller B, et al.: MT110: a novel bispecific single-chain antibody construct with high efficacy in eradicating established tumors, Mol. Immunol. 43:1129-43, 2006

Madden D R, Garboczi D N, Wiley DC: The antigenic identity of peptide-MHC complexes: a comparison of the conformations of five viral peptides presented by HLA-A2, Cell 75:693-708, 1993

Thorpe I F, Brooks C L, 3rd: Molecular evolution of affinity and flexibility in the immune system, Proc. Natl. Acad. Sci. U.S.A 104:8821-6, 2007

Maloney D G, Grillo-López A J, White C A et al.: IDEC-C2B8 (Rituximab) anti-CD20 monoclonal antibody therapy in patients with relapsed low-grade non-Hodgkin's lymphoma, Blood 90(6):2188-95, 1997

Donermeyer D L, Weber K S, Kranz D M, Allen P M, 2006, The study of high-affinity TCRs reveals duality in T cell recognition of antigen: specificity and degeneracy, J. Immunol. 177(10):6911-9

Xu, H, Cheng M, Guo H, Chen Y, Huse M, and Cheung N K, 2015, Retargeting T cells to GD2 pentasaccharide on human tumors using Bispecific humanized antibody, Cancer Immunol. Res. 3(3):266-77.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

The invention claimed is:

1. An isolated nucleic acid molecule encoding a human antibody agent that binds an EBV-LMP2/HLA peptide complex, wherein the human antibody agent comprises:
   (a) heavy chain CDR1 of SEQ ID NO:31, heavy chain CDR2 of SEQ ID NO:33, heavy chain CDR3 of SEQ ID NO:35; light chain CDR1 of SEQ ID NO:73, light chain CDR2 of SEQ ID NO:75 and light chain CDR3 of SEQ ID NO:77;
   (b) heavy chain CDR1 of SEQ ID NO:37, heavy chain CDR2 of SEQ ID NO:39, heavy chain CDR3 of SEQ ID NO:41, light chain CDR1 of SEQ ID NO:79, light chain CDR2 of SEQ ID NO:81, and light chain CDR3 of SEQ ID NO:83;
   (c) heavy chain CDR1 of SEQ ID NO:43, heavy chain CDR2 of SEQ ID NO:45, heavy chain CDR3 of SEQ ID NO:47, light chain CDR1 of SEQ ID NO:85, light chain CDR2 of SEQ ID NO:87, and light chain CDR3 of SEQ ID NO:89;
   (d) heavy chain CDR1 of SEQ ID NO:49, heavy chain CDR2 of SEQ ID NO:51, heavy chain CDR3 of SEQ ID NO:53, light chain CDR1 of SEQ ID NO:91, light chain CDR2 of SEQ ID NO:93, and light chain CDR3 of SEQ ID NO:95;
   (e) heavy chain CDR1 of SEQ ID NO:55, heavy chain CDR2 of SEQ ID NO:57, heavy chain CDR3 of SEQ ID NO:59, light chain CDR1 of SEQ ID NO:97, light chain CDR2 of SEQ ID NO:99, and light chain CDR3 of SEQ ID NO:101;
   (f) heavy chain CDR1 of SEQ ID NO:61, heavy chain CDR2 of SEQ ID NO:63, heavy chain CDR3 of SEQ ID NO:65, light chain CDR1 of SEQ ID NO:103, light chain CDR2 of SEQ ID NO:105, and light chain CDR3 of SEQ ID NO:107;
   (g) heavy chain CDR1 of SEQ ID NO:67, heavy chain CDR2 of SEQ ID NO:69, heavy chain CDR3 of SEQ ID NO:71, light chain CDR1 of SEQ ID NO:109, light chain CDR2 of SEQ ID NO:111, and light chain CDR3 of SEQ ID NO:113; or
   (h) heavy chain CDR1 of SEQ ID NO:43, heavy chain CDR2 of SEQ ID NO:45 or a sequence that differs from SEQ ID NO:45 in an I51V substitution, heavy chain CDR3 of SEQ ID NO:47, light chain CDR1 of SEQ ID NO:85, light chain CDR2 of SEQ ID NO:87 or a sequence that differs from SEQ ID NO:87 in a S52G substitution, and light chain CDR3 of SEQ ID NO:89 or a sequence that differs from SEQ ID NO:89 in a N95I substitution.

2. A recombinant vector comprising the nucleic acid molecule of claim 1.

3. The isolated nucleic acid molecule of claim 1, wherein the encoded human antibody agent comprises:
   (i) a heavy chain variable region having a sequence at least 95% identical to a heavy chain variable region sequence as set forth in any one of SEQ ID NOs: 5, 9, 13, 17, 21, 25, and 29, and
   (ii) a light chain variable region having a sequence at least 95% identical to a light chain variable region sequence as set forth in any one of SEQ ID NOs: 3, 7, 11, 15, 19, 23, and 27.

4. The isolated nucleic acid molecule of claim 1, wherein the encoded human antibody agent comprises:
   (i) a heavy chain variable region comprising a sequence as set forth in any one of SEQ ID NOs: 5, 9, 13, 17, 21, 25, and 29, and
   (ii) a light chain variable region comprising a sequence as set forth in any one of SEQ ID NOs: 3, 7, 11, 15, 19, 23, and 27.

5. The isolated nucleic acid molecule of claim 1, wherein the encoded human antibody agent comprises:
   (a) a light chain variable region as set forth in SEQ ID NO:3 and a heavy chain variable region as set forth in SEQ ID NO:5;
   (b) a light chain variable region as set forth in SEQ ID NO:7 and a heavy chain variable region as set forth in SEQ ID NO:9;
   (c) a light chain variable region as set forth in SEQ ID NO:11 and a heavy chain variable region as set forth in SEQ ID NO:13;
   (d) a light chain variable region as set forth in SEQ ID NO:15 and a heavy chain variable region as set forth in SEQ ID NO:17;
   (e) a light chain variable region as set forth in SEQ ID NO:19 and a heavy chain variable region as set forth in SEQ ID NO:21;
   (f) a light chain variable region as set forth in SEQ ID NO:23 and a heavy chain variable region as set forth in SEQ ID NO:25; or
   (g) a light chain variable region as set forth in SEQ ID NO:27 and a heavy chain variable region as set forth in SEQ ID NO:29.

6. The isolated nucleic acid molecule of claim 1, wherein the encoded human antibody agent comprises:
   (i) heavy chain CDR1 of SEQ ID NO:43, heavy chain CDR2 of SEQ ID NO:45 or a sequence that differs from SEQ ID NO:45 in an I51V substitution, and heavy chain CDR3 of SEQ ID NO:47; and
   (ii) light chain CDR1 of SEQ ID NO:85, light chain CDR2 of SEQ ID NO:87 or a sequence that differs from SEQ ID NO:87 in a S52G substitution, and light chain CDR3 of SEQ ID NO:89 or a sequence that differs from SEQ ID NO:89 in a N95I substitution.

7. The isolated nucleic acid molecule of claim 1, wherein the encoded human antibody agent comprises:
   (i) a light chain variable region sequence that comprises a sequence of SEQ ID NO: 11 or a sequence that differs from SEQ ID NO:11 in one or more amino acid substitutions selected from I48V, S52G, P55H, K66R and N95I; and
   (ii) a heavy chain variable region that comprises a sequence of SEQ ID NO: 13 or a sequence that differs from SEQ ID NO:13 in one or more amino acid substitutions selected from V5E, E10D, G26E, I51V and V78A.

8. The isolated nucleic acid molecule of claim 1, wherein the encoded human antibody agent comprises:
   (i) a light chain variable region having a sequence at least 95% identical to a light chain variable region sequence as set forth in SEQ ID NO:11; and
   (ii) a heavy chain variable region having a sequence at least 95% identical to a heavy chain variable region sequence as set forth in SEQ ID NO:13.

9. The isolated nucleic acid molecule of claim 1, wherein the encoded human antibody agent comprises:
   (i) a light chain variable region having a sequence as set forth in SEQ ID NO:11; and
   (ii) a heavy chain variable region having a sequence as set forth in SEQ ID NO:13.

10. The isolated nucleic acid molecule of claim 1, wherein the CDR sequences of the encoded human antibody agent comprise DNA sequences as set forth in:
    (a) SEQ ID NOs: 30, 32, 34, 72, 74, and 76;
    (b) SEQ ID NOs: 36, 38, 40, 78, 80, and 82;
    (c) SEQ ID NOs: 42, 44, 46, 84, 86, and 88;
    (d) SEQ ID NOs: 48, 50, 52, 90, 92, and 94;
    (e) SEQ ID NOs: 54, 56, 58, 96, 98, and 100;
    (f) SEQ ID NOs: 60, 62, 64, 102, 104, and 106; or
    (g) SEQ ID NOs: 66, 68, 70, 108, 110, and 112.

11. The isolated nucleic acid molecule of claim 1, comprising:
    (i) a human heavy chain variable region that comprises a DNA sequence that is at least 95% identical to a sequence set forth in any one of SEQ ID NOs: 4, 8, 12, 16, 20, 24, and 28; and
    (ii) a human light chain variable region that comprises a DNA sequence that is at least 95% identical to a sequence set forth in any one of SEQ ID NOs: 2, 6, 10, 14, 18, 22, and 26.

12. The isolated nucleic acid molecule of claim 1, comprising:
    (a) a human heavy chain variable region that comprises a DNA sequence as set forth in any one of SEQ ID NOs: 4, 8, 12, 16, 20, 24, and 28; and
    (b) a human light chain variable region that comprises a DNA sequence as set forth in any one of SEQ ID NOs: 2, 6, 10, 14, 18, 22, and 26.

13. The isolated nucleic acid molecule of claim 1, comprising:
    (a) a light chain variable region comprising a DNA sequence as set forth in SEQ ID NO:2 and a heavy chain variable region comprising a DNA sequence as set forth in SEQ ID NO:4;
    (b) a light chain variable region comprising a DNA sequence as set forth in SEQ ID NO:6 and a heavy chain variable region comprising a DNA sequence as set forth in SEQ ID NO:8;
    (c) a light chain variable region comprising a DNA sequence as set forth in SEQ ID NO:10 and a heavy chain variable region comprising a DNA sequence as set forth in SEQ ID NO:12;
    (d) a light chain variable region comprising a DNA sequence as set forth in SEQ ID NO:14 and a heavy chain variable region comprising a DNA sequence as set forth in SEQ ID NO:16;
    (e) a light chain variable region comprising a DNA sequence as set forth in SEQ ID NO:18 and a heavy chain variable region comprising a DNA sequence as set forth in SEQ ID NO:20;
    (f) a light chain variable region comprising a DNA sequence as set forth in SEQ ID NO:22 and a heavy chain variable region comprising a DNA sequence as set forth in SEQ ID NO:24; or
    (g) a light chain variable region comprising a DNA sequence as set forth in SEQ ID NO:26 and a heavy chain variable region comprising a DNA sequence as set forth in SEQ ID NO:28.

14. A recombinant vector comprising the nucleic acid molecule of claim 4.

15. A recombinant vector comprising the nucleic acid molecule of claim 6.

16. A recombinant vector comprising the nucleic acid molecule of claim 13.

* * * * *